(12) United States Patent
Lisanti et al.

(10) Patent No.: US 10,022,372 B2
(45) Date of Patent: Jul. 17, 2018

(54) CAVEOLIN-1 RELATED METHODS FOR TREATING GLIOBLASTOMA WITH TEMOZOLOMIDE

(71) Applicants: THOMAS JEFFERSON UNIVERSITY, Philadelphia, PA (US); Michael P. Lisanti, Withington, Manchester (GB)

(72) Inventors: Michael P. Lisanti, Withington (GB); Jean-Francois Jasmin, Philadelphia, PA (US); Kevin Quann, Pittsburgh, PA (US)

(73) Assignee: THOMAS JEFFERSON UNIVERSITY, Philadelphia, PA (US)

( * ) Notice: Subject to any disclaimer, the term of this patent is extended or adjusted under 35 U.S.C. 154(b) by 0 days.

(21) Appl. No.: 14/785,553

(22) PCT Filed: Apr. 18, 2014

(86) PCT No.: PCT/US2014/034639
§ 371 (c)(1),
(2) Date: Oct. 19, 2015

(87) PCT Pub. No.: WO2014/172627
PCT Pub. Date: Oct. 23, 2014

(65) Prior Publication Data
US 2016/0074389 A1  Mar. 17, 2016

Related U.S. Application Data

(60) Provisional application No. 61/813,724, filed on Apr. 19, 2013.

(51) Int. Cl.
| | | |
|---|---|---|
| *A61K 31/495* | (2006.01) | |
| *A61N 5/10* | (2006.01) | |
| *C12Q 1/6886* | (2018.01) | |
| *G01N 33/574* | (2006.01) | |

(52) U.S. Cl.
CPC ............. *A61K 31/495* (2013.01); *A61N 5/10* (2013.01); *C12Q 1/6886* (2013.01); *G01N 33/57407* (2013.01); *C12Q 2600/106* (2013.01); *C12Q 2600/158* (2013.01); *G01N 2333/705* (2013.01)

(58) Field of Classification Search
CPC .................................................... A61K 31/495
See application file for complete search history.

(56) References Cited

U.S. PATENT DOCUMENTS

| | | |
|---|---|---|
| 4,981,785 A | 1/1991 | Nayak |
| 5,124,246 A | 6/1992 | Urdea et al. |
| 5,358,691 A | 10/1994 | Clark et al. |
| 5,359,100 A | 10/1994 | Urdea et al. |
| 5,545,730 A | 8/1996 | Urdea et al. |
| 5,571,670 A | 11/1996 | Urdea et al. |
| 5,580,731 A | 12/1996 | Chang et al. |
| 5,591,584 A | 1/1997 | Chang et al. |
| 5,594,117 A | 1/1997 | Urdea et al. |
| 5,594,118 A | 1/1997 | Urdea et al. |
| 5,597,909 A | 1/1997 | Urdea et al. |
| 5,624,802 A | 4/1997 | Urdea et al. |
| 5,635,352 A | 6/1997 | Urdea et al. |
| 5,681,697 A | 10/1997 | Urdea et al. |
| 5,681,702 A | 10/1997 | Collins et al. |
| 5,693,617 A | 12/1997 | Stein et al. |
| 5,756,764 A | 5/1998 | Fenteany et al. |
| 5,780,454 A | 7/1998 | Adams et al. |
| 5,885,530 A | 3/1999 | Babson et al. |
| 6,018,020 A | 1/2000 | Attwood et al. |
| 6,066,730 A | 5/2000 | Adams et al. |
| 6,075,150 A | 6/2000 | Wang et al. |
| 6,083,903 A | 7/2000 | Adams et al. |
| 6,096,778 A | 8/2000 | Chatterjee et al. |
| 6,147,223 A | 11/2000 | Fenteany et al. |
| 6,159,750 A | 12/2000 | Edmonds |
| 6,297,217 B1 | 10/2001 | Adams et al. |
| 6,310,057 B1 | 10/2001 | Chatterjee et al. |

(Continued)

FOREIGN PATENT DOCUMENTS

| | | |
|---|---|---|
| WO | 1991013904 A1 | 1/1991 |
| WO | 1997027212 A1 | 7/1997 |

(Continued)

OTHER PUBLICATIONS

Cohen et al., Clin. Cancer Res. 11, 6767-71 (2005).*

(Continued)

*Primary Examiner* — Theodore R. West
(74) *Attorney, Agent, or Firm* — Cozen O'Connor

(57) ABSTRACT

This invention provides a method for treating a subject afflicted with glioblastoma multiforme comprising administering a therapeutically effective regimen of temoxolomide to be glioblastoma multiforme-afflicted subject, wherein the subject's glioblastoma multiforme cells are known to be caveolin-1-positive. This invention also provides a method for determining whether a subject afflicted with glioblastoma multiforme is likely to progress therapeutically in response to a therapeutically effective regimen of temoxolomide comprising determining whether the subject's glioblastoma multiforme cells are caveolin-1-positive, whereby if the subject's glioblastoma multiforme cells are caveolin-1-positive, the subject is likely to progress therapeutically in response to a therapeutically effective regimen of temozolomide.

9 Claims, 6 Drawing Sheets

(56) References Cited

U.S. PATENT DOCUMENTS

| | | |
|---|---|---|
| 6,335,358 B1 | 1/2002 | Fenteany et al. |
| 6,432,662 B1 | 8/2002 | Davis et al. |
| 6,465,433 B1 | 10/2002 | Adams et al. |
| 6,548,668 B2 | 4/2003 | Adams et al. |
| 6,617,317 B1 | 9/2003 | Adams et al. |
| 6,645,999 B1 | 11/2003 | Schreiber et al. |
| 6,747,150 B2 | 6/2004 | Adams et al. |
| 6,781,000 B1 | 8/2004 | Wang et al. |
| 6,831,099 B1 | 12/2004 | Crews et al. |
| 2003/0135033 A1 | 7/2003 | Klippel-Giese et al. |
| 2003/0165895 A1 | 9/2003 | Czerniak et al. |
| 2003/0166572 A1 | 9/2003 | Furet et al. |
| 2004/0043004 A1 | 3/2004 | Bender et al. |
| 2004/0167337 A1 | 8/2004 | Furet et al. |
| 2004/0186167 A1 | 9/2004 | Dou et al. |
| 2004/0234979 A1 | 11/2004 | Sun et al. |
| 2005/0032135 A1 | 2/2005 | Zerangue et al. |
| 2005/0203162 A1 | 9/2005 | Xiao et al. |
| 2006/0019256 A1 | 1/2006 | Clarke et al. |
| 2006/0183141 A1 | 8/2006 | Chang et al. |
| 2006/0275844 A1 | 12/2006 | Linke et al. |
| 2006/0281122 A1 | 12/2006 | Bryant et al. |
| 2007/0020297 A1 | 1/2007 | Wheeler et al. |
| 2007/0122856 A1 | 5/2007 | Georges et al. |
| 2008/0064055 A1 | 3/2008 | Bryant et al. |
| 2008/0138345 A1 | 6/2008 | De Sauvage et al. |
| 2009/0047215 A1 | 2/2009 | Harris |
| 2009/0092553 A1 | 4/2009 | Zerangue et al. |
| 2009/0220551 A1 | 9/2009 | Sampson et al. |
| 2009/0317392 A1 | 12/2009 | Nakamura et al. |
| 2010/0086922 A1 | 4/2010 | Bryant et al. |
| 2010/0255004 A1 | 10/2010 | DePinho et al. |
| 2010/0330106 A1 | 12/2010 | Noguera-Troise et al. |
| 2012/0039805 A1 | 2/2012 | Lisanti et al. |
| 2012/0039811 A1 | 2/2012 | Admon et al. |

FOREIGN PATENT DOCUMENTS

| | | |
|---|---|---|
| WO | 1999030707 A1 | 6/1999 |
| WO | 2002030973 A2 | 4/2002 |
| WO | 2002096933 A1 | 12/2002 |
| WO | 2003018557 A1 | 3/2003 |
| WO | 2004022070 A1 | 3/2004 |
| WO | 2004064755 A2 | 8/2004 |
| WO | 2004065394 A1 | 8/2004 |
| WO | 2004071382 A2 | 8/2004 |
| WO | 2005002572 A2 | 1/2005 |
| WO | 2005003137 A1 | 1/2005 |
| WO | 2005005601 A2 | 1/2005 |
| WO | 2005016859 A2 | 2/2005 |
| WO | 2005021558 A2 | 3/2005 |
| WO | 2005030707 A1 | 4/2005 |
| WO | 2005099687 A2 | 10/2005 |
| WO | 2005105826 A1 | 11/2005 |
| WO | 2005111008 A2 | 11/2005 |
| WO | 2005115431 A2 | 12/2005 |
| WO | 2006045066 A2 | 4/2006 |
| WO | 2008067065 A2 | 6/2008 |
| WO | 2010089580 A1 | 8/2010 |
| WO | 2010096627 A1 | 8/2010 |
| WO | 2011123788 A1 | 6/2011 |

OTHER PUBLICATIONS

Quann et al., Cell Cycle 12, 1510-20 (published online Apr. 17, 2013).*

Abulrob, A., et al., "Interactions of EGFR and Caveolin-1 in Human Glioblastoma Cells: Evidence that Tyrosine Phosphorylation regulates EGFR association with caveolae", Oncogene, vol. 23, pp. 6967-6979, 2004.

Ashburner, M., et al., "Gene Ontology: Tool for the Unification of Biology. The Gene Ontology Consortium", Nature Genetics, vol. 25, pp. 25-29, 2000.

Barresi, V., et al., "Caveolin-1 Expression in Diffuse Gliomas: Correlation with the Proliferation Index, Epidermal Growth Factor Receptor, p53, and 1p/19q status", Hum Pathol, vol. 40, pp. 1738-1746, 2009.

Brada, M., et al., "Multicenter Phase II Trial of Temozolomide in Patients with Glioblastoma Multiforme at First Relapse", Annals of Oncology, vol. 12, pp. 259-266, 2001.

Bruyere, C., et al., "Temozolomide modifies caveolin-1 expression in experimental malignant gliomas in vitro and in vivo", Translational Oncology, vol. 4, pp. 92-100, 2011.

Buckner, J.C., et al., "Central Nervous System Tumors", Mayo Clin Proc, vol. 82, pp. 1271-1286, 2007.

Cameron, A.W., et al., "Caveolin-1 Expression is Maintained in Rat and HumanAstroglioma Cell Lines", Gilia, vol. 37, pp. 275-290, 2002.

Cassoni, P., et al., "Caveolin-1 Expression is Variably Displayed in Astroglial-Derived Tumors and Absent in Oligodendrogliomas: Concrete Premises for a New Reliable Diagnostic Marker in Gliomas", Am J Surg Pathol, vol. 31, pp. 760-769, 2007.

Cohen, A.W., et al., "Caveolin-1 Null Mice Develop Cardiac Hypertrophy with Hyperactivation of p42/44 MAP Kinase in Cardiac Fibroblasts", Am J Physiol Cell Physiol, vol. 284, pp. C457-C474, 2003.

Cosset, E.C., et al., "Involvement of the TGFbeta Pathway in the Regulation of Alpha5 Beta1 Integrins by Caveolin-1 in Human Glioblastoma", International Journal of Cancer, vol. 131, pp. 601-611, 2012.

Deeken, J.F., et al., "The blood-brain barrier and cancer: transporters, treatment, and Trojan horses", Clin Cancer Res, vol. 13, pp. 1663-1674, 2007.

Engelman, J.A., et al., "Caveolin-mediated regulation of signaling along the p42/44 MAP kinase cascade in vivo. A role for the caveolin-scaffolding domain", FEBS letters, vol. 428, Issue 3, pp. 205-211, 1998.

Feng, S., et al., "Caveolin-1 gene silencing promotes the activation of P13K/AKT dependent on Eralpha36 and the transformation of MCF10ACE", Science China Life Sciences, vol. 53, pp. 598-605, 2010.

Forget, M.A., et al., "The expression of rho proteins decreases with human brain tumor progression: potential tumor markers", Clinical & Experimental Metastasis, vol. 19, pp. 9-15, 2002.

Garcia-Cardena, G., et al., "Dissecting the interaction between nitric oxide synthase (NOS) and caveolin. Functional significance of the nos caveolin binding doman in vivo", J Biol Chem, vol. 272, No. 41, pp. 25437-25440, 1997.

Goetz, J.G., "Caveolin-1 in tumor progression: the good, the bad and the ugly", Cancer Metastasis Rev, vol. 27, pp. 715-735, 2008.

Guo, Z., et al., "Expression and clinical significance of multidrug resistance proteins in brain tumors", Journal of Experimental & Clinical Cancer Research, vol. 29, No. 1, 122 (6 pages).

Han, F., et al., "Caveolin-1 acts as a tumor suppressor by down-regulating epidermal growth factor receptor-mitogen-activated protein kinase signaling pathway in pancreatic carcinoma cell lines", Pancreas, vol. 38, pp. 766-774, 2009.

Han, F., et al., "Caveolin-1 regulating the invasion and expression of matrix metalloproteinase (MMPs) in pancreatic carcinoma cells", The Journal of Surgical Research, vol. 159, pp. 443-450, 2010.

Ho, C.C., et al., "Caveolin-1 expression is significantly associated with drug resistance and poor prognosis in advanced non-small cell lung cancer patients treated with gemcitabine-based chemotherapy", Lung Cancer, vol. 59, pp. 105-110, 2008.

Hulit, J., et al., "The cyclin D1 gene is transcriptionally repressed by caveolin-1", J. Biol Chem, vol. 275, pp. 21203-21209, 2000.

Huse, J.T., et al., "Targeting brain cancer: advances in the molecular pathology of malignant glioma and medulloblastoma", Nat Rev Cancer, vol. 10, pp. 319-331, 2010.

Jodoin, J., et al., "P-glycoprotein in blood-brain barrier endothelial cells: interaction and oligomerization with caveolins", Journal of Neurochemistry, vol. 87, pp. 1010-1023, 2003.

Kim, H.N., et al., "Caveolin-1 inhibits membrane-type 1 matrix metalloproteinase activity", BMB Reports, vol. 41, pp. 858-862, 2008.

(56) References Cited

OTHER PUBLICATIONS

Kim, S., et al., "Basal and UV-induced MMP-1 expression are inhibited by p53 in human dermal fibroblasts", Experimental Dermatology, vol. 17, pp. 939-945, 2008.
Kita, D., et al., "PIK3CA alterations in primary (de novo) and secondary glioblastomas", Acta Neuropathologica, vol. 113, pp. 295-302, 2007.
Lin, M.I., et al., "Caveolin-1-deficient mice have increased tumor microvascular permeability, angiogenesis, and growth", Cancer Res, vol. 67, pp. 2849-2856, 2007.
Lopez-Gines, C. et al., "The activation of ERK1/2 MAP kinases in glioblastoma pathobiology and its relationship with EGFR amplification". Neuropathology: Official Journal of the Japanese Society of Neuropathology, vol. 28, No. 5, pp. 507-515, 2008.
Louis, D.N., "Molecular pathology of malignant gliomas", Annu Rev Pathol, vol. 1, pp. 97-117, 2006.
Martin, S., et al., "Caveolin-1 regulates glioblastoma aggressiveness through the control of alpha(5)beta(1) integrin expression and modulates glioblastoma responsiveness to SJ749, an alpha(5)beta(1) integrin antagonist", Biochim Biophys Acta, vol. 1793, Issue 2, pp. 354-367, 2009.
Mercier, I., et al., "Caveolin-1 and accelerated host aging in the breast tumor microenvironment: chemoprevention with rapamycin, an mTOR inhibitor and anti-aging drug", Am J Pathol, vol. 181, pp. 278-293, 2012.
Mizoguchi, M., et al. "Activation of STAT3, MAPK, and AKT in malignant astrocytic gliomas: correlation with EGFR status, tumor grade, and survival", J Neuropathol Exp Neurol, vol. 65, pp. 1181-1188, 2006.
Nakatani, K., et al., "Expression of caveolin-1 and its correlation with cisplatin sensitivity in oral squamous cell carcinoma", Journal of Cancer Research and Clinical Oncology, vol. 131, pp. 445-452, 2005.
Navarro, A., et al., "A role for caveolae in cell migration", FASEB J, vol. 18, pp. 1801-1811, 2004.
Ohgaki, H., et al., "Genetic pathways to primary and secondary glioblastoma", Am J Pathol, vol. 170, No. 5, pp. 1445-1453, 2007.
Parat, M.O., et al., "Caveolin-1, caveolae, and gliboblastoma", Neuro Oncol, vol. 14, No. 6, pp. 679-688, 2012.
Park, J., et al., "RNA interference-directed caveolin-1 knockdown sensitizes SN12CPM6 cells to doxorubicin-induced apoptosis and reduces lung metastasis", Tumour Biol, vol. 31, pp. 643-650, 2010.
Parton, R.G., et al., "The multiple faces of caveolae", Nat Rev Mol Cell Biol, vol. 8, pp. 185-194, 2007.
Patel, H.H., et al., "Caveolae as organizers of pharmacologically relevant signal transduction molecules", Annual Review of Pharmacology and Toxicology, vol. 48, pp. 359-391, 2008.
Quann, K., et al., "Caveolin-1 is a negative regulator of tumor growth in glioblastoma and modulates chemosensitivity to temozolomide", Cell Cycle, vol. 12, No. 10, pp. 1510-1520, 2013. 79-688, 2012.
Razani, B., et al., "Caveolae: from cell biology to animal physiology", Pharmacological Reviews, vol. 54, pp. 431-467, 2002.
Reunanen, N. et al., "Enhancement of fibroblast collagenase (matrix metalloproteinase-1)gene expression by ceramide is mediated by extracellular signal-regulated and stress-activated protein kinase pathways", J Biol Chem, vol. 273, pp. 5237-5145, 1998.
Schmitz, M., et al., "Effect of cavtratin, a caveolin-1 scaffolding domain peptide, on oligodendroglial signaling cascades", Cellular and Molecular Neurobiology, vol. 31, pp. 991-997, 2011.
Senetta, R., et al., "Caveolin 1 expression independently predicts shorter survival in oligodendrogliomas", J Neuropathol Exp Neurol, vol. 68, pp. 425-431, 2009.
Shetty, P., et al., "Urokinase expression by tumor suppressor protein p53: a novel role in mRNA turnover", American Journal of Respiratory Cell and Molecular Biology, vol. 39, pp. 364-372, 2008.
Stupp, R., et al., Effects of radiotherapy with concomitant and adjuvant temozolomide versus radiotherapy alone on survival in glioblastoma in a randomised phase III study: 5-year analysis of the EORTC-NCIC trial, Lancet Oncol, vol. 10, pp. 459-466, 2009.

Subramanian, A., et al., "Gene set enrichment analysis: a knowledge-based approach for interpreting genome-wide expression profiles", Proc Natl Acad Sci USA, vol. 102, pp. 15545-15550, 2005.
Sun, Y., et al., p53 down-regulates human matrix metalloproteinase-1 (Collagenase-1) gene expression, J Biol Chem, vol. 274, pp. 11535-11540, 1999.
Sunayama, J., et al., "Crosstalk between the pI3K/mTOR and MEK/ERK pathways involved in the maintenance of self-renewal and tumorigenicity of glioblastoma stem-like cells", Stem Cells, vol. 28, pp. 1930-1939, 2010.
Torres, V.A., et al., "Caveolin-1 controls cell proliferation and cell death by suppressing expressin of the inhibitor of apoptosis protein survivin", Journal of Cell Science, vol. 119, pp. 1812-1823, 2006.
Van Deurs, B., et al., "Caveolae: anchored, multifunctional platforms in the lipid ocean", Trends in Cell Biology, vol. 13, pp. 92-100, 2003.
Williams, T.M., et al., "Caveolin-1 gene disruption promotes mammary tumorigenesis and dramatically enhances long metastasis in vivo. Role of Cav-1 in cell invasiveness and matrix metalloproteinase (MMP-2/9) secretion", J Biol Chem, vol. 279, No. 49, pp. 51630-51646, 2004.
Williams, T.M., et al., "Caveolin-1 in oncogenic transformation, cancer, and metastasis", Am J Physiol Cell Physiol, vol. 288, pp. C494-C506, 2005.
Xia, H., "Pathologic caveolin-1 regulation of PTEN in idiopathic pulmonary fibrosis", Am J Pathol, vol. 176, pp. 2626-2637, 2010.
Yang, X., et al., "Higher expression of Caveolin-1 inhibits human small cell cancer (SCLC) apoptosis in vitro", Cancer Invest, vol. 30, pp. 453-462, 2012.
Zhang, M., et al., "Deletion of caveolin-1 protects hyperoxia-induced apoptosis via survivin-mediated pathways", American Journal of Physiology Lung Cellular and Molecular Physiology, vol. 297, pp. L945-L953, 2009.
Zhang, M., et al., "Caveolin-1 mediates Fas-BID signaling in hyperoxia-induced apoptosis", Free Radical Biology & Medicine, vol. 50, No. 10, pp. 1252-1262, 2011.
Mercier, I., et al., "Human breast cancer-associated fibroblasts (CAFs) show caveolin-1 downregulation and RB tumor suppressor functional inactivation: Implications for the response to hormonal therapy", Cancer Biology & Therapy, vol. 7, pp. 1212-1225, 2008.
International Search Report issued in International Application No. PCT/US2010/024606 dated May 4, 2010.
International Search Report issued in International Application No. PCT/US2011/048467 dated Dec. 22, 2011.
International Search Report issued in International Application No. PCT/US2012/022933 dated May 2, 2012.
International Search Report issued in International Application No. PCT/US2013/023209 dated Apr. 9, 2013.
International Search Report issued in International Application No. PCT/US2013/059679 dated Mar. 4, 2014.
International Search Report issued in International Application No. PCT/US2014/034639 dated Aug. 26, 2014.
Iqbal, M., et al., "Potent Inhibitors of Proteasome", J. Med. Chem., vol. 38, No. 13, pp. 2276-2277, 1995.
Jordan, V.C., "A current view of tamoxifen for the treatment and prevention of breast cancer", British Journal of Pharmacology, vol. 110, No. 2, pp. 507-517, 1993.
Joseph, P., et al., "Oncogenic potential of mouse translation elongation factor-1 delta, a novel cadmium-responsive proto-oncogene", J Biol Chem, vol. 277, pp. 6131-6136, 2002.
Kawase, A., et al., "Podoplanin expression by cancer associated fibroblasts predicts poor prognosis of lung adenocarcinoma", Int. J. Cancer, vol. 123, pp. 1053-1059, 2008.
Kay, R.A., et al., "The expression of migration stimulating factor, a potent oncofetal cytokine, is uniquely controlled by 3'-untranslated region-dependent nuclear sequestration of its precursor messenger RNA", Cancer Res, vol. 65, pp. 10742-10749, 2005.
Keown, W.A., et al., "Methods for Introducing DNA into mammalian cells", Methods in Enzymology, vol. 185, pp. 527-537, 1990.
Kerbel, R., et al., "Clinical translation of angiogenesis inhibitors", Nature Reviews, vol. 2, pp. 727-739, 2002.
Ko, Y.H., et al., "Glutamine fuels a vicious cycle of autophagy in the tumor stroma and oxidative mitochondrial metabolism in epithelial

(56) References Cited

OTHER PUBLICATIONS cancer cells: Implications for preventing chemotherapy resistance", Cancer Biol Ther, vol. 12, No. 12, pp. 1085-1097, 2011.

Koguchi, Y., et al., "TMC-95A, B, C, and D, Novel Proteasome Inhibitors Produced by Apiospora montagnei Sacc. TC 1093 Taxonomy, Production, Isolation, and Biological Activities", The Journal of Antibiotics (Tokyo), vol. 53, No. 2, pp. 105-109, 2000.

Kojima, Y., et al., "Autocrine TGF-beta and stromal cell-derived factor-1 (SDF-1) signaling drives the evolution of tumor-promoting mammary stromal myofibroblasts", Proc Natl Acad Sci USA, vol. 107, pp. 20009-20014, 2010.

Koo, J.S., et al., "The impact of caveolin protein expression in tumor stroma on prognosis of breast cancer.", Tumour Biol, vol. 32, pp. 787-799, 2011.

Kroll, M. "The secondary fungal metabolite gliotoxin targets proteolytic activities of the proteasome", Chemistry & Biology, vol. 6, No. 10, pp. 689-698, 1999.

Lee, J., et al., "Pyruvate kinase isozyme type M2 (PKM2) interacts and cooperates with Oct-4 in regulating transcription", Int J Biochem Cell Biol, vol. 40, No. 5, pp. 1043-1054, 2008.

Lei, Y. et al., "Blocking the translation elongation factor-1δ with its antisense mRNA results in a significant reversal of its oncogenic potential", Teratogenesis, Carcinogenesis, and Mutagenesis, vol. 22, No. 5, pp. 377-383, 2002.

Levy, L., et al., "Alterations in components of the TGF-beta superfamily signaling pathways in human cancer", Cytokine Growth Factor Rev, vol. 17, pp. 41-58, 2006.

Lisanti, M.P., et al., "Accelerated aging in the tumor microenvironment: connecting aging, inflammation and cancer metabolism with personalized medicine", Cell Cycle,, vol. 10, No. 13, pp. 2059-2063, 2011.

Lisanti, M.P., et al., "Hydrogen peroxide fuels aging, inflammation, cancer metabolism and metastasis: the seed and soil also needs 'fertilizer'", Cell Cycle, vol. 10, No. 15, pp. 2440-2449, 2011.

Lohr, M., et al., "Transforming growth factor-beta1 induces desmoplasia in an experimental model of human pancreatic carcinoma", Cancer Res, vol. 61, pp. 550-555, 2001.

Magistretti, P.J., et al., "The contribution of astrocytes to the 18F-2-deoxyglucose signal in PET activation studies", Mol Psychiatry, vol. 1, pp. 445-452, 1996.

Magistretti, P.J., "Role of Neuron-glia metabolic coupling and plasticity", J Exp Biol, vol. 209, pp. 2304-2311, 2006.

Magistretti, P.J., "Role of glutamate in neuron-glia metabolic coupling", Am J Clin Nutr, vol. 90, pp. 875S-880S, 2009.

Marastoni, M., et al., "Peptidyl Vinyl Ester Derivatives: New Class of Selective Inhibitors of Proteasome Trypsin-Like Activity", Journal of Medicinal Chemistry, vol. 48, No. 15, pp. 5038-5042, 2005.

Martinez-Outschoorn, U.E., et al., "The autophagic tumor stroma model of cancer or 'battery-operated tumor growth': A simple solution to the autophagy paradox", Cell Cycle, vol. 9, No. 21, pp. 4297-4306, 2010.

Martinez-Outschoorn, U.E., et al., "Tumor cells induce the cancer associated fibroblast phenotype via caveolin-1 degradation: Implications for breast cancer and DCIS therapy with autophagy inhibitors", Cell Cycle, vol. 9, No. 12, pp. 2423-2433, 2010.

Martinez-Outschoorn, U.E., et al., "Oxidative stress in cancer associated fibroblasts drives tumor-stroma co-evolution: A new paradigm for understanding tumor metabolism, the field effect and genomic instability in cancer cells", Cell Cycle, vol. 9, No. 16, pp. 3256-3276, 2010.

Martinez-Outschoorn, U.E., et al., "Autophagy in cancer associated fibroblasts promotes tumor cell survival: Role of hypoxia, HIF1 induction and NFkappaB activation in the tumor stromal microenvironment", Cell Cycle, vol. 9, No. 17, pp. 3515-3533, 2010.

Martinez-Outschoorn, U.E., et al., "Energy transfer in 'parasitic' cancer metabolism: Mitochondria are the powerhouse and Achilles' heel of tumor cells", Cell Cycle, vol. 10, No. 24, 4208-4216, 2011.

Martinez-Outschoorn, U.E., et al., "Stromal-epithelial metabolic coupling in cancer: integrating autophagy and metabolism in the tumor microenvironment", Int J Biochem Cell Biol, vol. 43, pp. 1045-1051, 2011.

Martinez-Outschoorn, U.E., et al., "Mitochondrial biogenesis drives tumor cell proliferation", Am J Pathol, vol. 178, pp. 1949-1952, 2011.

Martinez-Outschoorn, U.E., et al., "Cancer cells metabolically 'fertilize' the tumor microenvironment with hydrogen peroxide, driving the Warburg effect: Implications for PET imaging of human tumors", Cell Cycle, vol. 10, No. 15, 2504-2520, 2011.

Martinez-Outschoorn, U.E., et al., "Cytokine production and inflammation drive autophagy in the tumor microenvironment: role of stromal caveolin-1 as a key regulator", Cell Cycle, vol. 10, No. 11, pp. 1784-1793, 2011.

Martinez-Outschoorn, U.E., et al., "Ketones and lactate increase cancer cell 'stemness', driving recurrence, metastasis and poor clinical outcome in breast cancer, Achieving personalized medicine via metabolo-genomics", Cell Cycle, vol. 10, No. 8, pp. 1271-1286, 2011.

Martinez-Outschoorn, U.E., et al., "Anti-estrogen resistance in breast cancer is induced by the tumor microenvironment and can be overcome by inhibiting mitochondrial function in epithelial cancer cells", Cancer Biol Ther, vol. 12, No. 10, pp. 924-938, 2011.

Martinez-Outschoorn, U.E., et al., "Understanding the metabolic basis of drug resistance: Therapeutic induction of the Warburg effect kills cancer cells", Cell Cycle, vol. 10, No. 15, pp. 2521-2528, 2011.

Martinez-Outschoorn, U.E., et al., Power Surge: Supporting Cells 'Fuel' Cancer Cell Mitochondria, Cell Metab, vol. 15, pp. 4-5, 2012.

Massague, J., "TGFbeta in Cancer", Cell, vol. 134, pp. 215-230, 2008.

Massague, J., "TGF-beta signaling in development and disease", FEBS Lett, vol. 586, p. 1833, 2012.

McConnell, A.A., et al., "An unusual case of shock in a young woman", Postgrad Med J, vol. 65, No. 120, 1989.

Meng, L., et al., "Epoxomicin, a potent and selective proteasome inhibitor, exhibits in vivo antiinflammatory activity", Proc. Natl. Acad. Sci., vol. 96, No. 18, pp. 10403-10408, 1999.

Meng, L., et al., "Eponemycin Exerts Its Antitumor Effect through the Inhibition of Proteasome Function", Cancer Research, vol. 59, pp. 2798-2801, 1999.

Migita, T., et al., "ATP Citrate Lyase: 1-20 Activation and Therapeutic Implications in Non-Small Cell Lung Cancer", Cancer Research, vol. 68, No. 20, pp. 8547-8554, Oct. 15, 2008.

Millis, R.R., et al., "Immunohistochemical evaluation of biological markers in mammary carcinoma in situ: correlation with morphological features and recently proposed schemes for histological classification", The Breast, vol. 5, No. 3, pp. 113-122, 1996.

Mishra, P.J., et al., "Carcinoma-associated fibroblast-like differentiation of human mesenchymal stem cells", Cancer Res, vol. 68, pp. 4331-4339, 2008.

Monypenny, J., et al., "Cdc42 and Rac family GTPases regulate mode and speed but not direction of primary fibroblast migration during platelet-derived growth factor-dependent chemotaxis", Mol Cell Biol, vol. 29, pp. 2730-2747, 2009.

Anderson, R.L., et al., "Stromal expression of caveolin-1 regulates breast cancer progression", Journal of Bone and Mineral Research, vol. 19, No. 9, p. 1580, Sep. 2004.

Balliet, R.M., et al., "Mitochondrial oxidative stress in cancer-associated fibroblasts drives lactate production, promoting breast cancer tumor growth: Understanding the aging and cancer connection", Cell Cycle, vol. 10, No. 23, pp. 4065-4073, 2011.

Beckner, M.E., et al., "Identification of ATP Citrate Lyase as a Positive Regulator of Glycolytic Function in Glioblastomas", International Journal of Cancer, vol. 126, No. 10, pp. 2282-2295, May 15, 2010.

Bergersen, L.H., "Is lactate food for neurons? Comparison of monocarboxylate transporter subtypes in brain and muscle", Neuroscience, vol. 145, pp. 11-19, 2007.

Bogyo, M., et al., "Covalent modification of the active site threonine of proteasomal β subunits and the *Escherichia coli* homolog HslV by a new class of inhibitors", Proc. Natl. Acad. Sci. vol. 94, 6629-6634, 1997.

(56) References Cited

OTHER PUBLICATIONS

Bonuccelli, G., et al., "The reverse Warburg effect: Glycolysis inhibitor prevent the tumor promoting effects of caveolin-1 deficient cancer associated fibroblasts", Cell Cycle, vol. 9, No. 10, pp. 1960-1971, 2010.

Boring, C.C., et al., "Cancer statistics, 1993", CA Cancer J Clin, 1993, vol. 43, pp. 7-26.

Bouget, K., et al., "Hydrazino-aza and N-azapeptoids with therapeutic potential as anticancer agents", Bioorg. Med. Chem., vol. 11, pp. 4881-4889, 2003.

Brennan, et al., "Contribution of DNA and tissue microarray technology to the identification and validation of biomarkers and personalized medicine in breast cancer", Cancer Genomics & Proteomics, vol. 4, pp. 121-134, 2007.

Brizel, D.M., et al., "Elevated tumor lactate concentrations predict for an increased risk of metastases in head-and-neck cancer", Int J Radiat Oncol Biol Phys, vol. 51, No. 2, pp. 349-353, 2001.

Brooks, G.A., "Current concepts in lactate exchange", Med Sci Sports Exerc, vol. 23, No. 8, pp. 895-906, 1991.

Brooks, G.A., "Lactate shuttles in nature", Biochem Soc Trans, vol. 30, Part 2, pp. 258-264, 2002.

Bueno, V., et al., "The specific monocarboxylate transporter (MCT1) inhibitor, AR-C117977, a novel Immunosuppressant, prolongs allograft survival in the mouse", Transplantation, vol. 84, pp. 1204-1207, 2007.

Burgermeister, E., et al., "Caveats of caveolin-1 in cancer progression", Cancer Letters, vol. 268, No. 2, pp. 187-201, Sep. 18, 2008.

Carito, V., et al., "Metabolic Remodeling of the Tumor Microenvironment: Migration Stimulating Factor (MSF) Reprograms Myofibroblasts toward Lactate Production, fueling Anabolic Tumor Growth", Cell Cycle, vol. 11, No. 18, pp. 3403-3414, 2012.

Casey, T.M., et al., "Cancer associated fibroblasts stimulated by transforming growth factor beta 1 (TGF-beta 1) Increase invasion rate of tumor cells: a population study", Breast Cancer Res Treat, vol. 110, pp. 39-49, 2008.

Chen, C., et al., "Gene expression profiling identifies genes predictive of oral squamous cell carcinoma", Cancer Epidemiology Biomarkers & Prevention, vol. 17, No. 8, pp. 2152-2162, Aug. 2008.

Cheng, J.C., et al., "Severe lactic acidosis in a 14-year-old female with metastatic undifferentiated carcinoma of unknown primary", J. Pediatr Hematol Oncol, vol. 26, No. 11, pp. 780-782, 2004.

Chiavarina, B., et al., "HIF1-alpha functions as a tumor promoter in cancer associated fibroblasts, and as a tumor suppressor in breast cancer cells: Autophagy drives compartment-specific oncogenesis", Cell Cycle, vol. 9, No. 17, pp. 3534-3551, 2010.

Chiavarina, B., et al., "Pyruvate kinase expression (PKMI and PKM2) in cancer-associated fibroblasts drives stromal nutrient production and tumor growth", Cancer Biol Ther, vol. 12, No. 12, pp. 1101-1113, 2011.

Christofk, H.R., et al., "Pyruvate kinase M2 is a phosphotyrosine-binding protein", Nature 452, pp. 181-186, 2008.

Christofk, H.R., et al., "The M2 splice isoform of pyruvate kinase is important for cancer metabolism and tumour growth", Nature, vol. 452, pp. 230-233, 2008.

Colletta, A.A., et al., "Anti-oestrogens induce the secretion of active transforming growth factor beta from human fetal fibroblasts", Br J Cancer, vol. 62, pp. 405-409, 1990.

Daly, M.B., "Tamoxifen in ductal carcinoma in situ", Seminars in Oncology, vol. 33, pp. 647-649, Dec. 2006.

Deffieu, M., et al., "Glutathione participates in the regulation of mitophagy in yeast", Journal of Biological Chemistry, vol. 284, No. 22, pp. 14828-14837, 2009.

Desmouliere, A., et al., "Transforming growth factor-beta 1 induces alpha-smooth muscle action expression in granulation tissue myofibroblasts and in quiescent and growing cultured fibroblasts", J Cell Biol, vol. 122, pp. 103-111, 1993.

Dimmer, K.S., et al., "The low-affinity monocarboxylate transporter MCT4 is adapted to the export of lactate in highly glycolytic cells", Biochem J, vol. 350, Part 1, pp. 219-227, 2000.

Direkze, N.C., et al., "Bone marrow contribution to tumor-associated myofibroblasts and fibroblasts", Cancer Res, vol. 64, pp. 8492-8495, 2004.

Di Vizio, D., et al., "An absence of stromal caveolin-1 is associated with advanced prostate cancer, metastatic disease and epithelial Akt activation", Cell Cycle, vol. 8, No. 15, pp. 2420-2424, Aug. 2009.

El-Gendi, S.M., et al., "Stromal Caveolin-1 Expression in Breast Carcinoma. Correlation with Early Tumor Recurrence and Clinical Outcome", Pathol Oncol Res, vol. 18, pp. 459-469, 2012; DOI 10.1007/sl2253-011-9469-5: In Press.

Ellis, I., et al., "Antagonistic effects of TGF-beta 1 and MSF on fibroblast migration and hyaluronic acid synthesis. Possible implications for dermal wound healing", J Cell Sci, vol. 102 (Pt 3), pp. 447-456, 1992.

Engelman, J.A., et al., "Reciprocal regulation of Neu tyrosine kinase activity and caveolin-1 protein expression in vitro and in vivo", The Journal of Biological Chemistry, vol. 273, No. 32, pp. 20448-20455, 1998.

Ertel, A., et al., "Is cancer a metabolic rebellion against host aging? In the quest for immortality, tumor cells try to save themselves by boosting mitochondrial metabolism", Cell Cycle, vol. 11, No. 2, pp. 253-263, 2012.

Esteva, F.J., et al., "Integration of systemic chemotherapy in the management of primary breast cancer", The Oncologist, vol. 3, pp. 300-313, 1998.

Evans, T.R., et al., "Lactic acidosis. A presentation of metastatic breast cancer arising in pregnancy", Cancer, vol. 69, No. 2, pp. 453-456, 1992.

Fenteany, G., et al., "A beta-lactone related to lactacystin induces neurite outgrowth in a neuroblastoma cell line and inhibits cell cycle progression in an osteosarcoma cell line", Proc. Natl. Acad. Sci. USA, vol. 91, No. 8, pp. 3358-3362, 1994.

Fisher, B., et al., "Tamoxifen in the treatment of intraductal breast cancer: National surgical adjuvant breast and bowel project B-24 randomised controlled trial", The Lancet, vol. 353, pp. 1993-2000, Jun. 1999.

Frank, R., et al., "Clinical biomarkers in drug discovery and development", Nature Reviews, vol. 2, pp. 566-580, 2003.

Fry, D.W., et al., "Specific inhibition of cyclin-dependent kinase 4/6 by PD 0332991 and associated antitumor activity in human tumor xenografts", Mol Cancer Ther, vol. 3, pp. 1427-1438, 2004.

Furuta, E., et al., "Metabolic Genes in Cancer: Their Roles in Tumor Progression and Clinical Implications", Biochim Biophys Acta, vol. 1805, No. 2, pp. 141-152, 2010.

Gallagher, S.M., et al., "Monocarboxylate transporter 4 regulates maturation and trafficking of CD147 to the plasma membrane in the metastatic breast cancer cell line MDA-MB-231", Cancer Research, vol. 67, pp. 4182-4189, 2007.

Garcia, S., et al., "Poor prognosis in breast carcinomas correlates with increased expression of targetable CD146 and c-Met and with proteomic basal-like phenotype", Human Pathology, vol. 38, pp. 830-841, 2007.

Grey, A.M., et al., "Purification of the migration stimulating factor produced by fetal and breast cancer patient fibroblasts", Proc Natl Acad Sci, vol. 86, pp. 2438-2442, 1989.

Haggie, J.A., et al., "Fibroblasts from relatives of patients with hereditary breast cancer show fetal-like behaviour in vitro", Lancet, vol. 1, pp. 1455-1457, 1987.

Haraguchi, M., et al., "Sensitivity of Human KB Cells Expressing Platelet-derived Endothelial Cell Growth Factor to Pyrimidine Antimetabolites", Cancer Res., vol. 53, pp. 5680-5682, 1993.

Hart, I.R., et al., "Role of organ selectivity in the determination of metastatic patterns of B16 melanoma", Cancer Research, vol. 40, pp. 2281-2287, 1980.

Hart, I.R., et al., "Seed and soil revisited: mechanisms of site-specific metastasis", Cancer Metastasis Rev, vol. 1, pp. 5-16, 1982.

Heasman, S.J., et al., "GTPases: new insights into their functions from in vivo studies", Nat Rev Mol Cell Biol 2008, vol. 9, pp. 690-701.

Heid, C.A., et al., "Real time quantitative PCT", Genome Res., vol. 6, No. 10, pp. 986-994, 1996.

International Breast Cancer Study Group, "Toremifene and tamoxifen are equally effective for early-stage breast cancer: first

(56) References Cited

OTHER PUBLICATIONS results of International Breast Cancer Study Group Trials 12-93 and 14-93", Annals of Oncology, vol. 15, No. 12, pp. 1749-1759, 2004.
Surowiak, P., et al., "Occurrence of stromal myofibroblasts in the invasive ductal breast cancer tissue is an unfavourable prognostic factor", Anticancer Res, vol. 27, pp. 2917-2924, 2007.
Themeau, T., original Splus->R port by T. Lumley. Survival: Survival analysis, including penalised likelihood. R package version 236-9 2011; http://CRAN.R-project.org/package-survival.
Toullec, A., et al., Oxidative stress promotes myofibroblast differentiation and tumour spreading, EMBO Mol Med, vol. 2, pp. 211-230, 2010.
Trimmer, C., et al., "Caveolin-1 and mitochondrial SOD2 (MnSOD) function as tumor suppressors in the stromal microenvironment: A new genetically tractable model for human cancer associated fibroblasts", Cancer Biol Ther, vol. 11, No. 4, pp. 383-394, 2011.
Tsujino, T., et al., "Stromal myofibroblasts predict diseases recurrence for colorectal cancer", Clin Cancer Res, vol. 13, pp. 2082-2090, 2007.
Ullah, M.S., et al., "The plasma membrane lactate transporter MCT4, but not MCT1, is up-regulated by hypoxia through a HIF-1alpha-dependent mechanism", J Biol Chem, vol. 281, pp. 9030-9037, 2006.
Vander Heiden, M.G., et al., "Understanding the Warburg effect: the metabolic requirements of cell proliferation", Science, vol. 324, pp. 1029-1033, 2009.
Varanasi, U.R., et al., "Lactic acidosis associated with metastatic breast carcinoma", Cancer Treat Rep, vol. 64, pp. 1283-1285, 1980.
Vozenin-Brotons, M.C., et al., "Antifibotic action of Cu/Zn SOD is mediated by TGF-beta 1 repression and phenotype reversion of myofibroblasts", Free Radic Biol Med, vol. 30, pp. 30-42, 2001.
Waghray, M., et al., "Hydrogen peroxide is a diffusible paracrine signal for the induction of epithelial cell death by activated myofibroblasts", FASEB J, vol. 19, pp. 854-856, 2005.
Walenta, S., et al., "Correlation of high lactate levels in head and neck tumors with incidence of metastasis", Am J Pathol, vol. 150, No. 2, pp. 409-415, 1997.
Walenta, S., et al., "High lactate levels predict likelihood of metastases, tumor recurrence, and restricted patient survival in human cervical cancers", Cancer Res, vol. 60, pp. 916-921, 2000.
Walenta, S., et al., "Lactate: mirror and motor of tumor malignancy", Semin Radiat Oncol, vol. 14, No. 3, pp. 267-274, 2004.
Warburg, O., "On the origin of cancer cells", Science, vol. 123, pp. 309-314, 1956.
Warburg, O., "On respiratory impairment in cancer cells", Science, vol. 124, pp. 269-270, 1956.
Warner, E., "Type B lactic acidosis and metastatic breast cancer", Breast Cancer Res Treat, vol. 24, pp. 75-79, 1992.
Whitaker-Menezes, D., et al., "Evidence for a stromal-epithelial "lactate shuttle" in human tumors: MCT4 is a marker of oxidative stress in cancer-associated fibroblasts", Cell Cycle, vol. 10, No. 11, pp. 1772-1783, 2011.
Whitaker-Menezes, D., et al., "Hyperactivation of Oxidative Mitochondrial Metabolism in Epithelial Cancer Cells In Situ: Visualizing the Therapeutic Effects of Metformin in Tumor Tissue", Cell Cycle, vol. 10, No. 13, pp. 4047-4064, 2011.
Witkiewicz, A.K., et al., "Stromal caveolin-1 levels predict early DCIS progression to invasive breast cancer", Cancer Biology & Therapy, vol. 8, No. 11, pp. 1071-1079, 2009.
Witkiewicz, A.K., et al., "Loss of Caveolin-1 Expression in Breast Cancer Associated Fibroblasts Correlates with Tumor Aggressiveness", Laboratory Investigation, vol. 89, Supplement, pp. 74A-75A, 2009.
Witkiewicz, A.K., et al., "An Absence of Stromal Caveolin-1 Expression Predicts Early Tumor Recurrence and Poor Clinical Outcome in Human Breast Cancers", The American Journal of Pathology, vol. 174, No. 6, pp. 2023-2034, 2009.
Witkiewicz, A.K., et al., "Towards a new 'stroma-based' classification system for human breast cancer prognosis and therapy", Cell Cycle, vol. 8, No. 11, pp. 1654-1658, 2009.
Witkiewicz, A.K., et al., "Loss of stromal caveolin-1 expression predicts poor clinical outcome in triple negative and basal-like breast cancers", Cancer Biol Ther, vol. 10, No. 2, pp. 135-143, 2010.
Witkiewicz, A.K., et al., "Molecular profiling of a lethal tumor microenvironment, as defined by stromal caveolin-1 status in breast cancers", Cell Cycle, vol. 10, No. 11, pp. 1794-1809, 2011.
Wu, K.N., "Loss of stromal caveolin-1 expression in malignant melanoma metastases predicts poor survival", Cell Cycle, vol. 10, No. 24, pp. 4250-4255, 2011.
Yamamoto, Y., et al., "Combination effect of an angiogenesis inhibitor AGM-1470 with 5'-deoxy-5-fluorouridine, and with hormonal drugs in DMBA-induced rat mammary-tumors", Oncology Reports, vol. 2, No. 5, pp. 793-796, 1995.
Yancy, H.F., et al., "Metastatic Progression and Gene Expression Between Breast Cancer Cell Lines from African American and Caucasian Women", Journal of Carcinogenesis, Biomed Central, vol. 6, No. 8, pp. 1-12, May 1, 2007.
Zeisberg, E.M., et al., "Discovery of endothelial to mesenchymal transition as a source for carcinoma-associated fibroblasts", Cancer Research, vol. 67, pp. 10123-10128, 2007.
Zhong, L., et al., "Autoantibodies as potential biomarkers for breast cancer", Breast Cancer Research, vol. 10, pp. 1-8.
Zu, X.L., et al., "Cancer metabolism: facts, fantasy, and fiction", Biochem Biophys Res Commun, vol. 313, pp. 459-465, 2004.
Paget, S., "The distribution of secondary growths in cancer of the breast", Cancer Metastasis Rev, vol. 8, pp. 98-101, 1989.
Nam, S., "Ester Bond-containing Tea Polyphenols Potently Inhibit Proteasome Activity in Vitro and in Vivo", The Journal of Biological Chemistry, vol. 276, pp. 13322-13330, 2001.
Nowak, G., et al., "Autocrine production and TGF-beta 1-mediated effects on metabolism and viability in renal cells", Am J Physiol, vol. 271, pp. F689-F697, 1996.
Oikawa, et al., "Angiogenic activity of rat mammary carcinomas induced by 7,12-dimethylbenz[a]anthracene and its inhibition by medroxyprogesterone acetate: possible involvement of antiangiogenic action of medroxyprogesterone acetate in its tumor growth inhibition", Cancer Letters, vol. 43, pp. 85-92, 1988.
O'Reilly, M.S., et al., "Angiostatin: A novel angiogenesis inhibitor that mediates the suppression of metastases by a lewis lung carcinoma", Cell, vol. 79, No. 2, pp. 315-328, 1994.
Ovens, M.J., et al., "AR-C155858 is a potent inhibitor of monocarboxylate transporters MCTI and MCT2 that binds to an intracellular site involving transmembrane helices 7-10", Biochem J, vol. 425, pp. 523-530, 2010.
Ovens, M.J., et al., "The inhibition of monocarboxylate transporter 2 (MCT2) by AR-C155858 is modulated by the associated ancillary protein", Biochem. J., vol. 431, pp. 217-225, 2010.
Pavlides, S., et al., "The reverse Warburg effect: Aerobic glycolysis in cancer associated fibroblasts and the tumor stroma", Cell Cycle, vol. 8, No. 23, pp. 3984-4001, 2009.
Pavlides, S., et al., "Loss of stromal caveolin-1 leads to oxidative stress, mimics hypoxia and drives inflammation in the tumor microenvironment, conferring the 'reverse Warburg effect': A transcriptional informatics analysis with validation", Cell Cycle, vol. 9, No. 11, pp. 2201-2219, 2010.
Pavlides, S., et al., "The autophagic tumor stroma model of cancer: Role of oxidative stress and ketone production in fueling tumor cell metabolism", Cell Cycle, vol. 9, No. 17, pp. 3485-3505, 2010.
Pavlides, S., et al., "Warburg Meets Autophagy: Cancer-Associated Fibroblasts Accelerate Tumor Growth and Metastasis via Oxidative Stress, Mitophagy, and Aerobic Glycolysis", Antioxid Redox Signal, vol. 16, No. 1, pp. 1264-1284, 2012.
Pepe, M.S., et al., "Limitations of the odds ratio in gaugin the performance of a diagnostic, prognostic, or screening marker", American Journal of Epidemiology, vol. 159, No. 9, pp. 882-890, 2004.
Perrone, G., et al., "COX-2 localization within plasma membrane caveolae-like structures in human lobular intrapeithelical neoplasia of the breast", Virchows Archiv: an international journal of pathology, vol. 451, No. 6, pp. 1039-1045, 2007.
Pertega-Gomes, N., et al., "Monocarboxylate transporter 4 (MCT4) and CD147 overexpression is associated with poor prognosis in prostate cancer", BMC Cancer, vol. 11, No. 312, pp. 1-9, 2011.

(56) References Cited

OTHER PUBLICATIONS

Petersen, O.W., et al., "Epithelial to mesenchymal transition in human breast cancer can provide a nonmalignant stroma", Am J Pathol, vol. 162, pp. 391-402, 2003.
Picardo, M., et al., "Migration stimulating activity in serum of breast cancer patients", Lancet, vol. 337, pp. 130-133, 1991.
Pierre, K., et al., "Monocarboxylate transporters in the central nervous system: distribution, regulation and function", J Neurochem, vol. 94, pp. 1-14, 2005.
Qian, N., et al., "Prognostic signifigance of tumor/stromal caveolin-1 expression in breast cancer patients", Cancer Sci, vol. 102, No. 8, pp. 1590-1596, 2011.
R-Development-Core-Team. R: A language and environment for statistical computing, R Foundation for Statistical Computing, Vienna, Austria 2011; ISBN: 3-900051-07-0. http://www.R-project.org.
Racker, E., et al., "Glycolysis and methylaminoisobutyrate uptake in rat-1 cells transfected with ras or myc oncogenes", Proc Natl Acad Sci USA, vol. 82, pp. 3535-3538, 1985.
Ronnov-Jessen, L., et al., "Induction of alpha-smooth muscle actin by transforming growth factor-beta 1 in quiescent human breast gland fibroblasts. Implications for myofibroblast generation in breast neoplasia", Lab Invest, vol. 68, pp. 696-707, 1993.
Ronnov-Jessen, L., et al., "Cellular changes involved in conversion of normal to malignant breast: importance of the stromal reaction." Physiol Rev, vol. 76, pp. 69-125, 1996.
Rydzewski, R.M., et al., "Optimization of Subsite Binding to the β5 Subunit of the Human 20S Proteasome Using Vinyl Sulfones and 2-Keto-1,3,4-oxadiazoles: Syntheses and Cellular Properties of Potent, Selective Proteasome Inhibitors", Journal of Medicinal Chemistry, vol. 49, No. 10, pp. 2953-2968, 2006.
Sagara, Y., et al., "Clinical significance of caveolin-1, caveolin-2 and HER2/neu mRNA expression in human breast cancer", British Journal of Cancer, vol. 91, No. 5, pp. 959-965, 2004.
Sakr, R., et al., "Ductal carcinoma in situ: Value of sentinel lymph node biopsy", Journal of Surgical Oncology, vol. 94, pp. 426-430, 2006.
Salerno, M., et al., "Inhibition of signal transduction by the nm23 metastasis suppressor: Possible mechanisms", Clinical & Experimental Metastasis, vol. 20, No. 1, pp. 3-10, 2003.
Santos, A.M., et al., "Targeting fibroblast activation protein inhibits tumor stromagenesis and growth in mice.", J Clin Invest, vol. 119, pp. 3613-3625, 2009.
Savage, K., et al., "Caveolin 1 is overexpressed and amplified in a subset of basal-like and metaplastic breast carcinomas: A morphologic, ultrastructural, immunohistochemical, and in situ hybridization analysis", Clinical Cancer Research, vol. 13, No. 1, pp. 90-101, 2007.
Schor, A.M., et al., "Phenotypic heterogeneity in breast fibroblasts: functional anomaly in fibroblasts from histologically normal tissue adjacent to carcinoma", Int J Cancer, vol. 59, pp. 25-32, 1994.
Schor, S.L., et al., "Occurrence of a fetal fibroblast phenotype in familial breast cancer", Int J Cancer, vol. 37, pp. 831-836, 1986.
Schor, S.L., et al., "Hypothesis: persistent expression of fetal phenotypic characteristics by fibroblasts is associated with an increased susceptibility to neoplastic disease", Exp Cell Biol, vol. 55, pp. 11-17, 1987.
Schor, S.L., et al., "Foetal-to-adult transitions in fibroblast phenotype: their possible relevance to the pathogenesis of cancer", J Cell Sci Suppl, vol. 8, pp. 165-180, 1987.
Schor, S.L., et al., "Foetal and cancer patient fibroblasts produce an autocrine migration-stimulating factor not made by normal adult cells", J Cell Sci, vol. 90 (Pt 3), pp. 391-399, 1988.
Schor, S.L., et al., "Fibroblasts from cancer patients display a mixture of both foetal and adult-like phenotypic characteristics", J Cell Sci, vol. 90 (Pt 3), pp. 401-407, 1988.
Schor, S.L., et al., "Mechanism of action of the migration stimulating factor produced by fetal and cancer patient fibroblasts: effect on hyaluronic and synthesis", In Vitro Cell Dev Biol, vol. 25, pp. 737-746, 1989.
Schor, S.L., et al., "Characterization of migration-stimulating factor (MSF): evidence for its role in cancer pathogenesis", Cancer Invest, vol. 8, pp. 665-667, 1990.
Schor, S.L., et al., "Heterogeneity amongst fibroblasts in the production of migration stimulating factor (MSF): implications for cancer pathogenesis", Exs, vol. 59, pp. 127-146, 1991.
Schor, S.L., et al., "Migration stimulating factor (MSF): its structure, mode of action and possible function in health and disease", Symp Soc Exp Biol, vol. 47, pp. 235-251, 1993.
Schor, S.L., et al., "Fetal-like fibroblasts: their production of migration-stimulating factor and role in tumor progression", Cancer Treat Res, vol. 71, pp. 277-298, 1994.
Schor, S.L., et al., "Fibroblast subpopulations as accelerators of tumor progression: the role of migrating stimulating factor", Exs, vol. 74, pp. 273-296, 1995.
Schor, S.L., et al., "Phenotypic and genetic alterations in mammary stroma: implications for tumour progression", Breast Cancer Res, vol. 3, pp. 373-379, 2001.
Schor, S.L., et al., "Migration-stimulating factor: a genetically truncated onco-fetal fibronectin isoform expressed by carcinoma and tumor-associated stromal cells", Cancer Res, vol. 63, pp. 8827-8836, 2003.
Sculier, J.P., et al., "Lactic acidosis: a metabolic complication of extensive metastatic cancer", Eur J Cancer Clin Oncol, vol. 19, No. 5, pp. 597-601, 1983.
Sieweke, M.H., et al., "Mediation of wound-related Rous sarcoma virus tumorigenesis by TGF-beta", Science, vol. 248, 1656-1660, 1990.
Sieweke, M.H., et al., "The tumor-promoting effect of wounding: a possible role for TGF-beta-induced stromal alterations", Crit Rev Oncog, vol. 5, pp. 297-311, 1994.
Simpkins, S., et al., "The role of stromal caveolin-1 in breast cancer progression", NCRI Cancer Conference 2011; Abstract #A222:http://www.neri.org.uk/ nericonference/2011abstracts/abstracts/A222.html.
Sloan, E.K., et al., "Stromal Cell Expression of Caveolin-1 Predicts Outcome in Breast Cancer", The American Journal of Pathology, vol. 174, No. 6, pp. 2035-2043, 2009.
Solinas, G., et al., "Tumor-Conditioned Macrophages Secrete Migration-Stimulating Factor: A New Marker for M2-Polarization, influencing Tumor Cell Motility", The Journal of Immunology, vol. 185, pp. 642-652, 2010.
Sotgia, F., et al., "Understanding the Warburg effect and the prognostic value of stromal caveolin-1 as a marker of a lethal tumor microenvironment", Breast Cancer Research, vol. 13, No. 213, pp. 1-13, 2011.
Sotgia, F., et al., "Caveolin-1 and Cancer Metabolism in the Tumor Microenvironment: Markers, Models, and Mechanisms", Annu Rev Pathol, vol. 7, pp. 423-467, 2012.
Spaltenstein, A., et al., "Design and synthesis of novel protease inhibitors: Tripeptide α',β'-epoxyketones as nanomolar inactivators of the proteasome", Tetrahedron Letters, vol. 37, No. 9, 1343-1346, 1996.
Belanger, M.M., et al., "Up-regulation of caveolin expression cytotoxic agents in drug-sensitive cancer cells", Anti-Cancer Drugs, vol. 14, No. 4, pp. 281-287, 2003.
Herzog, M., et al., "Knockdown of caveolin-1 decreases activity of breast cancer resistance protein (BCRP/ABCG2) and Increases chemotherapeutic sensitivity", Naunyn-Schmied Arch Pharmacol, vol. 383, pp. 1-11, 2011.
Ho, Chao-Chi, et al., "Caveolin-1 expression is significantly associated with drug resistance and poor progosis in advanced non-small cell lung cancer patients treated with gemcitabine-based chemotherapy", Lung Cancer, vol. 59, pp. 105-110, 2008.
Lavie,Y., et al., "Up-regulation of Caveolae Caveolkar Constituents in Multidrug-resistant Cancer Cells", The Journal of Biological Chemistry, vol. 273, No. 49, pp. 32380-32383, 1998.
Senetta, R., et al., "Caveolin 1 Expression Independently Predicts Shorter Survival in Oligodendrogliomas", J Neuropathol Exp Neurol, vol. 68, No. 4, pp. 425-431, 2009.

(56) References Cited

OTHER PUBLICATIONS

Senetta, R., et al., "Epidermal growth factor receptor and caveolin-1 coexpression Identifies adult supratentorial ependymomas with rapid unfavorable outcomes", Neuro-Oncology, vol. 13, No. 2, pp. 176-183, 2011.

Thompson, T.C., et al., "Caveolin-1, a metastasis-related gene that promotes cell survival in prostate cancer", Apoptosis, vol. 4, No. 4, pp. 233-237, 1999.

Yang, C.-P.H., et al., "Upregulation of caveolin-1 and caveolae organelles in Taxol-resistant A549 cells", FEBS Letters, vol. 439, pp. 368-372, 1998.

Yoo, Seong-Ho, et al., Expression of caveolin-1 is associated with poor prognosis of patients with squamous cell carcinoma of the lung, Lung Cancer, vol. 42, pp. 19-202, 2003.

* cited by examiner

A

B

CAVEOLIN-1 RELATED METHODS FOR TREATING GLIOBLASTOMA WITH TEMOZOLOMIDE

This application claims priority of U.S. Provisional Application No. 61/813,724, filed Apr. 19, 2013, the contents of which are incorporated herein by reference in their entirety.

Throughout this application, various publications are cited. The disclosure of these publications is hereby incorporated by reference into this application to describe more fully the state of the art to which this invention pertains.

BACKGROUND OF THE INVENTION

Glioblastoma multiforme (GBM) is the most common and most deadly primary brain tumor affecting adults. Despite advancements made in surgical, radiological, and chemo-therapies for this grade IV astrocytoma, prognoses have remained very poor: median survival time from diagnosis remains at 9-15 months with less than 10% of patients surviving beyond 5 years.1, 2 Caveolin-1 (Cav-1) is the principle structural protein responsible for the formation of caveolae, or invaginating microdomains in the cell membrane. The capacity for Cav-1 to associate with a wide variety of proteins has implicated it in a number of processes ranging from vesicular transport and cholesterol homeostasis to nitric oxide production and cell migration, among others.3-7 Its ability to regulate cell cycle progression and intracellular signal transduction have resulted in the substantial characterization of Cav-1 in many cancers, where it has been shown to act as both a tumor suppressor and tumor promoter depending on the tissue type.8-11 In gliomas, expression of Cav-1 appears to increase proportionally to tumor grade, with most GBM lesions exhibiting more intense Cav-1 immunoreactivity than their grade II and III counterparts. 12-14 However, little is currently known as to the role of Cav-1 as it relates to GBM in vivo. Recent in vitro studies conducted using the GBM-derived cell line U-87MG have demonstrated that Cav-1 acts as a putative tumor suppressor in GBM by downregulating α5β1 integrin expression and subsequent TGFβ/SMAD pathway activity.[15][16]

SUMMARY OF THE INVENTION

This invention provides a method for treating a subject afflicted with glioblastoma multiforme comprising administering a therapeutically effective regimen of temozolomide to the glioblastoma multiforme-afflicted subject, wherein the subject's glioblastoma multiforme cells are known to be caveolin-1-positive.

This invention also provides a method for determining whether a subject afflicted with glioblastoma multiforme is likely to progress therapeutically in response to a therapeutically effective regimen of temozolomide comprising determining whether the subject's glioblastoma multiforme cells are caveolin-1-positive, whereby if the subject's glioblastoma multiforme cells are caveolin-1-positive, the subject is likely to progress therapeutically in response to a therapeutically effective regimen of temozolomide.

DETAILED DESCRIPTION OF THE INVENTION

Figure 1:
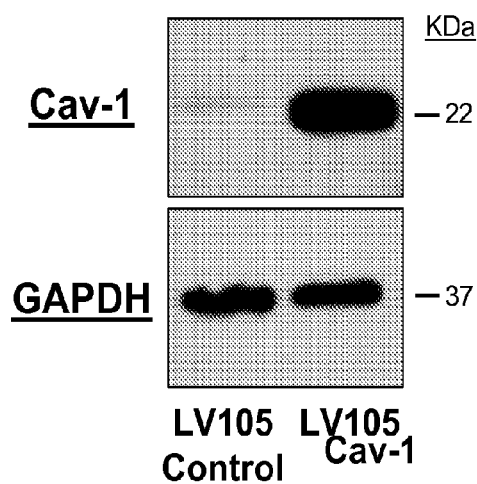
FIG. 1. Stable Expression of Cav-1 in U-87MG Cells. (A) Expression levels of Cav-1 measured by immunoblot analyses of U-87MG cells transduced with either LV105 control or LV105 Cav-1 lentivirus. (B) Immunofluorescent staining of Cav-1 in transduced U-87MG cells. Magnification=40×.
Figure 1:
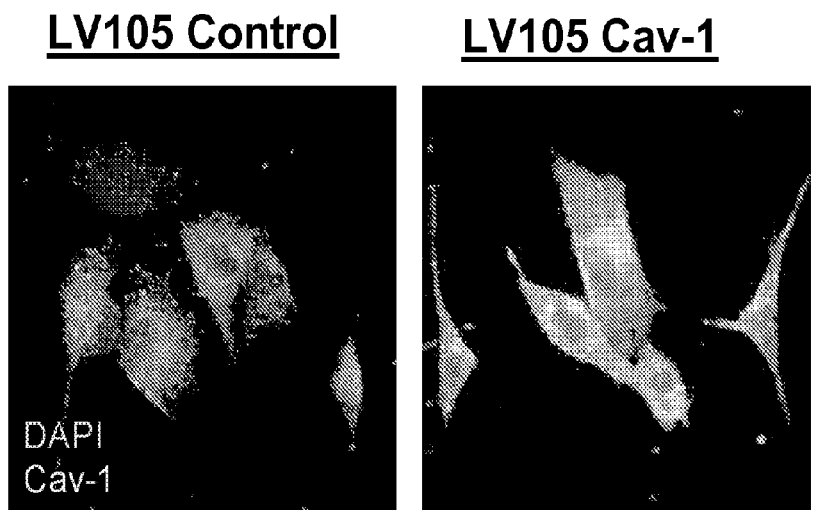

This invention provides a method for treating a subject afflicted with glioblastoma multiforme comprising administering a therapeutically effective regimen of temozolomide to the glioblastoma multiforme-afflicted subject, wherein the subject's glioblastoma multiforme cells are known to be caveolin-1-positive.

Preferably, the subject is human, and the glioblastoma multiforme is newly diagnosed in the subject.

This invention also provides a method for determining whether a subject afflicted with glioblastoma multiforme is likely to progress therapeutically in response to a therapeutically effective regimen of temozolomide comprising determining whether the subject's glioblastoma multiforme cells are caveolin-1-positive, whereby if the subject's glioblastoma multiforme cells are caveolin-1-positive, the subject is likely to progress therapeutically in response to a therapeutically effective regimen of temozolomide.

Preferably, the subject is human, and the glioblastoma multiforme is newly diagnosed in the subject.

The subject can be any animal capable of being afflicted with glioblastoma multiforme.

In this invention, cells that are caveolin-1-positive are determined to be such according to methods known in the art. Such methods include the antibody-based methods described herein.

In one embodiment, the subject's glioblastoma multiforme cells known to be caveolin-1-positive express an amount of caveolin-1 that is a percentage of the amount of caveolin-1 expressed by the lentiviral transduced caveolin-1-overexpressing U-87MG cells described herein, wherein the percentage is selected from below 10%, 10%-20%, 20%-30%, 30%-40%, 40%0-50%, 50%-60%, 60%-70%, 70%-80%, 80%-90%, 90%-100%, 100%-120%, 120%-140%, 140%-160%, 160%-180%, 180%-200%, and above 200%.

Temozolomide (available from Schering-Plough as Temodar® ("Temodar")) is a known therapeutic for treating glioblastoma multiforme. Typically, it is administered in conjunction with radiotherapy and/or surgery. Although numerous regimens of temozolomide are possible, the regimens set forth in in the Temodar label are preferred. Certain portions of that label are reproduced below, although the label's contents at http://www.accessdata.fda.gov/drugsatfda_docs/label/2006/021029s0121bI.pdf are incorporated herein in their entirety.

Temodar Description

Temodar Capsules for oral administration contain temozolomide, an imidazotetrazine derivative. The chemical name of temozolomide is 3,4-dihydro-3-methyl-4-oxoimidazo[5,1-d]-αs-tetrazine-8-carboxamide.

The material is a white to light tan/light pink powder with a molecular formula of $C_6H_6N_6O_2$ and a molecular weight of 194.15. The molecule is stable at acidic pH (<5), and labile at pH>7, hence Temodar can be administered orally. The prodrug, temozolomide, is rapidly hydrolyzed to the active 5-(3-methyltriazen-1-yl)imidazole-4-carboxamide (MTIC) at neutral and alkaline pH values, with hydrolysis taking place even faster at alkaline pH.

Each capsule contains either 5 mg, 20 mg, 100 mg, 140 mg, 180 mg, or 250 mg of temozolomide. The inactive ingredients for Temodar Capsules are lactose anhydrous, colloidal silicon dioxide, sodium starch glycolate, tartaric acid, and stearic acid. The 5 mg, 20 mg, 100 mg, and 250 mg gelatin capsule shells contain titanium dioxide. The capsules are white and imprinted with pharmaceutical ink. The body of the capsules for the 140 mg and 180 mg strengths is made of gelatin, and is opaque white. The cap is also made of gelatin, and the colors vary based on the dosage strength.

Temodar 5 mg: green imprint contains pharmaceutical grade shellac, anhydrous ethyl alcohol, isopropyl alcohol, n-butyl alcohol, propylene glycol, ammonium hydroxide, titanium dioxide, yellow iron oxide, and FD&C Blue #2 aluminum lake.

Temodar 20 mg: brown imprint contains pharmaceutical grade shellac, anhydrous ethyl alcohol, isopropyl alcohol, n-butyl alcohol, propylene glycol, purified water, ammonium hydroxide, potassium hydroxide, titanium dioxide, black iron oxide, yellow iron oxide, brown iron oxide, and red iron oxide.

Temodar 100 mg: blue imprint contains pharmaceutical glaze (modified) in an ethanol/shellac mixture, isopropyl alcohol, n-butyl alcohol, propylene glycol, titanium dioxide, and FD&C Blue #2 aluminum lake.

Temodar 140 mg: The blue cap contains gelatin, sodium lauryl sulfate, FD&C Blue #2, and titanium dioxide. The capsule body and cap are imprinted with pharmaceutical branding ink, which contains shellac, dehydrated alcohol, isopropyl alcohol, butyl, alcohol, propylene glycol, purified water, strong ammonia solution, potassium hydroxide, and ferric oxide.

Temodar 180 mg: The red cap contains gelatin, sodium lauryl sulfate, titanium dioxide, iron oxide red and iron oxide yellow. The capsule body and cap are imprinted with pharmaceutical branding ink, which contains shellac, dehydrated alcohol, isopropyl alcohol, butyl alcohol, propylene glycol, purified water, strong ammonia solution, potassium hydroxide, and ferric oxide.

Temodar 250 mg: black imprint contains pharmaceutical grade shellac, anhydrous ethyl alcohol, isopropyl alcohol, n-butyl alcohol, propylene glycol, purified water, ammonium hydroxide, potassium hydroxide, and black iron oxide.

Temodar Clinical Studies

Newly Diagnosed Glioblastoma Multiforme. Five hundred and seventy three patients were randomized to receive either Temodar (TMZ)+Radiotherapy (RT) (n=287) or RT alone (n=286). Patients in the Temodar+RT arm received concomitant Temodar (75 mg/m2) once daily, starting the first day of RT until the last day of RT, for 42 days (with a maximum of 49 days). This was followed by 6 cycles of Temodar alone (150 or 200 mg/m2) on Day 1-5 of every 28-day cycle, starting 4 weeks after the end of RT. Patients in the control arm received RT only. In both arms, focal radiation therapy was delivered as 60 Gy/30 fractions. Focal RT includes the tumor bed or resection site with a 2-3 cm margin. *Pneumocystis carinii* pneumonia (PCP) prophylaxis was required during the TMZ+radiotherapy treatment, regardless of lymphocyte count, and was to continue until recovery of lymphocyte count to less than or equal to Grade 1.

At the time of disease progression, Temodar was administered as salvage therapy in 161 patients of the 282 (57%) in the RT alone arm, and 62 patients of the 277 (22%) in the Temodar+RT arm. The addition of concomitant and maintenance Temodar to radiotherapy in the treatment of patients with newly diagnosed GBM showed a statistically significant improvement in overall survival compared to radiotherapy alone (FIG. 1). The hazard ratio (HR) for overall survival was 0.63 (95% CI for HR=0.52-0.75) with a logrank p<0.0001 in favor of the Temodar arm. The median survival was increased by 2½ months in the Temodar arm.

Temodar Indications and Usage

Temodar (temozolomide) Capsules are indicated for the treatment of adult patients with newly diagnosed glioblastoma multiforme concomitantly with radiotherapy and then as maintenance treatment.

Temodar Dosage and Administration

Dosage of Temodar Capsules must be adjusted according to nadir neutrophil and platelet counts in the previous cycle and the neutrophil and platelet counts at the time of initiating the next cycle. For Temodar dosage calculations based on body surface area (BSA) see assigned Table. For suggested capsule combinations on a daily dose see assigned Table.

Patients with Newly Diagnosed High Grade Glioma: Concomitant Phase

Temodar is administered orally at 75 mg/m2 daily for 42 days concomitant with focal radiotherapy (60 Gy administered in 30 fractions) followed by maintenance Temodar for 6 cycles. Focal RT includes the tumor bed or resection site with a 2-3 cm margin. No dose reductions are recommended during the concomitant phase; however, dose interruptions or discontinuation may occur based on toxicity. The Temodar dose should be continued throughout the 42 day concomitant period up to 49 days if all of the following conditions are met: absolute neutrophil count ≥1.5×10$^9$/L platelet count ≥100×109/L common toxicity criteria (CTC) non-hematological toxicity ≤Grade 1 (except for alopecia, nausea, and vomiting). During treatment, a complete blood count should be obtained weekly. Temozolomide dosing should be interrupted or discontinued during concomitant phase according to the hematological and non-hematological toxicity criteria. PCP prophylaxis is required during the concomitant administration of Temodar and radiotherapy and should be continued in patients who develop lymphocytopenia until recovery from lymphocytopenia (CTC grade ≤1).

Maintenance Phase Cycle 1:

Four weeks after completing the Temodar+RT phase, Temodar is administered for an additional 6 cycles of maintenance treatment. Dosage in Cycle 1 (maintenance) is 150 mg/m2 once daily for 5 days followed by 23 days without treatment.

Cycles 2-6:

At the start of Cycle 2, the dose is escalated to 200 mg/m2, if the CTC non hematologic toxicity for Cycle 1 is Grade ≤2 (except for alopecia, nausea, and vomiting), absolute neutrophil count (ANC) is ≥1.5×109/L, and the platelet count is ≥100×109/L. The dose remains at 200 mg/m2 per day for the first 5 days of each subsequent cycle except, if toxicity occurs. If the dose was not escalated at Cycle 2, escalation should not be done in subsequent cycles.

Dose reduction or discontinuation during maintenance:

During treatment, a complete blood count should be obtained on Day 22 (21 days after the first dose of Temodar) or within 48 hours of that day, and weekly until the ANC is above 1.5×109/L, (1,500/μL) and the platelet count exceeds 100×10$^9$/L (100,000/μL). The next cycle of Temodar should not be started until the ANC and platelet count exceed these levels. Dose reductions during the next cycle should be based on the lowest blood counts and worst non-hematologic toxicity during the previous cycle.

This invention will be better understood by reference to the Experimental Details which follow, but those skilled in the art will readily appreciate that the specific experiments detailed are only illustrative of the invention as described more fully in the claims which follow thereafter.

EXPERIMENTAL DETAILS

Abbreviations

Caveolin-1 (Cav-1), glioblastoma multiforme (GBM), mitogen activated protein kinase (MAPK), phosphatidylinositol 3-kinase (PI3K), ribosomal protein S6 (RPS6), mammalian target of rapamycin (mTOR), temozolomide (TMZ), transforming growth factor beta (TGFβ), transforming growth motor beta receptor I (TGFβRI), tumor protein 53 (TP53), phosphate and tensin homolog (PTEN), permeability glycoprotein (p-gp)

Synopsis

Caveolin-1 (Cav-1) is a critical regulator of tumor progression in a variety of cancers where it has been shown to act as either a tumor suppressor or tumor promoter. In glioblastoma multiforme, it has been previously demonstrated to function as a putative tumor suppressor. Our studies here, using the human glioblastoma-derived cell line U-87MG, further support the role of Cav-1 as a negative regulator of tumor growth. Using a lentiviral transduction approach, we were able to stably overexpress Cav-1 in U-87MG cells. Gene expression microarray analyses demonstrated significant enrichment in gene signatures corresponding to downregulation of MAPK, PI3K/AKT, and mTOR signaling, as well as activation of apoptotic pathways in Cav-1 overexpressing U-87MG cells. These same gene signatures were later confirmed at the protein level in vitro. To explore the ability of Cav-1 to regulate tumor growth in vivo, we further show that Cav-1 overexpressing U-87MG cells display reduced tumorigenicity in an ectopic xenograft mouse model, with marked hypoactivation of MAPK and PI3K/mTOR pathways. Finally, we demonstrate that Cav-1 overexpression confers sensitivity to the most commonly used chemotherapy for glioblastoma, temozolomide. In conclusion, Cav-1 negatively regulates key cell growth and survival pathways and may be an effective biomarker for predicting response to chemotherapy in glioblastoma.

Results

Stable Expression of Cav-1 in U-87MG Cells

In order to establish durable expression of Cav-1 over time in a cell line model, we chose to use a lentiviral transduction approach over the transient transfection methods used in previous in vitro studies.15,16 After selection with puromycin, U-87MG cells transduced with lentiviral constructs stably expressing full length Cav-1 cDNA (LV105 Cav-1) were shown to effectively upregulate Cav-1 compared to an empty control lentivirus (LV105 Control) as demonstrated by western immunoblot (FIG. 1A). Changes in Cav-1 protein expression were also confirmed by immunofluorescence, where overexpressing cells demonstrated increased cytoplasmic and membrane localization of Cav-1 following lentiviral transduction (FIG. 1B).

Cav-1 Regulates Cancer-Associated Gene Expression

Using a microarray consisting of >20,000 transcript probes, we were able to identify 2,001 genes (~10%) significantly modulated by Cav-1 overexpression (Tables 1, 2, S1 and S2). Gene set enrichment analyses performed on microarray expression data obtained from LV105 Control and LV105 Cav-1 U-87MG cells indicates that Cav-1 expression corresponds to changes in a variety of cancer-associated gene signatures. Specifically, by comparing expression data to biological process gene ontology sets, it was found that Cav-1-overexpressing U-87MG cells demonstrated significant (p<0.001) enrichment among gene sets related to negative regulation of signal transduction, MAP-kinase activity, cell proliferation, and transcription (Tables 2 and S1). Signatures related to caspase activation, apoptosis, and the transforming growth factor β pathway were also highly enriched (Tables 2 and S1). When expression data was compared to a curated canonical pathway database, gene sets related to PI3K/AKT, mTOR, and ERK signaling, as well as cell death and extracellular matrix signaling were found to be significantly enriched (Tables 2 and S1).

Cav-1 Mediates Major Proliferative and Cell-Survival Pathways

Figure 2:
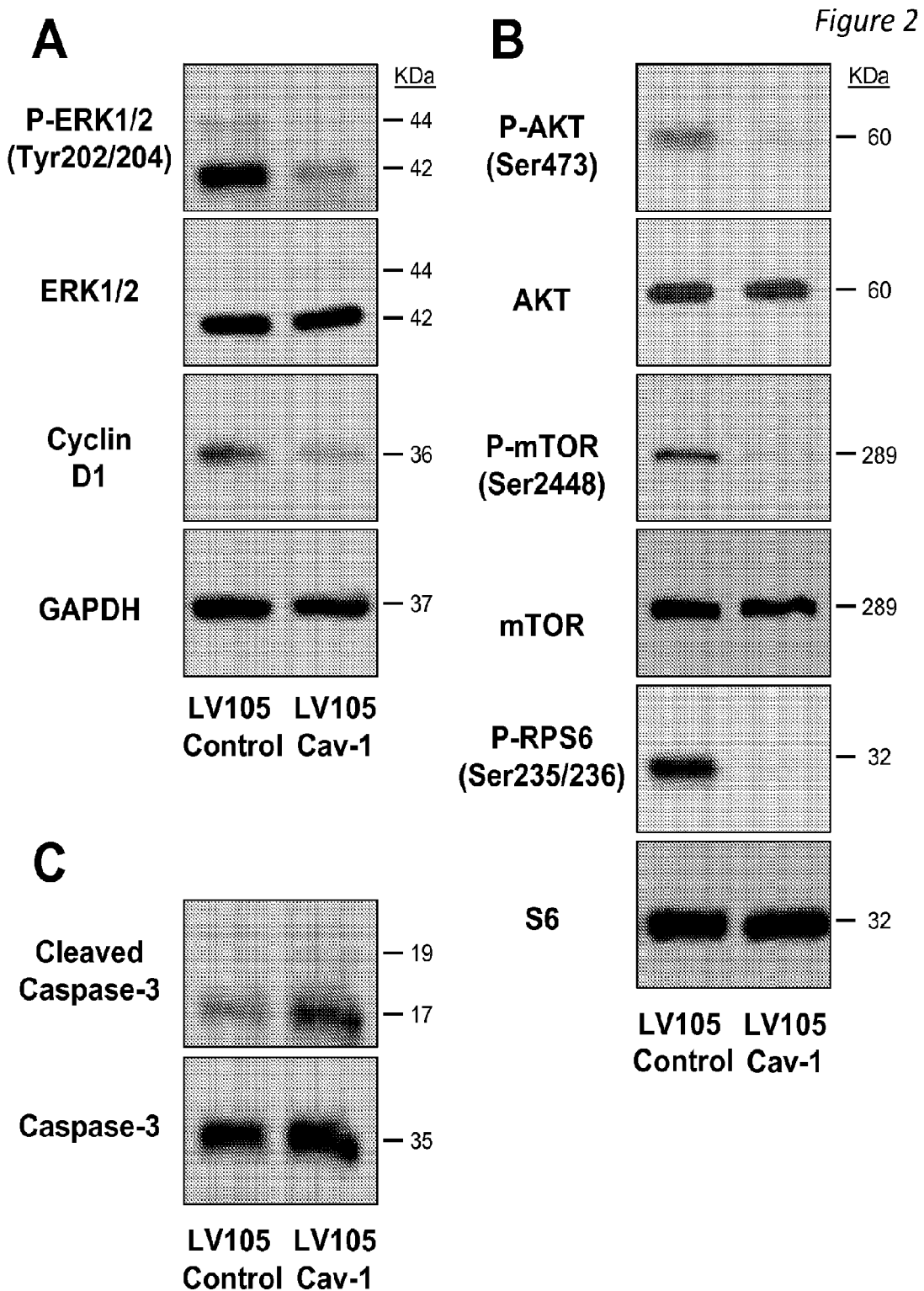
FIG. 2. Cav-1 Mediates Major Proliferative and Cell-Survival Pathways. Western immunoblot analysis of LV105 control and LV105 Cav-1 U-87MG cells showing cyclin D1 and cleaved caspase-3 expression as well as phosphorylation status of ERK1/2, AKT, mTOR and RPS6 pathways, with respective total protein levels for loading controls. Total caspase 3 and GAPDH serve as loading controls for cleaved caspase-3 and cyclin D1, respectively.

To validate the results obtained from our microarray analyses, we next sought to confirm Cav-1 mediated modulation of intracellular signaling pathways at the protein level. Overexpression of Cav-1 in U-87MG cells results in abrogated activity of proliferative pathways as shown by reduced phosphorylation of ERK1/2 and decreased expression of the cell cycle driver cyclin D1 when compared to control as shown by western immunoblot (FIG. 2A). Overexpression of Cav-1 further reduced the activity of protein synthesis pathways as shown by reduced activation of the AKT/mTOR/ribosomal protein S6 (RPS6) signaling pathways (FIG. 2B). Additionally, U-87MG cells overexpressing Cav-1 demonstrated increased presence of the apoptosis activator cleaved caspase 3 (FIG. 2C).

U-87MG Cells Stably Overexpressing Cav-1 Exhibit Decreased Tumor Growth In Vivo

Figure 3:
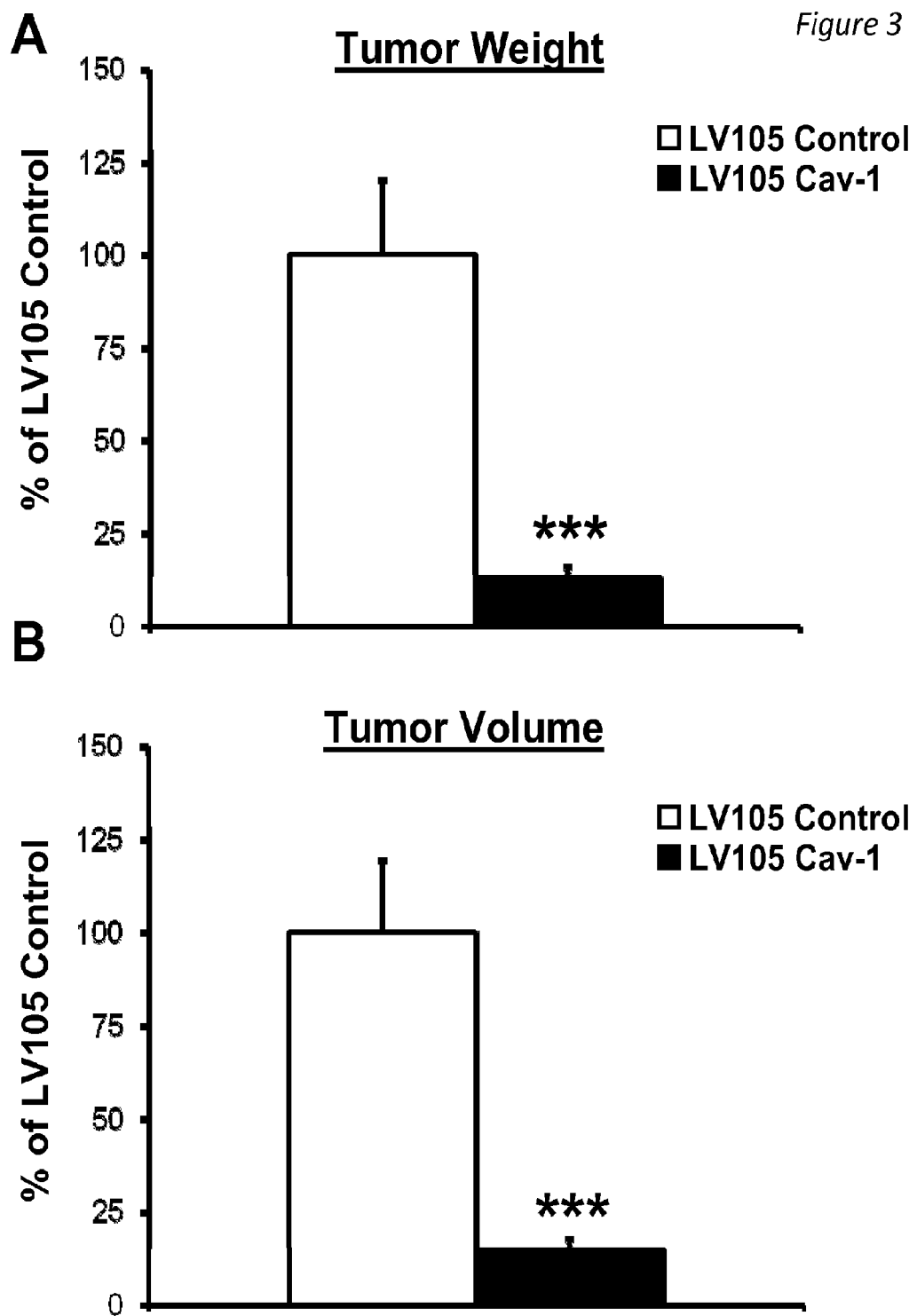
FIG. 3. U-87MG Cells Stably Overexpressing Cav-1 Exhibit Decreased Tumor Growth In Vivo. (A) Tumor weight and (B) tumor volume of U-87MG xenografts grown in athymic nu/nu male mice after 4 weeks (n=30 per group, ***$p<0.001$).

To evaluate the ability of Cav-1 to regulate tumorigenicity in vivo, U-87MG cells infected with either Cav-1-expressing or control lentivirus were injected subcutaneously into the flanks of athymic nu/nu male mice. After 4 weeks, mice were sacrificed and tumors were collected, weighed, and measured. Importantly, mice harboring Cav-1 overexpressing tumors demonstrated markedly reduced (~7 fold) tumor weights and volumes as compared to their control counterparts ($p<0.001$, FIGS. 3A and 3B).

Cav-1 Overexpressing Tumors Show Reduced Signaling Activity In Vivo

Figure 4:
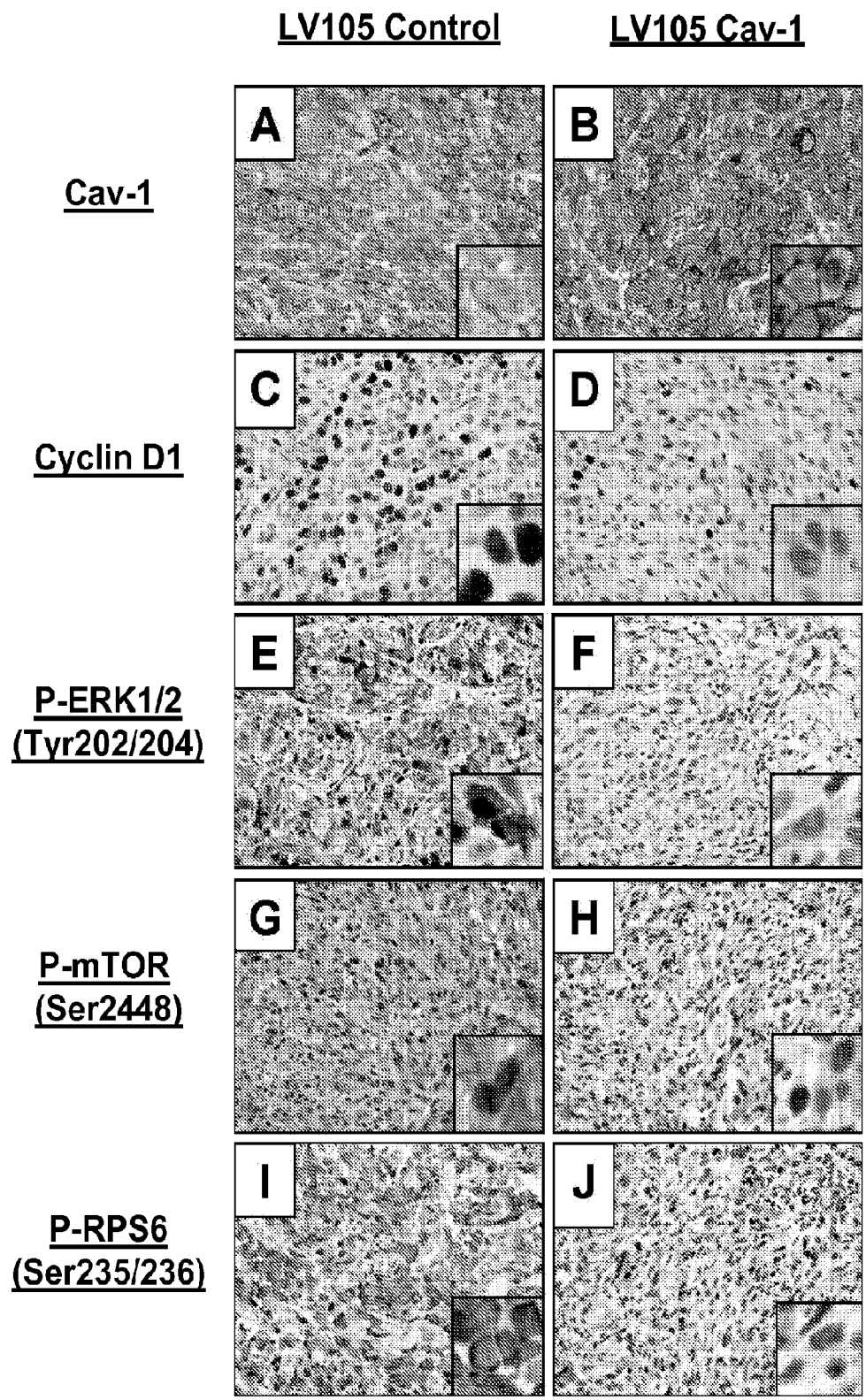
FIG. 4. Cav-1 Overexpressing Tumors Show Reduced Signaling Activity In Vivo. Immunohistochemical staining of explained tumors for Cav-1, cyclin D1, and phosphorylated ERK1/2, mTOR, and RPS6 (magnification=60×).

Similar to results obtained in vitro, our immunohistochemical analyses show that explanted xenograft tumors overexpressing Cav-1 demonstrate fewer cells staining positive for Phospho-ERK1/2 and cyclin D1 (FIG. 4). Additionally, RPS6 and MTOR pathways were shown to be silenced in LV105 Cav-1 tumors as shown by the absence of their active, phosphorylated isoforms (FIG. 4).

Cav-1 Confers Chemosensitivity in U-87MG Cells

Figure 5:
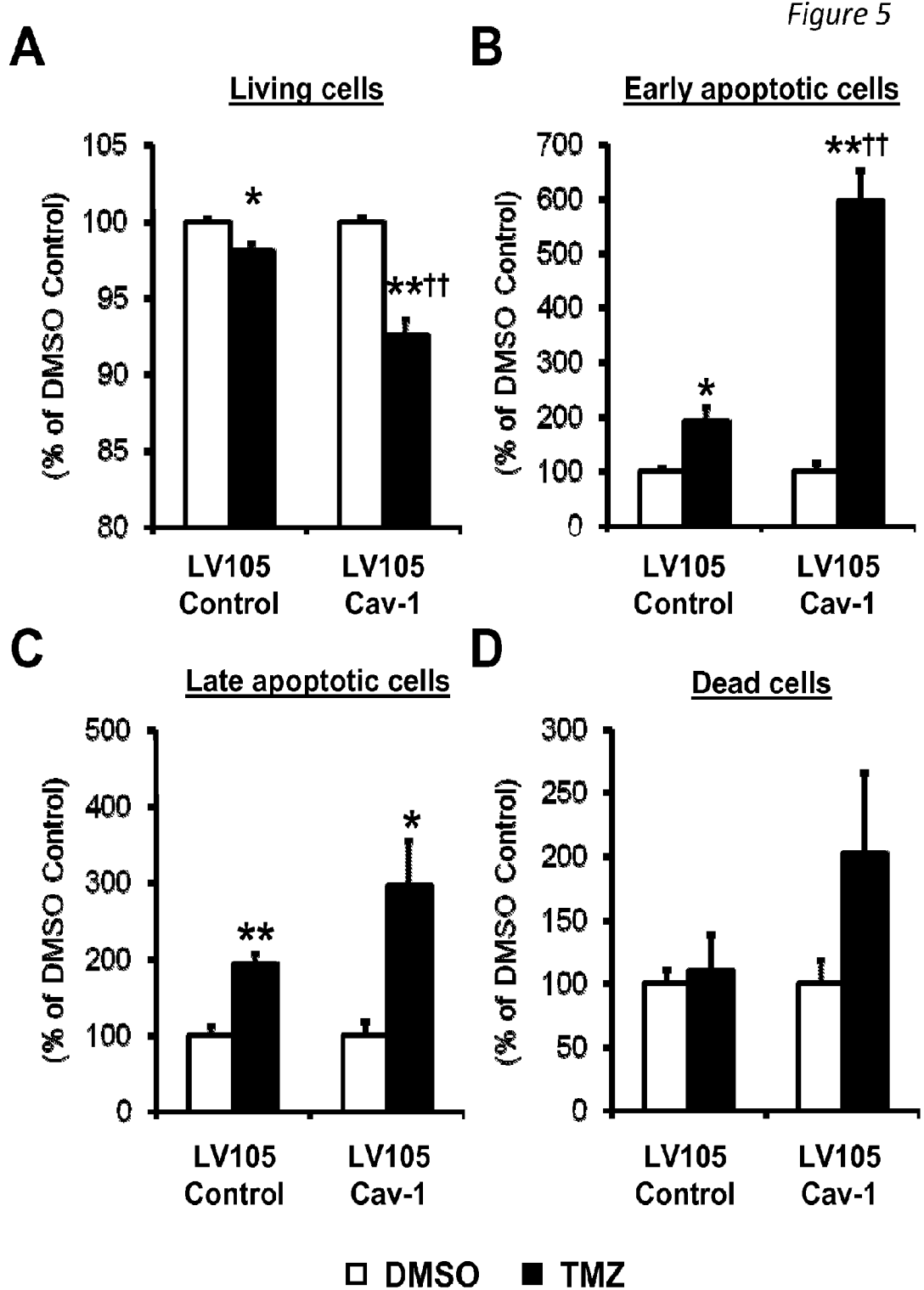
FIG. 5. Cav-1 Confers Chemosensitivity in U-87MG Cells. Annexin V and propidium iodide staining of U-87MG cells treated with either DMSO control or 500 µm TMZ reveals percentages of (A) live cells, (B) early apoptotic cells, (C) late apoptotic cells, and (D) dead cells as measured by flow cytometry. Each group is normalized to its own DMSO control (*$p<0.05$ and **$p<0.01$ vs internal DMSO control, \p<0.01 vs TMZ treated LV105 control, n=3 per group).
Figure 6:
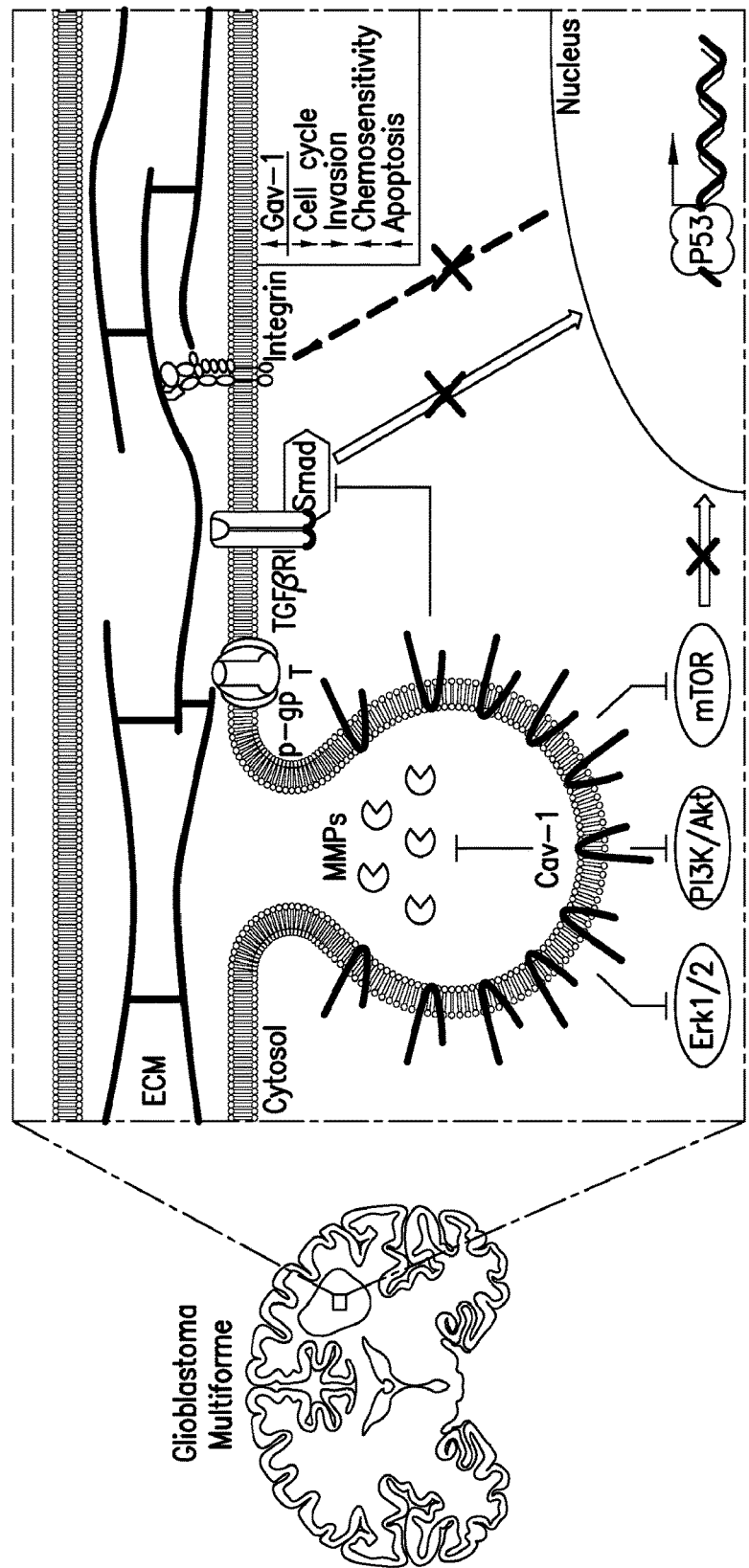
FIG. 6. Schematic Representation of the Role of Cav-1 in Glioblastoma. Gliomas are highly heterogeneous tumors that have been demonstrated to contain populations of cells with varied levels of Cav-1 expression. In this case, enhanced Cav-1 expression among a tumor cell prevents the activation of the TGFBRI/SMAD pathway, which in turn suppresses, at the transcriptional level, expression of integrin subunits and their subsequent signaling activity. Increased Cav-1 expression is also correlated with a decrease in the availability of matrix metallopeptidases, downregulated activity of the Erk1/2, PI3K/Akt and mTOR signaling pathways as well as the inhibition of the transmembrane drug exporter p-gp. Together, this may implicate that tumors with increased Cav-1 levels are less likely to progress through the cell cycle or invade into surrounding tissues and are primed to undergo P53 mediated apoptosis, making these cells more easily targeted by standard chemotherapy regimens.

To further examine the effect of Cav-1 on chemotherapeutic-induced apoptosis, U-87MG cells were stained for the cell death marker Annexin V and measured by flow cytometry. Cav-1 overexpressing U-87MG cells cultured for 72 hours in the presence of 500 μM of temozolomide (TMZ), the most commonly used chemotherapeutic for GBM, showed significant reductions in cell viability when compared to TMZ treated LV105 control cells (5.5%, $p<0.01$, FIG. 5A). This effect was found to be most pronounced among cells initiating apoptosis, as Cav-1-overexpressing U-87MG cells treated with TMZ demonstrated >400% increase in early apoptotic cells compared to TMZ-treated LV105 control cells ($p<0.01$, FIG. 5B). Interestingly, although not statistically significant, overexpression of Cav-1 yielded expanded late-apoptotic and dead cells after 72 hours of TMZ treatment (FIG. 5C, D).

Discussion

Although it has been, demonstrated that Cav-1 expression in glioma increases variably in accordance with grade, little is currently known about its biological effects on tumor onset and progression.12-14, 17, 18 Previous in vitro studies using transient transfection techniques have shown that loss of Cav-1 in U-87MG cells resulted in the adoption of a more proliferative and invasive phenotype whereas its forced overexpression conferred the opposite effects.15 In line with previous studies, we here show that Cav-1 functions as a putative tumor suppressor in glioblastoma. Using a novel lentivirus transduction system we created a stable Cav-1 overexpressing cell line based on the U-87MG background.

By subjecting transiently transfected U-87MG cells to a panel of reverse transcription-PCR printers, Martin et al. identified genes pertaining to cell invasion, metastasis, and cell adhesion as those being the most differentially regulated by Cav-1 expression. Particularly, they showed the integrin genes ITGA1, ITGA3, ITGA5, ITGAV, ITGB1, and ITGB5 were significantly down regulated in Cav-1 overexpressing cells, with cells treated with Cav-1 specific siRNA demonstrating marked upregulation of these same genes. Matrix metallopeptidase genes MMP1 and MMP2, as well as transforming growth factor beta receptor I (TGFRBI) were also shown to be significantly modulated by Cav-1.15 A follow up study using Cav-1 silenced U-87MG cells further clarified a mechanism in which Cav-1 acts as a negative regulator of integrin signaling by inhibiting the expression of these integrins themselves as well as sequestering downstream TGFβ/TGFβRI/SMAD2 and ERK pathways.16 Here, we implemented a similar, albeit much more expansive microarray-based approach to study gene perturbations as a result of Cav-1 overexpression. Using gene set enrichment analyses, we indeed show similar expression profiles to those found previously, with gene sets related to integrin interactions, as well as regulation of TGFβ receptor/SMAD pathways showing significant enrichment. In our study, however, we detected a multitude of other significantly enriched gene sets which have not been demonstrated previously in Cav-1 expressing GBM cells. For instance, U-87MG cells overexpressing Cav-1 demonstrated significant upregulation of genes responsible for negative regulation of signal transduction, particularly within ERK, PI3K/AKT, and mTOR pathways. Although it has long been known that Cav-1 serves to negatively regulate the activity of p42/p44 (ERK1/2) signaling proteins of the MAPK pathway, our evidence also suggests it has the capability to sequester PI3K and mTOR activity.20-26 This is notable due to the fact that ERK, PI3K and mTOR signaling axes are frequently unregulated in GBM, suggesting that loss of Cav-1 could lead to unchecked activation of these pathways.27-31 Two of the most commonly silenced genes in GBM are the tumor suppressor proteins PTEN and TP53, which serve to antagonize the PI3K/AKT/mTOR pathway and regulate cell cycle, response to DNA damage and cell death, respectively.32 Of note is that these two genes were among the most unregulated in cells overexpressing Cav-1, which would likely explain the gene signatures corresponding to downregulation of signaling pathways and reduced invasiveness.

A major hallmark of GBM is the ability of tumor cells to invariably metastasize to distant sites in the CNS despite aggressive treatment. This is often attributed to the excessive release of matrix metallopeptidases and urokinase plasminogen activator.33 Here we show that the genes MMP1, MMP3, and PLAU (urokinase plasminogen activator) are highly downregulated in our Cav-1 overexpressing U-87MG cells, which is consistent with reports that Cav-1 negatively regulates tumor invasiveness.15, 34-36 These genes have been shown to be regulated by Erk and TP53, therefore, their reduction may be secondary to Cav-1 modulation of these pathways.37-40

Of note, we also found that genes responsible for sequestering cell cycle progression and transcription were overexpressed in LV105 Cav-1 cells (FOXN3, HDAC5, VHL, CDKN1C, among others). Conversely, genes responsible for progression through cell cycle such as CCND1 (cyclin D1) were found to be significantly downregulated in Cav-1 overexpressing cells, consistent with previous reports that Cav-1 transcriptionally represses cyclin D1.8 Perhaps our most notable finding, however, is that a substantial number of genes involved in the activation of apoptotic and cell death pathways are increased as a result of Cav-1 overexpression (TP53, MOAP1, CASP3, CASP9, BCL2L11, BAK1, BID among others). Although the role of Cav-1 in apoptosis is contentious, with reports indicating both pro- and anti-cell death roles, it may be possible that expression of Cav-1 promotes apoptotic activity in U-87MG cells by inhibiting the BIRC5 gene product, survivin, as is suggested here and in previous reports.41-45 In support of these microarray data, we were able to demonstrate, at the protein level, silencing of ERK, AKT, mTOR, RPS6, and cyclin D1 pathways with corresponding activation and cleavage of the key apoptosis initiator caspase 3.

Importantly, we here show for the first time that forced expression of Cav-1 in vivo results in a dramatic reduction of tumor burden in U-87MG xenografts. Although Cosset et al. have demonstrated that explanted human glioma tissue lacking Cav-1 expression results in increased expression of α5β1 integrin subunits, we were able to demonstrate a direct inverse relationship with Cav-1 expression and cell proliferation in an animal model.16 In line with our in vitro data, these xenograft tumors displayed reduced activity of ERK, RPS6, and mTOR pathways. As these pathways have been previously shown to play major roles in glioma progression, it is likely that Cav-1 could act as a critical regulator of tumor growth and protein synthesis in a clinical setting. As examples of this, studies have shown that exogenous administration of cavtratin, or a soluble peptide consisting of the Cav-1 scaffolding domain fused to an internalization domain, results in reduced MAPK activity in oligodendroglial cells in vivo, as well as reduced tumor volumes in a xenograft model of Lewis Lung Carcinoma.23,46 A separate study demonstrated that in vitro administration of full length Cav-1 prevented invasion of three different GBM-derived cell lines using a Boyden-chamber assay.47 In this regard, it may be suggested that Cav-1 be explored as a therapeutic agent in GBM.

Lastly, we have also demonstrated that expression of Cav-1 confers sensitivity to the most commonly used chemotherapeutic in GBM, temozolomide. This could be due in part to the action of the permeability glycoprotein (P-gp) transporter, a multidrug exporter which normally prevents the influx of drugs across the blood brain barrier. However, cancerous cells can also express this protein, rendering treatment of GBM with conventional chemotherapeutics less effective.48 Cav-1 has been shown to associate with P-gp and negatively regulate its activity, therefore overexpression of Cav-1 most likely results in improved access of TMZ to the intracellular compartment of U-87MG cells in our model.49, 50 Interestingly, a separate study showed that treatment with TMZ resulted in upregulation of Cav-1 expression in vivo using orthotopic GBM xenograft models.47 In light of our data, this could suggest a positive feedback loop exists in which treatment with TMZ serves to auto-sensitize GBM cells through a Cav-1 dependent mechanism. This finding implicates Cav-1 as a potential biomarker predicting response to chemotherapies for GBM as it has been shown for other cancers such as breast, lung, and oral squamous cell carcinomas.51-53

Taken together, these studies confirm and expand upon previous work identifying Cav-1 as a putative tumor suppressor in GBM. We here show that stable overexpression of Cav-1 in a widely used model of GBM results in silencing of key proliferative and cell survival pathways in vitro as well as in vivo. Additionally, we have demonstrated its ability to modulate sensitivity to commonplace chemotherapeutics for GBM. These findings highlight the potential of Cav-1 to serve as a novel biomarker indicating potential response to therapy and also a candidate therapy for treatment of GBM.

Materials and Methods
Cell Lines and Reagents

The human glioblastoma-derived cell line U-87MG was obtained from American Type Culture Collection (ATCC) and cultured in Eagle's Modified Essential Medium (EMEM, ATCC) supplemented with 10% fetal bovine serum and 1% penicillin/streptomycin (Life Technologies). Cells were cultured in the presence of 5% CO2 at 37° C. Temozolomide (TMZ) was obtained from Sigma-Aldrich and dissolved in DMSO to a concentration of 100 mM. The following antibodies were used: mouse anti-Caveolin-1 (2297, BD Bioscience), rabbit anti-Caveolin-1 (N-20), mouse anti-cyclin D1 (DCS-6, Santa Cruz Biotechnology), rabbit anti-phospho mTOR (Se2448, D9C2, Cell Signaling), rabbit anti-phospho-ERK1/2 (Thr202/Tyr204, Cell Signaling), rabbit anti-phospho-AKT (Ser473, D9E, Cell Signaling), rabbit anti-phospho-ribosomal S6 (Ser235/236, 91B2, Cell Signaling) rabbit anti-ERK1/2 (Cell Signaling), rabbit anti-AKT (Cell Signaling), rabbit anti-ribosomal S6 (5G10, Cell Signaling), rabbit anti-cleaved caspase 3 (Asp175, Cell Signaling), rabbit anti-caspase 3 (Cell Signaling), and mouse anti-GAPDH (6C5, Fitzgerald Industries).

Stable Lentiviral Transduction of U-87MG Cells

Plasmids Ex-Neg-LV105 (empty control vector) and Ex-D0159-LV105 (Cav-1 c-DNA vector) were obtained from Genecopoeia and transfected into the packaging cell line Genecopoeia 293Ta using the Lenti-Pac HIV Expression Packaging Kit as per manufacturer's instructions, 48 hours post-transfection, lentivirus containing supernatants were collected and centrifuged at 500×g for 10 minutes to clear cellular debris. U-87MG cells were cultured in viral supernatants supplemented with 5 μg/ml polybrene (Santa Cruz) for 24 hours prior to changing back into complete medium containing 2.5 μg/ml puromycin hydrochloride (Santa Cruz) to select for lentiviral-transduced cells. After one week of selection, cells were allowed to grow in complete medium without puromycin.

Western Immunoblot

Cells at 70% confluence were collected, pelleted at 300× g, washed twice with Dulbecco's PBS (DPBS) and resuspended in RIPA lysis buffer (50 mM Tris, 150 mM NaCl, 0.5% sodium deoxycholate, 1% Triton X-100, 0.1% SDS, pH 7.5) including Complete Protease Inhibitor Cocktail (Roche Diagnostics) and Halt Phosphatase Inhibitor Cocktail (Thermo-Scientific). Lysates were sonicated and centrifuged at 10,000×g for 10 min to clear cellular debris prior to protein quantification by BCA assay (Thermo-Scientific) as per manufacturer's instructions. Proteins were separated by sodium dodecyl sulfate polyacrylamide gel electrophoresis (SDS-PAGE; 8-12% acrylamide), transferred to nitrocellulose membranes (Whatman), and blocked for 1 hour in TBST (10 mM Tris, 150 mM NaCl, 0.05% Tween-20, pH 8.0) with 5% bovine serum albumin (BSA). Membranes were incubated with primary antibodies diluted in TBST+ 1% BSA overnight at 4° C. followed by incubation in either horseradish peroxidase (HRP) conjugated anti-mouse (Thermo-Scientific) or anti-rabbit (BD Biosciences) antibodies. Detection of bound antibodies was accomplished with the use of Supersignal chemiluminescent substrates (Thermo-Scientific).

Immunofluorescence Analysis

U-87MG cells grown on glass coverslips in 6-well plates were fixed in ice-cold methanol for 20 min, washed with PBS, and incubated with anti-Cav-1 primary antibody (BD Bioscience) in immunofluorescence (IF) buffer (PBS+5% BSA, 0.5% NP40) for 30 min at 37° C. before incubation with secondary fluorescein isothiocyanate (FITC)-conjugated anti-mouse antibody (Jackson Labs) in IF buffer. Cells were counterstained with Hoechst nuclear dye (Life Technologies) prior to coverslipping and visualization with a Zeiss LSM 510 confocal microscope (Carl Zeiss Microscopy).

Gene Array

DNA microarray analysis was performed using the Human Whole Genome OneArray v2 (Phalanx Biotech, Belmont, Calif.). RNA quality and integrity were determined utilizing an Agilent 2100 Bioanalyzer (Agilent Technologies) and absorbance at A260/A280. Only high quality RNA, having a RIN of >7.0, and an A260/280 absorbance ratio of >1.8, was utilized for further experimentation, RNA was synthesized to double-stranded cDNA and amplified using in vitro transcription that included amino-allyl UTP, and the aRNA product was subsequently conjugated with with Cy5 NHS ester (GE Healthcare Lifesciences). Fragmented aRNA was hybridized at 42° C. overnight using the HybBag mixing system with 1× OneArray Hybridization Buffer (Phalanx Biotech), 0.01 mg/ml sheared salmon sperm DNA (Promega), at a concentration of 0.025 mg/ml labeled target. After hybridization, the arrays were washed according to the OneArray protocol. Raw intensity signals for each microarray were captured using a Molecular Dynamics™ Axon 4100A scanner, measured using GenePixPro™ Software. Significantly up- or down-regulated genes in LV105 Cav-1 cells were identified as having normalized intensities above background (>50), a fold change of ±1.5 compared to control, and p<0.05.

Gene Set Enrichment Analyses

Pre-processed expression data was subjected to Gene Set Enrichment Analysis using C5.BP.V3.0 (gene ontology: biological processes) and C2.CP.V3.0 (canonical pathways) MSigDB gene sets.54,55 Genes expression data were ordered based on a signal-2-noise metric and compared statistically to existing gene sets at a resolution of 1,000 permutations. Statistical significance of gene set enrichment was assumed at nominal p<0.05, with a false discovery rate (FDR) q<0.25.

Tumor Xenografts

All animal studies were conducted in accordance with the guidelines set forth by the National Institutes of Health and the Thomas Jefferson University Institutional Animal Care and Use Committee (IACUC). Briefly, U-87MG cells were washed with DPBS, trypsinized, counted, and resuspended in a volume of complete medium yielding 1×106 cells/50 µl, which was subsequently injected subcutaneously into the flanks of 6-8 week old male athymic nu/nu mice (NCI). After 4 weeks, mice were sacrificed and tumors were excised, weighed and measured prior to further processing.

Immunohistochemistry

Explanted xenograft tumors were fixed in 10% phosphate buffered formalin solution for 24 hours prior to dehydration in 70% ethanol, paraffin embedding, and sectioning onto slides. Following xylene deparaffinizaiton and rehydration, slides were subjected to 10 minutes of heat antigen retrieval in 10 mM sodium citrate buffer pH 6.0 and endogenous peroxide quenching in 3% hydrogen peroxide for 20 min. Tissues were blocked in 10% normal goat serum (NGS, Vector Labs, Burlingame, Calif.) for 1 hour at room temperature and incubated overnight with primary antibody in 10% NGS at 4° C. Slides were then washed in PBS and blocked with Biotin-Blocking System (Dako) before incubating with the appropriate secondary antibody in PBS and developing with 3,3-diaminobenzidine (DAB) substrate (Dako). Slides were counterstained with hematoxylin (Sigma), dehydrated, and coverslipped prior to imaging with an Olympus BX51 light microscope equipped with a Micropublisher 5.0 CCD camera (QImaging).

Flow Cytometry

U-87MG cells (50,000/well) were plated in 12-well tissue culture dishes and allowed to attach overnight prior to changing their medium into complete EMEM containing either 500 µM TMZ or DMSO control and culturing them for an additional 72 hours. Cells were then trypsinized, centrifuged at 300×g for 5 min and resuspended in binding buffer with APC-conjugated anti-Annexin V antibody (BP Biosciences) and 0.33 µg/ml Propidium Iodide (PI, KPL, Gaithersburg, Md.). All samples were run on a BD FACSCalibur flow cytometer (BD Biosciences). Cells were quantified according to staining as follows: viable (Annexin V negative, PI negative), early apoptotic (Annexin V positive, PI negative), late apoptotic (Annexin V positive, PI positive), and dead (Annexin V negative, PI positive).

Statistical Analysis

All data were expressed as mean±SEM Differences between groups were evaluated by either unpaired Student's t-test or one-way ANOVA followed by Tukey's multiple-group comparisons test, where appropriate. Statistical significance was assumed at p<0.05.

Table 1: Differential Gene Expression of Cav-1 Overexpressing U-87MG Cells

Top 100 microarray hits demonstrating the most significantly up- and downregulated genes in Cav-1 overexpressing U-87MG cells. For a complete list see Table S2. (n=3 samples from each group).

Table 2: Cav-1 Regulates Cancer-Associated Gene Expression

Enrichment score (ES), normalized enrichment score (NES), nominal p-value, and false discovery rate (FDR) q-value for selected gene sets enriched in LV105 Cav-1 cells vs control using (A) gene ontology: biological process and (B) canonical pathway molecular signature databases (n=3 samples from each group). For a detailed list of genes see Table S1.

Table S1: Gene Set Enrichment Data

Expanded Gene Set Enrichment Analysis for (A) gene ontology: biological process and (B) canonical pathway molecular signature databases (n=3 samples from each group).

Table S2: Differential Gene Expression of Cav-1 Overexpression U-87MG Cells

Top microarray hits demonstrating, the most significantly up- and downregulated genes in Cav-1 overexpressing U-87MG cells (fold change >±1.5 vs LV105 control, p<0.05, n=3 samples from each group).

REFERENCES

1. Buckner J C, Brown P D, O'Neill B P, Meyer F B, Wetmore C J, Uhm J H. Central nervous system tumors. Mayo Clin Proc 2007; 82:1271-86.
2. Stupp R, Hegi M E, Mason W P, van den Bent M J, Taphoorn M J, Janzer R C, et al. Effects of radiotherapy with concomitant and adjuvant temozolomide versus radiotherapy alone on survival in glioblastoma in a randomised phase III study: 5-year analysis of the EORTC-NCIC trial. Lancet Oncol 2009; 10:459-66.
3. van Deurs B, Roepstorff K, Hommelgaard A M, Sandvig K. Caveolae: anchored, multifunctional platforms in the lipid ocean. Trends in cell biology 2003; 13:92-100.
4. Garcia-Cardena G, Martasek P, Masters B S, Skidd P M, Couet J, Li S, et al. Dissecting the interaction between nitric oxide synthase (NOS) and caveolin. Functional significance of the nos caveolin binding domain in vivo. J Biol Chem 1997; 272:25437-40.
5. Navarro A, Anand-Apte B, Parat M O. A role for caveolae in cell migration. FASEB J 2004; 18:1801-11.
6. Parton R G, Simons K. The multiple faces of caveolae. Nat Rev Mol Cell Biol 2007; 8:185-94.
7. Razani B, Woodman S E, Lisanti M P. Caveolae: from cell biology to animal physiology. Pharmacological reviews 2002: 54:431-67.
8. Hulit J, Bash T, Fu M, Galbiati F, Albanese C, Sage D R, et al. The cyclin D1 gene is transcriptionally repressed by caveolin-1. J Biol Chem 2000; 275:21203-9.

9. Patel H H, Murray F, Insel P A. Caveolae as organizers of pharmacologically relevant signal transduction molecules. Annual review of pharmacology and toxicology 2008; 48:359-91.
10. Williams T M, Lisanti M P. Caveolin-1 in oncogenic transformation, cancer, and metastasis. Am J Physiol Cell Physiol 2005; 288:C494-506.
11. Goetz J G, Lajoie P, Wiseman S M, Nabi I R. Caveolin-1 in tumor progression: the good, the bad and the ugly. Cancer Metastasis Rev 2008; 27:715-35.
12. Cassoni P, Senetta R, Castellano I, Ortolan E, Bosco M, Magnani I, et al. Caveolin-1 expression is variably displayed in astroglial-derived tumors and absent in oligodendrogliomas; concrete premises for a new reliable diagnostic marker in gliomas. Am J Surg Pathol 2007; 31:760-9.
13. Barresi V, Buttarelli F R, Vitarelli E E, Arcella A, Antonelli M, Giangaspero F. Caveolin-1 expression in diffuse gliomas: correlation with the proliferation index, epidermal growth factor receptor, p53, and 1p/19q status. Hum Pathol 2009; 40:1738-46.
14. Senetta R, Trevisan E, Ruda R, Maldi E, Molinaro L, Lefranc F, et al. Caveolin 1 expression independently predicts shorter survival in oligodendrogliomas. J Neuropathol Exp Neurol 2009; 68:425-31.
15. Martin S, Cosset E C, Terrand J, Maglott A, Takeda K, Dontenwill M. Caveolin-1 regulates glioblastoma aggressiveness through the control of alpha(5)beta(1) integrin expression and modulates glioblastoma responsiveness to SJ749, an alpha(5)beta(1) integrin antagonist. Biochim Biophys Acta 2009; 1793:354-67.
16. Cosset E C, Godet J, Entz-Werle N, Guerin E, Guenot D, Froelich S, et al. Involvement of the TGFbeta pathway in the regulation of alpha5 beta1 integrins by caveolin-1 in human glioblastoma. International journal of cancer Journal international du cancer 2012; 131:601-11.
17. Abulrob A, Giuseppin S, Andrade M F, McDermid A, Moreno M, Stanimirovic D. Interactions of EGFR and caveolin-1 in human glioblastoma cells: evidence that tyrosine phosphorylation regulates EGFR association with caveolae. Oncogene 2004; 23:6967-79.
18. Forget M A, Desrosiers R R, Del M, Moumdjian R, Shedid D, Berthelet F, et al. The expression of rho proteins decreases with human brain tumor progression: potential tumor markers. Clinical & experimental metastasis 2002; 19:9-15.
19. Cameron P L, Liu C, Smart D K, Hantus S T, Fick J R, Cameron R S. Caveolin-1 expression is maintained in rat and human astroglioma cell lines. Glia 2002; 37:275-90.
20. Engelman J A, Chu C, Lin A, Jo H, Ikezu T, Okamoto T, et al. Caveolin-mediated regulation of signaling along the p42/44 MAP kinase cascade in vivo. A role for the caveolin-scaffolding domain. FEBS letters 1998; 428: 205-11.
21. Cohen A W, Park D S, Woodman S E, Williams T M, Chandra M, Shirani J, et al. Caveolin-1 null mice develop cardiac hypertrophy with hyperactivation of p42/44 MAP kinase in cardiac fibroblasts. Am J Physiol Cell Physiol 2003; 284:C457-74.
22. Han F, Gu D, Chen Q, Zhu H. Caveolin-1 acts as a tumor suppressor by down-regulating epidermal growth factor receptor-mitogen-activated protein kinase signaling pathway in pancreatic carcinoma cell lines. Pancreas 2009; 38:766-74.
23. Schmitz M, Zerr I, Althaus H H. Effect of cavtratin, a caveolin-1 scaffolding domain peptide, on oligodendroglial signaling cascades. Cellular and molecular neurobiology 2011; 31:991-7.
24. Xia H, Khalil W, Kahm J, Jessurun J, Kleidon J, Henke C A. Pathologic caveolin-1 regulation of PTEN in idiopathic pulmonary fibrosis. Am J Pathol 2010; 176:2626-37.
25. Feng S, Wang Y, Wang X, Wang Z, Cui Y, Lin J, et al. Caveolin-1 gene silencing promotes the activation of PI3K/AKT dependent on Eralpha36 and the transformation of MCF10ACE. Science China Life sciences 2010; 53:598-605.
26. Mercier I, Camacho J, Titchen K, Gonzales D M, Quann K, Bryant K G, et al. Caveolin-1 and accelerated host aging in the breast tumor microenvironment: chemoprevention with rapamycin, an mTOR inhibitor and antiaging drug. Am J Pathol 2012; 181:278-93.
27. Huse J T, Holland E C. Targeting brain cancer: advances in the molecular pathology of malignant glioma and medulloblastoma. Nat Rev Cancer 2010; 10:319-31.
28. Kita D, Yonekawa Y, Weller M, Ohgaki H. PIK3CA alterations in primary (de novo) and secondary glioblastomas. Acta neuropathologica 2007; 113:295-302.
29. Sunayama J, Matsuda K, Sato A, Tachibana K, Suzuki K, Narita Y, et al. Crosstalk between the PI3K/mTOR and MEK/ERK pathways involved in the maintenance of self-renewal and tumorigenicity of glioblastoma stem-like cells. Stem Cells 2010; 28:1930-9.
30. Mizoguchi M, Betensky R A, Batchelor T T, Bernay D C, Louis D N, Nutt C L. Activation of STAT3, MAPK, and AKT in malignant astrocytic gliomas: correlation with EGFR status, tumor grade, and survival. J Neuropathol Exp Neurol 2006; 65:1181-8.
31. Lopez-Gines C, Gil-Benso R, Benito R, Mata M, Pereda J, Sasire J, et al. The activation of ERK1/2 MAP kinases in glioblastoma pathobiology and its relationship with EGFR amplification. Neuropathology: official journal of the Japanese Society of Neuropathology 2008; 28:507-15.
32. Ohgaki H, Kleihues P. Genetic pathways to primary and secondary glioblastoma. Am J Pathol 2007; 170:1445-53.
33. Louis D N. Molecular pathology of malignant gliomas. Annu Rev Pathol 2006; 1:97-117.
34. Williams T M, Medina F, Badano I, Hazan R B, Hutchinson J, Muller W J, et al. Caveolin-1 gene disruption promotes mammary tumorigenesis and dramatically enhances lung metastasis in vivo. Role of Cav-1 in cell invasiveness and matrix metalloproteinase (MMP-2/9) secretion. J Biol Chem 2004; 279:51630-46.
35. Kim H N, Chung H S. Caveolin-1 inhibits membrane-type 1 matrix metalloproteinase activity. BMB reports 2008; 41:858-62.
36. Han F, Zhu H G. Caveolin-1 regulating the invasion and expression of matrix metalloproteinase (MMPs) in pancreatic carcinoma cells. The Journal of surgical research 2010; 159:443-50.
37. Reunanen N, Westermarck J, Hakkinen L, Holmstrom T H, Elo I, Eriksson J E, et al. Enhancement of fibroblast collagenase (matrix metalloproteinase-1) gene expression by ceramide is mediated by extracellular signal-regulated and stress-activated protein kinase pathways. J Biol Chem 1998; 273:5137-45.
38. Kim S, Lee Y, Lee D H, Kim Y, Cho K H, Chung J H. Basal and UV-induced MMP-1 expression are inhibited by p53 in human dermal fibroblasts. Experimental dermatology 2008; 17:939-45.

39. Sun Y, Wenger L, Rutter J L, Brinckerhoff C E, Cheung H S, p53 down-regulates human matrix metalloproteinase-1 (Collagenase-1) gene expression. J Biol Chem 1999; 274:11535-40.
40. Shetty P, Velusamy T, Bhandary Y P, Shetty R S, Liu M C, Shetty S. Urokinase expression by tumor suppressor protein p53: a novel role in mRNA turnover. American journal of respiratory cell and molecular biology 2008; 39:364-72.
41. Park J, Bae E, Lee C, Yoon S S, Chae Y S, Ahn K S, et al. RNA interference-directed caveolin-1 knockdown sensitizes SN12CPM6 cells to doxorubicin-induced apoptosis and reduces lung metastasis. Tumour Biol 2010; 31:643-50.
42. Yang X, Xiong H, Guan Z Z, Okai I, Ye D, Song Y, et al. Higher expression of Caveolin-1 inhibits human small cell lung cancer (SCLC) apoptosis in vitro. Cancer Invest 2012; 30:453-62.
43. Zhang M, Lee S J, An C, Xu J F, Joshi B, Nabi I R, et al. Caveolin-1 mediates Fas-BID signaling in hyperoxia-induced apoptosis. Free radical biology & medicine 2011; 50:1252-62.
44. Torres V A, Tapia J C, Rodriguez D A, Parraga M, Lisboa P, Montoya M, et al. Caveolin-1 controls cell proliferation and cell death by suppressing expression of the inhibitor of apoptosis protein survivin. Journal of cell science 2000; 119:1812-23.
45. Zhang M, Lin L, Lee S J, Mo L, Cao J, Ifedigbo E, et al. Deletion of caveolin-1 protects hyperoxia-induced apoptosis via survivin-mediated pathways. American journal of physiology Lung cellular and molecular physiology 2009; 297:L945-53.
46. Lin M I, Yu J, Murata T, Sessa W C. Caveolin-1-deficient mice have increased tumor microvascular permeability, angiogenesis, and growth. Cancer Res 2007; 67:2849-56.
47. Bruyere C, Abeloos L, Lamoral-Theys D, Senetta R, Mathieu V, Le Mercier M, et al. Temozolomide modifies caveolin-1 expression in experimental malignant gliomas in vitro and in vivo. Translational oncology 2011; 4:92-100.
48. Deeken J F, Loscher W. The blood-brain barrier and cancer: transporters, treatment, and Trojan horses. Clin Cancer Res 2007; 13:1663-74.
49. Jodoin J, Demeule M, Fenart L, Cecchelli R, Farmer S, Linton K J, et al. P-glycoprotein in blood-brain barrier endothelial cells: interaction and oligomerization with caveolins. Journal of neurochemistry 2003; 87:1010-23.
50. Guo Z, Zhu J, Zhao L, Luo Q, Jin X. Expression and clinical significance of multidrug resistance proteins in brain tumors. Journal of experimental & clinical cancer research: CR 2010; 29:122.
51. Mercier I, Casimiro M C, Wang C, Rosenberg A L, Quong J, Minkeu A, et al. Human breast cancer-associated fibroblasts (CAFs) show caveolin-1 downregulation and RB tumor suppressor functional inactivation: Implications for the response to hormonal therapy. Cancer biology & therapy 2008; 7:1212-25.
52. Ho C C, Kuo S H, Huang P H, Huang H Y, Yang C H, Yang P C. Caveolin-1 expression is significantly associated with drug resistance and poor prognosis in advanced non-small cell lung cancer patients treated with gemcitabine-based chemotherapy. Lung Cancer 2008; 59:105-10.
53. Nakatani K, Wada T, Nakamura M, Uzawa K, Tanzawa H, Fujita S. Expression of caveolin-1 and its correlation with cisplatin sensitivity in oral squamous cell carcinoma. Journal of cancer research and clinical oncology 2005; 131:445-52.
54. Subramanian A, Tamayo P, Mootha V K, Mukherjee S, Ebert B L, Gillette M A, et al. Gene set enrichment analysis: a knowledge-based approach for interpreting genome-wide expression profiles. Proc Natl Acad Sci USA 2005; 102:15545-50.
55. Ashburner M, Ball C A, Blake J A, Botstein D, Butler H, Cherry J M, et al. Gene ontology: tool for the unification of biology. The Gene Ontology Consortium, Nature genetics 2000; 25:25-9.

TABLE 1

Differential Gene Expression of Cav-1 Overexpressing U-87MG Cells. Top 100 microarray hits demonstrating the most significantly up- and downregulated genes in Cav-1 overexpressing U-87MG cells. For a complete list see Table S2. (n = 3 samples from each group).

| PROBE | FOLD CHANGE | P-VALUE | DESCRIPTION |
| --- | --- | --- | --- |
| CCDC3 | 94.19 | 0.00E+00 | coiled-coil domain containing 3 |
| COL3A1 | 75.99 | 0.00E+00 | collagen, type III, alpha 1 |
| MTUS1 | 46.14 | 2.77E−10 | microtubule associated tumor suppressor 1 |
| NUP210 | 34.18 | 5.08E−24 | nucleoporin 210 kDa |
| COL4A1 | 30.33 | 1.38E−22 | collagen, type IV, alpha 1 |
| APOE | 24.59 | 0.00E+00 | apolipoprotein E |
| LRRC17 | 21.54 | 0.00E+00 | leucine rich repeat containing 17 |
| PRL | 16.66 | 1.07E−22 | prolactin |
| SULF1 | 16.35 | 5.88E−20 | sulfatase 1 |
| UBE2QL1 | 15.93 | 0.00E+00 | ubiquitin-conjugating enzyme E2Q family-like 1 |
| FAT3 | 14.40 | 0.00E+00 | FAT tumor suppressor homolog 3 (*Drosophila*) |
| CSAG1 | 13.78 | 0.00E+00 | chondrosarcoma associated gene 1 |
| SOX4 | 12.86 | 1.89E−26 | SRY (sex determining region Y)-box 4 |
| CTNNA2 | 12.75 | 0.00E+00 | catenin (cadherin-associated protein), alpha 2 |
| GPM6B | 11.94 | 1.51E−14 | glycoprotein M6B |
| CSAG1\|CSAG2\|CSAG3 | 11.88 | 1.42E−15 | chondrosarcoma associated gene 1\|CSAG family, member 2\|CSAG family, member 3 |
| COL1A2 | 11.26 | 0.00E+00 | collagen, type I, alpha 2 |
| RCAN2 | 11.10 | 7.01E−45 | regulator of calcineurin 2 |
| MAF | 10.52 | 2.69E−11 | v-maf musculoaponeurotic fibrosarcoma oncogene homolog (avian) |
| CGNL1 | 10.41 | 5.06E−16 | cingulin-like 1 |
| ARHGAP28 | 10.03 | 4.15E−29 | Rho GTPase activating protein 28 |
| MGAT4A | 9.69 | 7.01E−45 | mannosyl (alpha-1,3-)-glycoprotein beta-1,4-N-acetylglucosaminyltransferase, isozyme A |
| WISP2 | 9.27 | 4.48E−44 | WNT1 inducible signaling pathway protein 2 |
| SULF2 | 9.21 | 4.22E−15 | sulfatase 2 |
| CBLN2 | 8.73 | 1.58E−39 | cerebellin 2 precursor |
| CELF2 | 8.36 | 0.00E+00 | CUGBP, Elav-like family member 2 |

TABLE 1-continued

Differential Gene Expression of Cav-1 Overexpressing U-87MG Cells. Top 100 microarray hits demonstrating the most significantly up- and downregulated genes in Cav-1 overexpressing U-87MG cells. For a complete list see Table S2. (n = 3 samples from each group).

| PROBE | FOLD CHANGE | P-VALUE | DESCRIPTION |
| --- | --- | --- | --- |
| QPRT | 8.31 | 3.44E−39 | quinolinate phosphoribosyltransferase |
| CALCA | 7.63 | 3.89E−12 | calcitonin-related polypeptide alpha |
| ALX4 | 7.62 | 8.08E−32 | ALX homeobox 4 |
| EPHA3 | 7.53 | 0.00E+00 | EPH receptor A3 |
| CD33 | 7.53 | 1.37E−40 | CD33 molecule |
| TNFRSF9 | 7.12 | 0.00E+00 | tumor necrosis factor receptor superfamily, member 9 |
| KIT | 6.96 | 7.30E−37 | v-kit Hardy-Zuckerman 4 feline sarcoma viral oncogene homolog |
| FOXO1 | 6.82 | 1.16E−14 | forkhead box O1 |
| F2RL2 | 6.59 | 4.88E−33 | coagulation factor II (thrombin) receptor-like 2 |
| ZNF229 | 6.58 | 0.000241 | zinc finger protein 229 |
| CCDC69 | 6.55 | 2.06E−28 | coiled-coil domain containing 69 |
| MEX3A | 6.51 | 3.28E−21 | mex-3 homolog A (*C. elegans*) |
| CKB | 6.47 | 4.76E−42 | creatine kinase, brain |
| THY1 | 6.30 | 8.38E−18 | Thy-1 cell surface antigen |
| ABLIM1 | 6.12 | 1.62E−30 | actin binding LIM protein 1 |
| PCDH7 | 6.04 | 1.54E−29 | protocadherin 7 |
| SLC9A3R1 | 6.02 | 0.00E+00 | solute carrier family 9 (sodium/hydrogen exchanger), member 3 regulator 1 |
| BIRC7 | 5.98 | 2.51E−17 | baculoviral IAP repeat-containing 7 |
| MEF2C | 5.86 | 6.40E−43 | myocyte enhancer factor 2C |
| PIK3R3 | 5.80 | 2.36E−18 | phosphoinositide-3-kinase, regulatory subunit 3 (gamma) |
| CD24 | 5.61 | 4.33E−22 | CD24 molecule |
| CALCB | 5.58 | 0.00E+00 | calcitonin-related polypeptide beta |
| UGT2B4 | 5.56 | 9.90E−13 | UDP glucuronosyltransferase 2 family, polypeptide B4 |
| SGCD | 5.55 | 7.22E−35 | sarcoglycan, delta (35 kDa dystrophin-associated glycoprotein) |
| DLX4 | 5.50 | 0.00E+00 | distal-less homeobox 4 |
| TP53 | 5.49 | 1.54E−28 | tumor protein p53 |
| BCL2L11 | 5.33 | 1.26E−27 | BCL2-like 11 (apoptosis facilitator) |
| MDK | 5.33 | 2.69E−32 | midkine (neurite growth-promoting factor 2) |
| COL14A1 | 5.30 | 1.96E−19 | collagen, type XIV, alpha 1 |
| DPP4 | 5.25 | 8.24E−31 | dipeptidyl-peptidase 4 |
| FRMPD4 | 5.12 | 1.69E−10 | FERM and PDZ domain containing 4 |
| SORL1 | 5.06 | 5.16E−10 | sortilin-related receptor, L(DLR class) A repeats-containing |
| RCOR2 | 5.02 | 1.79E−18 | REST corepressor 2 |
| LCP1 | −4.95 | 1.89E−14 | lymphocyte cytosolic protein 1 (L-plastin) |
| EPHB2 | −4.99 | 3.43E−18 | EPH receptor B2 |
| LOC100509788 . . . | −5.04 | 1.15E−14 | hypothetical LOC100509788\|hypothetical LOC100507248 |
| ID1 | −5.06 | 4.56E−35 | inhibitor of DNA binding 1, dominant negative helix-loop-helix protein |
| IL13RA2 | −5.25 | 0.00E+00 | interleukin 13 receptor, alpha 2 |
| NAV2 | −5.25 | 0.00E+00 | neuron navigator 2 |
| TOX2 | −5.28 | 1.60E−37 | TOX high mobility group box family member 2 |
| HLA-DRB1 . . . | −5.30 | 9.97E−19 | major histocompatibility complex, class II, DR beta 1 . . . |
| FST | −5.32 | 5.01E−29 | follistatin |
| KRT15 | −5.33 | 3.11E−35 | keratin 15 |
| CRYM | −5.40 | 6.12E−17 | crystallin, mu |
| AFF3 | −5.52 | 7.41E−14 | AF4/FMR2 family, member 3 |
| NAMPT | −5.54 | 0.00E+00 | nicotinamide phosphoribosyltransferase |
| COL4A6 | −5.56 | 1.74E−21 | collagen, type IV, alpha 6 |
| HS3ST2 | −5.63 | 8.54E−29 | heparan sulfate (glucosamine) 3-O-sulfotransferase 2 |
| DNER | −5.92 | 9.79E−12 | delta/notch-like EGF repeat containing |
| C3orf14 | −5.94 | 4.38E−22 | chromosome 3 open reading frame 14 |
| TXNIP | −6.02 | 5.66E−32 | thioredoxin interacting protein |
| IL8 | −6.44 | 1.49E−36 | interleukin 8 |
| GALNT12 | −6.73 | 4.86E−30 | UDP-N-acetyl-alpha-D-galactosamine: polypeptide N-acetylgalactosaminyltransferase 12 (GalNAc-T12) |
| FAM133A | −6.93 | 4.20E−45 | family with sequence similarity 133, member A |
| ACPP | −7.14 | 5.48E−32 | acid phosphatase, prostate |
| PTX3 | −7.23 | 1.76E−35 | pentraxin 3, long |
| DCC | −7.24 | 6.16E−23 | deleted in colorectal carcinoma |
| FARP1 | −7.26 | 1.40E−24 | FERM, RhoGEF (ARHGEF) and pleckstrin domain protein 1 (chondrocyte-derived) |
| BDKRB1 | −7.27 | 0.00E+00 | bradykinin receptor B1 |
| TFPI2 | −7.56 | 0.00E+00 | tissue factor pathway inhibitor 2 |
| IL1RN | −8.00 | 5.74E−19 | interleukin 1 receptor antagonist |
| FOXF1 | −8.20 | 0.00E+00 | forkhead box F1 |
| DDIT4L | −8.25 | 2.01E−37 | DNA-damage-inducible transcript 4-like |
| COL13A1 | −8.38 | 0.00E+00 | collagen, type XIII, alpha 1 |
| VAT1L | −8.62 | 2.06E−29 | vesicle amine transport protein 1 homolog (*T. californica*)-like |
| PLAU | −9.17 | 4.46E−25 | plasminogen activator, urokinase |
| BEX1 | −9.73 | 4.20E−45 | brain expressed, X-linked 1 |
| MGC87042 | −13.51 | 2.14E−20 | STEAP family protein MGC87042 |
| TFAP2C | −13.77 | 0.00E+00 | transcription factor AP-2 gamma (activating enhancer binding protein 2 gamma) |
| STC1 | −15.24 | 2.80E−45 | stanniocalcin 1 |

TABLE 1-continued

Differential Gene Expression of Cav-1 Overexpressing U-87MG Cells. Top 100 microarray hits demonstrating the most significantly up- and downregulated genes in Cav-1 overexpressing U-87MG cells. For a complete list see Table S2. (n = 3 samples from each group).

| PROBE | FOLD CHANGE | P-VALUE | DESCRIPTION |
|---|---|---|---|
| SBSN | −16.74 | 0.00E+00 | suprabasin |
| MMP3 | −19.01 | 0.00E+00 | matrix metallopeptidase 3 (stromelysin 1, progelatinase) |
| IL1B | −25.20 | 0.00E+00 | interleukin 1, beta |
| MMP1 | −37.04 | 0.00E+00 | matrix metallopeptidase 1 (interstitial collagenase) |

TABLE 2

Cav-1 Regulates Cancer-Associated Gene Expression. Enrichment score (ES), normalized enrichment score (NES), nominal p-value, and false discovery rate (FDR) q-value for selected gene sets enriched in LV105 Cav-1 cells vs control using (A) gene ontology: biological process and (B) canonical pathway molecular signature databases (n = 3 samples from each group). For a detailed list of genes see Table S1.

| Gene Set | Enrichment Score (ES) | Normalized ES | Nominal p-value | FDR q-value |
|---|---|---|---|---|
| A. Gene Ontology: Biological Process | | | | |
| NEGATIVE_REGULATION_OF_SIGNAL_TRANSDUCTION | 0.500 | 2.023 | <0.001 | 0.092 |
| REGULATION_OF_TRANSFORMING_GROWTH_FACTOR_BETA_RECEPTOR_PATHWAY | 0.619 | 1.846 | <0.001 | 0.071 |
| CASPASE_ACTIVATION | 0.566 | 1.748 | <0.001 | 0.067 |
| NEGATIVE_REGULATION_OF_MAP_KINASE_ACTIVITY | 0.521 | 1.537 | <0.001 | 0.160 |
| NEGATIVE_REGULATION_OF_CELL_PROLIFERATION | 0.331 | 1.460 | <0.001 | 0.190 |
| NEGATIVE_REGULATION_OF_TRANSCRIPTION | 0.340 | 1.367 | <0.001 | 0.211 |
| APOPTOSIS_GO | 0.313 | 1.338 | <0.001 | 0.227 |
| POSITIVE_REGULATION_OF_CELL_ADHESION | 0.501 | 1.308 | <0.001 | 0.243 |
| B. Canonical Pathways | | | | |
| BIOCARTA_AKT_PATHWAY | 0.647 | 1.965 | <0.001 | 0.137 |
| SA_PROGRAMMED_CELL_DEATH | 0.739 | 1.923 | <0.001 | 0.142 |
| KEGG_ECM_RECEPTOR_INTERACTION | 0.496 | 1.857 | <0.001 | 0.158 |
| KEGG_MTOR_SIGNALING_PATHWAY | 0.487 | 1.831 | <0.001 | 0.125 |
| REACTOME_PI3K_AKT_SIGNALING | 0.479 | 1.682 | <0.001 | 0.144 |
| REACTOME_INTEGRIN_CELL_SURFACE_INTERACTIONS | 0.423 | 1.592 | <0.001 | 0.142 |
| BIOCARTA_ERK_PATHWAY | 0.493 | 1.583 | <0.001 | 0.151 |
| KEGG_APOPTOSIS | 0.360 | 1.521 | <0.001 | 0.169 |

Supplementary Table 1: Gene Set Enrichment Data.
Expanded Gene Set Enrichment Analysis for (A) gene ontology: biological process and (B) canonical pathway molecular signature databases (n = 3 samples from each group).

A. Gene Ontology: Biological Process

NEGATIVE_REGULATION_OF_SIGNAL_TRANSDUCTION

Description: Genes annotated by the GO term GO:0009968. Any process that stops, prevents or reduces the frequency, rate or extent of signal transduction.

| Enrichment Score (ES) | Normalized ES | Nominal p-value | FDR q-value | FWER p-value |
|---|---|---|---|---|
| 0.500 | 2.023 | <0.001 | 0.092 | 0.139 |

| PROBE | FOLD CHANGE | DESCRIPTION |
|---|---|---|
| THY1 | 8.45 | Thy-1 cell surface antigen |
| FRZB | 7.02 | frizzled-related protein |
| OTUD7B | 2.76 | OTU domain containing 7B |
| PEG10 | 2.74 | paternally expressed 10 |
| NF1 | 2.51 | neurofibromin 1 |
| PTEN | 2.16 | phosphatase and tensin homolog |
| CBY1 | 2.04 | chibby homolog 1 (*Drosophila*) |
| EID2 | 1.88 | EP300 interacting inhibitor of differentiation 2 |
| RHOH | 1.86 | ras homolog gene family, member H |
| TAX1BP3 | 1.57 | Tax1 (human T-cell leukemia virus type I) binding protein 3 |

Supplementary Table 1: Gene Set Enrichment Data.
Expanded Gene Set Enrichment Analysis for (A) gene ontology: biological
process and (B) canonical pathway molecular signature databases (n = 3 samples from each group).

REGULATION_OF_TRANSFORMING_GROWTH_FACTOR_BETA_RECEPTOR_PATHWAY

Description: Genes annotated by the GO term GO:0017015. Any process that modulates
the frequency, rate or extent of activity of any TGFbeta receptor signaling pathway.

| Enrichment Score (ES) | Normalized ES | Nominal p-value | FDR q-value | FWER p-value |
|---|---|---|---|---|
| 0.619 | 1.846 | <0.001 | 0.071 | 0.227 |

| PROBE | FOLD CHANGE | DESCRIPTION |
|---|---|---|
| CDKN1C | 12.43 | cyclin-dependent kinase inhibitor 1C (p57, Kip2) |
| PEG10 | 2.74 | paternally expressed 10 |
| SMAD4 | 1.92 | SMAD family member 4 |
| EID2 | 1.88 | EP300 interacting inhibitor of differentiation 2 |
| SMAD2 | 1.58 | SMAD family member 2 |
| SMAD3 | 1.53 | SMAD family member 3 |

CASPASE_ACTIVATION

Description: Genes annotated by the GO term GO:0006919. Upregulation of the activity
of a caspase, any of a group of cysteine proteases involved in apoptosis.

| Enrichment Score (ES) | Normalized ES | Nominal p-value | FDR q-value | FWER p-value |
|---|---|---|---|---|
| 0.566 | 1.748 | <0.001 | 0.067 | 0.274 |

| PROBE | FOLD CHANGE | DESCRIPTION |
|---|---|---|
| TP53 | 7.01 | tumor protein p53 |
| F2R | 4.40 | coagulation factor II (thrombin) receptor |
| CYCS | 3.06 | cytochrome c, somatic |
| MOAP1 | 2.76 | modulator of apoptosis 1 |
| CASP9 | 2.18 | caspase 9, apoptosis-related cysteine peptidase |
| STAT1 | 1.55 | signal transducer and activator of transcription 1, 91 kDa |
| SMAD3 | 1.53 | SMAD family member 3 |

NEGATIVE_REGULATION_OF_MAP_KINASE_ACTIVITY

Description: Genes annotated by the GO term GO:0043407. Any process that stops,
prevents or reduces the frequency, rate or extent of MAP kinase activity.

| Enrichment Score (ES) | Normalized ES | Nominal p-value | FDR q-value | FWER p-value |
|---|---|---|---|---|
| 0.521 | 1.537 | <0.001 | 0.160 | 0.858 |

| PROBE | FOLD CHANGE | DESCRIPTION |
|---|---|---|
| DUSP8 | 3.79 | dual specificity phosphatase 8 |
| DUSP9 | 2.70 | dual specificity phosphatase 9 |
| NF1 | 2.51 | neurofibromin 1 |
| GPS2 | 2.22 | G protein pathway suppressor 2 |
| RGS4 | 1.55 | regulator of G-protein signaling 4 |

NEGATIVE_REGULATION_OF_CELL_PROLIFERATION

Description: Genes annotated by the GO term GO:0008285. Any process that
stops, prevents or reduces the rate or extent of cell proliferation.

| Enrichment Score (ES) | Normalized ES | Nominal p-value | FDR q-value | FWER p-value |
|---|---|---|---|---|
| 0.331 | 1.460 | <0.001 | 0.190 | 0.900 |

| PROBE | FOLD CHANGE | DESCRIPTION |
|---|---|---|
| IFITM1 | 19.62 | interferon induced transmembrane protein 1 (9-27) |
| CDKN1C | 12.43 | cyclin-dependent kinase inhibitor 1C (p57, Kip2) |
| CD33 | 9.90 | CD33 molecule |
| TNFRSF8 | 5.42 | tumor necrosis factor receptor superfamily, member 8 |
| FABP3 | 4.69 | fatty acid binding protein 3, muscle and heart (mammary-derived growth inhibitor) |

Supplementary Table 1: Gene Set Enrichment Data.
Expanded Gene Set Enrichment Analysis for (A) gene ontology: biological
process and (B) canonical pathway molecular signature databases (n = 3 samples from each group).

| | | |
|---|---|---|
| SESN1 | 4.33 | sestrin 1 |
| BTG2 | 3.65 | BTG family, member 2 |
| NCK2 | 3.51 | NCK adaptor protein 2 |
| FABP6 | 2.78 | fatty acid binding protein 6, ileal |
| MXI1 | 2.40 | MAX interactor 1 |
| CDK6 | 2.31 | cyclin-dependent kinase 6 |
| ODZ1 | 2.27 | odz, odd Oz/ten-m homolog 1(*Drosophila*) |
| VHL | 2.25 | von Hippel-Lindau tumor suppressor |
| RARRES3 | 2.16 | retinoic acid receptor responder (tazarotene induced) 3 |
| PTEN | 2.16 | phosphatase and tensin homolog |
| PTHLH | 2.06 | parathyroid hormone-like hormone |
| TGFB1I1 | 2.06 | transforming growth factor beta 1 induced transcript 1 |
| ETS1 | 2.03 | v-ets erythroblastosis virus E26 oncogene homolog 1 (avian) |
| GHRL | 2.02 | ghrelin/obestatin prepropeptide |
| MAGED1 | 1.93 | melanoma antigen family D, 1 |
| TOB1 | 1.88 | transducer of ERBB2, 1 |
| SSTR3 | 1.84 | somatostatin receptor 3 |
| WARS | 1.83 | tryptophanyl-tRNA synthetase |
| RBBP4 | 1.79 | retinoblastoma binding protein 4 |
| SSTR4 | 1.78 | somatostatin receptor 4 |
| MDM4 | 1.72 | Mdm4 p53 binding protein homolog (mouse) |
| LDOC1 | 1.65 | leucine zipper, down-regulated in cancer 1 |
| ING5 | 1.64 | inhibitor of growth family, member 5 |
| SIRPG | 1.64 | signal-regulatory protein gamma |
| KLF11 | 1.61 | Kruppel-like factor 11 |
| ING1 | 1.61 | inhibitor of growth family, member 1 |
| GML | 1.57 | glycosylphosphatidylinositol anchored molecule like protein |
| CDH13 | 1.55 | cadherin 13, H-cadherin (heart) |
| BAP1 | 1.55 | BRCA1 associated protein-1 (ubiquitin carboxy-terminal hydrolase) |
| TOB2 | 1.54 | transducer of ERBB2, 2 |
| FABP7 | 1.51 | fatty acid binding protein 7, brain |
| PPM1D | 1.50 | protein phosphatase, Mg2+/Mn2+ dependent, 1D |

NEGATIVE_REGULATION_OF_TRANSCRIPTION

Description: Genes annotated by the GO term GO:0016481. Any process that
stops, prevents or reduces the frequency, rate or extent of transcription.

| Enrichment Score (ES) | Normalized ES | Nominal p-value | FDR q-value | FWER p-value |
|---|---|---|---|---|
| 0.340 | 1.367 | <0.001 | 0.211 | 0.900 |

| PROBE | FOLD CHANGE | DESCRIPTION |
|---|---|---|
| CALCA | 11.61 | calcitonin-related polypeptide alpha |
| FOXN3 | 7.06 | forkhead box N3 |
| HEXIM1 | 4.02 | hexamethylene bis-acetamide inducible 1 |
| HDAC5 | 3.87 | histone deacetylase 5 |
| POU2F1 | 3.53 | POU class 2 homeobox 1 |
| ARID5B | 3.04 | AT rich interactive domain 5B (MRF1-like) |
| NRG1 | 2.80 | neuregulin 1 |
| MYST4 | 2.79 | MYST histone acetyltransferase (monocytic leukemia) 4 |
| TWIST1 | 2.67 | twist homolog 1 (*Drosophila*) |
| LANCL2 | 2.41 | LanC lantibiotic synthetase component C-like 2 (bacterial) |
| VHL | 2.25 | von Hippel-Lindau tumor suppressor |
| ZHX1 | 2.19 | zinc fingers and homeoboxes 1 |
| MEIS2 | 2.07 | Meis homeobox 2 |
| CBY1 | 2.04 | chibby homolog 1 (*Drosophila*) |
| ZBTB16 | 2.03 | zinc finger and BTB domain containing 16 |
| GLIS3 | 1.95 | GLIS family zinc finger 3 |
| RUNX2 | 1.93 | runt-related transcription factor 2 |
| SMAD4 | 1.92 | SMAD family member 4 |
| ID2 | 1.89 | inhibitor of DNA binding 2, dominant negative helix-loop-helix protein |
| EID2 | 1.88 | EP300 interacting inhibitor of differentiation 2 |
| NDUFA13 | 1.86 | NADH dehydrogenase (ubiquinone) 1 alpha subcomplex, 13 |
| STAT3 | 1.84 | signal transducer and activator of transcription 3 (acute-phase response factor) |
| ZNF174 | 1.84 | zinc finger protein 174 |
| ERN2 | 1.83 | endoplasmic reticulum to nucleus signaling 2 |
| SMARCE1 | 1.80 | SWI/SNF related, matrix associated, actin dependent regulator of chromatin, subfamily e, member 1 |
| GLIS1 | 1.78 | GLIS family zinc finger 1 |
| HSBP1 | 1.78 | heat shock factor binding protein 1 |
| UBP1 | 1.76 | upstream binding protein 1 (LBP-1a) |

Supplementary Table 1: Gene Set Enrichment Data.
Expanded Gene Set Enrichment Analysis for (A) gene ontology: biological
process and (B) canonical pathway molecular signature databases (n = 3 samples from each group).

| | | |
|---|---|---|
| TRIM27 | 1.74 | tripartite motif-containing 27 |
| MDM4 | 1.72 | Mdm4 p53 binding protein homolog (mouse) |
| ZNF148 | 1.69 | zinc finger protein 148 |
| CREBZF | 1.67 | CREB/ATF bZIP transcription factor |
| SMARCC2 | 1.66 | SWI/SNF related, matrix associated, actin dependent regulator of chromatin, subfamily c, member 2 |
| MEN1 | 1.66 | multiple endocrine neoplasia I |
| EID1 | 1.66 | EP300 interacting inhibitor of differentiation 1 |
| MYST1 | 1.65 | MYST histone acetyltransferase 1 |
| PML | 1.65 | promyelocytic leukemia |
| HEXIM2 | 1.61 | hexamthylene bis-acetamide inducible 2 |
| BCLAF1 | 1.61 | BCL2-associated transcription factor 1 |
| KLF11 | 1.61 | Kruppel-like factor 11 |
| SIRT2 | 1.60 | sirtuin 2 |
| SMAD2 | 1.58 | SMAD family member 2 |
| SUMO1 | 1.58 | SMT3 suppressor of mif two 3 homolog 1 (*S. cerevisiae*) |
| ZNF157 | 1.57 | zinc finger protein 157 |
| LDB1 | 1.57 | LIM domain binding 1 |
| SIN3A | 1.55 | SIN3 homolog A, transcription regulator (yeast) |
| HDAC8 | 1.54 | histone deacetylase 8 |
| ZEB1 | 1.51 | zinc finger E-box binding homeobox 1 |
| BCL3 | 1.49 | B-cell CLL/lymphoma 3 |
| ZNF281 | 1.49 | zinc finger protein 281 |

APOPTOSIS_GO

Description: Genes annotated by the GO term GO:0006915. A form of programmed cell death.

| Enrichment Score (ES) | Normalized ES | Nominal p-value | FDR q-value | FWER p-value |
|---|---|---|---|---|
| 0.313 | 1.338 | <0.001 | 0.227 | 0.943 |

| PROBE | FOLD CHANGE | DESCRIPTION |
|---|---|---|
| APOE | 30.82 | apolipoprotein E |
| DAPK1 | 10.17 | death-associated protein kinase 1 |
| FOXO1 | 8.55 | forkhead box O1 |
| TP53 | 7.01 | tumor protein p53 |
| BCL2L11 | 6.76 | BCL2-like 11 (apoptosis facilitator) |
| SNCA | 6.48 | synuclein, alpha (non A4 component of amyloid precursor) |
| PRUNE2 | 6.19 | prune homolog 2 (*Drosophila*) |
| PROC | 5.53 | protein C (inactivator of coagulation factors Va and VIIIa) |
| TNFRSF8 | 5.42 | tumor necrosis factor receptor superfamily, member 8 |
| F2R | 4.40 | coagulation factor II (thrombin) receptor |
| ACVR1C | 4.08 | activin A receptor, type IC |
| TNFSF12 | 3.54 | tumor necrosis factor (ligand) superfamily, member 12 |
| IGFBP3 | 3.51 | insulin-like growth factor binding protein 3 |
| PPP1R13B | 3.42 | protein phosphatase 1, regulatory (inhibitor) subunit 13B |
| JMY | 3.38 | junction mediating and regulatory protein, p53 cofactor |
| TNFRSF25 | 3.25 | tumor necrosis factor receptor superfamily, member 25 |
| PYCARD | 3.08 | PYD and CARD domain containing |
| CYCS | 3.06 | cytochrome c, somatic |
| MOAP1 | 2.76 | modulator of apoptosis 1 |
| ADORA1 | 2.67 | adenosine A1 receptor |
| AHR | 2.67 | aryl hydrocarbon receptor |
| BAK1 | 2.53 | BCL2-antagonist/killer 1 |
| SOCS2 | 2.52 | suppressor of cytokine signaling 2 |
| DDAH2 | 2.51 | dimethylarginine dimethylaminohydrolase 2 |
| ASNS | 2.49 | asparagine synthetase (glutamine-hydrolyzing) |
| PDCD2 | 2.40 | programmed cell death 2 |
| CD70 | 2.32 | CD70 molecule |
| DHCR24 | 2.25 | 24-dehydrocholesterol reductase |
| NUAK2 | 2.21 | NUAK family, SNF1-like kinase, 2 |
| CASP9 | 2.18 | caspase 9, apoptosis-related cysteine peptidase |
| SGPL1 | 2.17 | sphingosine-1-phosphate lyase 1 |
| CASP6 | 2.17 | caspase 6, apoptosis-related cysteine peptidase |
| PTEN | 2.16 | phosphatase and tensin homolog |
| BID | 2.08 | BH3 interacting domain death agonist |
| CASP3 | 2.06 | caspase 3, apoptosis-related cysteine peptidase |
| AVEN | 2.05 | apoptosis, caspase activation inhibitor |
| BIRC6 | 2.05 | baculoviral IAP repeat-containing 6 |
| SRGN | 2.04 | serglycin |
| MX1 | 2.03 | myxovirus (influenza virus) resistance 1, interferon-inducible protein p78 (mouse) |

Supplementary Table 1: Gene Set Enrichment Data.
Expanded Gene Set Enrichment Analysis for (A) gene ontology: biological
process and (B) canonical pathway molecular signature databases (n = 3 samples from each group).

| | | |
|---|---|---|
| PSEN1 | 2.02 | presenilin 1 |
| GHRL | 2.02 | ghrelin/obestatin prepropeptide |
| DNAJB6 | 2.02 | DnaJ (Hsp40) homolog, subfamily B, member 6 |
| BAG4 | 2.02 | BCL2-associated athanogene 4 |
| DOCK1 | 2.01 | dedicator of cytokinesis 1 |
| MAGEH1 | 2.01 | melanoma antigen family H, 1 |
| PCBP4 | 1.98 | poly(rC) binding protein 4 |
| RHOT1 | 1.93 | ras homolog gene family, member T1 |
| MAGED1 | 1.93 | melanoma antigen family D, 1 |
| BRAF | 1.90 | v-raf murine sarcoma viral oncogene homolog B1 |
| NDUFA13 | 1.86 | NADH dehydrogenase (ubiquinone) 1 alpha subcomplex, 13 |
| MADD | 1.85 | MAP-kinase activating death domain |
| TRIAP1 | 1.85 | TP53 regulated inhibitor of apoptosis 1 |
| DYRK2 | 1.85 | dual-specificity tyrosine-(Y)-phosphorylation regulated kinase 2 |
| SH3GLB1 | 1.85 | SH3-domain GRB2-like endophilin B1 |
| SSTR3 | 1.84 | somatostatin receptor 3 |
| ERN2 | 1.83 | endoplasmic reticulum to nucleus signaling 2 |
| NDUFS3 | 1.79 | NADH dehydrogenase (ubiquinone) Fe—S protein 3, 30 kDa (NADH-coenzyme Q reductase) |
| ERCC3 | 1.79 | excision repair cross-complementing rodent repair deficiency, complementation group 3 (xeroderma pigmentosum group B complementing) |
| DNM1L | 1.77 | dynamin 1-like |
| MAPK8 | 1.76 | mitogen-activated protein kinase 8 |
| BCL2L2 | 1.76 | BCL2-like 2 |
| CRADD | 1.75 | CASP2 and RIPK1 domain containing adaptor with death domain |
| SMNDC1 | 1.74 | survival motor neuron domain containing 1 |
| RNF7 | 1.73 | ring finger protein 7 |
| MDM4 | 1.72 | Mdm4 p53 binding protein homolog (mouse) |
| BECN1 | 1.71 | beclin 1, autophagy related |
| VDAC1 | 1.71 | voltage-dependent anion channel 1 |
| ZNF346 | 1.69 | zinc finger protein 346 |
| BAG1 | 1.69 | BCL2-associated athanogene |
| FIS1 | 1.67 | fission 1 (mitochondrial outer membrane) homolog (*S. cerevisiae*) |
| HSPA9 | 1.66 | heat shock 70 kDa protein 9 (mortalin) |
| TRAF7 | 1.65 | TNF receptor-associated factor 7 |
| PML | 1.65 | promyelocytic leukemia |
| ABL1 | 1.63 | c-abl oncogene 1, non-receptor tyrosine kinase |
| UTP11L | 1.63 | UTP11-like, U3 small nucleolar ribonucleoprotein, (yeast) |
| RTKN | 1.62 | rhotekin |
| BRE | 1.61 | brain and reproductive organ-expressed (TNFRSF1A modulator) |
| BCLAF1 | 1.61 | BCL2-associated transcription factor 1 |
| AIFM2 | 1.60 | apoptosis-inducing factor, mitochondrion-associated, 2 |
| ANXA4 | 1.60 | Annexin A4 |
| PDCD6 | 1.60 | programmed cell death 6 |
| SRA1 | 1.60 | steroid receptor RNA activator 1 |
| RIPK1 | 1.57 | receptor (TNFRSF)-interacting serine-threonine kinase 1 |
| NFKB1 | 1.57 | nuclear factor of kappa light polypeptide gene enhancer in B-cells 1 |
| STK3 | 1.57 | serine/threonine kinase 3 |
| GML | 1.57 | glycosylphosphatidylinositol anchored molecule like protein |
| AIFM1 | 1.57 | apoptosis-inducing factor, mitochondrion-associated, 1 |
| FOXL2 | 1.57 | forkhead box L2 |
| TXNL1 | 1.56 | thioredoxin-like 1 |
| STAT1 | 1.55 | signal transducer and activator of transcription 1, 91 kDa |
| MRPS30 | 1.55 | mitochondrial ribosomal protein S30 |
| CDH13 | 1.55 | cadherin 13, H-cadherin (heart) |
| SON | 1.55 | SON DNA binding protein |
| CIAPIN1 | 1.53 | cytokine induced apoptosis inhibitor 1 |
| STK17B | 1.52 | serine/threonine kinase 17b |
| ACIN1 | 1.51 | apoptotic chromatin condensation inducer 1 |
| TSPO | 1.50 | translocator protein (18 kDa) |

Supplementary Table 1: Gene Set Enrichment Data.
Expanded Gene Set Enrichment Analysis for (A) gene ontology: biological
process and (B) canonical pathway molecular signature databases (n = 3 samples from each group).

| | | |
|---|---|---|
| TAX1BP1 | 1.50 | Tax1 (human T-cell leukemia virus type I) binding protein 1 |
| BCL3 | 1.49 | B-cell CLL/lymphoma 3 |

POSITIVE_REGULATION_OF_CELL_ADHESION

Description: Genes annotated by the GO term GO:0045785. Any process that activates or increases the frequency, rate or extent of cell adhesion.

| Enrichment Score (ES) | Normalized ES | Nominal p-value | FDR q-value | FWER p-value |
|---|---|---|---|---|
| 0.501 | 1.308 | <0.001 | 0.243 | 0.943 |

| PROBE | FOLD CHANGE | DESCRIPTION |
|---|---|---|
| CDK6 | 2.31 | cyclin-dependent kinase 6 |
| SAA1 | 2.17 | serum amyloid A1 |
| SIRPG | 1.64 | signal-regulatory protein gamma |
| CDH13 | 1.55 | cadherin 13, H-cadherin (heart) |

B. Canonical Pathways

BIOCARTA_AKT_PATHWAY

Description: AKT Signaling Pathway

| Enrichment Score (ES) | Normalized ES | Nominal p-value | FDR q-value | FWER p-value |
|---|---|---|---|---|
| 0.647 | 1.965 | <0.001 | 0.137 | 0.167 |

| PROBE | FOLD CHANGE | DESCRIPTION |
|---|---|---|
| GHR | 16.06 | growth hormone receptor |
| FOXO1 | 8.55 | forkhead box O1 |
| CASP9 | 2.18 | caspase 9, apoptosis-related cysteine peptidase |
| CHUK | 1.65 | conserved helix-loop-helix ubiquitous kinase |
| NFKB1 | 1.57 | nuclear factor of kappa light polypeptide gene enhancer in B-cells 1 |
| IKBKB | 1.54 | inhibitor of kappa light polypeptide gene enhancer in B-cells, kinase beta |

SA_PROGRAMMED_CELL_DEATH

Description: Programmed cell death, or apoptosis, eliminates damaged or unneeded cells.

| Enrichment Score (ES) | Normalized ES | Nominal p-value | FDR q-value | FWER p-value |
|---|---|---|---|---|
| 0.739 | 1.923 | <0.001 | 0.142 | 0.261 |

| PROBE | FOLD CHANGE | DESCRIPTION |
|---|---|---|
| BCL2L11 | 6.76 | BCL2-like 11 (apoptosis facilitator) |
| BAK1 | 2.53 | BCL2-antagonist/killer 1 |
| CASP9 | 2.18 | caspase 9, apoptosis-related cysteine peptidase |
| BID | 2.08 | BH3 interacting domain death agonist |

KEGG_ECM_RECEPTOR_INTERACTION

Description: ECM-receptor interaction

| Enrichment Score (ES) | Normalized ES | Nominal p-value | FDR q-value | FWER p-value |
|---|---|---|---|---|
| 0.496 | 1.857 | <0.001 | 0.158 | 0.362 |

| PROBE | FOLD CHANGE | DESCRIPTION |
|---|---|---|
| COL3A1 | 189.00 | collagen, type III, alpha 1 |
| COL4A1 | 38.67 | collagen, type IV, alpha 1 |
| COL1A2 | 14.75 | collagen, type I, alpha 2 |
| ITGB8 | 6.07 | integrin, beta 8 |
| COL5A2 | 5.95 | collagen, type V, alpha 2 |
| ITGA10 | 4.84 | integrin, alpha 10 |
| COL1A1 | 4.44 | collagen, type I, alpha 1 |

Supplementary Table 1: Gene Set Enrichment Data.
Expanded Gene Set Enrichment Analysis for (A) gene ontology: biological
process and (B) canonical pathway molecular signature databases (n = 3 samples from each group).

| | | |
|---|---|---|
| RELN | 3.89 | reelin |
| COL4A2 | 3.70 | collagen, type IV, alpha 2 |
| THBS3 | 3.12 | thrombospondin 3 |
| ITGA4 | 3.06 | integrin, alpha 4 (antigen CD49D, alpha 4 subunit of VLA-4 receptor) |
| THBS4 | 3.01 | thrombospondin 4 |
| SDC2 | 2.87 | syndecan 2 |
| ITGAV | 2.56 | integrin, alpha V (vitronectin receptor, alpha polypeptide, antigen CD51) |
| ITGB6 | 2.49 | integrin, beta 6 |
| COL5A1 | 2.47 | collagen, type V, alpha 1 |
| ITGA6 | 2.15 | integrin, alpha 6 |
| LAMA5 | 1.96 | laminin, alpha 5 |
| DAG1 | 1.81 | dystroglycan 1 (dystrophin-associated glycoprotein 1) |
| ITGB5 | 1.71 | integrin, beta 5 |
| LAMB1 | 1.69 | laminin, beta 1 |
| AGRN | 1.64 | agrin |

KEGG_MTOR_SIGNALING_PATHWAY

Description: mTOR signaling pathway

| Enrichment Score (ES) | Normalized ES | Nominal p-value | FDR q-value | FWER p-value |
|---|---|---|---|---|
| 0.487 | 1.831 | <0.001 | 0.125 | 0.362 |

| PROBE | FOLD CHANGE | DESCRIPTION |
|---|---|---|
| IGF1 | 13.36 | insulin-like growth factor 1 (somatomedin C) |
| PIK3R3 | 7.27 | phosphoinositide-3-kinase, regulatory subunit 3 (gamma) |
| AKT2 | 3.13 | v-akt murine thymoma viral oncogene homolog 2 |
| ULK1 | 2.79 | unc-51-like kinase 1 (*C. elegans*) |
| RPS6KA1 | 2.70 | ribosomal protein S6 kinase, 90 kDa, polypeptide 1 |
| RPS6KA3 | 2.62 | ribosomal protein S6 kinase, 90 kDa, polypeptide 3 |
| EIF4B | 2.35 | eukaryotic translation initiation factor 4B |
| STK11 | 2.31 | serine/threonine kinase 11 |
| EIF4E2 | 2.01 | eukaryotic translation initiation factor 4E family member 2 |
| BRAF | 1.90 | v-raf murine sarcoma viral oncogene homolog B1 |
| MTOR | 1.54 | mechanistic target of rapamycin (serine/threonine kinase) |

REACTOME_PI3K_AKT_SIGNALING

Description: Genes involved in PI3K/AKT signalling

| Enrichment Score (ES) | Normalized ES | Nominal p-value | FDR q-value | FWER p-value |
|---|---|---|---|---|
| 0.479 | 1.682 | <0.001 | 0.144 | 0.452 |

| PROBE | FOLD CHANGE | DESCRIPTION |
|---|---|---|
| FOXO1 | 8.55 | forkhead box O1 |
| AKT2 | 3.13 | v-akt murine thymoma viral oncogene homolog 2 |
| IRS1 | 2.43 | insulin receptor substrate 1 |
| CASP9 | 2.18 | caspase 9, apoptosis-related cysteine peptidase |
| PTEN | 2.16 | phosphatase and tensin homolog |
| TRIB3 | 1.84 | tribbles homolog 3 (*Drosophila*) |
| CHUK | 1.65 | conserved helix-loop-helix ubiquitous kinase |
| MTOR | 1.54 | mechanistic target of rapamycin (serine/threonine kinase) |
| CREB1 | 1.52 | cAMP responsive element binding protein 1 |

REACTOME_INTEGRIN_CELL_SURFACE_INTERACTIONS

Description: Genes involved in Integrin cell surface interactions

| Enrichment Score (ES) | Normalized ES | Nominal p-value | FDR q-value | FWER p-value |
|---|---|---|---|---|
| 0.423 | 1.592 | <0.001 | 0.142 | 0.759 |

| PROBE | FOLD CHANGE | DESCRIPTION |
|---|---|---|
| COL4A1 | 38.67 | collagen, type IV, alpha 1 |
| COL1A2 | 14.75 | collagen, type I, alpha 2 |
| ITGB8 | 6.07 | integrin, beta 8 |

Supplementary Table 1: Gene Set Enrichment Data.
Expanded Gene Set Enrichment Analysis for (A) gene ontology: biological
process and (B) canonical pathway molecular signature databases (n = 3 samples from each group).

| Probe | Fold Change | Description |
|---|---|---|
| ICAM2 | 5.58 | intercellular adhesion molecule 2 |
| ITGA10 | 4.84 | integrin, alpha 10 |
| COL1A1 | 4.44 | collagen, type I, alpha 1 |
| COL4A2 | 3.70 | collagen, type IV, alpha 2 |
| ITGA4 | 3.06 | integrin, alpha 4 (antigen CD49D, alpha 4 subunit of VLA-4 receptor) |
| ITGAV | 2.56 | integrin, alpha V (vitronectin receptor, alpha polypeptide, antigen CD51) |
| SRC | 2.53 | v-src sarcoma (Schmidt-Ruppin A-2) viral oncogene homolog (avian) |
| ITGB6 | 2.49 | integrin, beta 6 |
| MADCAM1 | 2.19 | mucosal vascular addressin cell adhesion molecule 1 |
| ITGA6 | 2.15 | integrin, alpha 6 |
| LAMA5 | 1.96 | laminin, alpha 5 |
| SOS1 | 1.84 | son of sevenless homolog 1 (*Drosophila*) |
| ITGB5 | 1.71 | integrin, beta 5 |
| LAMB1 | 1.69 | laminin, beta 1 |
| RAPGEF3 | 1.65 | Rap guanine nucleotide exchange factor (GEF) 3 |
| ITGAL | 1.65 | integrin, alpha L (antigen CD11A (p180), lymphocyte function-associated antigen 1; alpha polypeptide) |

BIOCARTA_ERK_PATHWAY

Description: Erk1/Erk2 Mapk Signaling pathway

| Enrichment Score (ES) | Normalized ES | Nominal p-value | FDR q-value | FWER p-value |
|---|---|---|---|---|
| 0.493 | 1.583 | <0.001 | 0.151 | 0.759 |

| PROBE | FOLD CHANGE | DESCRIPTION |
|---|---|---|
| NGFR | 10.07 | nerve growth factor receptor |
| PDGFRA | 7.22 | platelet-derived growth factor receptor, alpha polypeptide |
| RPS6KA1 | 2.70 | ribosomal protein S6 kinase, 90 kDa, polypeptide 1 |
| SRC | 2.53 | v-src sarcoma (Schmidt-Ruppin A-2) viral oncogene homolog (avian) |
| MKNK2 | 2.26 | MAP kinase interacting serine/threonine kinase 2 |
| MKNK1 | 2.24 | MAP kinase interacting serine/threonine kinase 1 |
| STAT3 | 1.84 | signal transducer and activator of transcription 3 (acute-phase response factor) |
| SOS1 | 1.84 | son of sevenless homolog 1 (*Drosophila*) |
| GNAS | 1.82 | GNAS complex locus |
| SHC1 | 1.74 | SHC (Src homology 2 domain containing) transforming protein 1 |
| RPS6KA5 | 1.71 | ribosomal protein S6 kinase, 90 kDa, polypeptide 5 |

KEGG_APOPTOSIS

Description: Apoptosis

| Enrichment Score (ES) | Normalized ES | Nominal p-value | FDR q-value | FWER p-value |
|---|---|---|---|---|
| 0.360 | 1.521 | <0.001 | 0.169 | 0.804 |

| PROBE | FOLD CHANGE | DESCRIPTION |
|---|---|---|
| PIK3R3 | 7.27 | phosphoinositide-3-kinase, regulatory subunit 3 (gamma) |
| TP53 | 7.01 | tumor protein p53 |
| AKT2 | 3.13 | v-akt murine thymoma viral oncogene homolog 2 |
| CYCS | 3.06 | cytochrome c, somatic |
| PRKACB | 2.79 | protein kinase, cAMP-dependent, catalytic, beta |
| CASP9 | 2.18 | caspase 9, apoptosis-related cysteine peptidase |
| CASP6 | 2.17 | caspase 6, apoptosis-related cysteine peptidase |
| BID | 2.08 | BH3 interacting domain death agonist |
| CASP3 | 2.06 | caspase 3, apoptosis-related cysteine peptidase |
| PPP3CA | 1.98 | protein phosphatase 3, catalytic subunit, alpha isozyme |
| CHP | 1.78 | calcium binding protein P22 |
| MYD88 | 1.75 | myeloid differentiation primary response gene (88) |
| ENDOD1 | 1.68 | endonuclease domain containing 1 |
| CHUK | 1.65 | conserved helix-loop-helix ubiquitous kinase |
| RIPK1 | 1.57 | receptor (TNFRSF)-interacting serine-threonine kinase 1 |
| NFKB1 | 1.57 | nuclear factor of kappa light polypeptide gene enhancer in B-cells 1 |
| AIFM1 | 1.57 | apoptosis-inducing factor, mitochondrion-associated, 1 |
| IKBKB | 1.54 | inhibitor of kappa light polypeptide gene enhancer in B-cells, kinase beta |
| PRKACA | 1.51 | protein kinase, cAMP-dependent, catalytic, alpha |

| Probe ID | Gene_symbol | Description | Fold Change | p-value | Entrez_gene |
|---|---|---|---|---|---|
| PH_hs_0004751 | MMP1 | matrix metallopeptidase 1 (interstitial collagenase) | −37.04 | 0.000E+00 | 4312 |
| PH_hs_0007166 | IL1B | interleukin 1, beta | −25.20 | 0.000E+00 | 3553 |
| PH_hs_0024245 | MMP3 | matrix metallopeptidase 3 (stromelysin 1, progelatinase) | −19.01 | 0.000E+00 | 4314 |
| PH_hs_0020125 | SBSN | suprabasin | −16.74 | 0.000E+00 | 374897 |
| PH_hs_0002254 | STC1 | stanniocalcin 1 | −15.24 | 2.803E-45 | 6781 |
| PH_hs_0020945 | TFAP2C | transcription factor AP-2 gamma (activating enhancer binding protein 2 gamma) | −13.77 | 0.000E+00 | 7022 |
| PH_hs_0036700 | MGC87042 | STEAP family protein MGC87042 | −13.51 | 2.139E-20 | 256227 |
| PH_hs_0016413 | BEX1 | brain expressed, X-linked 1 | −9.73 | 4.204E-45 | 55859 |
| PH_hs_0031336 | PLAU | plasminogen activator, urokinase | −9.17 | 4.462E-25 | 5328 |
| PH_hs_0002016 | VAT1L | vesicle amine transport protein 1 homolog (T. californica)-like | −8.62 | 2.057E-29 | 57687 |
| PH_hs_0012290 | COL13A1 | collagen, type XIII, alpha 1 | −8.38 | 0.000E+00 | 1305 |
| PH_hs_0005972 | DDIT4L | DNA-damage-inducible transcript 4-like | −8.25 | 2.013E-37 | 115265 |
| PH_hs_0004656 | FOXF1 | forkhead box F1 | −8.20 | 0.000E+00 | 2294 |
| PH_hs_0025658 | IL1RN | interleukin 1 receptor antagonist | −8.00 | 5.741E-19 | 3557 |
| PH_hs_0003282 | TFPI2 | tissue factor pathway inhibitor 2 | −7.56 | 0.000E+00 | 7980 |
| PH_hs_0003282 | BDKRB1 | bradykinin receptor B1 | −7.27 | 0.000E+00 | 623 |
| PH_hs_0003166 | FARP1 | FERM, RhoGEF (ARHGEF) and pleckstrin domain protein 1 (chondrocyte-derived) | −7.26 | 1.402E-24 | 10160 |
| PH_hs_0048377 | DCC | deleted in colorectal carcinoma | −7.24 | 6.156E-23 | 1630 |
| PH_hs_0000274 | PTX3 | pentraxin 3, long | −7.23 | 1.757E-35 | 5806 |
| PH_hs_0024475 | ACPP | acid phosphatase, prostate | −7.14 | 5.483E-32 | 55 |
| PH_hs_0006070 | FAM133A | family with sequence similarity 133, member A | −6.93 | 4.204E-45 | 286499 |
| PH_hs_0003348 | GALNT12 | UDP-N-acetyl-alpha-D-galactosamine: polypeptide N-acetylgalactosaminyltransferase 12 (GalNAc-T12) | −6.73 | 4.860E-30 | 79695 |
| PH_hs_0000069 | IL8 | interleukin 8 | −6.44 | 1.489E-36 | 3576 |
| PH_hs_0010634 | TXNIP | thioredoxin interacting protein | −6.02 | 5.663E-32 | 10628 |
| PH_hs_0003353 | C3orf14 | chromosome 3 open reading frame 14 | −5.94 | 4.380E-22 | 57415 |
| PH_hs_0012787 | DNER | delta/notch-like EGF repeat containing | −5.92 | 9.790E-12 | 92737 |
| PH_hs_0006337 | HS3ST2 | heparan sulfate (glucosamine) 3-O-sulfotransferase 2 | −5.63 | 8.543E-29 | 9956 |
| PH_hs_0000049 | COL4A6 | collagen, type IV, alpha 6 | −5.56 | 1.738E-21 | 1288 |
| PH_hs_0043284 | NAMPT | nicotinamide phosphoribosyltransferase | −5.54 | 0.000E+00 | 10135 |
| PH_hs_0049129 | AFF3 | AF4/FMR2 family, member 3 | −5.52 | 7.406E-21 | 3899 |
| PH_hs_0000116 | CRYM | crystallin, mu | −5.40 | 6.122E-17 | 1428 |
| PH_hs_0004626 | KRT15 | keratin 15 | −5.33 | 3.109E-35 | 3866 |
| PH_hs_0044664 | FST | follistatin | −5.32 | 5.014E-29 | 10468 |
| PH_hs_0028155 | HLA-DRB1|HLA-DRB3|LOC1002909 66|LOC100510495|L OC100294276|LOC 100507687 | major histocompatibility complex, class II, DR beta 1|major histocompatibility complex, class II, DR beta 3|HLA class II histocompatibility antigen, DRB1-13 beta chain-like|HLA class II histocompatibility antigen, DR beta 3 chain-like|HLA class II histocompatibility antigen, DRB1-3 chain-like|HLA class II histocompatibility antigen, DR beta 3 chain-like | −5.30 | 9.970E-19 | 3123|3125|1002 9096|100510049 5|100294276|10 0510687 |
| PH_hs_0002348 | TOX2 | TOX high mobility group box family member 2 | −5.28 | 1.597E-37 | 84969 |
| PH_hs_0046213 | NAV2 | neuron navigator 2 | −5.25 | 0.000E+00 | 89797 |
| PH_hs_0023876 | IL13RA2 | interleukin 13 receptor, alpha 2 | −5.25 | 0.000E+00 | 3598 |
| PH_hs_0024850 | ID1 | inhibitor of DNA binding 1, dominant negative helix-loop-helix protein | −5.06 | 4.560E-35 | 3397 |
| PH_hs_0012929 | LOC100509788|LO C100507248 | hypothetical LOC100509788|hypothetical LOC100507248 | −5.04 | 1.146E-14 | 100509788|1005 07248 |
| PH_hs_0007059 | EPHB2 | EPH receptor B2 | −4.99 | 3.432E-18 | 2048 |
| PH_hs_0018575 | LCP1 | lymphocyte cytosolic protein 1 (L-plastin) | −4.95 | 1.889E-14 | 3936 |
| PH_hs_0019600 | KCNS3 | potassium voltage-gated channel, delayed-rectifier, subfamily S, member 3 | −4.95 | 4.978E-11 | 3790 |
| PH_hs_0046498 | HLA-DRB5 | major histocompatibility complex, class II, DR beta 5 | −4.82 | 1.368E-34 | 3127 |
| PH_hs_0045183 | ZNF542 | zinc finger protein 542 | −4.81 | 4.141E-04 | 147947 |
| PH_hs_0014393 | TRPV2 | transient receptor potential cation channel, subfamily V, member 2 | −4.75 | 1.016E-28 | 51393 |

-continued

| Probe ID | Gene_symbol | Description | Fold Change | p-value | Entrez_gene |
|---|---|---|---|---|---|
| PH_hs_0043843 | AK4 | adenylate kinase 4 | -4.73 | 1.111E-08 | 205 |
| PH_hs_0024184 | CCND1 | cyclin D1 | -4.73 | 2.278E-30 | 595 |
| PH_hs_0001350 | SMOC1 | SPARC related modular calcium binding 1 | -4.70 | 9.249E-44 | 64093 |
| PH_hs_0030595 | CLDN14 | claudin 14 | -4.60 | 9.133E-14 | 23562 |
| PH_hs_0048613 | EPAS1 | endothelial PAS domain protein 1 | -4.59 | 5.806E-15 | 2034 |
| PH_hs_0031957 | SH2D5 | SH2 domain containing 5 | -4.48 | 0.000E+00 | 400745 |
| PH_hs_0043853 | CDCA7L | cell division cycle associated 7-like | -4.43 | 3.584E-39 | 55536 |
| PH_hs_0025481 | HOXB7 | homeobox B7 | -4.41 | 1.473E-30 | 3217 |
| PH_hs_0003918 | STEAP1 | six transmembrane epithelial antigen of the prostate 1 | -4.39 | 5.290E-23 | 26872 |
| PH_hs_0047837 | MARCH4 | membrane-associated ring finger (C3HC4) 4 | -4.36 | 4.245E-03 | 57574 |
| PH_hs_0011595 | PTGS2 | prostaglandin-endoperoxide synthase 2 (prostaglandin G/H synthase and cyclooxygenase) | -4.29 | 1.995E-13 | 5743 |
| PH_hs_0022271 | LTBP2 | latent transforming growth factor beta binding protein 2 | -4.19 | 1.999E-14 | 4053 |
| PH_hs_0024711 | SPINK1 | serine peptidase inhibitor, Kazal type 1 | -4.17 | 2.325E-03 | 6690 |
| PH_hs_0000694 | RND3 | Rho family GTPase 3 | -4.17 | 1.005E-13 | 390 |
| PH_hs_0048830 | DSG2 | desmoglein 2 | -4.08 | 1.174E-28 | 1829 |
| PH_hs_0048643 | ODZ4 | odz, odd Oz/ten-m homolog 4 (Drosophila) | -4.04 | 1.557E-08 | 26011 |
| PH_hs_0028383 | NMU | neuromedin U | -4.03 | 1.770E-05 | 10874 |
| PH_hs_0009260 | NT5E | 5'-nucleotidase, ecto (CD73) | -4.01 | 5.626E-19 | 4907 |
| PH_hs_0045633 | HGF | hepatocyte growth factor (hepapoietin A; scatter factor) | -4.00 | 7.332E-28 | 3082 |
| PH_hs_0001558 | DHRS3 | dehydrogenase/reductase (SDR family) member 3 | -3.96 | 8.375E-28 | 9249 |
| PH_hs_0005777 | RAGE | renal tumor antigen | -3.94 | 2.330E-26 | 5891 |
| PH_hs_0030089 | HLA-DRA | major histocompatibility complex, class II, DR alpha | -3.93 | 8.182E-28 | 3122 |
| PH_hs_0034480 | HLA-DRB1\|LOC1002909 66\|LOC100294276\| HLA-DRB3\|LOC1005104 95\|LOC100510687\|L OC100294468\|LOC 100507709\|LOC100 507709\|LOC100294 036\|HLA-DRB4\|LOC1005105 19\|LOC100509582\|L OC100509301 | major histocompatibility complex, class II, DR beta 1\|HLA class II histocompatibility antigen, DRB1-13 beta chain-like\|HLA class II histocompatibility antigen, DRB1-3 chain-like\|major histocompatibility complex, class II, DR beta 3\|HLA class II histocompatibility antigen, DR beta 3 chain-like\|HLA class II histocompatibility antigen, DRB1-9 beta chain-like\|HLA class II histocompatibility antigen, DRB1-7 beta chain-like\|HLA class II histocompatibility antigen, DRB1-9 beta chain-like\|major histocompatibility complex, class II, DR beta 4\|HLA class II histocompatibility antigen, DR beta 4 chain-like\|HLA class II histocompatibility antigen, DR beta 4 chain-like | -3.92 | 1.174E-30 | 3123\|100290966 \|100294276\|312 5\|100510495\|10 0510687\|100294 468\|100507714\| 100507709\|1002 94036\|312610\|0 510519\|1005095 82\|100509301 |
| PH_hs_0047929 | KLHL29 | kelch-like 29 (Drosophila) | -3.89 | 1.231E-25 | 114818 |
| PH_hs_0003691 | CDH18 | cadherin 18, type 2 | -3.77 | 1.171E-19 | 1016 |
| PH_hs_0042825 | RFX8 | regulatory factor X, 8 | -3.75 | 4.197E-10 | 731220 |
| PH_hs_0009039 | FAM196A | family with sequence similarity 196, member A | -3.73 | 3.004E-15 | 642938 |
| PH_hs_0030443 | PAPPA | pregnancy-associated plasma protein A, pappalysin 1 | -3.72 | 3.420E-17 | 5069 |
| PH_hs_0049346 | APLN | apelin | -3.71 | 2.559E-26 | 8862 |
| PH_hs_0046081 | MEG3 | maternally expressed 3 (non-protein coding) | -3.70 | 6.844E-10 | 55384 |
| PH_hs_0047648 | RALGPS2 | Ral GEF with PH domain and SH3 binding motif 2 | -3.66 | 1.152E-07 | 55103 |
| PH_hs_0033958 | MYO1D | myosin ID | -3.59 | 2.503E-14 | 4642 |
| PH_hs_0023142 | RRM2 | ribonucleotide reductase M2 | -3.55 | 1.203E-26 | 6241 |
| PH_hs_0024642 | NPC1 | Niemann-Pick disease, type C1 | -3.51 | 1.057E-14 | 4864 |
| PH_hs_0004482 | MTSS1 | metastasis suppressor 1 | -3.51 | 4.583E-20 | 9788 |
| PH_hs_0047208 | TIAM1 | T-cell lymphoma invasion and metastasis 1 | -3.49 | 1.613E-04 | 7074 |
| PH_hs_0048955 | LSAMP | limbic system-associated membrane protein | -3.46 | 3.920E-29 | 4045 |
| PH_hs_0035899 | TMTC1 | transmembrane and tetratricopeptide repeat containing 1 | -3.45 | 7.324E-25 | 83857 |
| PH_hs_0048963 | KCTD12 | potassium channel tetramerisation domain containing 12 | -3.43 | 3.396E-29 | 115207 |

-continued

| Probe ID | Gene_symbol | Description | Fold Change | p-value | Entrez_gene |
|---|---|---|---|---|---|
| PH_hs_0045043 | ZAK | sterile alpha motif and leucine zipper containing kinase AZK | −3.40 | 4.328E-17 | 51776 |
| PH_hs_0043556 | HMGA1 | high mobility group AT-hook 1 | −3.39 | 2.623E-22 | 3159 |
| PH_hs_0026117 | TIMP1 | TIMP metallopeptidase inhibitor 1 | −3.38 | 3.742E-24 | 7076 |
| PH_hs_0042141 | SPA17 | sperm autoantigenic protein 17 | −3.37 | 3.888E-12 | 53340 |
| PH_hs_0045771 | LTBP1 | latent transforming growth factor beta binding protein 1 | −3.37 | 1.411E-30 | 4052 |
| PH_hs_0028680 | SPP1 | secreted phosphoprotein 1 | −3.36 | 2.569E-40 | 6696 |
| PH_hs_0044741 | PLAUR | plasminogen activator, urokinase receptor | −3.35 | 1.082E-22 | 5329 |
| PH_hs_0033515 | ACOX2 | acyl-CoA oxidase 2, branched chain | −3.34 | 3.621E-18 | 8309 |
| PH_hs_0048917 | MAST4 | microtubule associated serine/threonine kinase family member 4 | −3.32 | 2.941E-15 | 375449 |
| PH_hs_0019975 | G0S2 | G0/G1switch 2 | −3.31 | 1.569E-21 | 50486 |
| PH_hs_0018587 | ATL3 | atlastin GTPase 3 | −3.29 | 7.670E-06 | 25923 |
| PH_hs_0044542 | MAPKAP1 | mitogen-activated protein kinase associated protein 1 | −3.26 | 3.340E-11 | 79109 |
| PH_hs_0023338 | LAMA1 | laminin, alpha 1 | −3.25 | 1.069E-14 | 284217 |
| PH_hs_0040322 | IL1F5 | interleukin 1 family, member 5 (delta) | −3.25 | 4.701E-10 | 26525 |
| PH_hs_0025294 | EEF1A2 | eukaryotic translation elongation factor 1 alpha 2 | −3.23 | 8.373E-06 | 1917 |
| PH_hs_0022250 | TFPI | tissue factor pathway inhibitor (lipoprotein-associated coagulation inhibitor) | −3.21 | 4.649E-13 | 7035 |
| PH_hs_0004525 | JUN | jun proto-oncogene | −3.19 | 4.458E-30 | 3725 |
| PH_hs_0011503 | GPRC5A | G protein-coupled receptor, family C, group 5, member A | −3.18 | 1.116E-08 | 9052 |
| PH_hs_0048091 | RUNDC3B | RUN domain containing 3B | −3.18 | 2.274E-12 | 154661 |
| PH_hs_0042114 | SVIP | small VCP/p97-interacting protein | −3.17 | 2.297E-19 | 258010 |
| PH_hs_0020544 | BACE2 | beta-site APP-cleaving enzyme 2 | −3.15 | 9.307E-18 | 25825 |
| PH_hs_0043471 | TMEM98 | transmembrane protein 98 | −3.13 | 1.548E-07 | 26022 |
| PH_hs_0000235 | IL1A | interleukin 1, alpha | −3.08 | 1.086E-14 | 3552 |
| PH_hs_0000061 | ISL1 | ISL LIM homeobox 1 | −3.06 | 4.290E-05 | 3670 |
| PH_hs_0028200 | CENPI | centromere protein I | −3.06 | 1.299E-06 | 2491 |
| PH_hs_0014153 | TUBB6 | tubulin, beta 6 | −3.05 | 1.029E-14 | 84617 |
| PH_hs_0048021 | GINS4 | GINS complex subunit 4 (Sld5 homolog) | −3.01 | 8.775E-19 | 84296 |
| PH_hs_0000309 | VSNL1 | visinin-like 1 | −2.97 | 3.279E-11 | 7447 |
| PH_hs_0019257 | AOX1 | aldehyde oxidase 1 | −2.92 | 7.321E-24 | 316 |
| PH_hs_0016443 | CDK1 | cyclin-dependent kinase 1 | −2.89 | 1.172E-13 | 983 |
| PH_hs_0048433 | GALNT9 | UDP-N-acetyl-alpha-D-galactosamine: polypeptide N-acetylgalactosaminyltransferase 9 (GalNAc-T9) | −2.86 | 1.302E-03 | 50614 |
| PH_hs_0046169 | VEPH1 | ventricular zone expressed PH domain homolog 1 (zebrafish) | −2.86 | 1.966E-19 | 79674 |
| PH_hs_0047588 | SPATS2L | spermatogenesis associated, serine-rich 2-like | −2.85 | 9.378E-11 | 26010 |
| PH_hs_0043250 | CPEB2 | cytoplasmic polyadenylation element binding protein 2 | −2.85 | 6.360E-14 | 132864 |
| PH_hs_0022243 | SLC43A3 | solute carrier family 43, member 3 | −2.84 | 2.557E-08 | 29015 |
| PH_hs_0049493 | AKAP2|PALM2-AKAP2 | A kinase (PRKA) anchor protein 2|PALM2-AKAP2 readthrough | −2.84 | 6.170E-08 | 11217/445815 |
| PH_hs_0029612 | FOSL1 | FOS-like antigen 1 | −2.82 | 4.720E-03 | 8061 |
| PH_hs_0001652 | SPRY2 | sprouty homolog 2 (Drosophila) | −2.79 | 1.427E-07 | 10253 |
| PH_hs_0031712 | DKK3 | dickkopf homolog 3 (Xenopus laevis) | −2.79 | 4.059E-12 | 27122 |
| PH_hs_0045179 | SMTN | smoothelin | −2.78 | 7.772E-13 | 6525 |
| PH_hs_0003694 | HAS1 | hyaluronan synthase 1 | −2.77 | 2.110E-17 | 3036 |
| PH_hs_0030777 | PTTG3P|PTTG1|PTTG2 | pituitary tumor-transforming 3 (pseudogene)|pituitary tumor-transforming 1|pituitary tumor-transforming 2 | −2.77 | 2.922E-12 | 26255|9232|10744 |
| PH_hs_0004390 | IER3 | immediate early response 3 | −2.76 | 3.726E-17 | 8870 |
| PH_hs_0033310 | HDHD1 | haloacid dehalogenase-like hydrolase domain containing 1 | −2.76 | 1.556E-15 | 8226 |
| PH_hs_0042294 | C16orf42 | chromosome 16 open reading frame 42 | −2.75 | 1.576E-18 | 115939 |
| PH_hs_0048024 | UBASH3B | ubiquitin associated and SH3 domain containing B | −2.75 | 3.406E-04 | 84959 |
| PH_hs_0048924 | PRKCE | protein kinase C, epsilon | −2.73 | 3.275E-08 | 5581 |
| PH_hs_0004761 | GNG11 | guanine nucleotide binding protein (G protein), gamma 11 | −2.69 | 1.688E-10 | 2791 |
| PH_hs_0043388 | SPTLC3 | serine palmitoyltransferase, long chain base subunit 3 | −2.67 | 1.248E-09 | 55304 |

-continued

| Probe ID | Gene_symbol | Description | Fold Change | p-value | Entrez_gene |
|---|---|---|---|---|---|
| PH_hs_0005822 | HJURP | Holliday junction recognition protein | −2.66 | 2.269E−05 | 55355 |
| PH_hs_0004404 | BRP44 | brain protein 44 | −2.66 | 6.919E−16 | 25874 |
| PH_hs_0004222 | FAH | fumarylacetoacetate hydrolase (fumarylacetoacetase) | −2.64 | 4.634E−20 | 2184 |
| PH_hs_0029022 | CLEC2B | C-type lectin domain family 2, member B | −2.63 | 1.767E−15 | 9976 |
| PH_hs_0045651 | KPNA2 | karyopherin alpha 2 (RAG cohort 1, importin alpha 1) | −2.62 | 2.055E−12 | 3838 |
| PH_hs_0046334 | C14orf80 | chromosome 14 open reading frame 80 | −2.60 | 5.543E−11 | 283643 |
| PH_hs_0015628 | FZD8 | frizzled homolog 8 (Drosophila) | −2.59 | 1.161E−24 | 8325 |
| PH_hs_0049449 | GPR39 | G protein-coupled receptor 39 | −2.59 | 2.531E−16 | 2863 |
| PH_hs_0010276 | DUSP1 | dual specificity phosphatase 1 | −2.59 | 2.180E−20 | 1843 |
| PH_hs_0027327 | CTPS | CTP synthase | −2.59 | 4.106E−16 | 1503 |
| PH_hs_0035997 | PVRL3 | poliovirus receptor-related 3 | −2.59 | 6.413E−15 | 25945 |
| PH_hs_0003012 | FJX1 | four jointed box 1 (Drosophila) | −2.59 | 6.317E−05 | 24147 |
| PH_hs_0049442 | SRGAP1 | SLIT-ROBO Rho GTPase activating protein 1 | −2.59 | 9.266E−06 | 57522 |
| PH_hs_0047372 | PCDHB16 | protocadherin beta 16 | −2.58 | 5.863E−11 | 57717 |
| PH_hs_0025406 | SQRDL | sulfide quinone reductase-like (yeast) | −2.57 | 8.690E−12 | 58472 |
| PH_hs_0032595 | CD44 | CD44 molecule (Indian blood group) | −2.57 | 1.850E−15 | 960 |
| PH_hs_0015371 | MLPH | melanophilin | −2.57 | 2.150E−21 | 79083 |
| PH_hs_0003937 | ANLN | anillin, actin binding protein | −2.57 | 3.082E−04 | 54443 |
| PH_hs_0000094 | HBEGF | heparin-binding EGF-like growth factor | −2.56 | 1.226E−14 | 1839 |
| PH_hs_0011672 | CAMK2N1 | calcium/calmodulin-dependent protein kinase II inhibitor 1 | −2.56 | 8.003E−09 | 55450 |
| PH_hs_0024092 | ZIC2 | Zic family member 2 (odd-paired homolog, Drosophila) | −2.56 | 7.400E−07 | 7546 |
| PH_hs_0024602 | CNIH3 | cornichon homolog 3 (Drosophila) | −2.55 | 7.390E−08 | 149111 |
| PH_hs_0033695 | EEF1A1P9 | eukaryotic translation elongation factor 1 alpha 1 pseudogene 9 | −2.55 | 6.865E−10 | 441032 |
| PH_hs_0004464 | PRKAR2B | protein kinase, cAMP-dependent, regulatory, type II, beta | −2.54 | 5.797E−09 | 5577 |
| PH_hs_0047795 | ADAMTS6 | ADAM metallopeptidase with thrombospondin type 1 motif, 6 | −2.54 | 1.053E−09 | 11174 |
| PH_hs_0000277 | VDR | vitamin D (1,25-dihydroxyvitamin D3) receptor | −2.52 | 1.733E−16 | 7421 |
| PH_hs_0029239 | VWA5A | von Willebrand factor A domain containing 5A | −2.52 | 2.493E−11 | 4013 |
| PH_hs_0047888 | SLC6A15 | solute carrier family 6 (neutral amino acid transporter), member 15 | −2.48 | 2.500E−15 | 55117 |
| PH_hs_0000691 | KIAA1644 | KIAA1644 | −2.48 | 5.986E−10 | 85352 |
| PH_hs_0010370 | AMPH | amphiphysin | −2.47 | 1.200E−13 | 273 |
| PH_hs_0000198 | SERPIND1 | serpin peptidase inhibitor, clade D (heparin cofactor), member 1 | −2.46 | 4.216E−13 | 3053 |
| PH_hs_0016332 | FXYD5 | FXYD domain containing ion transport regulator 5 | −2.46 | 2.891E−17 | 53827 |
| PH_hs_0004309 | SLC16A2 | solute carrier family 16, member 2 (monocarboxylic acid transporter 8) | −2.46 | 2.935E−04 | 6567 |
| PH_hs_0002224 | RNASEH2A | ribonuclease H2, subunit A | −2.45 | 2.694E−09 | 10535 |
| PH_hs_0002700 | OSGIN1 | oxidative stress induced growth inhibitor 1 | −2.45 | 1.973E−08 | 29948 |
| PH_hs_0043945 | SVIL | supervillin | −2.44 | 9.094E−05 | 6840 |
| PH_hs_0047542 | GCLM | glutamate-cysteine ligase, modifier subunit | −2.44 | 8.375E−05 | 2730 |
| PH_hs_0025078 | DUSP4 | dual specificity phosphatase 4 | −2.44 | 4.669E−11 | 1846 |
| PH_hs_0004975 | ERCC6L | excision repair cross-complementing rodent repair deficiency, complementation group 6-like | −2.44 | 5.934E−03 | 54821 |
| PH_hs_0001751 | MAMLD1 | mastermind-like domain containing 1 | −2.43 | 3.018E−15 | 10046 |
| PH_hs_0044594 | UBE2C | ubiquitin-conjugating enzyme E2C | −2.42 | 8.370E−07 | 11065 |
| PH_hs_0004080 | SPHK1 | sphingosine kinase 1 | −2.42 | 4.606E−06 | 8877 |
| PH_hs_0048946 | QKI | quaking homolog, KH domain RNA binding (mouse) | −2.41 | 5.859E−18 | 9444 |
| PH_hs_0019754 | SPC25 | SPC25, NDC80 kinetochore complex component, homolog (S. cerevisiae) | −2.41 | 1.395E−07 | 57405 |
| PH_hs_0024110 | RAB36 | RAB36, member RAS oncogene family | −2.40 | 9.658E−11 | 9609 |
| PH_hs_0010858 | MELK | maternal embryonic leucine zipper kinase | −2.40 | 6.167E−15 | 9833 |
| PH_hs_0047385 | SGOL1 | shugoshin-like 1 (S. pombe) | −2.39 | 9.663E−07 | 151648 |
| PH_hs_0018565 | CARS2 | cysteinyl-tRNA synthetase 2, mitochondrial (putative) | −2.39 | 1.167E−18 | 79587 |
| PH_hs_0043450 | TMEM233 | transmembrane protein 233 | −2.39 | 1.186E−17 | 387890 |
| PH_hs_0038499 | TMEM14B | transmembrane protein 14B | −2.39 | 1.940E−03 | 81853 |
| PH_hs_0004787 | CDKN3 | cyclin-dependent kinase inhibitor 3 | −2.38 | 1.403E−15 | 1033 |

-continued

| Probe ID | Gene_symbol | Description | Fold Change | p-value | Entrez_gene |
|---|---|---|---|---|---|
| PH_hs_0043158 | BASP1 | brain abundant, membrane attached signal protein 1 | −2.38 | 1.695E−12 | 10409 |
| PH_hs_0043350 | GSTO1 | glutathione S-transferase omega 1 | −2.38 | 1.213E−11 | 9446 |
| PH_hs_0047240 | RPS6KA2 | ribosomal protein S6 kinase, 90 kDa, polypeptide 2 | −2.38 | 3.127E−04 | 6196 |
| PH_hs_0023540 | ETS2 | v-ets erythroblastosis virus E26 oncogene homolog 2 (avian) | −2.38 | 9.062E−08 | 2114 |
| PH_hs_0009576 | NMNAT2 | nicotinamide nucleotide adenylyltransferase 2 | −2.38 | 3.015E−12 | 23057 |
| PH_hs_0002026 | BET1 | blocked early in transport 1 homolog (S. cerevisiae) | −2.38 | 9.314E−10 | 10282 |
| PH_hs_0026679 | FOXM1 | forkhead box M1 | −2.37 | 5.575E−04 | 2305 |
| PH_hs_0022545 | SFXN1 | sideroflexin 1 | −2.37 | 1.949E−15 | 94081 |
| PH_hs_0018161 | ANKRD29 | ankyrin repeat domain 29 | −2.37 | 4.278E−06 | 147463 |
| PH_hs_0029732 | NDRG1 | N-myc downstream regulated 1 | −2.35 | 1.520E−10 | 10397 |
| PH_hs_0045036 | ABCC9 | ATP-binding cassette, sub-family C (CFTR/MRP), member 9 | −2.34 | 7.504E−20 | 10060 |
| PH_hs_0053215 | TM4SF19 | transmembrane 4 L six family member 19 | −2.34 | 6.058E−10 | 116211 |
| PH_hs_0033475 | AHNAK2 | AHNAK nucleoprotein 2 | −2.33 | 8.839E−03 | 113146 |
| PH_hs_0010770 | ABHD11 | abhydrolase domain containing 11 | −2.33 | 6.707E−09 | 83451 |
| PH_hs_0045849 | TPBG | trophoblast glycoprotein | −2.33 | 5.527E−07 | 7162 |
| PH_hs_0034496 | PTTG3P | pituitary tumor-transforming 3 (pseudogene) | −2.33 | 1.490E−08 | 26255 |
| PH_hs_0047831 | BMP2 | bone morphogenetic protein 2 | −2.31 | 1.266E−05 | 650 |
| PH_hs_0043263 | CXCL2 | chemokine (C-X-C motif) ligand 2 | −2.31 | 5.565E−17 | 2920 |
| PH_hs_0031701 | GRB10 | growth factor receptor-bound protein 10 | −2.31 | 1.756E−22 | 2887 |
| PH_hs_0000530 | UBE2T | ubiquitin-conjugating enzyme E2T (putative) | −2.30 | 6.299E−15 | 29089 |
| PH_hs_0042493 | FOXH1 | forkhead box H1 | −2.30 | 5.361E−10 | 8928 |
| PH_hs_0028179 | CALM3 | calmodulin 3 (phosphorylase kinase, delta) | −2.30 | 2.881E−06 | 808 |
| PH_hs_0047872 | LMNB2 | lamin B2 | −2.28 | 2.423E−07 | 84823 |
| PH_hs_0048360 | ARL4C | ADP-ribosylation factor-like 4C | −2.28 | 1.560E−11 | 10123 |
| PH_hs_0009230 | ESPL1 | extra spindle pole bodies homolog 1 (S. cerevisiae) | −2.28 | 9.375E−05 | 9700 |
| PH_hs_0029660 | AKR1C1\|AKR1C2\|A KR1C3\|LOC100508 006\|AKR1C4 | aldo-keto reductase family 1, member C1 (dihydrodiol dehydrogenase 1; 20-alpha (3-alpha)-hydroxysteroid dehydrogenase)\|aldo-keto reductase family 1, member C2 (dihydrodiol dehydrogenase 2; bile acid binding protein; 3-alpha hydroxysteroid dehydrogenase, type III)\|aldo-keto reductase family 1, member C3 (3-alpha hydroxysteroid dehydrogenase, type II)\|aldo-keto reductase family 1 member C2-like\|aldo-keto reductase family 1, member C4 (chlordecone reductase; 3-alpha hydroxysteroid dehydrogenase, type I; dihydrodiol dehydrogenase 4) | −2.28 | 1.460E−04 | 1645\|1646\|8644\|1005080061109 |
| PH_hs_0013082 | ANKRD36BP1 | ankyrin repeat domain 36B pseudogene 1 | −2.27 | 3.058E−10 | 84832 |
| PH_hs_0002592 | C21orf63 | chromosome 21 open reading frame 63 | −2.27 | 8.729E−12 | 59271 |
| PH_hs_0031635 | ARPC5 | actin related protein 2/3 complex, subunit 5, 16 kDa | −2.27 | 2.376E−06 | 10092 |
| PH_hs_0013738 | XRN2 | 5'-3' exoribonuclease 2 | −2.26 | 5.621E−07 | 22803 |
| PH_hs_0049138 | KIAA1462 | KIAA1462 | −2.26 | 4.763E−05 | 57608 |
| PH_hs_0018468 | CHN1 | chimerin (chimaerin) 1 | −2.26 | 5.839E−04 | 1123 |
| PH_hs_0000776 | ETHE1 | ethylmalonic encephalopathy 1 | −2.26 | 8.624E−13 | 23474 |
| PH_hs_0049591 | CKS1B | CDC28 protein kinase regulatory subunit 1B | −2.25 | 2.768E−07 | 1163 |
| PH_hs_0048832 | PCLO | piccolo (presynaptic cytomatrix protein) | −2.25 | 2.646E−15 | 27445 |
| PH_hs_0028032 | C1orf159 | chromosome 1 open reading frame 159 | −2.23 | 7.672E−07 | 54991 |
| PH_hs_0048019 | RNF157 | ring finger protein 157 | −2.22 | 9.246E−04 | 114804 |
| PH_hs_0011490 | C1orf94 | chromosome 1 open reading frame 94 | −2.22 | 6.699E−07 | 84970 |
| PH_hs_0002603 | GFPT2 | glutamine-fructose-6-phosphate transaminase 2 | −2.22 | 2.939E−12 | 9945 |
| PH_hs_0003818 | POC1A | POC1 centriolar protein homolog A (Chlamydomonas) | −2.21 | 1.470E−14 | 25886 |
| PH_hs_0028708 | SOX9 | SRY (sex determining region Y)-box 9 | −2.21 | 1.279E−06 | 6662 |
| PH_hs_0033207 | MGLL | monoglyceride lipase | −2.21 | 2.492E−08 | 11343 |
| PH_hs_0045266 | PCDHGC3 | protocadherin gamma subfamily C, 3 | −2.20 | 2.332E−13 | 5098 |
| PH_hs_0026037 | NUMB | numb homolog (Drosophila) | −2.20 | 1.463E−06 | 8650 |
| PH_hs_0028884 | ADORA2B | adenosine A2b receptor | −2.20 | 8.315E−08 | 136 |
| PH_hs_0033588 | RPSA\|RPSAP58\|R PSAP9 | ribosomal protein SA\|ribosomal protein SA pseudogene 58\|ribosomal protein SA pseudogene 9 | −2.20 | 2.010E−03 | 3921\|388524\|653162 |

-continued

| Probe ID | Gene_symbol | Description | Fold Change | p-value | Entrez_gene |
|---|---|---|---|---|---|
| PH_hs_0046309 | SPATA13 | spermatogenesis associated 13 | −2.20 | 1.390E−05 | 221178 |
| PH_hs_0045586 | SERPINB8 | serpin peptidase inhibitor, clade B (ovalbumin), member 8 | −2.20 | 6.632E−06 | 5271 |
| PH_hs_0005026 | CPOX | coproporphyrinogen oxidase | −2.19 | 3.861E−06 | 1371 |
| PH_hs_0043149 | RIN1 | Ras and Rab interactor 1 | −2.19 | 1.491E−05 | 9610 |
| PH_hs_0010736 | TMEM9 | transmembrane protein 9 | −2.19 | 5.519E−04 | 252839 |
| PH_hs_0004852 | FADD | Fas (TNFRSF6)-associated via death domain | −2.18 | 1.129E−10 | 8772 |
| PH_hs_0000422 | HPCAL1 | hippocalcin-like 1 | −2.17 | 1.475E−06 | 3241 |
| PH_hs_0009969 | PYCRL | pyrroline-5-carboxylate reductase-like | −2.17 | 6.696E−13 | 65263 |
| PH_hs_0027745 | BRMS1 | breast cancer metastasis suppressor 1 | −2.17 | 2.293E−07 | 25855 |
| PH_hs_0043905 | DDX10 | DEAD (Asp-Glu-Ala-Asp) box polypeptide 10 | −2.17 | 3.363E−09 | 1662 |
| PH_hs_0022175 | HEXB | hexosaminidase B (beta polypeptide) | −2.17 | 4.700E−11 | 3074 |
| PH_hs_0027449 | NDC80 | NDC80 homolog, kinetochore complex component (S. cerevisiae) | −2.17 | 3.530E−05 | 10403 |
| PH_hs_0018109 | PRKCA | protein kinase C, alpha | −2.17 | 4.058E−04 | 5578 |
| PH_hs_0003673 | CDCA2 | cell division cycle associated 2 | −2.17 | 1.970E−13 | 157313 |
| PH_hs_0015815 | LAT2 | linker for activation of T cells family, member 2 | −2.16 | 1.108E−05 | 7462 |
| PH_hs_0022625 | PLEKHB2 | pleckstrin homology domain containing, family B (evectins) member 2 | −2.16 | 1.004E−09 | 55041 |
| PH_hs_0014339 | ABCA1 | ATP-binding cassette, sub-family A (ABC1), member 1 | −2.16 | 2.090E−13 | 19 |
| PH_hs_0022058 | PSMC3IP | PSMC3 interacting protein | −2.16 | 4.121E−09 | 29893 |
| PH_hs_0025401 | RAB27B | RAB27B, member RAS oncogene family | −2.16 | 4.423E−03 | 5874 |
| PH_hs_0013577 | C16orf55 | chromosome 16 open reading frame 55 | −2.15 | 4.138E−10 | 124045 |
| PH_hs_0022541 | NSMCE4A | non-SMC element 4 homolog A (S. cerevisiae) | −2.15 | 2.095E−14 | 54780 |
| PH_hs_0006106 | EMG1 | EMG1 nucleolar protein homolog (S. cerevisiae) | −2.15 | 6.127E−10 | 10436 |
| PH_hs_0009265 | RNF182 | ring finger protein 182 | −2.15 | 1.637E−05 | 221687 |
| PH_hs_0023213 | PHLDA2 | pleckstrin homology-like domain, family A, member 2 | −2.15 | 4.494E−15 | 7262 |
| PH_hs_0004905 | PCGF5 | polycomb group ring finger 5 | −2.15 | 5.154E−09 | 84333 |
| PH_hs_0025352 | ARHGAP22 | Rho GTPase activating protein 22 | −2.15 | 1.413E−14 | 58504 |
| PH_hs_0044342 | FANCG | Fanconi anemia, complementation group G | −2.15 | 1.996E−07 | 2189 |
| PH_hs_0000113 | BMPER | BMP binding endothelial regulator | −2.14 | 3.066E−06 | 168667 |
| PH_hs_0017518 | HLA-DPA1 | major histocompatibility complex, class II, DP alpha 1 | −2.14 | 5.009E−06 | 3113 |
| PH_hs_0003763 | CTNNAL1 | catenin (cadherin-associated protein), alpha-like 1 | −2.14 | 3.962E−06 | 8727 |
| PH_hs_0005570 | CKAP2L | cytoskeleton associated protein 2-like | −2.14 | 3.170E−10 | 150468 |
| PH_hs_0035466 | AKR1C3\|AKR1C1 | aldo-keto reductase family 1, member C3 (3-alpha hydroxysteroid dehydrogenase, type II)\|aldo-keto reductase family 1, member C1 (dihydrodiol dehydrogenase 1; 20-alpha (3-alpha)-hydroxysteroid dehydrogenase) | −2.14 | 2.305E−07 | 8644\|1645 |
| PH_hs_0004663 | HNRNPAB | heterogeneous nuclear ribonucleoprotein A/B | −2.13 | 2.522E−23 | 3182 |
| PH_hs_0005188 | TMEM14A | transmembrane protein 14A | −2.13 | 8.566E−13 | 28978 |
| PH_hs_0002013 | NCEH1 | neutral cholesterol ester hydrolase 1 | −2.13 | 2.530E−17 | 57552 |
| PH_hs_0000702 | MOXD1 | monooxygenase, DBH-like 1 | −2.13 | 1.089E−09 | 26002 |
| PH_hs_0005006 | PTPRG | protein tyrosine phosphatase, receptor type, G | −2.13 | 8.371E−04 | 5793 |
| PH_hs_0017518 | DTYMK | deoxythymidylate kinase (thymidylate kinase) | −2.12 | 1.088E−09 | 1841 |
| PH_hs_0042247 | TIPIN | TIMELESS interacting protein | −2.12 | 1.156E−06 | 54962 |
| PH_hs_0022289 | SLC20A1 | solute carrier family 20 (phosphate transporter), member 1 | −2.11 | 9.926E−06 | 6574 |
| PH_hs_0012791 | HEY1 | hairy/enhancer-of-split related with YRPW motif 1 | −2.11 | 8.887E−12 | 23462 |
| PH_hs_0028863 | MLF1IP | MLF1 interacting protein | −2.11 | 1.191E−03 | 79682 |
| PH_hs_0021993 | FAHD2A\|FAHD2B | fumarylacetoacetate hydrolase domain containing 2A\|fumarylacetoacetate hydrolase domain containing 2B | −2.10 | 6.159E−07 | 51011\|151313 |
| PH_hs_0002385 | RUSC2 | RUN and SH3 domain containing 2 | −2.10 | 6.746E−11 | 9853 |
| PH_hs_0043353 | KIAA1632 | KIAA1632 | −2.10 | 1.532E−07 | 57724 |
| PH_hs_0024885 | TMEM38B | transmembrane protein 38B | −2.09 | 7.526E−09 | 55151 |
| PH_hs_0009375 | LRRC23 | leucine rich repeat containing 23 | −2.09 | 1.860E−08 | 10233 |
| PH_hs_0044235 | DYRK3 | dual-specificity tyrosine-(Y)-phosphorylation regulated kinase 3 | −2.08 | 2.299E−10 | 8444 |
| PH_hs_0034798 | LOC100508969 | putative grifin-like | −2.08 | 9.554E−09 | 100508969 |
| PH_hs_0043204 | ODC1 | ornithine decarboxylase 1 | −2.08 | 5.220E−08 | 4953 |

-continued

| Probe ID | Gene_symbol | Description | Fold Change | p-value | Entrez_gene |
|---|---|---|---|---|---|
| PH_hs_0046065 | ANKHD1 | ankyrin repeat and KH domain containing 1 | -2.08 | 3.873E-12 | 54882 |
| PH_hs_0005412 | C11orf70 | chromosome 11 open reading frame 70 | -2.08 | 3.906E-07 | 85016 |
| PH_hs_0028482 | NASP | nuclear autoantigenic sperm protein (histone-binding) | -2.07 | 4.280E-11 | 4678 |
| PH_hs_0000915 | DLC1 | deleted in liver cancer 1 | -2.07 | 2.059E-03 | 10395 |
| PH_hs_0047678 | C12orf32 | chromosome 12 open reading frame 32 | -2.07 | 4.459E-06 | 83695 |
| PH_hs_0042321 | OR1I1 | olfactory receptor, family 1, subfamily I, member 1 | -2.06 | 9.113E-11 | 126370 |
| PH_hs_0048084 | PTPRS | protein tyrosine phosphatase, receptor type, S | -2.06 | 5.021E-07 | 5802 |
| PH_hs_0048842 | ZNF175 | zinc finger protein 175 | -2.06 | 1.297E-10 | 7728 |
| PH_hs_0048874 | ABCG2 | ATP-binding cassette, sub-family G (WHITE), member 2 | -2.05 | 5.595E-04 | 9429 |
| PH_hs_0024590 | C13orf27 | chromosome 13 open reading frame 27 | -2.05 | 8.181E-06 | 93081 |
| PH_hs_0024747 | LRP11 | low density lipoprotein receptor-related protein 11 | -2.05 | 1.488E-04 | 84918 |
| PH_hs_0012692 | E2F2 | E2F transcription factor 2 | -2.05 | 4.561E-05 | 1870 |
| PH_hs_0020095 | GINS2 | GINS complex subunit 2 (Psf2 homolog) | -2.04 | 7.200E-11 | 51659 |
| PH_hs_0025861 | AURKB | aurora kinase B | -2.04 | 2.424E-11 | 9212 |
| PH_hs_0019605 | IFT27 | intraflagellar transport 27 homolog (Chlamydomonas) | -2.04 | 4.429E-07 | 11020 |
| PH_hs_0048618 | AMMECR1 | Alport syndrome, mental retardation, midface hypoplasia and elliptocytosis chromosomal region gene 1 | -2.04 | 3.863E-03 | 9949 |
| PH_hs_0048119 | KLHL5 | kelch-like 5 (Drosophila) | -2.03 | 1.531E-08 | 51088 |
| PH_hs_0023361 | CD109 | CD109 molecule | -2.03 | 6.177E-03 | 135228 |
| PH_hs_0031183 | ZWINT | ZW10 interactor | -2.03 | 3.329E-17 | 11130 |
| PH_hs_0042874 | CENPW | centromere protein W | -2.03 | 6.423E-14 | 387103 |
| PH_hs_0026771 | EZR | ezrin | -2.03 | 1.974E-03 | 7430 |
| PH_hs_0024623 | PKIB | protein kinase (cAMP-dependent, catalytic) inhibitor beta | -2.03 | 6.098E-07 | 5570 |
| PH_hs_0043766 | C19orf60 | chromosome 19 open reading frame 60 | -2.03 | 2.310E-06 | 55049 |
| PH_hs_0002625 | ASB1 | ankyrin repeat and SOCS box-containing 1 | -2.02 | 2.490E-13 | 51665 |
| PH_hs_0028219 | SEPT10 | septin 10 | -2.02 | 2.490E-13 | 151011 |
| PH_hs_0024580 | HIPK2 | homeodomain interacting protein kinase 2 | -2.02 | 1.851E-10 | 28996 |
| PH_hs_0001552 | USP31 | ubiquitin specific peptidase 31 | -2.02 | 1.077E-05 | 57478 |
| PH_hs_0042401 | OPN1SW | opsin 1 (cone pigments), short-wave-sensitive | -2.01 | 1.865E-12 | 611 |
| PH_hs_0043636 | TEAD4 | TEA domain family member 4 | -2.01 | 4.500E-08 | 7004 |
| PH_hs_0045480 | PSME2 | proteasome (prosome, macropain) activator subunit 2 (PA28 beta) | -2.01 | 9.149E-05 | 5721 |
| PH_hs_0001205 | LRRC49 | leucine rich repeat containing 49 | -2.01 | 1.154E-04 | 54839 |
| PH_hs_0025052 | E2F7 | E2F transcription factor 7 | -2.01 | 3.557E-03 | 144455 |
| PH_hs_0000209 | NEDD4 | neural precursor cell expressed, developmentally down-regulated 4 | -2.01 | 1.640E-10 | 4734 |
| PH_hs_0044438 | GABPB1 | GA binding protein transcription factor, beta subunit 1 | -2.00 | 3.852E-03 | 2553 |
| PH_hs_0003218 | REL | v-rel reticuloendotheliosis viral oncogene homolog (avian) | -2.00 | 5.416E-06 | 5966 |
| PH_hs_0045994 | MTCH1 | mitochondrial carrier homolog 1 (C. elegans) | -2.00 | 5.971E-05 | 23787 |
| PH_hs_0003990 | PAK1 | p21 protein (Cdc42/Rac)-activated kinase 1 | -2.00 | 4.804E-04 | 5058 |
| PH_hs_0002555 | C5orf62 | chromosome 5 open reading frame 62 | -1.99 | 2.299E-11 | 85027 |
| PH_hs_0005864 | NPDC1 | neural proliferation, differentiation and control, 1 | -1.99 | 2.021E-09 | 56654 |
| PH_hs_0023813 | C13orf34 | chromosome 13 open reading frame 34 | -1.99 | 1.154E-10 | 79866 |
| PH_hs_0002005 | ARSJ | arylsulfatase family, member J | -1.98 | 1.017E-11 | 79642 |
| PH_hs_0044571 | CASP1 | caspase 1, apoptosis-related cysteine peptidase (interleukin 1, beta, convertase) | -1.98 | 3.026E-08 | 834 |
| PH_hs_0045863 | VEGFA | vascular endothelial growth factor A | -1.98 | 2.718E-06 | 7422 |
| PH_hs_0048736 | DUSP3 | dual specificity phosphatase 3 | -1.98 | 2.130E-04 | 1845 |
| PH_hs_0006705 | ASPM | asp (abnormal spindle) homolog, microcephaly associated (Drosophila) | -1.98 | 1.306E-12 | 259266 |
| PH_hs_0046513 | LILRB3 | leukocyte immunoglobulin-like receptor, subfamily B (with TM and ITIM domains), member 3 | -1.98 | 1.265E-12 | 11025 |
| PH_hs_0043795 | TAGLN3 | transgelin 3 | -1.98 | 3.099E-02 | 29114 |
| PH_hs_0049303 | CCNA2 | cyclin A2 | -1.97 | 6.573E-04 | 890 |
| PH_hs_0019549 | GRB14 | growth factor receptor-bound protein 14 | -1.97 | 3.374E-04 | 2888 |
| PH_hs_0015893 | DDX39 | DEAD (Asp-Glu-Ala-Asp) box polypeptide 39 | -1.97 | 4.474E-07 | 10212 |
| PH_hs_0002060 | KCTD4 | potassium channel tetramerisation domain containing 4 | -1.97 | 1.689E-03 | 386618 |

| Probe ID | Gene_symbol | Description | Fold Change | p-value | Entrez_gene |
|---|---|---|---|---|---|
| PH_hs_0048129 | PSMC3 | proteasome (prosome, macropain) 26S subunit, ATPase, 3 | −1.97 | 5.276E-16 | 5702 |
| PH_hs_0016660 | PRC1 | protein regulator of cytokinesis 1 | −1.97 | 1.588E-05 | 9055 |
| PH_hs_0044572 | TGM2 | transglutaminase 2 (C polypeptide, protein-glutamine-gamma-glutamyltransferase) | −1.97 | 1.335E-07 | 7052 |
| PH_hs_0000579 | NCAPD2 | non-SMC condensin I complex, subunit D2 | −1.96 | 5.770E-12 | 9918 |
| PH_hs_0029923 | DHX9 | DEAH (Asp-Glu-Ala-His) box polypeptide 9 | −1.96 | 7.066E-05 | 1660 |
| PH_hs_0005732 | RAB3IP | RAB3A interacting protein (rabin3) | −1.96 | 2.555E-15 | 117177 |
| PH_hs_0049709 | MAP1LC3B2 | microtubule-associated protein 1 light chain 3 beta 2 | −1.96 | 7.038E-06 | 643246 |
| PH_hs_0044611 | GLRX2 | glutaredoxin 2 | −1.96 | 4.009E-17 | 51022 |
| PH_hs_0015982 | CCDC123 | coiled-coil domain containing 123 | −1.96 | 4.099E-05 | 84902 |
| PH_hs_0004448 | MCM5 | minichromosome maintenance complex component 5 | −1.96 | 1.824E-06 | 4174 |
| PH_hs_0023978 | CARHSP1 | calcium regulated heat stable protein 1, 24 kDa | −1.96 | 1.397E-15 | 23589 |
| PH_hs_0045723 | FKBP1A | FK506 binding protein 1A, 12 kDa | −1.96 | 5.040E-06 | 2280 |
| PH_hs_0003169 | CLN6 | ceroid-lipofuscinosis, neuronal 6, late infantile, variant | −1.95 | 7.612E-08 | 54982 |
| PH_hs_0044805 | TTC4\|C1orf175-TTC4 | tetratricopeptide repeat domain 4\|C1orf175-TTC4 read-through transcript | −1.95 | 3.343E-07 | 7268\|100527960 |
| PH_hs_0032582 | C11orf24 | chromosome 11 open reading frame 24 | −1.95 | 4.562E-08 | 53838 |
| PH_hs_0013285 | AURKA | aurora kinase A | −1.95 | 1.390E-10 | 6790 |
| PH_hs_0003188 | CD164 | CD164 molecule, sialomucin | −1.95 | 1.611E-05 | 8763 |
| PH_hs_0006549 | FUT8 | fucosyltransferase 8 (alpha (1,6) fucosyltransferase) | −1.95 | 1.200E-04 | 2530 |
| PH_hs_0002901 | LIMK1 | LIM domain kinase 1 | −1.94 | 1.021E-09 | 3984 |
| PH_hs_0031490 | LOC728392 | hypothetical protein LOC728392 | −1.94 | 1.282E-04 | 728392 |
| PH_hs_0047667 | FOXL1 | forkhead box L1 | −1.94 | 3.480E-05 | 2300 |
| PH_hs_0031360 | SYPL1 | synaptophysin-like 1 | −1.94 | 8.342E-08 | 6856 |
| PH_hs_0003454 | ORC6 | origin recognition complex, subunit 6 | −1.94 | 6.145E-06 | 23594 |
| PH_hs_0035763 | CENPO | centromere protein O | −1.94 | 2.621E-09 | 79172 |
| PH_hs_0008727 | KIF13A | kinesin family member 13A | −1.94 | 3.486E-04 | 63971 |
| PH_hs_0017351 | C20orf71 | chromosome 20 open reading frame 71 | −1.94 | 5.213E-06 | 128861 |
| PH_hs_0006918 | SHCBP1 | SHC SH2-domain binding protein 1 | −1.94 | 6.876E-08 | 79801 |
| PH_hs_0020941 | RETSAT | retinol saturase (all-trans-retinol 13,14-reductase) | −1.94 | 1.177E-04 | 54884 |
| PH_hs_0024059 | CCT7 | chaperonin containing TCP1, subunit 7 (eta) | −1.94 | 7.956E-04 | 10574 |
| PH_hs_0024259 | MRPS27 | mitochondrial ribosomal protein S27 | −1.94 | 1.847E-03 | 23107 |
| PH_hs_0049318 | C10orf72 | chromosome 10 open reading frame 72 | −1.93 | 3.386E-08 | 196740 |
| PH_hs_0047318 | LIMCH1 | LIM and calponin homology domains 1 | −1.93 | 9.492E-08 | 22998 |
| PH_hs_0048683 | ALCAM | activated leukocyte cell adhesion molecule | −1.93 | 3.584E-06 | 214 |
| PH_hs_0033361 | ACOT7 | acyl-CoA thioesterase 7 | −1.92 | 9.630E-11 | 11332 |
| PH_hs_0035398 | DNTTIP1 | deoxynucleotidyltransferase, terminal, interacting protein 1 | −1.92 | 1.403E-07 | 116092 |
| PH_hs_0047381 | NCAM1 | neural cell adhesion molecule 1 | −1.92 | 1.741E-07 | 4684 |
| PH_hs_0037695 | GRAMD1C | GRAM domain containing 1C | −1.92 | 2.212E-04 | 54762 |
| PH_hs_0003590 | SLC1A1 | solute carrier family 1 (neuronal/epithelial high affinity glutamate transporter, system Xag), member 1 | −1.92 | 1.093E-10 | 6505 |
| PH_hs_0049714 | FAM72B\|LOC100507552\|FAM72A\|FAM72D | family with sequence similarity 72, member B\|hypothetical LOC100507552\|family with sequence similarity 72, member A\|family with sequence similarity 72, member D | −1.92 | 6.626E-09 | 653820\|100507552\|729533\|728833 |
| PH_hs_0045672 | ABL2 | v-abl Abelson murine leukemia viral oncogene homolog 2 | −1.92 | 2.253E-08 | 27 |
| PH_hs_0004737 | CETN2 | centrin, EF-hand protein, 2 | −1.92 | 5.190E-10 | 1069 |
| PH_hs_0036109 | DCTN3 | dynactin 3 (p22) | −1.92 | 3.644E-08 | 11258 |
| PH_hs_0033090 | MGST1 | microsomal glutathione S-transferase 1 | −1.91 | 4.232E-10 | 4257 |
| PH_hs_0047363 | PLSCR1 | phospholipid scramblase 1 | −1.91 | 2.171E-06 | 5359 |
| PH_hs_0013740 | RGS17 | regulator of G-protein signaling 17 | −1.91 | 6.442E-05 | 26575 |
| PH_hs_0043862 | CYB5A | cytochrome b5 type A (microsomal) | −1.90 | 2.075E-04 | 1528 |
| PH_hs_0026835 | MPZL1 | myelin protein zero-like 1 | −1.90 | 4.916E-11 | 9019 |
| PH_hs_0011511 | GCNT3 | glucosaminyl (N-acetyl) transferase 3, mucin type | −1.90 | 9.543E-14 | 9245 |

| Probe ID | Gene_symbol | Description | Fold Change | p-value | Entrez_gene |
|---|---|---|---|---|---|
| PH_hs_0048561 | NIPAL3 | NIPA-like domain containing 3 | −1.90 | 1.433E-02 | 57185 |
| PH_hs_0025231 | ADAM23 | ADAM metallopeptidase domain 23 | −1.90 | 2.611E-04 | 8745 |
| PH_hs_0043830 | CDC25C | cell division cycle 25 homolog C (S. pombe) | −1.90 | 3.887E-09 | 995 |
| PH_hs_0036785 | MAP1S | microtubule-associated protein 1S | −1.90 | 1.501E-09 | 55201 |
| PH_hs_0044920 | UBD | ubiquitin D | −1.90 | 5.255E-04 | 10537 |
| PH_hs_0030776 | SAMD9 | sterile alpha motif domain containing 9 | −1.90 | 1.061E-05 | 54809 |
| PH_hs_0045444 | GLRX | glutaredoxin (thioltransferase) | −1.89 | 1.265E-05 | 2745 |
| PH_hs_0023448 | GSK3B | glycogen synthase kinase 3 beta | −1.89 | 2.146E-11 | 2932 |
| PH_hs_0018571 | PSMB9 | proteasome (prosome, macropain) subunit, beta type, 9 (large multifunctional peptidase 2) | −1.89 | 8.196E-10 | 5698 |
| PH_hs_0004405 | BLVRB | biliverdin reductase B (flavin reductase (NADPH)) | −1.89 | 2.210E-13 | 645 |
| PH_hs_0047836 | DPF1 | D4, zinc and double PHD fingers family 1 | −1.88 | 1.901E-05 | 8193 |
| PH_hs_0004430 | FBXL7 | F-box and leucine-rich repeat protein 7 | −1.88 | 7.656E-06 | 23194 |
| PH_hs_0035271 | RNF181 | ring finger protein 181 | −1.88 | 4.517E-07 | 51255 |
| PH_hs_0049491 | RABL2B\|RABL2A | RAB, member of RAS oncogene family-like 2B\|RAB, member of RAS oncogene family-like 2A | −1.88 | 2.605E-02 | 11158\|11159 |
| PH_hs_0043330 | IFI44 | interferon-induced protein 44 | −1.88 | 1.016E-03 | 10561 |
| PH_hs_0045053 | HPS1 | Hermansky-Pudlak syndrome 1 | −1.88 | 2.971E-13 | 3257 |
| PH_hs_0047472 | ECT2 | epithelial cell transforming sequence 2 oncogene | −1.88 | 1.277E-05 | 1894 |
| PH_hs_0032652 | NPAS2 | neuronal PAS domain protein 2 | −1.87 | 1.303E-04 | 4862 |
| PH_hs_0001423 | PECI | peroxisomal D3,D2-enoyl-CoA isomerase | −1.87 | 3.689E-09 | 10455 |
| PH_hs_0004651 | MKI67 | antigen identified by monoclonal antibody Ki-67 | −1.87 | 7.102E-07 | 4288 |
| PH_hs_0026788 | FAM45A\|FAM45B | family with sequence similarity 45, member A\|family with sequence similarity 45, member A pseudogene | −1.87 | 3.004E-04 | 404636\|55855 |
| PH_hs_0010738 | C15orf23 | chromosome 15 open reading frame 23 | −1.87 | 7.301E-10 | 90417 |
| PH_hs_0001501 | SPAG5 | sperm associated antigen 5 | −1.86 | 2.747E-10 | 10615 |
| PH_hs_0026413 | HS3ST3A1 | heparan sulfate (glucosamine) 3-O-sulfotransferase 3A1 | −1.86 | 6.848E-12 | 9955 |
| PH_hs_0031096 | C17orf76 | chromosome 17 open reading frame 76 | −1.86 | 1.145E-05 | 388341 |
| PH_hs_0048770 | FGF2 | fibroblast growth factor 2 (basic) | −1.86 | 6.452E-04 | 2247 |
| PH_hs_0022078 | FLJ36031 | hypothetical protein FLJ36031 | −1.86 | 1.084E-09 | 168455 |
| PH_hs_0031719 | CCL26 | chemokine (C-C motif) ligand 26 | −1.86 | 5.373E-08 | 10344 |
| PH_hs_0026360 | UCK2 | uridine-cytidine kinase 2 | −1.85 | 2.753E-05 | 7371 |
| PH_hs_0044943 | CDC20 | cell division cycle 20 homolog (S. cerevisiae) | −1.85 | 7.409E-10 | 991 |
| PH_hs_0010421 | CSF1 | colony stimulating factor 1 (macrophage) | −1.85 | 3.797E-06 | 1435 |
| PH_hs_0025732 | RCN3 | reticulocalbin 3, EF-hand calcium binding domain | −1.85 | 2.576E-04 | 57333 |
| PH_hs_0022666 | LSM6 | LSM6 homolog, U6 small nuclear RNA associated (S. cerevisiae) | −1.85 | 9.879E-06 | 11157 |
| PH_hs_0027965 | C1orf97 | chromosome 1 open reading frame 97 | −1.85 | 9.451E-06 | 84791 |
| PH_hs_0023973 | ADK | adenosine kinase | −1.85 | 1.721E-08 | 132 |
| PH_hs_0046086 | TMEM48 | transmembrane protein 48 | −1.85 | 1.162E-02 | 55706 |
| PH_hs_0049587 | CTAG1C\|CTAG1B\|CTAG1A | cancer/testis antigen 1 B\|cancer/testis antigen 1A | −1.85 | 1.189E-09 | 30848\|1485\|246\|100 |
| PH_hs_0030319 | RPL14 | ribosomal protein L14 | −1.85 | 2.669E-03 | 9045 |
| PH_hs_0035526 | C6orf48 | chromosome 6 open reading frame 48 | −1.85 | 9.450E-07 | 50854 |
| PH_hs_0026290 | PPIL5 | peptidylprolyl isomerase (cyclophilin)-like 5 | −1.84 | 2.236E-07 | 122769 |
| PH_hs_0029180 | RPL39L | ribosomal protein L39-like | −1.84 | 3.416E-06 | 116832 |
| PH_hs_0027863 | LRRC45 | leucine rich repeat containing 45 | −1.84 | 5.992E-05 | 201255 |
| PH_hs_0026085 | SOAT1 | sterol O-acyltransferase 1 | −1.84 | 1.289E-05 | 6646 |
| PH_hs_0015035 | BIRC2 | baculoviral IAP repeat-containing 2 | −1.84 | 4.236E-09 | 329 |
| PH_hs_0001378 | CEP55 | centrosomal protein 55 kDa | −1.84 | 9.382E-09 | 55165 |
| PH_hs_0010763 | SQSTM1 | sequestosome 1 | −1.84 | 1.187E-04 | 8878 |
| PH_hs_0020300 | VCAN | versican | −1.84 | 6.305E-07 | 1462 |
| PH_hs_0022918 | GOPC | golgi-associated PDZ and coiled-coil motif containing | −1.84 | 2.346E-03 | 57120 |
| PH_hs_0031530 | MRPS11 | mitochondrial ribosomal protein S11 | −1.84 | 8.221E-07 | 64963 |
| PH_hs_0044325 | HSCB | HscB iron-sulfur cluster co-chaperone homolog (E. coli) | −1.84 | 9.898E-05 | 150274 |

-continued

| Probe ID | Gene_symbol | Description | Fold Change | p-value | Entrez_gene |
|---|---|---|---|---|---|
| PH_hs_0000567 | EVI2B | ecotropic viral integration site 2B | −1.84 | 1.489E−06 | 2124 |
| PH_hs_0002383 | RASSF1 | Ras association (RalGDS/AF-6) domain family member 1 | −1.84 | 2.824E−08 | 11186 |
| PH_hs_0048795 | HAUS2 | HAUS augmin-like complex, subunit 2 | −1.84 | 2.310E−07 | 55142 |
| PH_hs_0028864 | GREM1 | gremlin 1 | −1.84 | 4.913E−06 | 26585 |
| PH_hs_0009344 | EHD1 | EH-domain containing 1 | −1.84 | 1.397E−09 | 10938 |
| PH_hs_0037874 | C16orf46 | chromosome 16 open reading frame 46 | −1.84 | 4.630E−04 | 123775 |
| PH_hs_0020115 | SNHG1 | small nucleolar RNA host gene 1 (non-protein coding) | −1.83 | 8.180E−05 | 23642 |
| PH_hs_0019671 | MRPL11 | mitochondrial ribosomal protein L11 | −1.83 | 8.255E−09 | 65003 |
| PH_hs_0019243 | INPP4B | inositol polyphosphate-4-phosphatase, type II, 105 kDa | −1.83 | 3.265E−08 | 8821 |
| PH_hs_0045821 | ABCD3 | ATP-binding cassette, sub-family D (ALD), member 3 | −1.83 | 2.197E−03 | 5825 |
| PH_hs_0044849 | CHCHD3 | coiled-coil-helix-coiled-coil-helix domain containing 3 | −1.83 | 1.283E−03 | 54927 |
| PH_hs_0008982 | NEURL3 | neuralized homolog 3 (Drosophila) pseudogene | −1.83 | 1.881E−06 | 93082 |
| PH_hs_0035355 | HAT1 | histone acetyltransferase 1 | −1.83 | 3.987E−03 | 8520 |
| PH_hs_0007225 | DTL | denticleless homolog (Drosophila) | −1.83 | 1.196E−06 | 51514 |
| PH_hs_0002142 | DERA | deoxyribose-phosphate aldolase (putative) | −1.83 | 4.940E−07 | 51071 |
| PH_hs_0019274 | ORAOV1 | oral cancer overexpressed 1 | −1.83 | 8.843E−08 | 220064 |
| PH_hs_0004122 | FAM83D | family with sequence similarity 83, member D | −1.83 | 3.065E−05 | 81610 |
| PH_hs_0000218 | DPYD | dihydropyrimidine dehydrogenase | −1.82 | 2.018E−06 | 1806 |
| PH_hs_0025971 | PHB2 | prohibitin 2 | −1.82 | 8.339E−04 | 11331 |
| PH_hs_0028689 | CXCL1 | chemokine (C-X-C motif) ligand 1 (melanoma growth stimulating activity, alpha) | −1.82 | 2.606E−05 | 2919 |
| PH_hs_0045959 | TRIOBP | TRIO and F-actin binding protein | −1.82 | 1.330E−04 | 11078 |
| PH_hs_0001028 | SEC61G | Sec61 gamma subunit | −1.82 | 4.824E−03 | 23480 |
| PH_hs_0043402 | AEN | apoptosis enhancing nuclease | −1.82 | 5.822E−06 | 64782 |
| PH_hs_0047904 | TGFBR2 | transforming growth factor, beta receptor II (70/80 kDa) | −1.82 | 7.668E−05 | 7048 |
| PH_hs_0047735 | GPR115 | G protein-coupled receptor 115 | −1.82 | 2.161E−02 | 221393 |
| PH_hs_0004541 | THOP1 | thimet oligopeptidase 1 | −1.82 | 1.936E−10 | 7064 |
| PH_hs_0014145 | TP53TG1 | TP53 target 1 (non-protein coding) | −1.82 | 1.314E−02 | 11257 |
| PH_hs_0048262 | TBC1D2 | TBC1 domain family, member 2 | −1.81 | 9.123E−10 | 55357 |
| PH_hs_0031937 | C9orf30 | chromosome 9 open reading frame 30 | −1.81 | 1.613E−06 | 91283 |
| PH_hs_0019643 | POP7 | processing of precursor 7, ribonuclease P/MRP subunit (S. cerevisiae) | −1.81 | 1.387E−05 | 10248 |
| PH_hs_0005815 | PBK | PDZ binding kinase | −1.81 | 1.191E−09 | 55872 |
| PH_hs_0011459 | BRCA1 | breast cancer 1, early onset | −1.81 | 1.268E−09 | 672 |
| PH_hs_0035485 | NDUFS8 | NADH dehydrogenase (ubiquinone) Fe—S protein 8, 23 kDa (NADH-coenzyme Q reductase) | −1.81 | 5.947E−07 | 4728 |
| PH_hs_0000213 | BIRC5 | baculoviral IAP repeat-containing 5 | −1.81 | 1.085E−06 | 332 |
| PH_hs_0029069 | TMEM106C | transmembrane protein 106C | −1.81 | 2.577E−06 | 79022 |
| PH_hs_0046226 | TMEM44 | transmembrane protein 44 | −1.81 | 1.339E−04 | 93109 |
| PH_hs_0040139 | HSPA8 | heat shock 70 kDa protein 8 | −1.81 | 5.682E−05 | 3312 |
| PH_hs_0040244 | NPHP1 | nephronophthisis 1 (juvenile) | −1.81 | 3.673E−05 | 4867 |
| PH_hs_0043288 | RHEB | Ras homolog enriched in brain | −1.80 | 6.510E−06 | 6009 |
| PH_hs_0023555 | MCFD2 | multiple coagulation factor deficiency 2 | −1.80 | 1.300E−11 | 90411 |
| PH_hs_0002916 | ATF1 | activating transcription factor 1 | −1.80 | 3.830E−03 | 466 |
| PH_hs_0044140 | C1orf91 | chromosome 1 open reading frame 91 | −1.80 | 1.686E−02 | 56063 |
| PH_hs_0024428 | CD9 | CD9 molecule | −1.80 | 1.100E−08 | 928 |
| PH_hs_0025533 | VBP1 | von Hippel-Lindau binding protein 1 | −1.80 | 2.488E−04 | 7411 |
| PH_hs_0043687 | CENPM | centromere protein M | −1.80 | 7.674E−06 | 79019 |
| PH_hs_0003656 | NKX3-1 | NK3 homeobox 1 | −1.80 | 7.447E−06 | 4824 |
| PH_hs_0040733 | HSP90AA1 | heat shock protein 90 kDa alpha (cytosolic), class A member 1 | −1.80 | 6.393E−08 | 3320 |
| PH_hs_0044161 | LACTB | lactamase, beta | −1.80 | 2.174E−04 | 114294 |
| PH_hs_0001230 | AGTRAP | angiotensin II receptor-associated protein | −1.79 | 5.200E−11 | 57085 |
| PH_hs_0018569 | PPIF | peptidylprolyl isomerase F | −1.79 | 4.753E−09 | 10105 |
| PH_hs_0004341 | CENPE | centromere protein E, 312 kDa | −1.79 | 9.609E−10 | 1062 |

| Probe ID | Gene_symbol | Description | Fold Change | p-value | Entrez_gene |
|---|---|---|---|---|---|
| PH_hs_0025444 | VIM | vimentin | -1.79 | 9.111E-08 | 7431 |
| PH_hs_0049740 | SMPD4\|LOC150776 | sphingomyelin phosphodiesterase 4, neutral membrane (neutral sphingomyelinase-3)\|sphingomyelin phosphodiesterase 4, neutral membrane pseudogene | -1.79 | 1.051E-05 | 55627\|150776 |
| PH_hs_0028715 | LDHA | lactate dehydrogenase A | -1.79 | 6.701E-08 | 3939 |
| PH_hs_0000768 | EPN2 | epsin 2 | -1.79 | 4.737E-04 | 22905 |
| PH_hs_0005724 | LHX6 | LIM homeobox 6 | -1.79 | 1.203E-07 | 26468 |
| PH_hs_0025379 | CDKN2D | cyclin-dependent kinase inhibitor 2D (p19, inhibits CDK4) | -1.79 | 8.228E-06 | 1032 |
| PH_hs_0033319 | NPC2 | Niemann-Pick disease, type C2 | -1.78 | 4.591E-06 | 10577 |
| PH_hs_0029964 | MYADM | myeloid-associated differentiation marker | -1.78 | 3.356E-03 | 91663 |
| PH_hs_0037156 | GPD2 | glycerol-3-phosphate dehydrogenase 2 (mitochondrial) | -1.78 | 4.154E-06 | 2820 |
| PH_hs_0039916 | EEF1D | eukaryotic translation elongation factor 1 delta (guanine nucleotide exchange protein) | -1.78 | 4.429E-04 | 1936 |
| PH_hs_0010658 | PSMB8 | proteasome (prosome, macropain) subunit, beta type, 8 (large multifunctional peptidase 7) | -1.78 | 4.481E-04 | 5696 |
| PH_hs_0004776 | CKS2 | CDC28 protein kinase regulatory subunit 2 | -1.78 | 1.551E-10 | 1164 |
| PH_hs_0004583 | LHFPL2 | lipoma HMGIC fusion partner-like 2 | -1.77 | 1.061E-07 | 10184 |
| PH_hs_0000326 | SOD3 | superoxide dismutase 3, extracellular | -1.77 | 1.803E-06 | 6649 |
| PH_hs_0022094 | SAE1 | SUMO1 activating enzyme subunit 1 | -1.77 | 5.938E-05 | 10055 |
| PH_hs_0004711 | RGS3 | regulator of G-protein signaling 3 | -1.77 | 1.651E-05 | 5998 |
| PH_hs_0025677 | PRNP | prion protein | -1.77 | 5.259E-07 | 5621 |
| PH_hs_0000080 | CSTB | cystatin B (stefin B) | -1.77 | 2.512E-09 | 1476 |
| PH_hs_0045464 | NOP56 | NOP56 ribonucleoprotein homolog (yeast) | -1.76 | 1.089E-05 | 10528 |
| PH_hs_0047402 | RP2 | retinitis pigmentosa 2 (X-linked recessive) | -1.76 | 1.033E-04 | 6102 |
| PH_hs_0042943 | TCTEX1D2 | Tctex1 domain containing 2 | -1.76 | 4.658E-05 | 255758 |
| PH_hs_0024334 | CSF3R | colony stimulating factor 3 receptor (granulocyte) | -1.76 | 3.205E-02 | 1441 |
| PH_hs_0010296 | TROAP | trophinin associated protein (tastin) | -1.76 | 1.262E-10 | 10024 |
| PH_hs_0016806 | CECR4 | cat eye syndrome chromosome region, candidate 4 (non-protein coding) | -1.75 | 1.425E-03 | 100130717 |
| PH_hs_0005831 | ENC1 | ectodermal-neural cortex 1 (with BTB-like domain) | -1.75 | 6.045E-07 | 8507 |
| PH_hs_0022064 | PITRM1 | pitrilysin metallopeptidase 1 | -1.75 | 5.754E-08 | 10531 |
| PH_hs_0032378 | TRNAU1AP | tRNA selenocysteine 1 associated protein 1 | -1.75 | 1.843E-03 | 54952 |
| PH_hs_0045445 | HLA-F | major histocompatibility complex, class I, F | -1.75 | 8.434E-04 | 3134 |
| PH_hs_0032575 | CCR1 | chemokine (C-C motif) receptor 1 | -1.75 | 1.064E-05 | 1230 |
| PH_hs_0028584 | LIMS3\|LOC100288695 | LIM and senescent cell antigen-like domains 3\|LIM and senescent cell antigen-like-containing domain protein 3-like | -1.75 | 4.363E-04 | 96626\|100288869 |
| PH_hs_0047045 | PRR9 | proline rich 9 | -1.75 | 1.345E-03 | 574414 |
| PH_hs_0048792 | ETV1 | ets variant 1 | -1.75 | 1.341E-02 | 2115 |
| PH_hs_0015013 | NAA50 | N(alpha)-acetyltransferase 50, NatE catalytic subunit | -1.75 | 4.647E-04 | 80218 |
| PH_hs_0049044 | SOCS3 | suppressor of cytokine signaling 3 | -1.75 | 1.625E-09 | 9021 |
| PH_hs_0029118 | OASL | 2'-5'-oligoadenylate synthetase-like | -1.75 | 7.921E-04 | 8638 |
| PH_hs_0043563 | LYAR | Ly1 antibody reactive homolog (mouse) | -1.74 | 6.522E-04 | 55646 |
| PH_hs_0031222 | CDCA8 | cell division cycle associated 8 | -1.74 | 8.079E-04 | 55143 |
| PH_hs_0005155 | PITPNM1 | phosphatidylinositol transfer protein, membrane-associated 1 | -1.74 | 1.573E-04 | 9600 |
| PH_hs_0031307 | HSP90AB1\|HSP90AB3P\|HSP90AB2P | heat shock protein 90 kDa alpha (cytosolic), class B member 1\|heat shock protein 90 kDa alpha (cytosolic), class B member 3 (pseudogene)\|heat shock protein 90 kDa alpha (cytosolic), class B member 2 (pseudogene) | -1.74 | 3.888E-13 | 3326\|332713916\|34 |
| PH_hs_0019919 | PXMP2 | peroxisomal membrane protein 2, 22 kDa | -1.74 | 1.454E-03 | 5827 |
| PH_hs_0012993 | KATNAL1 | katanin p60 subunit A-like 1 | -1.74 | 1.110E-03 | 84056 |
| PH_hs_0031317 | TUBA4A | tubulin, alpha 4a | -1.74 | 9.686E-06 | 7277 |
| PH_hs_0004487 | AP3M2 | adaptor-related protein complex 3, mu 2 subunit | -1.74 | 2.334E-05 | 10947 |
| PH_hs_0047687 | SMC5 | structural maintenance of chromosomes 5 | -1.74 | 4.946E-03 | 23137 |
| PH_hs_0048496 | AKAP12 | A kinase (PRKA) anchor protein 12 | -1.74 | 1.603E-04 | 9590 |
| PH_hs_0037808 | USP18 | ubiquitin specific peptidase 18 | -1.74 | 6.540E-05 | 11274 |
| PH_hs_0001880 | TUBG1 | tubulin, gamma 1 | -1.73 | 3.335E-04 | 7283 |
| PH_hs_0030008 | PSMD2 | proteasome (prosome, macropain) 26S subunit, non-ATPase, 2 | -1.73 | 2.207E-08 | 5708 |

| Probe ID | Gene_symbol | Description | Fold Change | p-value | Entrez_gene |
|---|---|---|---|---|---|
| PH_hs_0001260 | SH2B3 | SH2B adaptor protein 3 | −1.73 | 1.612E-09 | 10019 |
| PH_hs_0049148 | OSMR | oncostatin M receptor | −1.73 | 5.617E-05 | 9180 |
| PH_hs_0048215 | HABP4 | hyaluronan binding protein 4 | −1.73 | 7.845E-05 | 22927 |
| PH_hs_0005068 | DOHH | deoxyhypusine hydroxylase/monooxygenase | −1.73 | 2.286E-08 | 83475 |
| PH_hs_0004488 | PKMYT1 | protein kinase, membrane associated tyrosine/threonine 1 | −1.73 | 6.837E-07 | 9088 |
| PH_hs_0025165 | COX7A2L | cytochrome c oxidase subunit VIIa polypeptide 2 like | −1.73 | 4.384E-03 | 9167 |
| PH_hs_0019824 | EIF1AD | eukaryotic translation initiation factor 1A domain containing | −1.73 | 7.705E-04 | 84285 |
| PH_hs_0002211 | NET1 | neuroepithelial cell transforming 1 | −1.73 | 1.880E-03 | 10276 |
| PH_hs_0024093 | DYNC1LI2 | dynein, cytoplasmic 1, light intermediate chain 2 | −1.73 | 7.944E-04 | 1783 |
| PH_hs_0048670 | CPEB1 | cytoplasmic polyadenylation element binding protein 1 | −1.72 | 5.658E-09 | 64506 |
| PH_hs_0008058 | C1QL1 | complement component 1, q subcomponent-like 1 | −1.72 | 2.978E-04 | 10882 |
| PH_hs_0009984 | C11orf82 | chromosome 11 open reading frame 82 | −1.72 | 6.784E-05 | 220042 |
| PH_hs_0003062 | MRPL22 | mitochondrial ribosomal protein L22 | −1.72 | 1.695E-09 | 29093 |
| PH_hs_0010617 | PSMD14 | proteasome (prosome, macropain) 26S subunit, non-ATPase, 14 | −1.72 | 1.516E-04 | 10213 |
| PH_hs_0000227 | GFPT1 | glutamine- fructose-6-phosphate transaminase 1 | −1.72 | 1.886E-06 | 2673 |
| PH_hs_0004454 | BTG3 | BTG family, member 3 | −1.72 | 5.605E-12 | 10950 |
| PH_hs_0003616 | MRPS28 | mitochondrial ribosomal protein S28 | −1.72 | 4.247E-03 | 28957 |
| PH_hs_0024325 | SNX25 | sorting nexin 25 | −1.72 | 1.708E-02 | 83891 |
| PH_hs_0030964 | S100A16 | S100 calcium binding protein A16 | −1.72 | 1.813E-06 | 140576 |
| PH_hs_0048970 | SFMBT1 | Scm-like with four mbt domains 1 | −1.72 | 1.226E-03 | 51460 |
| PH_hs_0004701 | KLF10 | Kruppel-like factor 10 | −1.71 | 1.449E-05 | 7071 |
| PH_hs_0035153 | APOBEC3A|LAIR1 | apolipoprotein B mRNA editing enzyme, catalytic polypeptide-like 3A|leukocyte-associated immunoglobulin-like receptor 1 | −1.71 | 6.693E-06 | 200315|3903 |
| PH_hs_0006320 | SRSF3 | serine/arginine-rich splicing factor 3 | −1.71 | 3.541E-05 | 6428 |
| PH_hs_0018698 | RRM1 | ribonucleotide reductase M1 | −1.71 | 2.107E-09 | 6240 |
| PH_hs_0005575 | FBL | fibrillarin | −1.71 | 4.280E-07 | 2091 |
| PH_hs_0004726 | POLD3 | polymerase (DNA-directed), delta 3, accessory subunit | −1.71 | 5.972E-05 | 10714 |
| PH_hs_0002377 | CECR5 | cat eye syndrome chromosome region, candidate 5 | −1.71 | 2.839E-03 | 27440 |
| PH_hs_0004290 | NDUFA9 | NADH dehydrogenase (ubiquinone) 1 alpha subcomplex, 9, 39 kDa | −1.71 | 5.775E-09 | 4704 |
| PH_hs_0000569 | ATP2A3 | ATPase, Ca++ transporting, ubiquitous | −1.71 | 1.598E-06 | 489 |
| PH_hs_0002795 | MCTP2 | multiple C2 domains, transmembrane 2 | −1.71 | 1.949E-06 | 55784 |
| PH_hs_0022309 | VPS26A | vacuolar protein sorting 26 homolog A (S. pombe) | −1.71 | 1.132E-04 | 9559 |
| PH_hs_0045852 | TPM3 | tropomyosin 3 | −1.70 | 2.380E-05 | 7170 |
| PH_hs_0014235 | CCDC107 | coiled-coil domain containing 107 | −1.70 | 1.839E-10 | 203260 |
| PH_hs_0048967 | RAPH1 | Ras association (RalGDS/AF-6) and pleckstrin homology domains 1 | −1.70 | 1.103E-07 | 65059 |
| PH_hs_0047307 | KIAA1524 | KIAA1524 | −1.70 | 7.213E-08 | 57650 |
| PH_hs_0037802 | GPC6 | glypican 6 | −1.70 | 4.865E-05 | 10082 |
| PH_hs_0044814 | KIF4A | kinesin family member 4A | −1.70 | 5.116E-07 | 24137 |
| PH_hs_0047818 | MAP4 | microtubule-associated protein 4 | −1.70 | 3.260E-04 | 4134 |
| PH_hs_0029774 | ELL | elongation factor RNA polymerase II | −1.69 | 5.895E-09 | 8178 |
| PH_hs_0026668 | ENO2 | enolase 2 (gamma, neuronal) | −1.69 | 1.119E-04 | 2026 |
| PH_hs_0000408 | TBC1D13 | TBC1 domain family, member 13 | −1.69 | 1.019E-06 | 54662 |
| PH_hs_0042797 | OR6N2 | olfactory receptor, family 6, subfamily N, member 2 | −1.69 | 3.217E-04 | 81442 |
| PH_hs_0022981 | PAPOLA | poly(A) polymerase alpha | −1.69 | 2.295E-05 | 10914 |
| PH_hs_0042225 | DUSP5 | dual specificity phosphatase 5 | −1.69 | 6.939E-05 | 1847 |
| PH_hs_0044747 | KPNA6 | karyopherin alpha 6 (importin alpha 7) | −1.69 | 4.891E-04 | 23633 |
| PH_hs_0025873 | CEP152 | centrosomal protein 152 kDa | −1.69 | 2.041E-03 | 22995 |
| PH_hs_0016481 | FANCI | Fanconi anemia, complementation group I | −1.69 | 7.607E-06 | 55215 |
| PH_hs_0012268 | MICB | MHC class I polypeptide-related sequence B | −1.69 | 9.435E-05 | 4277 |
| PH_hs_0024760 | DPY19L1 | dpy-19-like 1 (C. elegans) | −1.69 | 2.089E-04 | 23333 |
| PH_hs_0025234 | OXR1 | oxidation resistance 1 | −1.69 | 7.896E-05 | 55074 |
| PH_hs_0014119 | BRF2 | BRF2, subunit of RNA polymerase III transcription initiation factor, BRF1-like | −1.69 | 2.754E-03 | 55290 |

-continued

| Probe ID | Gene_symbol | Description | Fold Change | p-value | Entrez_gene |
|---|---|---|---|---|---|
| PH_hs_0049053 | ADAM9 | ADAM metallopeptidase domain 9 | -1.69 | 1.435E-03 | 8754 |
| PH_hs_0044243 | RRP1 | ribosomal RNA processing 1 homolog (S. cerevisiae) | -1.69 | 3.245E-03 | 8568 |
| PH_hs_0011720 | TMEM97 | transmembrane protein 97 | -1.69 | 2.101E-06 | 27346 |
| PH_hs_0023589 | ACOT9 | acyl-CoA thioesterase 9 | -1.68 | 4.467E-08 | 23597 |
| PH_hs_0043078 | PPPDE1 | PPPDE peptidase domain containing 1 | -1.68 | 4.404E-04 | 51029 |
| PH_hs_0006882 | CDT1 | chromatin licensing and DNA replication factor 1 | -1.68 | 1.422E-06 | 81620 |
| PH_hs_0000282 | EPS8 | epidermal growth factor receptor pathway substrate 8 | -1.68 | 7.106E-06 | 2059 |
| PH_hs_0024883 | PPP6R1 | protein phosphatase 6, regulatory subunit 1 | -1.68 | 1.260E-02 | 22870 |
| PH_hs_0033354 | PIN1 | peptidylprolyl cis/trans isomerase, NIMA-interacting 1 | -1.68 | 1.860E-06 | 5300 |
| PH_hs_0027206 | UHRF1 | ubiquitin-like with PHD and ring finger domains 1 | -1.68 | 2.378E-03 | 29128 |
| PH_hs_0000937 | KIF11 | kinesin family member 11 | -1.68 | 3.453E-05 | 3832 |
| PH_hs_0010330 | ARHGAP11A | Rho GTPase activating protein 11A | -1.68 | 8.275E-04 | 9824 |
| PH_hs_0027568 | FARSB | phenylalanyl-tRNA synthetase, beta subunit | -1.68 | 5.779E-06 | 10056 |
| PH_hs_0047336 | BMPR1B | bone morphogenetic protein receptor, type IB | -1.68 | 1.566E-05 | 658 |
| PH_hs_0007062 | SCAF4 | SR-related CTD-associated factor 4 | -1.67 | 7.028E-05 | 57466 |
| PH_hs_0007254 | PHLDB3 | pleckstrin homology-like domain, family B, member 3 | -1.67 | 8.289E-03 | 653583 |
| PH_hs_0033183 | CHAF1A | chromatin assembly factor 1, subunit A (p150) | -1.67 | 9.186E-10 | 10036 |
| PH_hs_0044932 | MAD2L1 | MAD2 mitotic arrest deficient-like 1 (yeast) | -1.67 | 5.315E-05 | 4085 |
| PH_hs_0047787 | ARRDC4 | arrestin domain containing 4 | -1.67 | 2.673E-05 | 91947 |
| PH_hs_0008721 | CPNE7 | copine VII | -1.67 | 7.112E-12 | 27132 |
| PH_hs_0008113 | SKA1 | spindle and kinetochore associated complex subunit 1 | -1.67 | 9.034E-09 | 220134 |
| PH_hs_0004580 | CD74 | CD74 molecule, major histocompatibility complex, class II invariant chain | -1.66 | 1.644E-10 | 972 |
| PH_hs_0047141 | BNIP3 | BCL2/adenovirus E1B 19 kDa interacting protein 3 | -1.66 | 4.822E-05 | 664 |
| PH_hs_0001261 | UVRAG | UV radiation resistance associated gene | -1.66 | 2.121E-05 | 7405 |
| PH_hs_0002556 | ETNK1 | ethanolamine kinase 1 | -1.66 | 3.075E-03 | 55500 |
| PH_hs_0024492 | RABL5 | RAB, member RAS oncogene family-like 5 | -1.66 | 8.791E-04 | 64792 |
| PH_hs_0035332 | PAFAH1B3 | platelet-activating factor acetylhydrolase 1b, catalytic subunit 3 (29 kDa) | -1.66 | 1.201E-03 | 5050 |
| PH_hs_0031400 | FMR1 | fragile X mental retardation 1 | -1.66 | 7.029E-05 | 2332 |
| PH_hs_0003608 | ZCCHC17 | zinc finger, CCHC domain containing 17 | -1.66 | 1.069E-04 | 51538 |
| PH_hs_0004961 | CENPQ | centromere protein Q | -1.66 | 3.290E-03 | 55166 |
| PH_hs_0022104 | DPP7 | dipeptidyl-peptidase 7 | -1.66 | 1.011E-03 | 29952 |
| PH_hs_0023179 | FOXP1 | forkhead box P1 | -1.66 | 1.860E-06 | 27086 |
| PH_hs_0005753 | RIPK2 | receptor-interacting serine-threonine kinase 2 | -1.66 | 3.304E-07 | 8767 |
| PH_hs_0044855 | SLC18A3 | solute carrier family 18 (vesicular acetylcholine), member 3 | -1.66 | 3.964E-02 | 6572 |
| PH_hs_0027806 | METRN | meteorin, glial cell differentiation regulator | -1.66 | 6.883E-04 | 79006 |
| PH_hs_0004239 | CASP4 | caspase 4, apoptosis-related cysteine peptidase | -1.65 | 5.104E-03 | 837 |
| PH_hs_0004095 | HAUS8 | HAUS augmin-like complex, subunit 8 | -1.65 | 1.813E-02 | 93323 |
| PH_hs_0035325 | EIF6 | eukaryotic translation initiation factor 6 | -1.65 | 6.351E-05 | 3692 |
| PH_hs_0049245 | SMC3 | structural maintenance of chromosomes 3 | -1.65 | 1.596E-03 | 9126 |
| PH_hs_0047576 | GXYLT1 | glucoside xylosyltransferase 1 | -1.65 | 1.824E-04 | 283464 |
| PH_hs_0035543 | H2AFZ | H2A histone family, member Z | -1.65 | 2.566E-05 | 3015 |
| PH_hs_0002639 | TMEM51 | transmembrane protein 51 | -1.65 | 3.158E-03 | 55092 |
| PH_hs_0023607 | CTTN | cortactin | -1.65 | 7.125E-08 | 2017 |
| PH_hs_0043741 | EEF1E1 | eukaryotic translation elongation factor 1 epsilon 1 | -1.65 | 3.436E-04 | 9521 |
| PH_hs_0010392 | DPYSL2 | dihydropyrimidinase-like 2 | -1.65 | 6.601E-04 | 1808 |
| PH_hs_0044640 | TAF13 | TAF13 RNA polymerase II, TATA box binding protein (TBP)-associated factor, 18 kDa | -1.65 | 4.779E-03 | 6884 |
| PH_hs_0000792 | DYNC1H1 | dynein, cytoplasmic 1, heavy chain 1 | -1.65 | 2.037E-10 | 1778 |
| PH_hs_0048854 | UTP15 | UTP15, U3 small nucleolar ribonucleoprotein, homolog (S. cerevisiae) | -1.65 | 2.575E-05 | 84135 |
| PH_hs_0012697 | WBP2 | WW domain binding protein 2 | -1.65 | 1.728E-03 | 23558 |
| PH_hs_0048257 | IRAK2 | interleukin-1 receptor-associated kinase 2 | -1.65 | 4.036E-09 | 3656 |
| PH_hs_0029627 | FAM195B | family with sequence similarity 195, member B | -1.65 | 5.379E-06 | 348262 |

| Probe ID | Gene_symbol | Description | Fold Change | p-value | Entrez_gene |
|---|---|---|---|---|---|
| PH_hs_0044919 | GLRX3 | glutaredoxin 3 | −1.65 | 7.437E−04 | 10539 |
| PH_hs_0035080 | LOC100508928 | hypothetical protein LOC100508928 | −1.64 | 2.930E−02 | 100508928 |
| PH_hs_0048932 | PCNX | pecanex homolog (Drosophila) | −1.64 | 2.578E−04 | 22990 |
| PH_hs_0045569 | NME1 | non-metastatic cells 1, protein (NM23A) expressed in | −1.64 | 5.426E−03 | 4830 |
| PH_hs_0044216 | PPPDE2 | PPPDE peptidase domain containing 2 | −1.64 | 2.451E−05 | 27351 |
| PH_hs_0004174 | HMMR | hyaluronan-mediated motility receptor (RHAMM) | −1.64 | 4.985E−03 | 3161 |
| PH_hs_0004526 | PSMD8 | proteasome (prosome, macropain) 26S subunit, non-ATPase, 8 | −1.64 | 1.259E−05 | 5714 |
| PH_hs_0021964 | GCNT2 | glucosaminyl (N-acetyl) transferase 2, I-branching enzyme (I blood group) | −1.64 | 5.447E−06 | 2651 |
| PH_hs_0024529 | NFKBIZ | nuclear factor of kappa light polypeptide gene enhancer in B-cells inhibitor, zeta | −1.64 | 3.357E−05 | 64332 |
| PH_hs_0047732 | PRDM8 | PR domain containing 8 | −1.64 | 3.460E−03 | 56978 |
| PH_hs_0033509 | RPL36AL/RPL36A | ribosomal protein L36a-like/ribosomal protein L36a | −1.64 | 8.830E−04 | 6166/6173 |
| PH_hs_0011496 | PEA15 | phosphoprotein enriched in astrocytes 15 | −1.64 | 1.557E−02 | 8682 |
| PH_hs_0006140 | SIVA1 | SIVA1, apoptosis-inducing factor | −1.64 | 1.912E−08 | 10572 |
| PH_hs_0034155 | LRRC8E | leucine rich repeat containing 8 family, member E | −1.64 | 6.525E−10 | 80131 |
| PH_hs_0005514 | AGPAT9 | 1-acylglycerol-3-phosphate O-acyltransferase 9 | −1.64 | 9.099E−07 | 84803 |
| PH_hs_0022980 | STMN4 | stathmin-like 4 | −1.64 | 3.410E−03 | 81551 |
| PH_hs_0027288 | DDA1 | DET1 and DDB1 associated 1 | −1.64 | 2.791E−05 | 79016 |
| PH_hs_0025525 | CLU | clusterin | −1.64 | 5.676E−05 | 1191 |
| PH_hs_0049199 | DDX6 | DEAD (Asp-Glu-Ala-Asp) box polypeptide 6 | −1.64 | 4.826E−08 | 1656 |
| PH_hs_0046136 | ALS2 | amyotrophic lateral sclerosis 2 (juvenile) | −1.64 | 4.555E−06 | 57679 |
| PH_hs_0025324 | TXNRD1 | thioredoxin reductase 1 | −1.64 | 6.177E−05 | 7296 |
| PH_hs_0032742 | MRPL14 | mitochondrial ribosomal protein L14 | −1.64 | 1.879E−05 | 64928 |
| PH_hs_0044203 | C20orf24/TGIF2-C20ORF24 | chromosome 20 open reading frame 24/TGIF2-C20orf24 read-through transcript | −1.64 | 5.281E−03 | 55969/100527943 |
| PH_hs_0044654 | LMNA | lamin A/C | −1.63 | 1.321E−04 | 4000 |
| PH_hs_0023583 | ATAD2 | ATPase family, AAA domain containing 2 | −1.63 | 1.061E−02 | 29028 |
| PH_hs_0043661 | DEPDC1 | DEP domain containing 1 | −1.63 | 1.637E−03 | 55635 |
| PH_hs_0042194 | EXOSC8 | exosome component 8 | −1.63 | 3.802E−04 | 11340 |
| PH_hs_0046189 | LAS1L | LAS1-like (S. cerevisiae) | −1.63 | 1.049E−04 | 81887 |
| PH_hs_0044204 | C3orf75 | chromosome 3 open reading frame 75 | −1.63 | 2.969E−02 | 54859 |
| PH_hs_0043707 | MEST | mesoderm specific transcript homolog (mouse) | −1.63 | 3.780E−04 | 4232 |
| PH_hs_0047544 | C1R | complement component 1, r subcomponent | −1.62 | 1.530E−04 | 715 |
| PH_hs_0012041 | SMAGP | small cell adhesion glycoprotein | −1.62 | 1.812E−05 | 57228 |
| PH_hs_0009437 | TOP2A | topoisomerase (DNA) II alpha 170 kDa | −1.62 | 4.278E−08 | 7153 |
| PH_hs_0007455 | PHTF2 | putative homeodomain transcription factor 2 | −1.62 | 8.711E−03 | 57157 |
| PH_hs_0049025 | TGFBR1 | transforming growth factor, beta receptor 1 | −1.62 | 9.826E−03 | 7046 |
| PH_hs_0048444 | VAV2 | vav 2 guanine nucleotide exchange factor | −1.62 | 3.484E−04 | 7410 |
| PH_hs_0042046 | STS | steroid sulfatase (microsomal), isozyme S | −1.62 | 5.977E−04 | 412 |
| PH_hs_0042789 | PITX1 | paired-like homeodomain 1 | −1.62 | 1.482E−02 | 5307 |
| PH_hs_0015031 | REEP4 | receptor accessory protein 4 | −1.62 | 5.035E−10 | 80346 |
| PH_hs_0003757 | FLNC | filamin C, gamma | −1.62 | 2.953E−05 | 2318 |
| PH_hs_0017279 | RPL28 | ribosomal protein L28 | −1.62 | 1.187E−05 | 6158 |
| PH_hs_0023492 | CAMK2N2 | calcium/calmodulin-dependent protein kinase II inhibitor 2 | −1.62 | 8.088E−09 | 94032 |
| PH_hs_0042165 | ANXA1 | annexin A1 | −1.62 | 2.539E−10 | 301 |
| PH_hs_0027828 | C11orf17 | chromosome 11 open reading frame 17 | −1.62 | 6.499E−05 | 56672 |
| PH_hs_0047497 | CEP120 | centrosomal protein 120 kDa | −1.62 | 5.099E−07 | 153241 |
| PH_hs_0016835 | RALGAPB | Ral GTPase activating protein, beta subunit (non-catalytic) | −1.62 | 2.171E−06 | 57148 |
| PH_hs_0005632 | COL12A1 | collagen, type XII, alpha 1 | −1.61 | 3.006E−03 | 1303 |
| PH_hs_0048738 | CCDC88A | coiled-coil domain containing 88A | −1.61 | 1.003E−05 | 55704 |
| PH_hs_0002640 | EFNB2 | ephrin-B2 | −1.61 | 1.286E−04 | 1948 |

-continued

| Probe ID | Gene_symbol | Description | Fold Change | p-value | Entrez_gene |
|---|---|---|---|---|---|
| PH_hs_0028809 | ATAD3A|ATAD3BL OC732419 | ATPase family, AAA domain containing 3A|ATPase family, AAA domain containing 3B|ATPase family AAA domain-containing protein 3B-like | -1.61 | 9.305E-06 | 55210|83858|73 2419 |
| PH_hs_0030980 | C22orf13 | chromosome 22 open reading frame 13 | -1.61 | 1.915E-02 | 83606 |
| PH_hs_0005089 | IMP4 | IMP4, U3 small nucleolar ribonucleoprotein, homolog (yeast) | -1.61 | 8.466E-03 | 92856 |
| PH_hs_0027124 | LPXN | leupaxin | -1.61 | 8.650E-05 | 9404 |
| PH_hs_0027049 | STRAP | serine/threonine kinase receptor associated protein | -1.61 | 9.166E-06 | 11171 |
| PH_hs_0025102 | AP1S1 | adaptor-related protein complex 1, sigma 1 subunit | -1.61 | 5.584E-07 | 1174 |
| PH_hs_0027140 | RAD54L | RAD54-like (S. cerevisiae) | -1.61 | 1.114E-03 | 8438 |
| PH_hs_0016469 | ANKRD13B | ankyrin repeat domain 13B | -1.61 | 1.169E-04 | 124930 |
| PH_hs_0020362 | CDCA5 | cell division cycle associated 5 | -1.61 | 1.999E-09 | 113130 |
| PH_hs_0024860 | LCMT1 | leucine carboxyl methyltransferase 1 | -1.61 | 1.182E-04 | 51451 |
| PH_hs_0012886 | CDKN1B | cyclin-dependent kinase inhibitor 1B (p27, Kip1) | -1.60 | 1.837E-05 | 1027 |
| PH_hs_0004483 | DLGAP5 | discs, large (Drosophila) homolog-associated protein 5 | -1.60 | 1.153E-07 | 9787 |
| PH_hs_0048190 | YOD1 | YOD1 OTU deubiquinating enzyme 1 homolog (S. cerevisiae) | -1.60 | 9.987E-04 | 55432 |
| PH_hs_0005179 | BLOC1S1-RDH5|BLOC1S1 | BLOC1S1-RDH5 read-through transcript|biogenesis of lysosomal organelles complex-1, subunit 1 | -1.60 | 1.485E-07 | 100528022|2647 |
| PH_hs_0048562 | EXOSC2 | exosome component 2 | -1.60 | 1.177E-02 | 23404 |
| PH_hs_0010222 | SEMA7A | semaphorin 7A, GPI membrane anchor (John Milton Hagen blood group) | -1.60 | 4.901E-04 | 8482 |
| PH_hs_0035730 | EFCAB7 | EF-hand calcium binding domain 7 | -1.60 | 3.417E-05 | 84455 |
| PH_hs_0022760 | C9orf30-TMEFF1 | chromosome 9 open reading frame 30|C9orf30-TMEFF1 read-through transcript | -1.60 | 4.727E-03 | 91283|10052669 4 |
| PH_hs_0043696 | SALL1 | sal-like 1 (Drosophila) | -1.60 | 8.071E-05 | 6299 |
| PH_hs_0031970 | TTLL4 | tubulin tyrosine ligase-like family, member 4 | -1.60 | 2.928E-03 | 9654 |
| PH_hs_0009664 | ARHGDIA | Rho GDP dissociation inhibitor (GDI) alpha | -1.60 | 4.801E-06 | 396 |
| PH_hs_0047984 | VPS26B | vacuolar protein sorting 26 homolog B (S. pombe) | -1.60 | 3.761E-02 | 112936 |
| PH_hs_0009153 | MAP3K5 | mitogen-activated protein kinase kinase kinase 5 | -1.60 | 3.131E-05 | 4217 |
| PH_hs_0048564 | PDE4DIP | phosphodiesterase 4D interacting protein | -1.60 | 2.391E-03 | 9659 |
| PH_hs_0008761 | PTGES | prostaglandin E synthase | -1.60 | 2.976E-02 | 9536 |
| PH_hs_0044962 | LOC100190939 | hypothetical LOC100190939 | -1.60 | 9.335E-06 | 100190939 |
| PH_hs_0023587 | PRPF40A | PRP40 pre-mRNA processing factor 40 homolog A (S. cerevisiae) | -1.60 | 1.105E-07 | 55660 |
| PH_hs_0000565 | TMEM164 | transmembrane protein 164 | -1.59 | 3.951E-05 | 84187 |
| PH_hs_0022049 | CHEK1 | CHK1 checkpoint homolog (S. pombe) | -1.59 | 4.785E-05 | 1111 |
| PH_hs_0044127 | RPL7L1 | ribosomal protein L7-like 1 | -1.59 | 1.230E-02 | 285855 |
| PH_hs_0030773 | FIGNL1 | fidgetin-like 1 | -1.59 | 3.760E-06 | 63979 |
| PH_hs_0025217 | MPRIP | myosin phosphatase Rho interacting protein | -1.59 | 3.941E-07 | 23164 |
| PH_hs_0029324 | TCEB2 | transcription elongation factor B (SIII), polypeptide 2 (18 kDa, elongin B) | -1.59 | 6.908E-04 | 6923 |
| PH_hs_0048518 | ZFP36L2 | zinc finger protein 36, C3H type-like 2 | -1.59 | 1.059E-02 | 678 |
| PH_hs_0045853 | TTK | TTK protein kinase | -1.59 | 8.529E-06 | 7272 |
| PH_hs_0009005 | ITGA5 | integrin, alpha 5 (fibronectin receptor, alpha polypeptide) | -1.59 | 2.606E-04 | 3678 |
| PH_hs_0001187 | GNPAT | glyceronephosphate O-acyltransferase | -1.59 | 4.097E-06 | 8443 |
| PH_hs_0031229 | LOC399959 | hypothetical LOC399959 | -1.59 | 7.124E-03 | 399959 |
| PH_hs_0025859 | MRPL38 | mitochondrial ribosomal protein L38 | -1.59 | 3.931E-02 | 64978 |
| PH_hs_0004760 | LOXL2 | lysyl oxidase-like 2 | -1.59 | 1.995E-10 | 4017 |
| PH_hs_0005216 | LLGL1 | lethal giant larvae homolog 1 (Drosophila) | -1.59 | 9.464E-03 | 3996 |
| PH_hs_0002641 | PMVK | phosphomevalonate kinase | -1.59 | 1.45E-06 | 10654 |
| PH_hs_0002255 | ELOVL1 | elongation of very long chain fatty acids (FEN1/Elo2, SUR4/Elo3, yeast)-like 1 | -1.58 | 6.869E-07 | 64834 |
| PH_hs_0045216 | EIF4E | eukaryotic translation initiation factor 4E | -1.58 | 3.365E-07 | 1977 |
| PH_hs_0030583 | TAF1A | TATA box binding protein (TBP)-associated factor, RNA polymerase I, A, 48 kDa | -1.58 | 1.399E-02 | 9015 |
| PH_hs_0026629 | CLK3 | CDC-like kinase 3 | -1.58 | 7.459E-03 | 1198 |
| PH_hs_0049736 | TUBA1B | tubulin, alpha 1b | -1.58 | 4.408E-06 | 10376 |
| PH_hs_0016555 | FDX1L | ferredoxin 1-like | -1.58 | 6.643E-07 | 112812 |

-continued

| Probe ID | Gene_symbol | Description | Fold Change | p-value | Entrez_gene |
|---|---|---|---|---|---|
| PH_hs_0032775 | FAM102A | family with sequence similarity 102, member A | -1.58 | 1.105E-02 | 399665 |
| PH_hs_0004360 | STX1A | syntaxin 1A (brain) | -1.58 | 5.134E-04 | 6804 |
| PH_hs_0047441 | STC2 | stanniocalcin 2 | -1.58 | 4.336E-04 | 8614 |
| PH_hs_0042579 | OR9G4 | olfactory receptor, family 9, subfamily G, member 4 | -1.58 | 1.585E-03 | 283189 |
| PH_hs_0005496 | CEBPB | CCAAT/enhancer binding protein (C/EBP), beta | -1.58 | 6.247E-06 | 1051 |
| PH_hs_0000972 | TPX2 | TPX2, microtubule-associated, homolog (Xenopus laevis) | -1.58 | 7.974E-07 | 22974 |
| PH_hs_0030976 | NFKBIB | nuclear factor of kappa light polypeptide gene enhancer in B-cells inhibitor, beta | -1.58 | 1.258E-02 | 4793 |
| PH_hs_0025894 | PSMD11 | proteasome (prosome, macropain) 26S subunit, non-ATPase, 11 | -1.58 | 6.282E-04 | 5717 |
| PH_hs_0035995 | IDH3B | isocitrate dehydrogenase 3 (NAD+) beta | -1.58 | 4.342E-03 | 3420 |
| PH_hs_0016737 | RNFT2 | ring finger protein, transmembrane 2 | -1.58 | 3.709E-05 | 84900 |
| PH_hs_0029014 | PSMB3 | proteasome (prosome, macropain) subunit, beta type, 3 | -1.58 | 5.940E-08 | 5691 |
| PH_hs_0022722 | XPO1 | exportin 1 (CRM1 homolog, yeast) | -1.58 | 2.317E-03 | 7514 |
| PH_hs_0017273 | CCDC80 | coiled-coil domain containing 80 | -1.58 | 4.779E-03 | 151887 |
| PH_hs_0034252 | GBA | glucosidase, beta, acid | -1.58 | 6.789E-05 | 2629 |
| PH_hs_0045439 | U2AF1 | U2 small nuclear RNA auxiliary factor 1 | -1.58 | 5.021E-04 | 7307 |
| PH_hs_0042037 | KIF5B | kinesin family member 5B | -1.58 | 8.342E-04 | 3799 |
| PH_hs_0033649 | C6orf191 | chromosome 6 open reading frame 191 | -1.57 | 3.539E-02 | 253582 |
| PH_hs_0043455 | CDKN2AIPNL | CDKN2A interacting protein N-terminal like | -1.57 | 4.900E-06 | 91368 |
| PH_hs_0000774 | ATP6V0B | ATPase, H+ transporting, lysosomal 21 kDa, V0 subunit b | -1.57 | 5.481E-07 | 533 |
| PH_hs_0014714 | GPN3 | GPN-loop GTPase 3 | -1.57 | 7.778E-04 | 51184 |
| PH_hs_0048167 | TGOLN2 | trans-golgi network protein 2 | -1.57 | 8.987E-03 | 10618 |
| PH_hs_0003647 | MRPL51 | mitochondrial ribosomal protein L51 | -1.57 | 1.079E-06 | 51258 |
| PH_hs_0000084 | IER2 | immediate early response 2 | -1.57 | 3.085E-03 | 9592 |
| PH_hs_0006093 | DEK | DEK oncogene | -1.57 | 4.785E-05 | 7913 |
| PH_hs_0049458 | ZNF367 | zinc finger protein 367 | -1.57 | 8.118E-06 | 195828 |
| PH_hs_0045731 | GAS6 | growth arrest-specific 6 | -1.57 | 2.941E-03 | 2621 |
| PH_hs_0042627 | HSD11B2 | hydroxysteroid (11-beta) dehydrogenase 2 | -1.57 | 4.076E-04 | 3291 |
| PH_hs_0045021 | AK2 | adenylate kinase 2 | -1.57 | 1.179E-09 | 204 |
| PH_hs_0019487 | SCN1B | sodium channel, voltage-gated, type I, beta | -1.57 | 9.110E-06 | 6324 |
| PH_hs_0031022 | SNRNP25 | small nuclear ribonucleoprotein 25 kDa (U11/U12) | -1.56 | 3.507E-04 | 79622 |
| PH_hs_0036212 | PREPL | prolyl endopeptidase-like | -1.56 | 1.834E-05 | 9581 |
| PH_hs_0047598 | SKA2 | spindle and kinetochore associated complex subunit 2 | -1.56 | 4.366E-04 | 348235 |
| PH_hs_0042314 | ITGB1BP3 | integrin beta 1 binding protein 3 | -1.56 | 2.862E-04 | 27231 |
| PH_hs_0028818 | FAM132B | family with sequence similarity 132, member B | -1.56 | 1.320E-02 | 151176 |
| PH_hs_0001900 | TCEAL7 | transcription elongation factor A (SII)-like 7 | -1.56 | 3.320E-08 | 56849 |
| PH_hs_0002232 | IRX5 | iroquois homeobox 5 | -1.56 | 1.028E-02 | 10265 |
| PH_hs_0005745 | DNASE1L2 | deoxyribonuclease 1-like 2 | -1.56 | 1.675E-02 | 1775 |
| PH_hs_0009654 | RHEBL1 | Ras homolog enriched in brain like 1 | -1.56 | 1.015E-03 | 121268 |
| PH_hs_0023170 | COL6A3 | collagen, type VI, alpha 3 | -1.56 | 5.901E-03 | 1293 |
| PH_hs_0012740 | HNRNPA2B1 | heterogeneous nuclear ribonucleoprotein A2/B1 | -1.56 | 6.334E-05 | 3181 |
| PH_hs_0045185 | APITD1|APITD1-CORT | apoptosis-inducing, TAF9-like domain 1|APITD1-CORT read-through | -1.56 | 1.837E-02 | 378708|1005267 39 |
| PH_hs_0019597 | SLC31A1 | solute carrier family 31 (copper transporters), member 1 | -1.56 | 1.821E-05 | 1317 |
| PH_hs_0004640 | MVP | major vault protein | -1.56 | 4.294E-03 | 9961 |
| PH_hs_0009331 | BCL6 | B-cell CLL/lymphoma 6 | -1.56 | 1.401E-05 | 604 |
| PH_hs_0047504 | SLC36A1 | solute carrier family 36 (proton/amino acid symporter), member 1 | -1.56 | 1.386E-02 | 206358 |
| PH_hs_0033324 | PDK1 | pyruvate dehydrogenase kinase, isozyme 1 | -1.56 | 1.322E-02 | 5163 |
| PH_hs_0016208 | WDR87 | WD repeat domain 87 | -1.56 | 4.877E-03 | 83889 |
| PH_hs_0025539 | NOM1 | nucleolar protein with MIF4G domain 1 | -1.56 | 1.313E-03 | 64434 |
| PH_hs_0044231 | TMEM205 | transmembrane protein 205 | -1.56 | 8.953E-08 | 374882 |
| PH_hs_0043161 | RPF2 | ribosome production factor 2 homolog (S. cerevisiae) | -1.56 | 5.915E-03 | 84154 |

-continued

| Probe ID | Gene_symbol | Description | Fold Change | p-value | Entrez_gene |
|---|---|---|---|---|---|
| PH_hs_0027173 | GADD45GIP1 | growth arrest and DNA-damage-inducible, gamma interacting protein 1 | −1.56 | 2.280E-08 | 90480 |
| PH_hs_0009338 | GNB5 | guanine nucleotide binding protein (G protein), beta 5 | −1.56 | 3.405E-03 | 10681 |
| PH_hs_0001609 | ORC1 | origin recognition complex, subunit 1 | −1.56 | 1.568E-03 | 4998 |
| PH_hs_0025441 | IGFBP7 | insulin-like growth factor binding protein 7 | −1.56 | 1.101E-04 | 3490 |
| PH_hs_0045832 | SCML1 | sex comb on midleg-like 1 (Drosophila) | −1.56 | 1.960E-03 | 6322 |
| PH_hs_0027330 | ITGA3 | integrin, alpha 3 (antigen CD49C, alpha 3 subunit of VLA-3 receptor) | −1.55 | 2.179E-04 | 3675 |
| PH_hs_0004485 | KNG1 | kininogen 1 | −1.55 | 1.097E-03 | 3827 |
| PH_hs_0044371 | DYNLT3 | dynein, light chain, Tctex-type 3 | −1.55 | 1.062E-03 | 6990 |
| PH_hs_0042113 | TDP2 | tyrosyl-DNA phosphodiesterase 2 | −1.55 | 1.367E-05 | 51567 |
| PH_hs_0048414 | LYPD1 | LY6/PLAUR domain containing 1 | −1.55 | 4.586E-06 | 116372 |
| PH_hs_0043504 | PRKD2 | protein kinase D2 | −1.55 | 3.743E-02 | 25865 |
| PH_hs_0029970 | RPL21|RPL21P28 | ribosomal protein L21|ribosomal protein L21 pseudogene 28 | −1.55 | 1.545E-05 | 6144|100131205 |
| PH_hs_0024955 | NUP205 | nucleoporin 205 kDa | −1.55 | 2.455E-04 | 23165 |
| PH_hs_0042301 | RPSAP58|RPSA | ribosomal protein SA pseudogene 58|ribosomal protein SA | −1.55 | 1.644E-07 | 388524|3921 |
| PH_hs_0032176 | FAM184B | family with sequence similarity 184, member B | −1.55 | 2.543E-03 | 27146 |
| PH_hs_0045064 | KIAA1715 | KIAA1715 | −1.55 | 1.243E-05 | 80856 |
| PH_hs_0028321 | ASCC3 | activating signal cointegrator 1 complex subunit 3 | −1.55 | 1.377E-04 | 10973 |
| PH_hs_0000362 | WDR5 | WD repeat domain 5 | −1.55 | 2.593E-03 | 11091 |
| PH_hs_0036525 | NDP | Norrie disease (pseudoglioma) | −1.55 | 1.991E-02 | 4693 |
| PH_hs_0042371 | LOC723972 | hepatopoietin PCn127 | −1.55 | 5.314E-03 | 723972 |
| PH_hs_0043178 | SRM | spermidine synthase | −1.55 | 8.957E-05 | 6723 |
| PH_hs_0012275 | MED25 | mediator complex subunit 25 | −1.55 | 1.898E-08 | 81857 |
| PH_hs_0002364 | TNFAIP3 | tumor necrosis factor, alpha-induced protein 3 | −1.55 | 4.993E-04 | 7128 |
| PH_hs_0023879 | FAM108C1 | family with sequence similarity 108, member C1 | −1.55 | 1.195E-04 | 58489 |
| PH_hs_0026052 | BCCIP | BRCA2 and CDKN1A interacting protein | −1.55 | 3.503E-05 | 56647 |
| PH_hs_0023309 | CD63 | CD63 molecule | −1.55 | 7.081E-04 | 967 |
| PH_hs_0005994 | PNO1 | partner of NOB1 homolog (S. cerevisiae) | −1.55 | 2.375E-07 | 56902 |
| PH_hs_0042994 | POLE3 | polymerase (DNA directed), epsilon 3 (p17 subunit) | −1.55 | 5.996E-05 | 54107 |
| PH_hs_0023297 | C17orf89 | chromosome 17 open reading frame 89 | −1.55 | 2.443E-06 | 284184 |
| PH_hs_0028985 | FEZ2 | fasciculation and elongation protein zeta 2 (zygin II) | −1.54 | 3.770E-08 | 9637 |
| PH_hs_0023879 | UCHL3 | ubiquitin carboxyl-terminal esterase L3 (ubiquitin thiolesterase) | −1.54 | 1.460E-02 | 7347 |
| PH_hs_0023515 | DCTN2 | dynactin 2 (p50) | −1.54 | 4.633E-04 | 10540 |
| PH_hs_0031357 | MMD | monocyte to macrophage differentiation-associated | −1.54 | 2.163E-02 | 23531 |
| PH_hs_0044653 | FZR1 | fizzy/cell division cycle 20 related 1 (Drosophila) | −1.54 | 6.402E-03 | 51343 |
| PH_hs_0029801 | RBPJ | recombination signal binding protein for immunoglobulin kappa J region | −1.54 | 5.075E-06 | 3516 |
| PH_hs_0001441 | ZCCHC9 | zinc finger, CCHC domain containing 9 | −1.54 | 4.844E-02 | 84240 |
| PH_hs_0044663 | PDE7A | phosphodiesterase 7A | −1.54 | 6.506E-04 | 5150 |
| PH_hs_0042297 | LOC728024 | chromosome X open reading frame 56 pseudogene | −1.54 | 2.346E-03 | 728024 |
| PH_hs_0036053 | HNRNPA1P10|HNRNPA1L2 | heterogeneous nuclear ribonucleoprotein A1 pseudogene 10|heterogeneous nuclear ribonucleoprotein A1-like 2 | −1.54 | 2.367E-04 | 664709|144983 |
| PH_hs_0004152 | ALKBH3 | alkB, alkylation repair homolog 3 (E. coli) | −1.54 | 4.653E-04 | 221120 |
| PH_hs_0001032 | EMP3 | epithelial membrane protein 3 | −1.54 | 5.502E-03 | 2014 |
| PH_hs_0007357 | HDGFRP3 | hepatoma-derived growth factor, related protein 3 | −1.54 | 3.829E-04 | 50810 |
| PH_hs_0025796 | DDX1 | DEAD (Asp-Glu-Ala-Asp) box polypeptide 1 | −1.54 | 2.149E-05 | 1653 |
| PH_hs_0005643 | MAST2 | microtubule associated serine/threonine kinase 2 | −1.54 | 1.655E-04 | 23139 |
| PH_hs_0044106 | C7orf44 | chromosome 7 open reading frame 44 | −1.54 | 1.777E-02 | 55744 |
| PH_hs_0005844 | AIM2 | absent in melanoma 2 | −1.54 | 1.492E-05 | 9447 |
| PH_hs_0003453 | UACA | uveal autoantigen with coiled-coil domains and ankyrin repeats | −1.54 | 1.379E-03 | 55075 |
| PH_hs_0024767 | MAPRE1 | microtubule-associated protein, RP/EB family, member 1 | −1.54 | 1.001E-06 | 22919 |
| PH_hs_0026523 | LAT | linker for activation of T cells | −1.54 | 2.833E-05 | 27040 |
| PH_hs_0030224 | LBR | lamin B receptor | −1.54 | 7.940E-04 | 3930 |

-continued

| Probe ID | Gene_symbol | Description | Fold Change | p-value | Entrez_gene |
|---|---|---|---|---|---|
| PH_hs_0016124 | CD82 | CD82 molecule | −1.54 | 7.113E-04 | 3732 |
| PH_hs_0047488 | RTTN | rotatin | −1.54 | 8.024E-04 | 25914 |
| PH_hs_0045751 | PRMT1 | protein arginine methyltransferase 1 | −1.54 | 5.335E-03 | 3276 |
| PH_hs_0014950 | ST6GALNAC2 | ST6 (alpha-N-acetyl-neuraminyl-2,3-beta-galactosyl-1,3)-N-acetylgalactosaminide alpha-2,6-sialyltransferase 2 | −1.54 | 5.043E-03 | 10610 |
| PH_hs_0042237 | ASAM | adipocyte-specific adhesion molecule | −1.53 | 2.390E-02 | 79827 |
| PH_hs_0010045 | TCTN2 | tectonic family member 2 | −1.53 | 2.124E-02 | 79867 |
| PH_hs_0005616 | CEP72 | centrosomal protein 72 kDa | −1.53 | 7.808E-04 | 55722 |
| PH_hs_0040108 | MRPS7 | mitochondrial ribosomal protein S7 | −1.53 | 1.221E-05 | 51081 |
| PH_hs_0043151 | TMEM126B | transmembrane protein 126B | −1.53 | 2.268E-03 | 55863 |
| PH_hs_0031377 | SUMO3 | SMT3 suppressor of mif two 3 homolog 3 (S. cerevisiae) | −1.53 | 2.405E-02 | 6612 |
| PH_hs_0027070 | CANT1 | calcium activated nucleotidase 1 | −1.53 | 2.427E-09 | 124583 |
| PH_hs_0003940 | GOLT1B | golgi transport 1B | −1.53 | 2.734E-03 | 51026 |
| PH_hs_0003882 | PSMC2 | proteasome (prosome, macropain) 26S subunit, ATPase, 2 | −1.53 | 2.074E-04 | 5701 |
| PH_hs_0042349 | UBE2S | ubiquitin-conjugating enzyme E2S | −1.53 | 1.020E-04 | 27338 |
| PH_hs_0033920 | RPS2/RPS2P32 | ribosomal protein S2/ribosomal protein S2 pseudogene 32 | −1.53 | 2.014E-04 | 6187/256355 |
| PH_hs_0035967 | SEPW1 | selenoprotein W, 1 | −1.53 | 8.249E-07 | 6415 |
| PH_hs_0013492 | C19orf48 | chromosome 19 open reading frame 48 | −1.53 | 3.217E-02 | 84798 |
| PH_hs_0024307 | RABGAP1L | RAB GTPase activating protein 1-like | −1.53 | 1.971E-06 | 9910 |
| PH_hs_0014633 | RELL1 | RELT-like 1 | −1.53 | 1.784E-04 | 768211 |
| PH_hs_0048556 | ABI2 | abl-interactor 2 | −1.53 | 2.139E-02 | 10152 |
| PH_hs_0042396 | CCDC55 | coiled-coil domain containing 55 | −1.53 | 1.609E-03 | 84081 |
| PH_hs_0025941 | EZH2 | enhancer of zeste homolog 2 (Drosophila) | −1.53 | 5.642E-04 | 2146 |
| PH_hs_0042302 | NFE2L3 | nuclear factor (erythroid-derived 2)-like 3 | −1.53 | 2.838E-03 | 9603 |
| PH_hs_0048073 | MID1 | midline 1 (Opitz/BBB syndrome) | −1.53 | 6.308E-05 | 4281 |
| PH_hs_0045238 | POMZP3 | POM121 and ZP3 fusion | −1.53 | 3.140E-02 | 22932 |
| PH_hs_0006055 | C6orf108 | chromosome 6 open reading frame 108 | −1.53 | 2.161E-05 | 10591 |
| PH_hs_0001067 | ADPGK | ADP-dependent glucokinase | −1.53 | 1.636E-03 | 83440 |
| PH_hs_0048983 | UGT8 | UDP glycosyltransferase 8 | −1.53 | 5.934E-06 | 7368 |
| PH_hs_0014217 | TRIML2 | tripartite motif family-like 2 | −1.53 | 3.721E-02 | 205860 |
| PH_hs_0022450 | ACP1 | acid phosphatase 1, soluble | −1.52 | 1.088E-05 | 52 |
| PH_hs_0038578 | TPI1P2 | triosephosphate isomerase 1 pseudogene 2 | −1.52 | 3.335E-04 | 286016 |
| PH_hs_0028259 | TUBGCP2 | tubulin, gamma complex associated protein 2 | −1.52 | 4.195E-03 | 10844 |
| PH_hs_0022623 | ATP12A | ATPase, H+/K+ transporting, nongastric, alpha polypeptide | −1.52 | 4.213E-02 | 479 |
| PH_hs_0001474 | C2CD2 | C2 calcium-dependent domain containing 2 | −1.52 | 5.457E-03 | 25966 |
| PH_hs_0024635 | DHX29 | DEAH (Asp-Glu-Ala-His) box polypeptide 29 | −1.52 | 2.895E-02 | 54505 |
| PH_hs_0046144 | SLC22A23 | solute carrier family 22, member 23 | −1.52 | 1.474E-06 | 63027 |
| PH_hs_0042374 | SPCS2 | signal peptidase complex subunit 2 homolog (S. cerevisiae) | −1.52 | 1.375E-04 | 9789 |
| PH_hs_0049062 | PTPRE | protein tyrosine phosphatase, receptor type, E | −1.52 | 1.076E-02 | 5791 |
| PH_hs_0004268 | TSN | translin | −1.52 | 3.016E-04 | 7247 |
| PH_hs_0044174 | CCDC34 | coiled-coil domain containing 34 | −1.52 | 1.696E-05 | 91057 |
| PH_hs_0000095 | HNRNPF | heterogeneous nuclear ribonucleoprotein F | −1.52 | 9.856E-03 | 3185 |
| PH_hs_0047557 | SMG1 | SMG1 homolog, phosphatidylinositol 3-kinase-related kinase (C. elegans) | −1.52 | 4.786E-03 | 23049 |
| PH_hs_0001034 | MRPL17 | mitochondrial ribosomal protein L17 | −1.52 | 1.608E-03 | 63875 |
| PH_hs_0028767 | ZNF205 | zinc finger protein 205 | −1.52 | 6.249E-04 | 7755 |
| PH_hs_0024960 | MAPKAPK5 | mitogen-activated protein kinase-activated protein kinase 5 | −1.52 | 1.010E-02 | 8550 |
| PH_hs_0048097 | WNK1 | WNK lysine deficient protein kinase 1 | −1.52 | 9.225E-04 | 65125 |
| PH_hs_0045887 | EDF1 | endothelial differentiation-related factor 1 | −1.52 | 3.984E-06 | 8721 |
| PH_hs_0022899 | RBBP6 | retinoblastoma binding protein 6 | −1.52 | 3.670E-02 | 5930 |
| PH_hs_0026178 | RHOV | ras homolog gene family, member V | −1.52 | 9.963E-04 | 171177 |
| PH_hs_0047826 | GNA12 | guanine nucleotide binding protein (G protein) alpha 12 | −1.52 | 5.094E-05 | 2768 |
| PH_hs_0043828 | RAB28 | RAB28, member RAS oncogene family | −1.52 | 3.772E-08 | 9364 |

-continued

| Probe ID | Gene_symbol | Description | Fold Change | p-value | Entrez_gene |
|---|---|---|---|---|---|
| PH_hs_0001647 | CDC42BPA | CDC42 binding protein kinase alpha (DMPK-like) | -1.52 | 1.093E-02 | 8476 |
| PH_hs_0036173 | PHLDA1 | pleckstrin homology-like domain, family A, member 1 | -1.52 | 6.756E-03 | 22822 |
| PH_hs_0014144 | IGFBP6 | insulin-like growth factor binding protein 6 | -1.51 | 1.443E-04 | 3489 |
| PH_hs_0002729 | RAB32 | RAB32, member RAS oncogene family | -1.51 | 3.247E-07 | 10981 |
| PH_hs_0024838 | HOMER3 | homer homolog 3 (Drosophila) | -1.51 | 1.595E-06 | 9454 |
| PH_hs_0004294 | CHAF1B | chromatin assembly factor 1, subunit B (p60) | -1.51 | 1.896E-04 | 8208 |
| PH_hs_0019868 | NUDT2 | nudix (nucleoside diphosphate linked moiety X)-type motif 2 | -1.51 | 2.029E-04 | 318 |
| PH_hs_0048583 | ARSB | arylsulfatase B | -1.51 | 7.077E-03 | 411 |
| PH_hs_0026399 | WSB2 | WD repeat and SOCS box-containing 2 | -1.51 | 3.959E-04 | 55884 |
| PH_hs_0009365 | GBF1 | golgi brefeldin A resistant guanine nucleotide exchange factor 1 | -1.51 | 7.727E-04 | 8729 |
| PH_hs_0002134 | EML2 | echinoderm microtubule associated protein like 2 | -1.51 | 6.098E-05 | 24139 |
| PH_hs_0004460 | PLP2 | proteolipid protein 2 (colonic epithelium-enriched) | -1.51 | 1.066E-03 | 5355 |
| PH_hs_0016002 | OSBPL6 | oxysterol binding protein-like 6 | -1.51 | 3.213E-04 | 114880 |
| PH_hs_0040227 | CCT2 | chaperonin containing TCP1, subunit 2 (beta) | -1.51 | 1.726E-03 | 10576 |
| PH_hs_0043346 | MMS22L | MMS22-like, DNA repair protein | -1.51 | 5.604E-03 | 253714 |
| PH_hs_0043854 | YWHAZ | tyrosine 3-monooxygenase/tryptophan 5-monooxygenase activation protein, zeta polypeptide | -1.51 | 5.534E-03 | 7534 |
| PH_hs_0028426 | CPSF2 | cleavage and polyadenylation specific factor 2, 100 kDa | -1.51 | 3.959E-05 | 53981 |
| PH_hs_0003307 | IFFO1 | intermediate filament family orphan 1 | -1.51 | 3.000E-03 | 25900 |
| PH_hs_0002624 | C1orf183 | chromosome 1 open reading frame 183 | -1.51 | 2.437E-02 | 55924 |
| PH_hs_0043283 | AVL9 | AVL9 homolog (S. cerevisiae) | -1.51 | 5.360E-03 | 23080 |
| PH_hs_0002454 | STK32C | serine/threonine kinase 32C | -1.51 | 1.680E-03 | 282974 |
| PH_hs_0023205 | NACC2 | NACC family member 2, BEN and BTB (POZ) domain containing | -1.51 | 4.284E-05 | 138151 |
| PH_hs_0022730 | AARS2 | alanyl-tRNA synthetase 2, mitochondrial (putative) | -1.51 | 8.329E-04 | 57505 |
| PH_hs_0022481 | SLC38A1 | solute carrier family 38, member 1 | -1.51 | 8.055E-03 | 81539 |
| PH_hs_0011979 | HELLS | helicase, lymphoid-specific | -1.51 | 5.647E-05 | 3070 |
| PH_hs_0023943 | DYNC1LI1 | dynein, cytoplasmic 1, light intermediate chain 1 | -1.51 | 2.582E-07 | 51143 |
| PH_hs_0048423 | MTHFD2L | methylenetetrahydrofolate dehydrogenase (NADP+ dependent) 2-like | -1.51 | 2.343E-05 | 441024 |
| PH_hs_0043722 | HSPE1 | heat shock 10 kDa protein 1 (chaperonin 10) | -1.51 | 1.243E-05 | 3336 |
| PH_hs_0046245 | RN7SK | RNA, 7SK small nuclear | -1.50 | 7.331E-03 | 125050 |
| PH_hs_0042076 | MND1 | meiotic nuclear divisions 1 homolog (S. cerevisiae) | -1.50 | 8.546E-04 | 84057 |
| PH_hs_0033252 | CCT8 | chaperonin containing TCP1, subunit 8 (theta) | -1.50 | 4.221E-04 | 10694 |
| PH_hs_0017250 | MRPL52 | mitochondrial ribosomal protein L52 | -1.50 | 1.191E-04 | 122704 |
| PH_hs_0004748 | CRYZ | crystallin, zeta (quinone reductase) | -1.50 | 1.292E-04 | 1429 |
| PH_hs_0048353 | DGKG | diacylglycerol kinase, gamma 90 kDa | -1.50 | 4.838E-03 | 1608 |
| PH_hs_0016106 | WDR54 | WD repeat domain 54 | -1.50 | 8.701E-07 | 84058 |
| PH_hs_0014646 | CENPN | centromere protein N | -1.50 | 3.810E-04 | 55839 |
| PH_hs_0046162 | ZNF655 | zinc finger protein 655 | -1.50 | 5.230E-03 | 79027 |
| PH_hs_0042329 | C14orf129 | chromosome 14 open reading frame 129 | -1.50 | 1.286E-02 | 51527 |
| PH_hs_0027429 | PGD | phosphogluconate dehydrogenase | -1.50 | 1.210E-02 | 5226 |
| PH_hs_0043881 | PAIP1 | poly(A) binding protein interacting protein 1 | 1.50 | 2.633E-04 | 10605 |
| PH_hs_0045400 | CLYBL | citrate lyase beta like | 1.50 | 4.115E-05 | 171425 |
| PH_hs_0043595 | CD2BP2 | CD2 (cytoplasmic tail) binding protein 2 | 1.50 | 1.797E-05 | 10421 |
| PH_hs_0048644 | UBFD1 | ubiquitin family domain containing 1 | 1.50 | 1.980E-04 | 56061 |
| PH_hs_0047552 | PHF20L1 | PHD finger protein 20-like 1 | 1.50 | 1.004E-04 | 51105 |
| PH_hs_0026183 | GGN | gametogenetin | 1.50 | 5.191E-03 | 199720 |
| PH_hs_0003403 | SCFD2 | sec1 family domain containing 2 | 1.50 | 1.088E-02 | 152579 |
| PH_hs_0048448 | CTSC | cathepsin C | 1.50 | 4.601E-04 | 1075 |
| PH_hs_0024651 | KIAA0564 | KIAA0564 | 1.50 | 2.283E-02 | 23078 |
| PH_hs_0003439 | BACE1 | beta-site APP-cleaving enzyme 1 | 1.50 | 1.051E-05 | 23621 |
| PH_hs_0043807 | SNORD36C | small nucleolar RNA, C/D box 36C | 1.50 | 2.005E-02 | 26813 |
| PH_hs_0006004 | APH1A | anterior pharynx defective 1 homolog A (C. elegans) | 1.50 | 4.814E-07 | 51107 |

-continued

| Probe ID | Gene_symbol | Description | Fold Change | p-value | Entrez_gene |
|---|---|---|---|---|---|
| PH_hs_0048482 | RNF41 | ring finger protein 41 | 1.51 | 3.158E-04 | 10193 |
| PH_hs_0025673 | POLI | polymerase (DNA directed) iota | 1.51 | 7.395E-05 | 11201 |
| PH_hs_0016735 | MTMR1 | myotubularin related protein 1 | 1.51 | 1.677E-03 | 8776 |
| PH_hs_0047917 | ZNF22 | zinc finger protein 22 (KOX 15) | 1.51 | 8.036E-05 | 7570 |
| PH_hs_0013712 | FLVCR2 | feline leukemia virus subgroup C cellular receptor family, member 2 | 1.51 | 3.284E-04 | 55640 |
| PH_hs_0043122 | C8orf58 | chromosome 8 open reading frame 58 | 1.51 | 1.542E-02 | 541565 |
| PH_hs_0004469 | COX10 | COX10 homolog, cytochrome c oxidase assembly protein, heme A: farnesyltransferase (yeast) | 1.51 | 1.901E-05 | 1352 |
| PH_hs_0032150 | ACO2 | aconitase 2, mitochondrial | 1.51 | 3.217E-05 | 50 |
| PH_hs_0002405 | LOC728769 | hypothetical LOC728769 | 1.51 | 2.871E-04 | 728769 |
| PH_hs_0047565 | SCAI | suppressor of cancer cell invasion | 1.51 | 4.964E-02 | 286205 |
| PH_hs_0020536 | PCNXL2 | pecanex-like 2 (Drosophila) | 1.51 | 8.610E-04 | 80003 |
| PH_hs_0004941 | LYPLAL1 | lysophospholipase-like 1 | 1.51 | 3.513E-05 | 127018 |
| PH_hs_0004372 | PDLIM1 | PDZ and LIM domain 1 | 1.51 | 1.027E-10 | 9124 |
| PH_hs_0001012 | NDFIP1 | Nedd4 family interacting protein 1 | 1.51 | 8.944E-06 | 80762 |
| PH_hs_0000383 | ZBTB6 | zinc finger and BTB domain containing 6 | 1.51 | 1.593E-04 | 10773 |
| PH_hs_0038333 | CD3D | CD3d molecule, delta (CD3-TCR complex) | 1.51 | 6.190E-03 | 915 |
| PH_hs_0014077 | PPP3CA | protein phosphatase 3, catalytic subunit, alpha isozyme | 1.51 | 3.067E-04 | 5530 |
| PH_hs_0023907 | LOC729678 | hypothetical LOC729678 | 1.51 | 7.940E-04 | 729678 |
| PH_hs_0010397 | LRRC8A | leucine rich repeat containing 8 family, member A | 1.51 | 7.358E-07 | 56262 |
| PH_hs_0010861 | ASPHD2 | aspartate beta-hydroxylase domain containing 2 | 1.51 | 2.650E-04 | 57168 |
| PH_hs_0003128 | CWC15 | CWC15 spliceosome-associated protein homolog (S. cerevisiae) | 1.51 | 9.358E-03 | 51503 |
| PH_hs_0000400 | HSPA6/HSPA7 | heat shock 70 kDa protein 6 (HSP70B')/heat shock 70 kDa protein 7 (HSP70B) | 1.51 | 3.097E-04 | 3310/3311 |
| PH_hs_0001871 | AGTPBP1 | ATP/GTP binding protein 1 | 1.51 | 9.026E-03 | 23287 |
| PH_hs_0000185 | EGR2 | early growth response 2 | 1.51 | 6.131E-03 | 1959 |
| PH_hs_0024220 | ARHGEF6 | Rac/Cdc42 guanine nucleotide exchange factor (GEF) 6 | 1.51 | 7.994E-04 | 9459 |
| PH_hs_0006447 | SLC22A1 | solute carrier family 22 (organic cation transporter), member 1 | 1.51 | 2.535E-02 | 6580 |
| PH_hs_0005008 | TKT | transketolase | 1.51 | 1.316E-05 | 7086 |
| PH_hs_0048391 | TNKS | tankyrase, TRF1-interacting ankyrin-related ADP-ribose polymerase | 1.52 | 3.244E-05 | 8658 |
| PH_hs_0004304 | UBE4A | ubiquitination factor E4A (UFD2 homolog, yeast) | 1.52 | 2.617E-06 | 9354 |
| PH_hs_0048671 | RSL1D1 | ribosomal L1 domain containing 1 | 1.52 | 4.283E-07 | 26156 |
| PH_hs_0048540 | PPAPDC1B | phosphatidic acid phosphatase type 2 domain containing 1B | 1.52 | 5.595E-05 | 84513 |
| PH_hs_0016168 | TBC1D17 | TBC1 domain family, member 17 | 1.52 | 1.279E-04 | 79735 |
| PH_hs_0015637 | KCTD10 | potassium channel tetramerisation domain containing 10 | 1.52 | 1.879E-05 | 83892 |
| PH_hs_0023033 | SPTBN1 | spectrin, beta, non-erythrocytic 1 | 1.52 | 6.840E-03 | 6711 |
| PH_hs_0016601 | MYLK3 | myosin light chain kinase 3 | 1.52 | 2.776E-02 | 91807 |
| PH_hs_0045413 | ISPD | isoprenoid synthase domain containing | 1.52 | 3.156E-03 | 729920 |
| PH_hs_0001800 | PCBP4 | poly(rC) binding protein 4 | 1.52 | 1.341E-03 | 57060 |
| PH_hs_0018078 | ZNF433 | zinc finger protein 433 | 1.52 | 1.872E-03 | 163059 |
| PH_hs_0004727 | THAP11 | THAP domain containing 11 | 1.52 | 3.289E-02 | 57215 |
| PH_hs_0045886 | ABCC3 | ATP-binding cassette, sub-family C (CFTR/MRP), member 3 | 1.52 | 4.111E-02 | 8714 |
| PH_hs_0048645 | JMJD6 | jumonji domain containing 6 | 1.52 | 4.753E-03 | 23210 |
| PH_hs_0004786 | EFR3A | EFR3 homolog A (S. cerevisiae) | 1.52 | 5.120E-03 | 23167 |
| PH_hs_0024084 | GMPR2 | guanosine monophosphate reductase 2 | 1.52 | 1.927E-02 | 51292 |
| PH_hs_0022118 | TSPAN6 | tetraspanin 6 | 1.52 | 8.438E-08 | 7105 |
| PH_hs_0024849 | SMAP1 | small ArfGAP 1 | 1.52 | 8.788E-06 | 60682 |
| PH_hs_0000168 | BMP1 | bone morphogenetic protein 1 | 1.52 | 2.780E-02 | 649 |
| PH_hs_0042131 | UNC5B | unc-5 homolog B (C. elegans) | 1.52 | 6.477E-05 | 219699 |
| PH_hs_0004107 | HMG20A | high-mobility group 20A | 1.52 | 3.115E-04 | 10363 |
| PH_hs_0005691 | DCAF12 | DDB1 and CUL4 associated factor 12 | 1.52 | 2.355E-05 | 25853 |
| PH_hs_0048600 | FAM83A | family with sequence similarity 83, member A | 1.52 | 6.789E-03 | 84985 |
| PH_hs_0032001 | C4orf3 | chromosome 4 open reading frame 3 | 1.53 | 8.890E-03 | 401152 |

-continued

| Probe ID | Gene_symbol | Description | Fold Change | p-value | Entrez_gene |
|---|---|---|---|---|---|
| PH_hs_0001041 | MLLT1 | myeloid/lymphoid or mixed-lineage leukemia (trithorax homolog, Drosophila); translocated to, 1 | 1.53 | 5.645E-03 | 4298 |
| PH_hs_0009558 | MOCOS | molybdenum cofactor sulfurase | 1.53 | 8.519E-03 | 55034 |
| PH_hs_0025759 | PINK1 | PTEN induced putative kinase 1 | 1.53 | 8.950E-03 | 65018 |
| PH_hs_0048966 | TET2 | tet oncogene family member 2 | 1.53 | 3.614E-05 | 54790 |
| PH_hs_0043745 | ERGIC3 | ERGIC and golgi 3 | 1.53 | 1.094E-04 | 51614 |
| PH_hs_0004918 | ALDH3B2 | aldehyde dehydrogenase 3 family, member B2 | 1.53 | 1.294E-04 | 222 |
| PH_hs_0000975 | CRELD1 | cysteine-rich with EGF-like domains 1 | 1.53 | 1.854E-03 | 78987 |
| PH_hs_0000785 | C19orf25 | chromosome 19 open reading frame 25 | 1.53 | 3.172E-05 | 148223 |
| PH_hs_0018872 | PRRC2B | proline-rich coiled-coil 2B | 1.53 | 1.716E-05 | 84726 |
| PH_hs_0015541 | ZNF688 | zinc finger protein 688 | 1.53 | 1.740E-02 | 146542 |
| PH_hs_0025301 | PREP | prolyl endopeptidase | 1.53 | 3.247E-02 | 5550 |
| PH_hs_0024410 | FBXO18 | F-box protein, helicase, 18 | 1.53 | 1.225E-02 | 84893 |
| PH_hs_0046233 | PWWP2A | PWWP domain containing 2A | 1.53 | 4.429E-05 | 114825 |
| PH_hs_0049034 | PRRC1 | proline-rich coiled-coil 1 | 1.53 | 4.088E-06 | 133619 |
| PH_hs_0046198 | KBTBD7 | kelch repeat and BTB (POZ) domain containing 7 | 1.53 | 2.960E-03 | 84078 |
| PH_hs_0030171 | HIGD2A\|LOC100506614 | HIG1 hypoxia inducible domain family, member 2A\|HIG1 domain family member 2A-like | 1.53 | 2.577E-04 | 192286\|100506614 |
| PH_hs_0022591 | METAP2 | methionyl aminopeptidase 2 | 1.53 | 4.749E-04 | 10988 |
| PH_hs_0042234 | AVEN | apoptosis, caspase activation inhibitor | 1.53 | 8.367E-05 | 57099 |
| PH_hs_0048476 | LOC284023 | hypothetical LOC284023 | 1.53 | 1.885E-04 | 284023 |
| PH_hs_0025536 | FAP | fibroblast activation protein, alpha | 1.53 | 1.381E-03 | 2191 |
| PH_hs_0004756 | C7orf36 | chromosome 7 open reading frame 36 | 1.53 | 1.277E-06 | 57002 |
| PH_hs_0044296 | EIF4E2 | eukaryotic translation initiation factor 4E family member 2 | 1.53 | 1.536E-03 | 9470 |
| PH_hs_0025084 | GIT2 | G protein-coupled receptor kinase interacting ArfGAP 2 | 1.53 | 8.645E-05 | 9815 |
| PH_hs_0044758 | N4BP2L2 | NEDD4 binding protein 2-like 2 | 1.53 | 2.744E-03 | 10443 |
| PH_hs_0049234 | VPS13D | vacuolar protein sorting 13 homolog D (S. cerevisiae) | 1.53 | 1.215E-04 | 55187 |
| PH_hs_0000638 | NAV1 | neuron navigator 1 | 1.53 | 1.732E-04 | 89796 |
| PH_hs_0009353 | ALDOC | aldolase C, fructose-bisphosphate | 1.53 | 7.378E-04 | 230 |
| PH_hs_0010455 | TMEM41B | transmembrane protein 41B | 1.53 | 3.761E-04 | 440026 |
| PH_hs_0027444 | TMEM183A\|TMEM183B | transmembrane protein 183A\|transmembrane protein 183B | 1.53 | 8.395E-08 | 92703\|653659 |
| PH_hs_0035954 | COX6B1 | cytochrome c oxidase subunit VIb polypeptide 1 (ubiquitous) | 1.54 | 5.741E-06 | 1340 |
| PH_hs_0047622 | PLEKHA2 | pleckstrin homology domain containing, family A (phosphoinositide binding specific) member 2 | 1.54 | 4.550E-04 | 59339 |
| PH_hs_0027276 | POLR2A | polymerase (RNA) II (DNA directed) polypeptide A, 220 kDa | 1.54 | 1.208E-05 | 5430 |
| PH_hs_0016038 | SAMD14 | sterile alpha motif domain containing 14 | 1.54 | 4.183E-06 | 201191 |
| PH_hs_0049628 | DNAJB6 | DnaJ (Hsp40) homolog, subfamily B, member 6 | 1.54 | 2.288E-04 | 10049 |
| PH_hs_0048596 | FBXW11 | F-box and WD repeat domain containing 11 | 1.54 | 3.613E-06 | 23291 |
| PH_hs_0044398 | KIAA0319L | KIAA0319-like | 1.54 | 6.188E-07 | 79932 |
| PH_hs_0020045 | EXOSC6 | exosome component 6 | 1.54 | 1.294E-05 | 118460 |
| PH_hs_0000767 | TFB2M | transcription factor B2, mitochondrial | 1.54 | 2.152E-07 | 64216 |
| PH_hs_0034852 | PCYT2 | phosphate cytidylyltransferase 2, ethanolamine | 1.54 | 5.404E-04 | 5833 |
| PH_hs_0033414 | DOCK1 | dedicator of cytokinesis 1 | 1.54 | 1.046E-03 | 1793 |
| PH_hs_0043219 | FAM49B | family with sequence similarity 49, member B | 1.54 | 3.796E-03 | 51571 |
| PH_hs_0033727 | UBE2E3 | ubiquitin-conjugating enzyme E2E 3 (UBC4/5 homolog, yeast) | 1.54 | 1.087E-04 | 10477 |
| PH_hs_0047945 | PDE4D | phosphodiesterase 4D, cAMP-specific | 1.54 | 8.361E-03 | 5144 |
| PH_hs_0009339 | CA2 | carbonic anhydrase II | 1.54 | 7.809E-04 | 760 |
| PH_hs_0047971 | ZC3H4 | zinc finger CCCH-type containing 4 | 1.54 | 2.618E-05 | 23211 |
| PH_hs_0049011 | GRIP1 | glutamate receptor interacting protein 1 | 1.54 | 1.326E-04 | 23426 |
| PH_hs_0032559 | GCN1L1 | GCN1 general control of amino-acid synthesis 1-like 1 (yeast) | 1.54 | 1.606E-03 | 10985 |
| PH_hs_0010814 | NOL6 | nucleolar protein family 6 (RNA-associated) | 1.54 | 3.008E-05 | 65083 |
| PH_hs_0005005 | PTHLH | parathyroid hormone-like hormone | 1.54 | 1.241E-03 | 5744 |

-continued

| Probe ID | Gene_symbol | Description | Fold Change | p-value | Entrez_gene |
|---|---|---|---|---|---|
| PH_hs_0030094 | LGALS3 | lectin, galactoside-binding, soluble, 3 | 1.54 | 1.676E-06 | 3958 |
| PH_hs_0029625 | B3GALT6 | UDP-Gal: betaGal beta 1,3-galactosyltransferase polypeptide 6 | 1.55 | 1.468E-04 | 126792 |
| PH_hs_0022323 | ST5 | suppression of tumorigenicity 5 | 1.55 | 7.224E-05 | 6764 |
| PH_hs_0009186 | GBAS | glioblastoma amplified sequence | 1.55 | 2.304E-04 | 2631 |
| PH_hs_0023193 | PLEKHA5 | pleckstrin homology domain containing, family A member 5 | 1.55 | 1.799E-03 | 54477 |
| PH_hs_0004643 | PCCA | propionyl CoA carboxylase, alpha polypeptide | 1.55 | 9.936E-08 | 5095 |
| PH_hs_0000531 | GMFG | glia maturation factor, gamma | 1.55 | 1.651E-03 | 9535 |
| PH_hs_0002963 | C18orf21 | chromosome 18 open reading frame 21 | 1.55 | 5.907E-03 | 83608 |
| PH_hs_0047295 | KLHL7 | kelch-like 7 (Drosophila) | 1.55 | 1.097E-05 | 55975 |
| PH_hs_0008777 | C1orf123 | chromosome 1 open reading frame 123 | 1.55 | 6.129E-07 | 54987 |
| PH_hs_0045514 | ATP5J | ATP synthase, H+ transporting, mitochondrial Fo complex, subunit F6 | 1.55 | 7.689E-05 | 522 |
| PH_hs_0004522 | ZNF133 | zinc finger protein 133 | 1.55 | 2.580E-06 | 7692 |
| PH_hs_0025950 | POU2F1 | POU class 2 homeobox 1 | 1.55 | 2.104E-02 | 5451 |
| PH_hs_0019788 | LOC100128239 | hypothetical LOC100128239 | 1.55 | 5.510E-04 | 100128239 |
| PH_hs_0048539 | BIRC6 | baculoviral IAP repeat-containing 6 | 1.55 | 2.960E-05 | 57448 |
| PH_hs_0110855 | FBXO21 | F-box protein 21 | 1.55 | 1.943E-05 | 23014 |
| PH_hs_0039715 | EIF2AK1 | eukaryotic translation initiation factor 2-alpha kinase 1 | 1.55 | 1.187E-04 | 27102 |
| PH_hs_0024999 | MEF2A | myocyte enhancer factor 2A | 1.55 | 4.262E-04 | 4205 |
| PH_hs_0028746 | SFRS18 | splicing factor, arginine/serine-rich 18 | 1.55 | 2.577E-03 | 25957 |
| PH_hs_0048431 | EBAG9 | estrogen receptor binding site associated, antigen, 9 | 1.55 | 4.614E-08 | 9166 |
| PH_hs_0016039 | LUZP1 | leucine zipper protein 1 | 1.55 | 4.034E-05 | 7798 |
| PH_hs_0036083 | HIST1H2BO | histone cluster 1, H2bo | 1.55 | 9.118E-03 | 8348 |
| PH_hs_0042922 | ZNRF1 | zinc and ring finger 1 | 1.55 | 7.343E-03 | 84937 |
| PH_hs_0048199 | LYRM5 | LYR motif containing 5 | 1.55 | 1.915E-06 | 144363 |
| PH_hs_0049208 | TMEM120B | transmembrane protein 120B | 1.55 | 8.962E-05 | 144404 |
| PH_hs_0022563 | RAB3GAP2 | RAB3 GTPase activating protein subunit 2 (non-catalytic) | 1.55 | 2.390E-08 | 25782 |
| PH_hs_0042429 | CASP3 | caspase 3, apoptosis-related cysteine peptidase | 1.55 | 3.907E-06 | 836 |
| PH_hs_0005685 | FDX1 | ferredoxin 1 | 1.56 | 8.693E-04 | 2230 |
| PH_hs_0024939 | NTN4 | netrin 4 | 1.56 | 2.472E-03 | 59277 |
| PH_hs_0031479 | ARHGAP18 | Rho GTPase activating protein 18 | 1.56 | 6.715E-04 | 93663 |
| PH_hs_0043827 | ZNF12 | zinc finger protein 12 | 1.56 | 1.858E-06 | 7559 |
| PH_hs_0049288 | SSBP3 | single stranded DNA binding protein 3 | 1.56 | 8.140E-05 | 23648 |
| PH_hs_0000824 | OPTN | optineurin | 1.56 | 9.636E-04 | 10133 |
| PH_hs_0049396 | AFTPH | aftiphilin | 1.56 | 1.799E-06 | 54812 |
| PH_hs_0048450 | C19orf12 | chromosome 19 open reading frame 12 | 1.56 | 1.255E-02 | 83636 |
| PH_hs_0026865 | CSRNP2 | cysteine-serine-rich nuclear protein 2 | 1.56 | 6.262E-05 | 81566 |
| PH_hs_0047426 | TTBK2 | tau tubulin kinase 2 | 1.56 | 1.531E-04 | 146057 |
| PH_hs_0004351 | CD58 | CD58 molecule | 1.56 | 6.131E-03 | 965 |
| PH_hs_0009296 | SS18L1 | synovial sarcoma translocation gene on chromosome 18-like 1 | 1.56 | 8.882E-05 | 26039 |
| PH_hs_0025428 | ATAD1 | ATPase family, AAA domain containing 1 | 1.56 | 2.530E-02 | 84896 |
| PH_hs_0048165 | HUWE1 | HECT, UBA and WWE domain containing 1 | 1.56 | 4.140E-02 | 10075 |
| PH_hs_0049522 | GCOM1|GRINL1A | GRINL1A complex locus|glutamate receptor, ionotropic, N-methyl D-aspartate-like 1A | 1.56 | 1.726E-07 | 145781|81488 |
| PH_hs_0026865 | IQCG | IQ motif containing G | 1.56 | 3.815E-05 | 84223 |
| PH_hs_0049719 | ZNF286A/ZNF286B | zinc finger protein 286A|zinc finger protein 286B | 1.56 | 1.631E-07 | 57335|729288 |
| PH_hs_0032018 | C14orf4 | chromosome 14 open reading frame 4 | 1.56 | 3.766E-02 | 64207 |
| PH_hs_0024650 | OGT | O-linked N-acetylglucosamine (GlcNAc) transferase (UDP-N-acetylglucosamine: polypeptide-N-acetylglucosaminyl transferase) | 1.56 | 2.950E-06 | 8473 |
| PH_hs_0017245 | GPT2 | glutamic pyruvate transaminase (alanine aminotransferase) 2 | 1.56 | 1.058E-07 | 84706 |
| PH_hs_0032724 | RHPN2 | rhophilin, Rho GTPase binding protein 2 | 1.56 | 8.249E-03 | 85415 |
| PH_hs_0045351 | CSNK1A1 | casein kinase 1, alpha 1 | 1.57 | 1.154E-02 | 1452 |
| PH_hs_0048038 | MAVS | mitochondrial antiviral signaling protein | 1.57 | 1.928E-02 | 57506 |

-continued

| Probe ID | Gene_symbol | Description | Fold Change | p-value | Entrez_gene |
|---|---|---|---|---|---|
| PH_hs_0004369 | GTF3C2 | general transcription factor IIIC, polypeptide 2, beta 110 kDa | 1.57 | 2.550E-05 | 2976 |
| PH_hs_0012636 | C12orf59 | chromosome 12 open reading frame 59 | 1.57 | 5.695E-04 | 120939 |
| PH_hs_0027047 | PSEN1 | presenilin 1 | 1.57 | 6.207E-08 | 5663 |
| PH_hs_0025563 | POLG2 | polymerase (DNA directed), gamma 2, accessory subunit | 1.57 | 4.194E-02 | 11232 |
| PH_hs_0044185 | SC4MOL | sterol-C4-methyl oxidase-like | 1.57 | 4.298E-05 | 6307 |
| PH_hs_0049284 | KCNE4 | potassium voltage-gated channel, Isk-related family, member 4 | 1.57 | 1.170E-04 | 23704 |
| PH_hs_0033019 | CLEC16A | C-type lectin domain family 16, member A | 1.57 | 2.175E-04 | 23274 |
| PH_hs_0004621 | G6PD | glucose-6-phosphate dehydrogenase | 1.57 | 4.259E-11 | 2539 |
| PH_hs_0008936 | CNFN | cornifelin | 1.57 | 2.439E-03 | 84518 |
| PH_hs_0011767 | SCAMP3 | secretory carrier membrane protein 3 | 1.57 | 9.620E-04 | 10067 |
| PH_hs_0016122 | SLC1A4 | solute carrier family 1 (glutamate/neutral amino acid transporter), member 4 | 1.57 | 2.182E-04 | 6509 |
| PH_hs_0022142 | TTC39B | tetratricopeptide repeat domain 39B | 1.57 | 4.096E-02 | 158219 |
| PH_hs_0045419 | C3orf74 | chromosome 3 open reading frame 74 | 1.57 | 9.866E-04 | 100128378 |
| PH_hs_0030874 | SRGN | serglycin | 1.57 | 1.624E-04 | 5552 |
| PH_hs_0048143 | CCDC28A | coiled-coil domain containing 28A | 1.58 | 9.407E-04 | 25901 |
| PH_hs_0044123 | C11orf1 | chromosome 11 open reading frame 1 | 1.58 | 1.074E-05 | 64776 |
| PH_hs_0004165 | TBC1D14 | TBC1 domain family, member 14 | 1.58 | 1.030E-04 | 57533 |
| PH_hs_0002175 | SH3D19 | SH3 domain containing 19 | 1.58 | 7.045E-06 | 152503 |
| PH_hs_0024840 | UBR5 | ubiquitin protein ligase E3 component n-recognin 5 | 1.58 | 2.780E-03 | 51366 |
| PH_hs_0022141 | AMACR | alpha-methylacyl-CoA racemase | 1.58 | 4.17E-03 | 23600 |
| PH_hs_0027132 | CELSR2 | cadherin, EGF LAG seven-pass G-type receptor 2 (flamingo homolog, Drosophila) | 1.58 | 3.447E-05 | 1952 |
| PH_hs_0013522 | FYCO1 | FYVE and coiled-coil domain containing 1 | 1.58 | 2.311E-06 | 79443 |
| PH_hs_0045034 | SP100 | SP100 nuclear antigen | 1.58 | 7.247E-03 | 6672 |
| PH_hs_0035085 | PPARA | peroxisome proliferator-activated receptor alpha | 1.58 | 2.721E-05 | 5465 |
| PH_hs_0031001 | ACTR3B\|LOC100290215 | ARP3 actin-related protein 3 homolog B (yeast)\|actin-related protein 3B-like | 1.58 | 9.928E-03 | 57180\|100290215 |
| PH_hs_0031048 | ZSCAN21 | zinc finger and SCAN domain containing 21 | 1.58 | 1.902E-02 | 7589 |
| PH_hs_0003114 | MSC | musculin | 1.58 | 1.337E-03 | 9242 |
| PH_hs_0043581 | AIMP1 | aminoacyl tRNA synthetase complex-interacting multifunctional protein 1 | 1.58 | 4.000E-05 | 9255 |
| PH_hs_0048354 | C20orf11 | chromosome 20 open reading frame 11 | 1.59 | 4.137E-05 | 54994 |
| PH_hs_0048878 | RAD1 | RAD1 homolog (S. pombe) | 1.59 | 2.970E-06 | 5810 |
| PH_hs_0016338 | ORAI3 | ORAI calcium release-activated calcium modulator 3 | 1.59 | 1.111E-03 | 93129 |
| PH_hs_0014922 | PLEKHA1 | pleckstrin homology domain containing, family A (phosphoinositide binding specific) member 1 | 1.59 | 1.421E-03 | 59338 |
| PH_hs_0023122 | KIAA0182 | KIAA0182 | 1.59 | 1.038E-03 | 23199 |
| PH_hs_0048307 | PLA2G12A | phospholipase A2, group XIIA | 1.59 | 6.881E-05 | 81579 |
| PH_hs_0023005 | SNAP23 | synaptosomal-associated protein, 23 kDa | 1.59 | 1.444E-09 | 8773 |
| PH_hs_0043617 | UQCR10 | ubiquinol-cytochrome c reductase, complex III subunit X | 1.59 | 1.171E-06 | 29796 |
| PH_hs_0022779 | ANKRD10 | ankyrin repeat domain 10 | 1.59 | 4.515E-07 | 55608 |
| PH_hs_0022328 | FOXRED2 | FAD-dependent oxidoreductase domain containing 2 | 1.59 | 6.057E-05 | 80020 |
| PH_hs_0044173 | MFAP3 | microfibrillar-associated protein 3 | 1.59 | 1.286E-06 | 4238 |
| PH_hs_0025588 | ATP10D | ATPase, class V, type 10D | 1.59 | 1.417E-03 | 57205 |
| PH_hs_0011594 | KIAA0240 | KIAA0240 | 1.59 | 1.693E-03 | 23506 |
| PH_hs_0001803 | LHPP | phospholysine phosphohistidine inorganic pyrophosphate phosphatase | 1.59 | 9.655E-03 | 64077 |
| PH_hs_0014304 | EIF4EBP2 | eukaryotic translation initiation factor 4E binding protein 2 | 1.59 | 6.835E-05 | 1979 |
| PH_hs_0003753 | C16orf91 | chromosome 16 open reading frame 91 | 1.59 | 6.459E-04 | 283951 |
| PH_hs_0022328 | BRP44L | brain protein 44-like | 1.59 | 4.158E-06 | 51660 |
| PH_hs_0014106 | DCAF13\|LOC100132724 | DDB1 and CUL4 associated factor 13\|DDB1 and CUL4 associated factor 13 pseudogene | 1.59 | 5.874E-11 | 25879\|100132724 |
| PH_hs_0015077 | ESCO1 | establishment of cohesion 1 homolog 1 (S. cerevisiae) | 1.59 | 1.047E-05 | 114799 |
| PH_hs_0014660 | RNPEP | arginyl aminopeptidase (aminopeptidase B) | 1.60 | 3.948E-03 | 6051 |
| PH_hs_0046336 | FAM154B | family with sequence similarity 154, member B | 1.60 | 1.957E-03 | 283726 |

-continued

| Probe ID | Gene_symbol | Description | Fold Change | p-value | Entrez_gene |
|---|---|---|---|---|---|
| PH_hs_0045874 | TFEB | transcription factor EB | 1.60 | 1.545E-02 | 7942 |
| PH_hs_0030122 | CLNS1A | chloride channel, nucleotide-sensitive, 1A | 1.60 | 6.918E-07 | 1207 |
| PH_hs_0009587 | MSI1 | musashi homolog 1 (*Drosophila*) | 1.60 | 2.309E-02 | 4440 |
| PH_hs_0048517 | RG9MTD3 | RNA (guanine-9-) methyltransferase domain containing 3 | 1.60 | 9.403E-03 | 158234 |
| PH_hs_0032912 | MAU2 | MAU2 chromatid cohesion factor homolog (*C. elegans*) | 1.60 | 1.497E-02 | 23383 |
| PH_hs_0049428 | CRTAP | cartilage associated protein | 1.60 | 1.593E-09 | 10491 |
| PH_hs_0026756 | RRM2B | ribonucleotide reductase M2 B (TP53 inducible) | 1.60 | 2.110E-02 | 50484 |
| PH_hs_0020075 | LOC100506710 | hypothetical LOC100506710 | 1.60 | 2.700E-02 | 100506710 |
| PH_hs_0049738 | WBP1 | WW domain binding protein 1 | 1.60 | 3.799E-03 | 23559 |
| PH_hs_0002279 | LPIN3 | lipin 3 | 1.60 | 3.974E-02 | 64900 |
| PH_hs_0009258 | CBFA2T2 | core-binding factor, runt domain, alpha subunit 2; translocated to, 2 | 1.60 | 8.097E-07 | 9139 |
| PH_hs_0031558 | MAN2A2 | mannosidase, alpha, class 2A, member 2 | 1.60 | 7.157E-08 | 4122 |
| PH_hs_0016092 | YIPF2 | Yip1 domain family, member 2 | 1.60 | 1.427E-07 | 78992 |
| PH_hs_0002228 | PRSS23 | protease, serine, 23 | 1.60 | 9.689E-03 | 11098 |
| PH_hs_0009253 | PUM1 | pumilio homolog 1 (*Drosophila*) | 1.60 | 1.256E-06 | 9698 |
| PH_hs_0045052 | PHF14 | PHD finger protein 14 | 1.60 | 1.267E-09 | 9678 |
| PH_hs_0047595 | ZSCAN29 | zinc finger and SCAN domain containing 29 | 1.60 | 1.517E-04 | 146050 |
| PH_hs_0048120 | XAF1 | XIAP associated factor 1 | 1.60 | 5.328E-05 | 54739 |
| PH_hs_0012489 | JHDM1D | jumonji C domain containing histone demethylase 1 homolog D (*S. cerevisiae*) | 1.60 | 1.549E-02 | 80853 |
| PH_hs_0027917 | FAM173A | family with sequence similarity 173, member A | 1.60 | 2.586E-02 | 65990 |
| PH_hs_0048982 | MTSS1L | metastasis suppressor 1-like | 1.60 | 8.727E-03 | 92154 |
| PH_hs_0049657 | DEAF1\|LOC100294411\|LOC100510366 | deformed epidermal autoregulatory factor 1 (*Drosophila*)\|deformed epidermal autoregulatory factor 1 homolog\|deformed epidermal autoregulatory factor 1 homolog | 1.60 | 2.179E-02 | 10522\|100294411\|100510366 |
| PH_hs_0044463 | LEPRE1 | leucine proline-enriched proteoglycan (leprecan) 1 | 1.60 | 6.830E-04 | 64175 |
| PH_hs_0019278 | ATP9A | ATPase, class II, type 9A | 1.60 | 6.232E-05 | 10079 |
| PH_hs_0011495 | EZH1 | enhancer of zeste homolog 1 (*Drosophila*) | 1.60 | 1.167E-02 | 2145 |
| PH_hs_0001383 | IFI30 | interferon, gamma-inducible protein 30 | 1.60 | 1.553E-07 | 10437 |
| PH_hs_0033907 | C3orf37 | chromosome 3 open reading frame 37 | 1.60 | 1.830E-06 | 56941 |
| PH_hs_0045429 | CARD14 | caspase recruitment domain family, member 14 | 1.61 | 6.212E-03 | 79092 |
| PH_hs_0004131 | NLGN1 | neuroligin 1 | 1.61 | 4.238E-06 | 22871 |
| PH_hs_0043769 | YME1L1 | YME1-like 1 (*S. cerevisiae*) | 1.61 | 4.313E-06 | 10730 |
| PH_hs_0047505 | REV1 | REV1 homolog (*S. cerevisiae*) | 1.61 | 3.377E-03 | 51455 |
| PH_hs_0033483 | SUV420H1 | suppressor of variegation 4-20 homolog 1 (*Drosophila*) | 1.61 | 2.386E-06 | 51111 |
| PH_hs_0009246 | SGMS1 | sphingomyelin synthase 1 | 1.61 | 1.451E-05 | 259230 |
| PH_hs_0023732 | ORC3 | origin recognition complex, subunit 3 | 1.61 | 5.159E-10 | 23595 |
| PH_hs_0044172 | TBX6 | T-box 6 | 1.61 | 4.391E-05 | 6911 |
| PH_hs_0009272 | JDP2 | Jun dimerization protein 2 | 1.61 | 1.257E-05 | 122953 |
| PH_hs_0047502 | LYST | lysosomal trafficking regulator | 1.61 | 3.861E-05 | 1130 |
| PH_hs_0011689 | UBE2D4 | ubiquitin-conjugating enzyme E2D 4 (putative) | 1.61 | 2.288E-07 | 51619 |
| PH_hs_0005789 | ZNF195 | zinc finger protein 195 | 1.61 | 1.791E-04 | 7748 |
| PH_hs_0001062 | LIMA1 | LIM domain and actin binding 1 | 1.62 | 1.284E-02 | 51474 |
| PH_hs_0037014 | LOC283788 | FSHD region gene 1 pseudogene | 1.62 | 1.236E-03 | 283788 |
| PH_hs_0045072 | DNMT3A | DNA (cytosine-5-)-methyltransferase 3 alpha | 1.62 | 9.633E-05 | 1788 |
| PH_hs_0024031 | MEIS2 | Meis homeobox 2 | 1.62 | 1.225E-08 | 4212 |
| PH_hs_0048988 | PTPRJ | protein tyrosine phosphatase, receptor type, J | 1.62 | 1.211E-03 | 5795 |
| PH_hs_0025758 | SLC37A3 | solute carrier family 37 (glycerol-3-phosphate transporter), member 3 | 1.62 | 3.277E-04 | 84255 |
| PH_hs_0049273 | CERKL | ceramide kinase-like | 1.62 | 2.574E-02 | 375298 |
| PH_hs_0004334 | ANXA11 | annexin A11 | 1.62 | 1.755E-05 | 311 |
| PH_hs_0048118 | ADRA1B | adrenergic, alpha-1B-, receptor | 1.62 | 1.722E-02 | 147 |
| PH_hs_0022987 | WDR3 | WD repeat domain 3 | 1.62 | 2.639E-06 | 10885 |
| PH_hs_0033950 | NTN1 | netrin 1 | 1.62 | 1.653E-04 | 9423 |

| Probe ID | Gene_symbol | Description | Fold Change | p-value | Entrez_gene |
|---|---|---|---|---|---|
| PH_hs_0000457 | IFT20 | intraflagellar transport 20 homolog (Chlamydomonas) | 1.62 | 8.098E-08 | 90410 |
| PH_hs_0025978 | KIAA0895L | KIAA0895-like | 1.62 | 2.220E-06 | 653319 |
| PH_hs_0015931 | KILLIN | killin protein | 1.62 | 1.676E-02 | 100144748 |
| PH_hs_0030138 | NCOA4 | nuclear receptor coactivator 4 | 1.62 | 3.169E-02 | 8031 |
| PH_hs_0044163 | DNAJC4 | DnaJ (Hsp40) homolog, subfamily C, member 4 | 1.63 | 5.787E-05 | 3338 |
| PH_hs_0029640 | DGAT1 | diacylglycerol O-acyltransferase 1 | 1.63 | 9.096E-03 | 8694 |
| PH_hs_0014146 | CPT2 | carnitine palmitoyltransferase 2 | 1.63 | 3.949E-06 | 1376 |
| PH_hs_0033101 | DDIT3 | DNA-damage-inducible transcript 3 | 1.63 | 4.381E-07 | 1649 |
| PH_hs_0004516 | MYCBP|GJA9-MYCBP | c-myc binding protein|GJA9-MYCBP read-through transcript | 1.63 | 6.147E-06 | 26292|100527950 |
| PH_hs_0047608 | CCNG1 | cyclin G1 | 1.63 | 2.089E-09 | 900 |
| PH_hs_0043207 | IDI1 | isopentenyl-diphosphate delta isomerase 1 | 1.63 | 4.124E-03 | 3422 |
| PH_hs_0044933 | RAB4A | RAB4A, member RAS oncogene family | 1.63 | 2.044E-04 | 5867 |
| PH_hs_0049089 | ANKIB1 | ankyrin repeat and IBR domain containing 1 | 1.63 | 3.147E-05 | 54467 |
| PH_hs_0031757 | ZNF358 | zinc finger protein 358 | 1.63 | 5.418E-06 | 140467 |
| PH_hs_0047479 | PAFAH2 | platelet-activating factor acetylhydrolase 2, 40 kDa | 1.63 | 1.509E-04 | 5051 |
| PH_hs_0004550 | BTD | biotinidase | 1.63 | 1.471E-07 | 686 |
| PH_hs_0028609 | ZNF883 | zinc finger protein 883 | 1.63 | 5.789E-04 | 169834 |
| PH_hs_0043810 | TUT1 | terminal uridylyl transferase 1, U6 snRNA-specific | 1.63 | 1.455E-06 | 64852 |
| PH_hs_0035910 | C2orf79 | chromosome 2 open reading frame 79 | 1.63 | 1.321E-05 | 391356 |
| PH_hs_0000943 | PCOLCE2 | procollagen C-endopeptidase enhancer 2 | 1.63 | 9.240E-04 | 26577 |
| PH_hs_0019224 | CCDC137 | coiled-coil domain containing 137 | 1.63 | 7.104E-03 | 339230 |
| PH_hs_0045600 | ZDHHC15 | zinc finger, DHHC-type containing 15 | 1.63 | 1.855E-02 | 158866 |
| PH_hs_0044912 | HOXA4 | homeobox A4 | 1.64 | 1.112E-07 | 3201 |
| PH_hs_0002170 | KIAA0907 | KIAA0907 | 1.64 | 6.458E-10 | 22889 |
| PH_hs_0046354 | FAM149B1 | family with sequence similarity 149, member B1 | 1.64 | 8.722E-03 | 317662 |
| PH_hs_0000723 | PIGG | phosphatidylinositol glycan anchor biosynthesis, class G | 1.64 | 1.007E-07 | 54872 |
| PH_hs_0005689 | MADCAM1 | mucosal vascular addressin cell adhesion molecule 1 | 1.64 | 4.911E-04 | 8174 |
| PH_hs_0013010 | SLC2A6 | solute carrier family 2 (facilitated glucose transporter), member 6 | 1.64 | 3.664E-05 | 11182 |
| PH_hs_0029552 | IMMT | inner membrane protein, mitochondrial | 1.64 | 4.872E-05 | 10989 |
| PH_hs_0045062 | OAS2 | 2'-5'-oligoadenylate synthetase 2, 69/71 kDa | 1.64 | 1.995E-02 | 4939 |
| PH_hs_0023084 | ITGA6 | integrin, alpha 6 | 1.64 | 2.871E-02 | 3655 |
| PH_hs_0026675 | NT5DC1 | 5'-nucleotidase domain containing 1 | 1.64 | 3.635E-06 | 221294 |
| PH_hs_0029676 | BID | BH3 interacting domain death agonist | 1.64 | 2.786E-05 | 637 |
| PH_hs_0033245 | KLHDC2 | kelch domain containing 2 | 1.64 | 6.251E-07 | 23588 |
| PH_hs_0044326 | ZDHHC4 | zinc finger, DHHC-type containing 4 | 1.64 | 2.436E-07 | 55146 |
| PH_hs_0002393 | RCBTB2 | regulator of chromosome condensation (RCC1) and BTB (POZ) domain containing protein 2 | 1.64 | 1.148E-03 | 1102 |
| PH_hs_0002304 | TRPS1 | trichorhinophalangeal syndrome I | 1.64 | 8.441E-03 | 7227 |
| PH_hs_0049353 | NPR2 | natriuretic peptide receptor B/guanylate cyclase B (atrionatriuretic peptide receptor B) | 1.64 | 1.536E-08 | 4882 |
| PH_hs_0031026 | SGPL1 | sphingosine-1-phosphate lyase 1 | 1.64 | 2.770E-06 | 8879 |
| PH_hs_0004553 | C9orf23 | chromosome 9 open reading frame 23 | 1.64 | 1.784E-04 | 138716 |
| PH_hs_0028801 | AKAP1 | A kinase (PRKA) anchor protein 1 | 1.64 | 1.502E-05 | 8165 |
| PH_hs_0018576 | WDR45 | WD repeat domain 45 | 1.64 | 3.369E-03 | 11152 |
| PH_hs_0044278 | GABARAP | GABA(A) receptor-associated protein | 1.65 | 1.937E-08 | 11337 |
| PH_hs_0003532 | RAD51C | RAD51 homolog C (S. cerevisiae) | 1.65 | 2.771E-05 | 5889 |
| PH_hs_0024179 | TUG1 | taurine upregulated 1 (non-protein coding) | 1.65 | 7.814E-06 | 55000 |
| PH_hs_0010786 | ZNF227 | zinc finger protein 227 | 1.65 | 6.551E-04 | 7770 |
| PH_hs_0032689 | LOC100506469 | hypothetical LOC100506469 | 1.65 | 1.617E-04 | 100506469 |
| PH_hs_0029827 | ACAD10 | acyl-CoA dehydrogenase family, member 10 | 1.65 | 7.588E-04 | 80724 |
| PH_hs_0003364 | COX6C | cytochrome c oxidase subunit Vic | 1.65 | 3.069E-09 | 1345 |
| | WDR91 | WD repeat domain 91 | 1.65 | 3.741E-04 | 29062 |

-continued

| Probe ID | Gene_symbol | Description | Fold Change | p-value | Entrez_gene |
|---|---|---|---|---|---|
| PH_hs_0012404 | PAPD4 | PAP associated domain containing 4 | 1.65 | 2.586E-03 | 167153 |
| PH_hs_0016855 | C1orf131 | chromosome 1 open reading frame 131 | 1.65 | 4.999E-09 | 128061 |
| PH_hs_0022679 | BAZ2A | bromodomain adjacent to zinc finger domain, 2A | 1.65 | 2.181E-05 | 11176 |
| PH_hs_0023824 | CASP9 | caspase 9, apoptosis-related cysteine peptidase | 1.65 | 3.389E-07 | 842 |
| PH_hs_0045990 | MKRN1 | makorin ring finger protein 1 | 1.65 | 1.028E-07 | 23608 |
| PH_hs_0033427 | TPST2 | tyrosylprotein sulfotransferase 2 | 1.65 | 1.672E-05 | 8459 |
| PH_hs_0048332 | ZFP41 | zinc finger protein 41 homolog (mouse) | 1.65 | 1.482E-02 | 286128 |
| PH_hs_0005443 | CCDC88B | coiled-coil domain containing 88B | 1.65 | 9.200E-05 | 283234 |
| PH_hs_0045165 | KLF8 | Kruppel-like factor 8 | 1.65 | 8.970E-03 | 11279 |
| PH_hs_0004785 | APPBP2 | amyloid beta precursor protein (cytoplasmic tail) binding protein 2 | 1.65 | 7.063E-09 | 10513 |
| PH_hs_0025597 | NECAP2 | NECAP endocytosis associated 2 | 1.65 | 3.159E-05 | 55707 |
| PH_hs_0047382 | PTEN | phosphatase and tensin homolog | 1.65 | 4.096E-06 | 5728 |
| PH_hs_0016640 | EXOSC4 | exosome component 4 | 1.65 | 4.486E-09 | 54512 |
| PH_hs_0004539 | ZNF32 | zinc finger protein 32 | 1.65 | 1.262E-05 | 7580 |
| PH_hs_0043379 | TUBA1A | tubulin, alpha 1a | 1.66 | 9.471E-10 | 7846 |
| PH_hs_0027148 | SSR2 | signal sequence receptor, beta (translocon-associated protein beta) | 1.66 | 6.356E-06 | 6746 |
| PH_hs_0003841 | C19orf54 | chromosome 19 open reading frame 54 | 1.66 | 2.926E-08 | 284325 |
| PH_hs_0001589 | FLJ40852 | hypothetical LOC285962 | 1.66 | 6.666E-07 | 6046 |
| PH_hs_0004295 | BRD2 | bromodomain containing 2 | 1.66 | 7.008E-03 | 23387 |
| PH_hs_0049162 | SIK3 | SIK family kinase 3 | 1.66 | 2.242E-03 | 64924 |
| PH_hs_0044636 | SLC30A5 | solute carrier family 30 (zinc transporter), member 5 | 1.66 | 2.571E-07 | 11244 |
| PH_hs_0001241 | ZHX1 | zinc fingers and homeoboxes 1 | 1.66 | 1.463E-02 | 285962 |
| PH_hs_0017041 | HTR3C | 5-hydroxytryptamine (serotonin) receptor 3, family member C | 1.66 | 2.256E-04 | 170572 |
| PH_hs_0042819 | HRCT1 | histidine rich carboxyl terminus 1 | 1.66 | 4.303E-03 | 646962 |
| PH_hs_0043608 | FUT2 | fucosyltransferase 2 (secretor status included) | 1.66 | 4.174E-03 | 2524 |
| PH_hs_0044026 | LOC100129999 | hypothetical LOC100129999 | 1.66 | 3.297E-03 | 100129999 |
| PH_hs_0004373 | PCK2 | phosphoenolpyruvate carboxykinase 2 (mitochondrial) | 1.66 | 3.785E-06 | 5106 |
| PH_hs_0002243 | TGFB1I1 | transforming growth factor beta 1 induced transcript 1 | 1.66 | 6.547E-03 | 7041 |
| PH_hs_0000401 | CASP6 | caspase 6, apoptosis-related cysteine peptidase | 1.66 | 6.378E-09 | 839 |
| PH_hs_0011914 | RING1 | ring finger protein 1 | 1.66 | 4.582E-08 | 6015 |
| PH_hs_0026387 | TIGD7 | tigger transposable element derived 7 | 1.66 | 3.100E-02 | 91151 |
| PH_hs_0006967 | HAGHL | hydroxyacylglutathione hydrolase-like | 1.66 | 1.243E-06 | 84264 |
| PH_hs_0004292 | SEC14L1 | SEC14-like 1 (S. cerevisiae) | 1.66 | 4.703E-05 | 6397 |
| PH_hs_0022822 | RNF14 | ring finger protein 14 | 1.66 | 7.217E-06 | 9604 |
| PH_hs_0043191 | ESRRA | estrogen-related receptor alpha | 1.66 | 1.592E-05 | 2101 |
| PH_hs_0045284 | LOC100287188 | protein FAM104B-like | 1.66 | 3.688E-06 | 100287188 |
| PH_hs_0004376 | MLLT11 | myeloid/lymphoid or mixed-lineage leukemia (trithorax homolog, Drosophila); translocated to, 11 | 1.66 | 1.706E-10 | 10962 |
| PH_hs_0006941 | FBXO46 | F-box protein 46 | 1.66 | 1.841E-02 | 23403 |
| PH_hs_0047422 | AHR | aryl hydrocarbon receptor | 1.67 | 5.562E-10 | 196 |
| PH_hs_0020904 | MAN2A1 | mannosidase, alpha, class 2A, member 1 | 1.67 | 7.157E-08 | 4124 |
| PH_hs_0043712 | ENO3 | enolase 3 (beta, muscle) | 1.67 | 8.931E-04 | 2027 |
| PH_hs_0012892 | ANKRA2 | ankyrin repeat, family A (RFXANK-like), 2 | 1.67 | 1.064E-06 | 57763 |
| PH_hs_0047216 | C21orf91 | chromosome 21 open reading frame 91 | 1.67 | 4.654E-04 | 54149 |
| PH_hs_0004414 | SLC38A3 | solute carrier family 38, member 3 | 1.67 | 1.446E-02 | 10991 |
| PH_hs_0001741 | SYF2 | SYF2 homolog, RNA splicing factor (S. cerevisiae) | 1.67 | 1.989E-07 | 25949 |
| PH_hs_0043728 | ZNF706 | zinc finger protein 706 | 1.67 | 5.606E-05 | 51123 |
| PH_hs_0042863 | ZXDB | zinc finger, X-linked, duplicated B | 1.67 | 1.290E-06 | 158586 |
| PH_hs_0018969 | PAIP2 | poly(A) binding protein interacting protein 2 | 1.68 | 4.624E-09 | 51247 |
| PH_hs_0048231 | TMEM8B | transmembrane protein 8B | 1.68 | 2.743E-05 | 51754 |
| PH_hs_0029146 | HCN2 | hyperpolarization activated cyclic nucleotide-gated potassium channel 2 | 1.68 | 2.037E-03 | 610 |
| PH_hs_0026554 | FADS1 | fatty acid desaturase 1 | 1.68 | 3.140E-05 | 3992 |

-continued

| Probe ID | Gene_symbol | Description | Fold Change | p-value | Entrez_gene |
|---|---|---|---|---|---|
| PH_hs_0004683 | GYPC | glycophorin C (Gerbich blood group) | 1.68 | 2.865E-07 | 2995 |
| PH_hs_0008452 | ZBTB33 | zinc finger and BTB domain containing 33 | 1.68 | 6.550E-10 | 10009 |
| PH_hs_0013065 | SNRNP200 | small nuclear ribonucleoprotein 200 kDa (U5) | 1.68 | 5.073E-09 | 23020 |
| PH_hs_0043268 | COQ9 | coenzyme Q9 homolog (S. cerevisiae) | 1.68 | 4.103E-05 | 57017 |
| PH_hs_0002081 | MST4 | serine/threonine protein kinase MST4 | 1.68 | 2.108E-13 | 51765 |
| PH_hs_0010871 | SLC7A5 | solute carrier family 7 (cationic amino acid transporter, y+ system), member 5 | 1.68 | 3.951E-06 | 8140 |
| PH_hs_0028376 | INSIG1 | insulin induced gene 1 | 1.68 | 2.145E-05 | 3638 |
| PH_hs_0025814 | DDR2 | discoidin domain receptor tyrosine kinase 2 | 1.68 | 1.638E-05 | 4921 |
| PH_hs_0048961 | VPS36 | vacuolar protein sorting 36 homolog (S. cerevisiae) | 1.68 | 2.591E-04 | 51028 |
| PH_hs_0023950 | FCGR2A | Fc fragment of IgG, low affinity IIa, receptor (CD32) | 1.68 | 1.289E-03 | 2212 |
| PH_hs_0017080 | CDC42EP3 | CDC42 effector protein (Rho GTPase binding) 3 | 1.68 | 4.681E-09 | 10602 |
| PH_hs_0047312 | FAM200B | family with sequence similarity 200, member B | 1.68 | 2.126E-03 | 285550 |
| PH_hs_0023658 | RUFY1 | RUN and FYVE domain containing 1 | 1.68 | 1.233E-06 | 80230 |
| PH_hs_0042175 | ZNF7 | zinc finger protein 7 | 1.69 | 4.552E-04 | 7553 |
| PH_hs_0048105 | FAM117B | family with sequence similarity 117, member B | 1.69 | 1.004E-07 | 150864 |
| PH_hs_0027115 | C6orf203 | chromosome 6 open reading frame 203 | 1.69 | 6.111E-03 | 51250 |
| PH_hs_0049463 | UBTD2 | ubiquitin domain containing 2 | 1.69 | 5.780E-04 | 92181 |
| PH_hs_0043760 | GPS2 | G protein pathway suppressor 2 | 1.69 | 2.336E-07 | 2874 |
| PH_hs_0023932 | ATP5SL | ATP5S-like | 1.69 | 3.430E-09 | 55101 |
| PH_hs_0002159 | EFS | embryonal Fyn-associated substrate | 1.69 | 1.152E-02 | 10278 |
| PH_hs_0005189 | MCEE | methylmalonyl CoA epimerase | 1.69 | 1.962E-05 | 84693 |
| PH_hs_0022191 | MKNK1 | MAP kinase interacting serine/threonine kinase 1 | 1.69 | 5.955E-08 | 8569 |
| PH_hs_0033268 | VHL | von Hippel-Lindau tumor suppressor | 1.69 | 1.565E-06 | 7428 |
| PH_hs_0048569 | SORBS2 | sorbin and SH3 domain containing 2 | 1.69 | 2.761E-06 | 8470 |
| PH_hs_0004274 | TRIM9 | tripartite motif-containing 9 | 1.69 | 2.128E-05 | 114088 |
| PH_hs_0044328 | CAPS2 | calcyphosine 2 | 1.69 | 1.140E-04 | 84698 |
| PH_hs_0015555 | KIAA0513 | KIAA0513 | 1.69 | 7.975E-03 | 9764 |
| PH_hs_0014078 | DHRS2 | dehydrogenase/reductase (SDR family) member 2 | 1.69 | 9.406E-03 | 10202 |
| PH_hs_0005896 | JRKL | jerky homolog-like (mouse) | 1.69 | 7.156E-03 | 8690 |
| PH_hs_0022115 | SNTB2 | syntrophin, beta 2 (dystrophin-associated protein A1, 59 kDa, basic component 2) | 1.70 | 6.213E-05 | 6645 |
| PH_hs_0005461 | PUS3 | pseudouridylate synthase 3 | 1.70 | 1.796E-02 | 83480 |
| PH_hs_0042603 | OR10AG1 | olfactory receptor, family 10, subfamily AG, member 1 | 1.70 | 3.130E-02 | 282770 |
| PH_hs_0044545 | ATP2A2 | ATPase, Ca++ transporting, cardiac muscle, slow twitch 2 | 1.70 | 4.425E-03 | 488 |
| PH_hs_0030085 | GTF2I|GTF2IP1|LOC100093631 | general transcription factor II general transcription factor II, pseudogene 1|general transcription factor III, pseudogene | 1.70 | 1.888E-03 | 2969|297011000 93631 |
| PH_hs_0016043 | ABHD8 | abhydrolase domain containing 8 | 1.70 | 4.693E-06 | 79575 |
| PH_hs_0032403 | UTP14A | UTP14, U3 small nucleolar ribonucleoprotein, homolog A (yeast) | 1.70 | 6.697E-05 | 10813 |
| PH_hs_0048328 | GOLM1 | golgi membrane protein 1 | 1.70 | 2.841E-16 | 51280 |
| PH_hs_0047201 | JAK3 | Janus kinase 3 | 1.70 | 3.679E-04 | 3718 |
| PH_hs_0044054 | MGC4294 | hypothetical MGC4294 | 1.70 | 1.113E-05 | 79160 |
| PH_hs_0044881 | AASS | aminoadipate-semialdehyde synthase | 1.70 | 1.813E-08 | 10157 |
| PH_hs_0000201 | SDC2 | syndecan 2 | 1.70 | 8.975E-08 | 6383 |
| PH_hs_0022040 | EPC2 | enhancer of polycomb homolog 2 (Drosophila) | 1.70 | 3.370E-04 | 26122 |
| PH_hs_0042218 | CPSF1 | cleavage and polyadenylation specific factor 1, 160 kDa | 1.70 | 7.951E-07 | 29894 |
| PH_hs_0026618 | LILRA6 | leukocyte immunoglobulin-like receptor, subfamily A (with TM domain), member 6 | 1.70 | 1.974E-04 | 79168 |
| PH_hs_0042180 | FAM195A | family with sequence similarity 195, member A | 1.71 | 1.447E-04 | 84331 |
| PH_hs_0023317 | GSTT1 | glutathione S-transferase theta 1 | 1.71 | 5.419E-03 | 2952 |
| PH_hs_0048580 | SLC8A1 | solute carrier family 8 (sodium/calcium exchanger), member 1 | 1.71 | 2.217E-04 | 6546 |
| PH_hs_0047777 | LOC283070 | hypothetical LOC283070 | 1.71 | 8.572E-04 | 283070 |
| PH_hs_0049052 | NEK9 | NIMA (never in mitosis gene a)-related kinase 9 | 1.71 | 6.992E-08 | 91754 |
| PH_hs_0000635 | DAK | dihydroxyacetone kinase 2 homolog (S. cerevisiae) | 1.71 | 3.821E-07 | 26007 |

| Probe ID | Gene_symbol | Description | Fold Change | p-value | Entrez_gene |
|---|---|---|---|---|---|
| PH_hs_0010665 | LONRF1 | LON peptidase N-terminal domain and ring finger 1 | 1.71 | 4.253E-03 | 91694 |
| PH_hs_0017204 | CYB561 | cytochrome b-561 | 1.71 | 4.352E-04 | 1534 |
| PH_hs_0005010 | EPHX1 | epoxide hydrolase 1, microsomal (xenobiotic) | 1.71 | 4.868E-04 | 2052 |
| PH_hs_0004348 | DHCR24 | 24-dehydrocholesterol reductase | 1.71 | 4.708E-06 | 1718 |
| PH_hs_0048984 | ARHGAP26 | Rho GTPase activating protein 26 | 1.71 | 2.205E-04 | 23092 |
| PH_hs_0049038 | CYP2U1 | cytochrome P450, family 2, subfamily U, polypeptide 1 | 1.71 | 3.685E-03 | 113612 |
| PH_hs_0006005 | HAAO | 3-hydroxyanthranilate 3,4-dioxygenase | 1.71 | 4.998E-04 | 23498 |
| PH_hs_0048317 | SSH1 | slingshot homolog 1 (Drosophila) | 1.71 | 4.971E-04 | 54434 |
| PH_hs_0028961 | GJA1 | gap junction protein, alpha 1, 43 kDa | 1.71 | 6.654E-10 | 2697 |
| PH_hs_0037684 | SPRR2C\|SPRR2F\|SPRR2A\|SPRR2D\|SPRR2B | small proline-rich protein 2C (pseudogene)\|small proline-rich protein 2F\|small proline-rich protein 2A\|small proline-rich protein 2D\|small proline-rich protein 2B | 1.71 | 8.339E-03 | 6702\|6705\|6701\|6703\|6701 |
| PH_hs_0022089 | RHOBTB3 | Rho-related BTB domain containing 3 | 1.72 | 2.189E-11 | 22836 |
| PH_hs_0044498 | PDLIM5 | PDZ and LIM domain 5 | 1.72 | 1.826E-04 | 10611 |
| PH_hs_0049222 | CDK6 | cyclin-dependent kinase 6 | 1.72 | 1.062E-03 | 1021 |
| PH_hs_0005169 | FZD1 | frizzled homolog 1 (Drosophila) | 1.72 | 3.611E-07 | 8321 |
| PH_hs_0015651 | SDF2L1 | stromal cell-derived factor 2-like 1 | 1.72 | 9.778E-12 | 23753 |
| PH_hs_0027861 | CCNL2 | cyclin L2 | 1.72 | 8.564E-07 | 81669 |
| PH_hs_0002696 | PRDX5 | peroxiredoxin 5 | 1.72 | 9.925E-08 | 25824 |
| PH_hs_0048461 | ANKH | ankylosis, progressive homolog (mouse) | 1.73 | 6.258E-04 | 56172 |
| PH_hs_0008852 | ZNF331 | zinc finger protein 331 | 1.73 | 4.777E-04 | 55422 |
| PH_hs_0000005 | PTN | pleiotrophin | 1.73 | 2.386E-03 | 5764 |
| PH_hs_0001196 | NAP1L5 | nucleosome assembly protein 1-like 5 | 1.73 | 3.798E-06 | 266812 |
| PH_hs_0042738 | TTC32 | tetratricopeptide repeat domain 32 | 1.73 | 3.957E-04 | 130502 |
| PH_hs_0027325 | TPM4 | tropomyosin 4 | 1.73 | 2.504E-05 | 7171 |
| PH_hs_0031502 | PARM1 | prostate androgen-regulated mucin-like protein 1 | 1.74 | 9.257E-04 | 25849 |
| PH_hs_0002223 | ARAP3 | ArfGAP with RhoGAP domain, ankyrin repeat and PH domain 3 | 1.74 | 5.100E-09 | 64411 |
| PH_hs_0004678 | AUH | AU RNA binding protein/enoyl-CoA hydratase | 1.74 | 9.569E-07 | 549 |
| PH_hs_0009955 | TBX15 | T-box 15 | 1.74 | 6.616E-09 | 6913 |
| PH_hs_0047896 | USP2 | ubiquitin specific peptidase 2 | 1.74 | 2.468E-02 | 9099 |
| PH_hs_0010764 | NHP2L1 | NHP2 non-histone chromosome protein 2-like 1 (S. cerevisiae) | 1.74 | 7.337E-06 | 4809 |
| PH_hs_0024042 | SELO | selenoprotein O | 1.74 | 1.844E-08 | 83642 |
| PH_hs_0048599 | STX17 | syntaxin 17 | 1.74 | 4.209E-07 | 55014 |
| PH_hs_0047314 | RINL | Ras and Rab interactor-like | 1.74 | 2.707E-03 | 126432 |
| PH_hs_0016467 | ACY1\|ABHD14A-ACY1 | aminoacylase 1\|ABHD14A-ACY1 read-through transcript | 1.74 | 2.152E-04 | 95\|100526760 |
| PH_hs_0002734 | ZNF395 | zinc finger protein 395 | 1.74 | 5.218E-11 | 55893 |
| PH_hs_0048639 | ARHGAP23 | Rho GTPase activating protein 23 | 1.74 | 5.289E-07 | 57636 |
| PH_hs_0018415 | TFDP2 | transcription factor Dp-2 (E2F dimerization partner 2) | 1.74 | 2.317E-05 | 7029 |
| PH_hs_0026721 | MKNK2 | MAP kinase interacting serine/threonine kinase 2 | 1.75 | 1.161E-06 | 2872 |
| PH_hs_0002278 | SYTL1 | synaptotagmin-like 1 | 1.75 | 2.669E-04 | 84958 |
| PH_hs_0035906 | MRPS21 | mitochondrial ribosomal protein S21 | 1.75 | 3.374E-05 | 54460 |
| PH_hs_0032572 | TRIM45 | tripartite motif-containing 45 | 1.75 | 4.049E-07 | 80263 |
| PH_hs_0033001 | TMEM173 | transmembrane protein 173 | 1.75 | 1.796E-10 | 340061 |
| PH_hs_0002554 | COLEC12 | collectin sub-family member 12 | 1.75 | 3.852E-03 | 81035 |
| PH_hs_0030672 | HSP90B3P\|HSP90B1 | heat shock protein 90 kDa beta (Grp94), member 3 (pseudogene)\|heat shock protein 90 kDa beta (Grp94), member 1 | 1.75 | 3.486E-04 | 3434\|7184 |
| PH_hs_0043173 | AHSA2 | AHA1, activator of heat shock 90 kDa protein ATPase homolog 2 (yeast) | 1.76 | 1.216E-04 | 130872 |
| PH_hs_0043127 | RPL37 | ribosomal protein L37 | 1.76 | 1.916E-02 | 6167 |
| PH_hs_0047769 | FBXW7 | F-box and WD repeat domain containing 7 | 1.76 | 1.167E-04 | 55294 |
| PH_hs_0027424 | SPRY3 | sprouty homolog 3 (Drosophila) | 1.76 | 1.958E-02 | 10251 |

-continued

| Probe ID | Gene_symbol | Description | Fold Change | p-value | Entrez_gene |
|---|---|---|---|---|---|
| PH_hs_0048217 | SETX | senataxin | 1.76 | 3.813E-07 | 23064 |
| PH_hs_0032014 | SSX3\|SSX2B\|SSX2\|SSX1\|SSX6\|SSX8\|SSX4B\|SSX5\|SSX4 | synovial sarcoma, X breakpoint 3\|synovial sarcoma, X breakpoint 2B\|synovial sarcoma, X breakpoint 2\|synovial sarcoma, X breakpoint 1\|synovial sarcoma, X breakpoint 6 (pseudogene)\|synovial sarcoma, X breakpoint 8\|synovial sarcoma, X breakpoint 4B\|synovial sarcoma, X breakpoint 5\|synovial sarcoma, X breakpoint 4 | 1.76 | 7.266E-09 | 10214\|727837\|6757\|6756\|28065\|7\|28065\|954831\|3\|6758\|6759 |
| PH_hs_0004403 | REEP6 | receptor accessory protein 6 | 1.77 | 3.483E-08 | 92840 |
| PH_hs_0023957 | TBC1D24 | TBC1 domain family, member 24 | 1.77 | 3.544E-08 | 57465 |
| PH_hs_0003835 | DAPL1 | death associated protein-like 1 | 1.77 | 1.584E-09 | 92196 |
| PH_hs_0014780 | C14orf159 | chromosome 14 open reading frame 159 | 1.77 | 9.423E-06 | 80017 |
| PH_hs_0001843 | SMARCAD1 | SWI/SNF-related, matrix-associated actin-dependent regulator of chromatin, subfamily a, containing DEAD/H box 1 | 1.77 | 1.737E-02 | 56916 |
| PH_hs_0023854 | CDH2 | cadherin 2, type 1, N-cadherin (neuronal) | 1.77 | 3.258E-06 | 1000 |
| PH_hs_0049386 | TBC1D4 | TBC1 domain family, member 4 | 1.77 | 2.277E-05 | 9882 |
| PH_hs_0004699 | ELF2 | E74-like factor 2 (ets domain transcription factor) | 1.77 | 9.693E-06 | 1998 |
| PH_hs_0030842 | LEPREL4 | leprecan-like 4 | 1.77 | 3.572E-11 | 10609 |
| PH_hs_0020913 | NBL1 | neuroblastoma, suppression of tumorigenicity 1 | 1.77 | 8.672E-13 | 4681 |
| PH_hs_0006583 | APCDD1L | adenomatosis polyposis coli down-regulated 1-like | 1.77 | 5.450E-08 | 164284 |
| PH_hs_0021012 | YIPF3 | Yip1 domain family, member 3 | 1.77 | 1.860E-06 | 25844 |
| PH_hs_0003910 | LOC400657 | hypothetical LOC400657 | 1.77 | 1.397E-03 | 400657 |
| PH_hs_0000273 | SLC25A4 | solute carrier family 25 (mitochondrial carrier; adenine nucleotide translocator), member 4 | 1.78 | 2.834E-13 | 291 |
| PH_hs_0043494 | HDAC10 | histone deacetylase 10 | 1.78 | 2.214E-08 | 83933 |
| PH_hs_0049183 | GDPD1 | glycerophosphodiester phosphodiesterase domain containing 1 | 1.78 | 3.658E-04 | 284161 |
| PH_hs_0036875 | LOC25845 | hypothetical LOC25845 | 1.78 | 2.096E-11 | 6929 |
| PH_hs_0003199 | PARVA | parvin, alpha | 1.78 | 5.602E-07 | 25845 |
| PH_hs_0009907 | NDUFA2 | NADH dehydrogenase (ubiquinone) 1 alpha subcomplex, 2, 8 kDa | 1.78 | 1.868E-06 | 55742 |
| PH_hs_0010303 | ADAM10 | ADAM metallopeptidase domain 10 | 1.78 | 3.057E-11 | 4695 |
| PH_hs_0032660 | IP6K2 | inositol hexakisphosphate kinase 2 | 1.78 | 3.479E-05 | 102 |
| PH_hs_0016846 | ODZ1 | odz, odd Oz/ten-m homolog 1(Drosophila) | 1.78 | 1.123E-06 | 51447 |
| PH_hs_0025907 | FECH | ferrochelatase | 1.79 | 1.634E-05 | 10178 |
| PH_hs_0044270 | FAM135A | family with sequence similarity 135, member A | 1.79 | 6.082E-08 | 2235 |
| PH_hs_0044958 | UCKL1-AS1 | UCKL1 antisense RNA 1 (non-protein coding) | 1.79 | 1.628E-06 | 57579 |
| PH_hs_0015564 | STK11 | serine/threonine kinase 11 | 1.79 | 1.856E-03 | 100113386 |
| PH_hs_0029967 | C20orf30 | chromosome 20 open reading frame 30 | 1.79 | 9.915E-09 | 6794 |
| PH_hs_0017531 | PDCD2 | programmed cell death 2 | 1.79 | 1.179E-10 | 29058 |
| PH_hs_0002291 | PRMT6 | protein arginine methyltransferase 6 | 1.79 | 5.583E-08 | 5134 |
| PH_hs_0030709 | TDG | thymine-DNA glycosylase | 1.79 | 1.007E-10 | 55170 |
| PH_hs_0004669 | ZCCHC14 | zinc finger, CCHC domain containing 14 | 1.79 | 1.029E-09 | 6996 |
| PH_hs_0000425 | ASXL1 | additional sex combs like 1 (Drosophila) | 1.80 | 1.622E-05 | 23174 |
| PH_hs_0037100 | MAPKSP1 | MAPK scaffold protein 1 | 1.80 | 1.899E-08 | 171023 |
| PH_hs_0006026 | DPM2 | dolichyl-phosphate mannosyltransferase polypeptide 2, regulatory subunit | 1.80 | 2.270E-08 | 8649 |
| PH_hs_0010270 | USP11 | ubiquitin specific peptidase 11 | 1.80 | 2.652E-08 | 8818 |
| PH_hs_0042311 | ACAP1 | ArfGAP with coiled-coil, ankyrin repeat and PH domains 1 | 1.80 | 1.344E-04 | 8237 |
| PH_hs_0049092 | AGGF1 | angiogenic factor with G patch and FHA domains 1 | 1.80 | 3.659E-10 | 9744 |
| PH_hs_0009177 | MTHFR | methylenetetrahydrofolate reductase (NAD(P)H) | 1.80 | 3.362E-08 | 55109 |
| PH_hs_0028356 | C9orf16 | chromosome 9 open reading frame 16 | 1.80 | 1.486E-03 | 4524 |
| PH_hs_0049348 | UNG | uracil-DNA glycosylase | 1.80 | 5.328E-07 | 79095 |
| PH_hs_0024775 | MRPS36 | mitochondrial ribosomal protein S36 | 1.80 | 7.338E-12 | 7374 |
| PH_hs_0025554 | KIAA0355 | KIAA0355 | 1.81 | 1.174E-05 | 92259 |
| PH_hs_0032654 | SYVN1 | synovial apoptosis inhibitor 1, synoviolin | 1.81 | 1.469E-06 | 9710 |
| PH_hs_0047771 | PSME4 | proteasome (prosome, macropain) activator subunit 4 | 1.81 | 2.419E-04 | 84447 |
| PH_hs_0045596 | NTM | neurotrimin | 1.81 | 3.705E-08 | 23198 |
|  |  |  |  | 2.755E-03 | 50863 |

-continued

| Probe ID | Gene_symbol | Description | Fold Change | p-value | Entrez_gene |
|---|---|---|---|---|---|
| PH_hs_0004676 | MGST2 | microsomal glutathione S-transferase 2 | 1.81 | 2.881E-17 | 4258 |
| PH_hs_0004332 | TP53INP1 | tumor protein p53 inducible nuclear protein 1 | 1.81 | 3.598E-12 | 94241 |
| PH_hs_0024698 | FKBP1B | FK506 binding protein 1B, 12.6 kDa | 1.81 | 9.010E-05 | 2281 |
| PH_hs_0024427 | PTPN13 | protein tyrosine phosphatase, non-receptor type 13 (APO-1/CD95 (Fas)-associated phosphatase) | 1.81 | 8.794E-04 | 5783 |
| PH_hs_0015577 | LMO3 | LIM domain only 3 (rhombotin-like 2) | 1.81 | 1.340E-02 | 55885 |
| PH_hs_0004637 | STAT4 | signal transducer and activator of transcription 4 | 1.82 | 5.915E-03 | 6775 |
| PH_hs_0003386 | RCHY1 | ring finger and CHY zinc finger domain containing 1 | 1.82 | 2.475E-03 | 25898 |
| PH_hs_0048542 | SNX1 | sorting nexin 1 | 1.82 | 2.439E-13 | 6642 |
| PH_hs_0002269 | ATP6V0A2 | ATPase, H+ transporting, lysosomal V0 subunit a2 | 1.82 | 5.328E-06 | 23545 |
| PH_hs_0049460 | DCAF16 | DDB1 and CUL4 associated factor 16 | 1.82 | 2.320E-15 | 54876 |
| PH_hs_0023908 | SLC35C2 | solute carrier family 35, member C2 | 1.82 | 1.119E-11 | 51006 |
| PH_hs_0006395 | AKR1B10 | aldo-keto reductase family 1, member B10 (aldose reductase) | 1.82 | 1.963E-06 | 57016 |
| PH_hs_0006538 | MXI1 | MAX interactor 1 | 1.82 | 2.678E-11 | 4601 |
| PH_hs_0047616 | RHOBTB1 | Rho-related BTB domain containing 1 | 1.82 | 4.322E-04 | 9886 |
| PH_hs_0043877 | COMMD5 | COMM domain containing 5 | 1.82 | 6.384E-04 | 28991 |
| PH_hs_0023544 | NCOA7 | nuclear receptor coactivator 7 | 1.82 | 3.973E-12 | 135112 |
| PH_hs_0011642 | PGCP | plasma glutamate carboxypeptidase | 1.82 | 2.757E-07 | 10404 |
| PH_hs_0045568 | NSUN5|NSUN5P1 | NOP2/Sun domain family, member 5|NOP2/Sun domain family, member 5 pseudogene 1 | 1.83 | 1.676E-02 | 55695|155400 |
| PH_hs_0047570 | THNSL1 | threonine synthase-like 1 (S. cerevisiae) | 1.83 | 3.818E-03 | 79896 |
| PH_hs_0031414 | EIF4B | eukaryotic translation initiation factor 4B | 1.83 | 1.642E-10 | 1975 |
| PH_hs_0003988 | PROS1 | protein S (alpha) | 1.83 | 6.746E-08 | 5627 |
| PH_hs_0048500 | WDR52 | WD repeat domain 52 | 1.83 | 6.038E-11 | 55779 |
| PH_hs_0047575 | LRRC15 | leucine rich repeat containing 15 | 1.84 | 4.693E-09 | 131578 |
| PH_hs_0043182 | INPP5J | inositol polyphosphate-5-phosphatase J | 1.84 | 2.135E-03 | 27124 |
| PH_hs_0047843 | SIKE1 | suppressor of IKBKE 1 | 1.84 | 8.761E-03 | 80143 |
| PH_hs_0046804 | TXNRD3 | thioredoxin reductase 3 | 1.84 | 3.504E-05 | 114112 |
| PH_hs_0027161 | RGL1 | ral guanine nucleotide dissociation stimulator-like 1 | 1.84 | 3.076E-07 | 23179 |
| PH_hs_0048693 | LANCL2 | LanC lantibiotic synthetase component C-like 2 (bacterial) | 1.84 | 5.401E-05 | 55915 |
| PH_hs_0037413 | SCD | stearoyl-CoA desaturase (delta-9-desaturase) | 1.84 | 1.155E-04 | 6319 |
| PH_hs_0025293 | MYL9 | myosin, light chain 9, regulatory | 1.84 | 1.836E-02 | 10398 |
| PH_hs_0048520 | MTR | 5-methyltetrahydrofolate-homocysteine methyltransferase | 1.85 | 7.931E-05 | 4548 |
| PH_hs_0048400 | C14orf37 | chromosome 14 open reading frame 37 | 1.85 | 1.658E-03 | 145407 |
| PH_hs_0024444 | RXRB | retinoid X receptor, beta | 1.85 | 1.285E-02 | 6257 |
| PH_hs_0045401 | C9orf47 | chromosome 9 open reading frame 47 | 1.85 | 4.062E-06 | 286223 |
| PH_hs_0022284 | ZFHX3 | zinc finger homeobox 3 | 1.85 | 2.090E-04 | 463 |
| PH_hs_0033290 | ANAPC16 | anaphase promoting complex subunit 16 | 1.85 | 4.920E-06 | 119504 |
| PH_hs_0031856 | MLYCD | malonyl-CoA decarboxylase | 1.86 | 6.542E-09 | 23417 |
| PH_hs_0001569 | RPL32 | ribosomal protein L32 | 1.86 | 7.861E-10 | 6161 |
| PH_hs_0047272 | UTP23 | UTP23, small subunit (SSU) processome component, homolog (yeast) | 1.86 | 4.335E-05 | 84294 |
| PH_hs_0043952 | HOXC4 | homeobox C4 | 1.86 | 6.202E-05 | 3221 |
| PH_hs_0019723 | HOXD11 | homeobox D11 | 1.86 | 4.758E-06 | 3237 |
| PH_hs_0043477 | FHL1 | four and a half LIM domains 1 | 1.86 | 6.556E-11 | 2273 |
| PH_hs_0000067 | FUCA1 | fucosidase, alpha-L-1, tissue | 1.86 | 1.128E-08 | 2517 |
| PH_hs_0002731 | INPP1 | inositol polyphosphate-1-phosphatase | 1.86 | 2.943E-09 | 3628 |
| PH_hs_0019227 | CREB3L1 | cAMP responsive element binding protein 3-like 1 | 1.86 | 3.369E-11 | 90993 |
| PH_hs_0048324 | ZBTB42 | zinc finger and BTB domain containing 42 | 1.86 | 8.390E-03 | 100128927 |
| PH_hs_0047553 | TTC17 | tetratricopeptide repeat domain 17 | 1.86 | 2.515E-07 | 55761 |
| PH_hs_0047553 | C14orf147 | chromosome 14 open reading frame 147 | 1.86 | 8.254E-04 | 171546 |
| PH_hs_0049187 | LYRM7 | Lyrm7 homolog (mouse) | 1.87 | 8.952E-09 | 90624 |
| PH_hs_0020051 | RALGPS1 | Ral GEF with PH domain and SH3 binding motif 1 | 1.87 | 4.566E-10 | 9649 |
| PH_hs_0047566 | ZNF252 | zinc finger protein 252 | 1.87 | 1.657E-08 | 286101 |

| Probe ID | Gene_symbol | Description | Fold Change | p-value | Entrez_gene |
|---|---|---|---|---|---|
| PH_hs_0000336 | AVPR2 | arginine vasopressin receptor 2 | 1.87 | 1.010E-03 | 554 |
| PH_hs_0005562 | TRIM66 | tripartite motif-containing 66 | 1.87 | 4.678E-08 | 9866 |
| PH_hs_0006529 | MRGPRF | MAS-related GPR, member F | 1.87 | 1.895E-05 | 116535 |
| PH_hs_0004529 | PRUNE | prune homolog (Drosophila) | 1.87 | 7.967E-08 | 58497 |
| PH_hs_0022051 | ZKSCAN1 | zinc finger with KRAB and SCAN domains 1 | 1.87 | 2.720E-07 | 7586 |
| PH_hs_0046005 | TIMM8B | translocase of inner mitochondrial membrane 8 homolog B (yeast) | 1.87 | 8.474E-12 | 26521 |
| PH_hs_0032414 | SGSM2 | small G protein signaling modulator 2 | 1.87 | 7.506E-05 | 9905 |
| PH_hs_0001748 | RXRA | retinoid X receptor, alpha | 1.87 | 1.042E-04 | 6256 |
| PH_hs_0009027 | RPS6KA1 | ribosomal protein S6 kinase, 90 kDa, polypeptide 1 | 1.87 | 2.210E-02 | 6195 |
| PH_hs_0011507 | DIRAS3 | DIRAS family, GTP-binding RAS-like 3 | 1.87 | 8.847E-06 | 9077 |
| PH_hs_0001519 | PODXL | podocalyxin-like | 1.87 | 3.383E-12 | 5420 |
| PH_hs_0008047 | C6orf226 | chromosome 6 open reading frame 226 | 1.87 | 6.461E-04 | 441150 |
| PH_hs_0049316 | COL5A1 | collagen, type V, alpha 1 | 1.87 | 1.013E-07 | 1289 |
| PH_hs_0042093 | C11orf10 | chromosome 11 open reading frame 10 | 1.87 | 7.744E-06 | 746 |
| PH_hs_0045836 | SIPA1 | signal-induced proliferation-associated 1 | 1.87 | 6.350E-08 | 6494 |
| PH_hs_0009068 | KLF9 | Kruppel-like factor 9 | 1.87 | 2.083E-03 | 687 |
| PH_hs_0022757 | SMARCC1 | SWI/SNF related, matrix associated, actin dependent regulator of chromatin, subfamily c, member 1 | 1.88 | 2.366E-06 | 6599 |
| PH_hs_0035301 | SPIN2B\|SPIN2A | spindlin family, member 2B\|spindlin family, member 2A | 1.88 | 1.382E-04 | 474343\|54466 |
| PH_hs_0048289 | UBTF | upstream binding transcription factor, RNA polymerase I | 1.88 | 1.653E-09 | 7343 |
| PH_hs_0005203 | FAM8A1 | family with sequence similarity 8, member A1 | 1.88 | 9.793E-05 | 51439 |
| PH_hs_0046157 | TNS3 | tensin 3 | 1.88 | 5.242E-07 | 64759 |
| PH_hs_0002295 | PSMA5 | proteasome (prosome, macropain) subunit, alpha type, 5 | 1.88 | 2.276E-07 | 5686 |
| PH_hs_0006488 | MTHFS\|ST20-MTHFS | 5,10-methenyltetrahydrofolate synthetase (5-formyltetrahydrofolate cyclo-ligase)\|ST20-MTHFS read-through transcript | 1.88 | 5.184E-09 | 10588\|100528021 |
| PH_hs_0001105 | CTSF | cathepsin F | 1.88 | 2.149E-10 | 8722 |
| PH_hs_0043405 | C2orf64 | chromosome 2 open reading frame 64 | 1.88 | 9.922E-08 | 493753 |
| PH_hs_0049170 | MLLT6 | myeloid/lymphoid or mixed-lineage leukemia (trithorax homolog, Drosophila); translocated to, 6 | 1.89 | 1.853E-05 | 4302 |
| PH_hs_0047825 | FAM43A | family with sequence similarity 43, member A | 1.89 | 8.101E-04 | 131583 |
| PH_hs_0028077 | GALNT1 | UDP-N-acetyl-alpha-D-galactosamine: polypeptide N-acetylgalactosaminyltransferase 1 (GalNAc-T1) | 1.89 | 1.023E-04 | 2589 |
| PH_hs_0046019 | LOC152217 | hypothetical LOC152217 | 1.89 | 6.150E-06 | 152217 |
| PH_hs_0006554 | CSTF3 | cleavage stimulation factor, 3' pre-RNA, subunit 3, 77 kDa | 1.89 | 4.945E-06 | 23331 |
| PH_hs_0045139 | CNST | consortin, connexin sorting protein | 1.89 | 7.321E-04 | 1479 |
| PH_hs_0047482 | MT1E | metallothionein 1E | 1.89 | 1.097E-05 | 163882 |
| PH_hs_0010158 | CYTH3 | cytohesin 3 | 1.89 | 1.056E-12 | 4493 |
| PH_hs_0040048 | RBM47 | RNA binding motif protein 47 | 1.89 | 1.366E-08 | 9265 |
| PH_hs_0005209 | ATXN3 | ataxin 3 | 1.89 | 7.857E-06 | 54502 |
| PH_hs_0045780 | MCTS1 | malignant T cell amplified sequence 1 | 1.90 | 2.327E-11 | 4287 |
| PH_hs_0016827 | TTC28 | tetratricopeptide repeat domain 28 | 1.90 | 4.097E-08 | 28985 |
| PH_hs_0048634 | GSN | gelsolin | 1.90 | 5.759E-09 | 2934 |
| PH_hs_0024657 | MBD1 | methyl-CpG binding domain protein 1 | 1.90 | 4.190E-05 | 4152 |
| PH_hs_0046391 | RGL2 | ral guanine nucleotide dissociation stimulator-like 2 | 1.90 | 2.737E-07 | 5863 |
| | LOC389834\|LOC100510339\|LOC100509956 | ankyrin repeat domain 57 pseudogene\|hypothetical LOC100510339\|hypothetical LOC100509956 | 1.90 | | 389834\|100510339\|100509956 |
| PH_hs_0043844 | EXTL2 | exostoses (multiple)-like 2 | 1.90 | 3.831E-07 | 2135 |
| PH_hs_0045850 | TPM2 | tropomyosin 2 (beta) | 1.90 | 8.897E-12 | 7169 |
| PH_hs_0046287 | ALDH1L2 | aldehyde dehydrogenase 1 family, member L2 | 1.90 | 2.363E-06 | 160428 |
| PH_hs_0043249 | BAK1 | BCL2-antagonist/killer 1 | 1.90 | 2.484E-11 | 578 |
| PH_hs_0000315 | JUP | junction plakoglobin | 1.90 | 1.837E-02 | 3728 |
| PH_hs_0002107 | ERMN | ermin, ERM-like protein | 1.90 | 9.838E-06 | 57471 |
| PH_hs_0009163 | SMARCA1 | SWI/SNF related, matrix associated, actin dependent regulator of chromatin, subfamily a, member 1 | 1.91 | 5.003E-10 | 6594 |

| Probe ID | Gene_symbol | Description | Fold Change | p-value | Entrez_gene |
|---|---|---|---|---|---|
| PH_hs_0034349 | PLSCR3 | phospholipid scramblase 3 | 1.91 | 7.262E-11 | 57048 |
| PH_hs_0048416 | ENAH | enabled homolog (Drosophila) | 1.91 | 1.555E-08 | 55740 |
| PH_hs_0033391 | MANF | mesencephalic astrocyte-derived neurotrophic factor | 1.91 | 5.051E-09 | 7873 |
| PH_hs_0033911 | MZF1 | myeloid zinc finger 1 | 1.91 | 1.191E-05 | 7593 |
| PH_hs_0019842 | GPIHBP1 | glycosylphosphatidylinositol anchored high density lipoprotein binding protein 1 | 1.91 | 2.811E-04 | 338328 |
| PH_hs_0003154 | TTC14 | tetratricopeptide repeat domain 14 | 1.91 | 8.569E-10 | 151613 |
| PH_hs_0013097 | DDAH2 | dimethylarginine dimethylaminohydrolase 2 | 1.91 | 2.184E-07 | 23564 |
| PH_hs_0047815 | FAM46A | family with sequence similarity 46, member A | 1.91 | 5.944E-07 | 55603 |
| PH_hs_0004256 | TJP1 | tight junction protein 1 (zona occludens 1) | 1.92 | 1.259E-04 | 7082 |
| PH_hs_0004673 | TNFRSF11B | tumor necrosis factor receptor superfamily, member 11b | 1.92 | 7.208E-11 | 4982 |
| PH_hs_0013717 | SNX4 | sorting nexin 4 | 1.92 | 1.718E-03 | 8723 |
| PH_hs_0042038 | RPS23 | ribosomal protein S23 | 1.92 | 7.523E-09 | 6228 |
| PH_hs_0023373 | USP4 | ubiquitin specific peptidase 4 (proto-oncogene) | 1.92 | 1.294E-09 | 7375 |
| PH_hs_0004467 | ANTXR1 | anthrax toxin receptor 1 | 1.92 | 4.346E-05 | 84168 |
| PH_hs_0029280 | C10orf11 | chromosome 10 open reading frame 11 | 1.92 | 1.242E-08 | 83938 |
| PH_hs_0001672 | MRPS26 | mitochondrial ribosomal protein S26 | 1.92 | 6.277E-04 | 64949 |
| PH_hs_0011402 | SETD6 | SET domain containing 6 | 1.92 | 8.076E-05 | 79918 |
| PH_hs_0022248 | GOLGA1 | golgin A1 | 1.92 | 1.566E-11 | 2800 |
| PH_hs_0026107 | ASNS | asparagine synthetase (glutamine-hydrolyzing) | 1.92 | 1.037E-13 | 440 |
| PH_hs_0049653 | C1GALT1 | core 1 synthase, glycoprotein-N-acetylgalactosamine 3-beta-galactosyltransferase, 1 | 1.92 | 3.093E-05 | 56913 |
| PH_hs_0023051 | POMT1 | protein-O-mannosyltransferase 1 | 1.92 | 7.706E-08 | 10585 |
| PH_hs_0020406 | NISCH | nischarin | 1.92 | 5.466E-14 | 11188 |
| PH_hs_0047101 | LOC642414 | putative tripartite motif-containing protein 64B-like | 1.93 | 2.876E-05 | 642414 |
| PH_hs_0006318 | ZNF213 | zinc finger protein 213 | 1.93 | 3.268E-06 | 7760 |
| PH_hs_0028823 | SRRM3 | serine/arginine repetitive matrix 3 | 1.93 | 3.023E-02 | 222183 |
| PH_hs_0047860 | PURB | purine-rich element binding protein B | 1.93 | 2.893E-13 | 5814 |
| PH_hs_0017235 | TMEM127 | transmembrane protein 127 | 1.93 | 8.235E-12 | 55654 |
| PH_hs_0023953 | PAM | peptidylglycine alpha-amidating monooxygenase | 1.93 | 3.004E-11 | 5066 |
| PH_hs_0024186 | PPP1R13B | protein phosphatase 1, regulatory (inhibitor) subunit 13B | 1.93 | 2.494E-05 | 23368 |
| PH_hs_0045707 | DLG3 | discs, large homolog 3 (Drosophila) | 1.93 | 2.644E-08 | 1741 |
| PH_hs_0011504 | NFS1 | NFS1 nitrogen fixation 1 homolog (S. cerevisiae) | 1.94 | 4.496E-12 | 9054 |
| PH_hs_0032829 | TRNP1 | TMF1-regulated nuclear protein 1 | 1.94 | 5.053E-03 | 388610 |
| PH_hs_0047930 | NUMBL | numb homolog (Drosophila)-like | 1.94 | 9.113E-09 | 9253 |
| PH_hs_0012900 | PDCD11 | programmed cell death 11 | 1.94 | 3.969E-04 | 22984 |
| PH_hs_0029814 | KCNK15 | potassium channel, subfamily K, member 15 | 1.94 | 1.817E-04 | 60598 |
| PH_hs_0047221 | LPAR1 | lysophosphatidic acid receptor 1 | 1.94 | 5.820E-11 | 1902 |
| PH_hs_0019226 | SOCS2 | suppressor of cytokine signaling 2 | 1.94 | 4.846E-04 | 8835 |
| PH_hs_0004725 | CCDC106 | coiled-coil domain containing 106 | 1.94 | 5.882E-10 | 29903 |
| PH_hs_0024622 | FBXO32 | F-box protein 32 | 1.94 | 1.591E-04 | 114907 |
| PH_hs_0042800 | IER5L | immediate early response 5-like | 1.95 | 3.788E-08 | 389792 |
| PH_hs_0020451 | ATP13A1 | ATPase type 13A1 | 1.95 | 2.001E-09 | 57130 |
| PH_hs_0000889 | C11orf54 | chromosome 11 open reading frame 54 | 1.95 | 6.146E-11 | 28970 |
| PH_hs_0028088 | DMBT1 | deleted in malignant brain tumors 1 | 1.95 | 1.821E-11 | 1755 |
| PH_hs_0049298 | RPS6KA3 | ribosomal protein S6 kinase, 90 kDa, polypeptide 3 | 1.95 | 5.253E-10 | 6197 |
| PH_hs_0048277 | FXC1 | fracture callus 1 homolog (rat) | 1.95 | 4.129E-08 | 26515 |
| PH_hs_0043125 | UL16BP1 | UL16 binding protein 1 | 1.95 | 6.756E-06 | 80329 |
| PH_hs_0026363 | CHPF | chondroitin polymerizing factor | 1.95 | 5.633E-15 | 79586 |
| PH_hs_0024014 | TCF4 | transcription factor 4 | 1.96 | 5.984E-05 | 6925 |
| PH_hs_0001088 | ERRFI1 | ERBB receptor feedback inhibitor 1 | 1.96 | 2.665E-11 | 54206 |
| PH_hs_0024993 | DECR1 | 2,4-dienoyl CoA reductase 1, mitochondrial | 1.96 | 1.066E-12 | 1666 |
| PH_hs_0004400 | AK1 | adenylate kinase 1 | 1.96 | 6.811E-14 | 203 |

-continued

| Probe ID | Gene_symbol | Description | Fold Change | p-value | Entrez_gene |
|---|---|---|---|---|---|
| PH_hs_0046216 | KLHL13 | kelch-like 13 (Drosophila) | 1.96 | 4.875E-09 | 90293 |
| PH_hs_0048810 | NCOA1 | nuclear receptor coactivator 1 | 1.96 | 1.170E-13 | 8648 |
| PH_hs_0002369 | C1orf198 | chromosome 1 open reading frame 198 | 1.97 | 5.537E-05 | 84886 |
| PH_hs_0013583 | LOC100509177|LOC100507143 | hypothetical LOC100509177|hypothetical LOC100507143 | 1.97 | 1.420E-05 | 100509177|100507143 |
| PH_hs_0048372 | KIAA0368 | KIAA0368 | 1.97 | 3.641E-07 | 23392 |
| PH_hs_0002565 | PPAPDC2 | phosphatidic acid phosphatase type 2 domain containing 2 | 1.97 | 4.478E-10 | 403313 |
| PH_hs_0049716 | ZNF84 | zinc finger protein 84 | 1.97 | 4.885E-10 | 7637 |
| PH_hs_0049733 | FOXO3|FOXO3B | forkhead box O3|forkhead box O3B pseudogene | 1.98 | 7.907E-07 | 2309|2310 |
| PH_hs_0043347 | AIG1 | androgen-induced 1 | 1.98 | 1.289E-10 | 51390 |
| PH_hs_0035778 | C22orf9 | chromosome 22 open reading frame 9 | 1.98 | 6.161E-14 | 23313 |
| PH_hs_0022930 | CMBL | carboxymethylenebutenolidase homolog (Pseudomonas) | 1.98 | 6.780E-06 | 134147 |
| PH_hs_0022134 | BEND6 | BEN domain containing 6 | 1.98 | 6.104E-08 | 221336 |
| PH_hs_0047693 | SFT2D3 | SFT2 domain containing 3 | 1.98 | 2.169E-10 | 84826 |
| PH_hs_0049131 | ITGAV | integrin, alpha V (vitronectin receptor, alpha polypeptide, antigen CD51) | 1.99 | 9.064E-09 | 3685 |
| PH_hs_0047284 | LRP4 | low density lipoprotein receptor-related protein 4 | 1.99 | 9.963E-04 | 4038 |
| PH_hs_0001027 | TRMT12 | tRNA methyltransferase 12 homolog (S. cerevisiae) | 1.99 | 5.773E-10 | 55039 |
| PH_hs_0036686 | VCY|VCY1B | variable charge, Y-linked|variable charge, Y-linked 1B | 1.99 | 2.141E-08 | 9084|353513 |
| PH_hs_0004062 | TWIST1 | twist homolog 1 (Drosophila) | 1.99 | 2.279E-10 | 7291 |
| PH_hs_0025209 | TMEM165 | transmembrane protein 165 | 1.99 | 7.612E-06 | 55858 |
| PH_hs_0011591 | ECH1 | enoyl CoA hydratase 1, peroxisomal | 1.99 | 4.743E-06 | 1891 |
| PH_hs_0000821 | LOC730101 | hypothetical LOC730101 | 1.99 | 3.922E-09 | 730101 |
| PH_hs_0004614 | RPIA | ribose 5-phosphate isomerase A | 2.00 | 8.202E-12 | 22934 |
| PH_hs_0004782 | MOGS | mannosyl-oligosaccharide glucosidase | 2.00 | 1.991E-02 | 7841 |
| PH_hs_0014094 | PCIF1 | PDX1 C-terminal inhibiting factor 1 | 2.00 | 4.306E-06 | 63935 |
| PH_hs_0023807 | NRBF2 | nuclear receptor binding factor 2 | 2.00 | 8.640E-05 | 29982 |
| PH_hs_0043177 | TSHZ1 | teashirt zinc finger homeobox 1 | 2.00 | 1.768E-02 | 10194 |
| PH_hs_0047673 | ATP8B2 | ATPase, class I, type 8B, member 2 | 2.00 | 4.409E-07 | 57198 |
| PH_hs_0003316 | EPDR1 | ependymin related protein 1 (zebrafish) | 2.01 | 6.066E-05 | 54749 |
| PH_hs_0005942 | CALB2 | calbindin 2 | 2.01 | 1.063E-05 | 794 |
| PH_hs_0034220 | ZFP62 | zinc finger protein 62 homolog (mouse) | 2.01 | 1.520E-04 | 643836 |
| PH_hs_0023507 | TMEM184A | transmembrane protein 184A | 2.01 | 2.001E-03 | 202915 |
| PH_hs_0046412 | FLJ44606 | glutaredoxin-like protein YDR286C homolog | 2.02 | 3.321E-02 | 401207 |
| PH_hs_0003641 | RIPK4 | receptor-interacting serine-threonine kinase 4 | 2.02 | 6.652E-03 | 54101 |
| PH_hs_0023807 | CASD1 | CAS1 domain containing 1 | 2.02 | 1.538E-06 | 64921 |
| PH_hs_0013600 | C1orf63 | chromosome 1 open reading frame 63 | 2.02 | 2.198E-10 | 57035 |
| PH_hs_0017020 | NANOS1 | nanos homolog 1 (Drosophila) | 2.02 | 4.103E-03 | 340719 |
| PH_hs_0015639 | GLIPR2 | GLI pathogenesis-related 2 | 2.02 | 3.212E-13 | 152007 |
| PH_hs_0043550 | C1QTNF6 | C1q and tumor necrosis factor related protein 6 | 2.03 | 3.959E-06 | 114904 |
| PH_hs_0033165 | IL28B|IL28A|IL29 | interleukin 28B (interferon, lambda 3)|interleukin 28A (interferon, lambda 2)|interleukin 29 (interferon, lambda 1) | 2.03 | 6.546E-03 | 282617|282616|282618 |
| PH_hs_0022868 | NUB1 | negative regulator of ubiquitin-like proteins 1 | 2.03 | 4.660E-08 | 51667 |
| PH_hs_0020917 | CORO2A | coronin, actin binding protein, 2A | 2.03 | 1.062E-03 | 7464 |
| PH_hs_0047989 | MAZ | MYC-associated zinc finger protein (purine-binding transcription factor) | 2.03 | 3.244E-10 | 4150 |
| PH_hs_0025770 | SERP1 | stress-associated endoplasmic reticulum protein 1 | 2.03 | 1.051E-10 | 27230 |
| PH_hs_0033036 | ZNF45 | zinc finger protein 45 | 2.03 | 2.056E-05 | 7596 |
| PH_hs_0019863 | CA11 | carbonic anhydrase XI | 2.04 | 4.911E-08 | 770 |
| PH_hs_0002737 | DTX3 | deltex homolog 3 (Drosophila) | 2.04 | 1.470E-11 | 196403 |
| PH_hs_0035189 | ZNF251 | zinc finger protein 251 | 2.04 | 9.418E-04 | 90987 |
| PH_hs_0020096 | C22orf39 | chromosome 22 open reading frame 39 | 2.04 | 1.243E-14 | 128977 |
| PH_hs_0042520 | RNASE7 | ribonuclease, RNase A family, 7 | 2.05 | 6.778E-06 | 84659 |

-continued

| Probe ID | Gene_symbol | Description | Fold Change | p-value | Entrez_gene |
|---|---|---|---|---|---|
| PH_hs_0032160 | C17orf49 | chromosome 17 open reading frame 49 | 2.05 | 1.966E-12 | 124944 |
| PH_hs_0006209 | PARD6A | par-6 partitioning defective 6 homolog alpha (C. elegans) | 2.05 | 4.258E-12 | 50855 |
| PH_hs_0020138 | FSTL1 | follistatin-like 1 | 2.05 | 1.168E-12 | 11167 |
| PH_hs_0014474 | ROM1 | retinal outer segment membrane protein 1 | 2.05 | 2.580E-09 | 6094 |
| PH_hs_0005160 | MPZ | myelin protein zero | 2.06 | 3.136E-07 | 4359 |
| PH_hs_0009397 | C3AR1 | complement component 3a receptor 1 | 2.06 | 1.371E-06 | 719 |
| PH_hs_0000410 | PKIG | protein kinase (cAMP-dependent, catalytic) inhibitor gamma | 2.06 | 8.581E-09 | 11142 |
| PH_hs_0044100 | PEG10 | paternally expressed 10 | 2.06 | 1.512E-08 | 23089 |
| PH_hs_0044325 | LNX1 | ligand of numb-protein X 1 | 2.06 | 3.386E-14 | 84708 |
| PH_hs_0010102 | BAALC | brain and acute leukemia, cytoplasmic | 2.07 | 1.745E-14 | 79870 |
| PH_hs_0001121 | HMGCR | 3-hydroxy-3-methylglutaryl-CoA reductase | 2.07 | 1.507E-04 | 3156 |
| PH_hs_0014732 | HMOX2 | heme oxygenase (decycling) 2 | 2.07 | 5.674E-04 | 3163 |
| PH_hs_0030241 | VASN | vasorin | 2.07 | 5.365E-07 | 114990 |
| PH_hs_0013514 | PCYOX1L | prenylcysteine oxidase 1 like | 2.07 | 1.923E-11 | 78991 |
| PH_hs_0046338 | C17orf58 | chromosome 17 open reading frame 58 | 2.07 | 8.241E-13 | 284018 |
| PH_hs_0049703 | TRIM16\|TRIM16L | tripartite motif-containing 16\|tripartite motif-containing 16-like | 2.08 | 8.751E-19 | 10626\|47166 |
| PH_hs_0000736 | SEMA4C | sema domain, immunoglobulin domain (Ig), transmembrane domain (TM) and short cytoplasmic domain, (semaphorin) 4C | 2.08 | 4.931E-09 | 54910 |
| PH_hs_0014418 | PAN2 | PAN2 poly(A) specific ribonuclease subunit homolog (S. cerevisiae) | 2.08 | 1.261E-05 | 9924 |
| PH_hs_0027093 | PTPRU | protein tyrosine phosphatase, receptor type, U | 2.08 | 4.672E-14 | 10076 |
| PH_hs_0043466 | PRAF2 | PRA1 domain family, member 2 | 2.08 | 9.335E-20 | 11230 |
| PH_hs_0034204 | LOC100510699\|LOC100505643 | putative beta-glucuronidase-like protein FLJ75429-like\|hypothetical LOC100505643 | 2.08 | 3.868E-05 | 100510699\|100505643 |
| PH_hs_0004397 | CDH5 | cadherin 5, type 2 (vascular endothelium) | 2.08 | 9.410E-09 | 1003 |
| PH_hs_0012803 | ACOT11 | acyl-CoA thioesterase 11 | 2.09 | 6.960E-07 | 26027 |
| PH_hs_0049095 | C6orf89 | chromosome 6 open reading frame 89 | 2.09 | 6.783E-11 | 221477 |
| PH_hs_0044597 | RNLS | renalase, FAD-dependent amine oxidase | 2.09 | 1.558E-08 | 55328 |
| PH_hs_0043819 | INO80C | INO80 complex subunit C | 2.09 | 2.613E-17 | 125476 |
| PH_hs_0031263 | C21orf119 | chromosome 21 open reading frame 119 | 2.09 | 3.737E-08 | 84996 |
| PH_hs_0023822 | OTUD7B | OTU domain containing 7B | 2.09 | 1.545E-11 | 56957 |
| PH_hs_0003929 | C1orf213 | chromosome 1 open reading frame 213 | 2.10 | 4.394E-04 | 148898 |
| PH_hs_0019488 | MAP1LC3A | microtubule-associated protein 1 light chain 3 alpha | 2.10 | 5.281E-09 | 84557 |
| PH_hs_0048987 | TEP1 | telomerase-associated protein 1 | 2.10 | 7.392E-12 | 7011 |
| PH_hs_0036845 | ZFP90 | zinc finger protein 90 homolog (mouse) | 2.10 | 3.656E-04 | 146198 |
| PH_hs_0000451 | COQ10A | coenzyme Q10 homolog A (S. cerevisiae) | 2.10 | 2.841E-15 | 93058 |
| PH_hs_0030457 | C14orf132 | chromosome 14 open reading frame 132 | 2.10 | 5.548E-11 | 56967 |
| PH_hs_0032425 | FLJ41649 | hypothetical LOC401260 | 2.10 | 3.776E-02 | 401260 |
| PH_hs_0004437 | PDIA5 | protein disulfide isomerase family A, member 5 | 2.11 | 4.807E-12 | 10954 |
| PH_hs_0049358 | DKFZp686O24166 | hypothetical protein DKFZp686O24166 | 2.11 | 7.020E-09 | 374383 |
| PH_hs_0023823 | GPC1 | glypican 1 | 2.11 | 3.373E-11 | 2817 |
| PH_hs_0002176 | MOAP1 | modulator of apoptosis 1 | 2.11 | 1.302E-17 | 64112 |
| PH_hs_0003194 | PELI2 | pellino homolog 2 (Drosophila) | 2.12 | 4.454E-05 | 57161 |
| PH_hs_0048515 | SHROOM3 | shroom family member 3 | 2.12 | 2.480E-05 | 57619 |
| PH_hs_0016793 | TLCD1 | TLC domain containing 1 | 2.12 | 4.102E-11 | 116238 |
| PH_hs_0044378 | ZNF34 | zinc finger protein 34 | 2.13 | 2.273E-11 | 80778 |
| PH_hs_0047462 | C20orf112 | chromosome 20 open reading frame 112 | 2.13 | 1.145E-07 | 140688 |
| PH_hs_0033256 | MAGEA6\|MAGEA3\|MAGEA2\|MAGEA12\|MAGEA5 | melanoma antigen family A, 6\|melanoma antigen family A, 3\|melanoma antigen family A, 2\|melanoma antigen family A, 12\|melanoma antigen family A, 5 | 2.13 | 4.248E-04 | 4105\|4102\|4101\|266740\|4111\|4104 |
| PH_hs_0036772 | DUSP5P | dual specificity phosphatase 5 pseudogene | 2.13 | 9.343E-10 | 574029 |
| PH_hs_0048572 | UBAP2L | ubiquitin associated protein 2-like | 2.13 | 1.197E-08 | 9898 |

-continued

| Probe ID | Gene_symbol | Description | Fold Change | p-value | Entrez_gene |
|---|---|---|---|---|---|
| PH_hs_0035164 | RPL22L1 | ribosomal protein L22-like 1 | 2.14 | 1.362E-05 | 200916 |
| PH_hs_0049240 | TANC1 | tetratricopeptide repeat, ankyrin repeat and coiled-coil containing 1 | 2.14 | 6.461E-12 | 85461 |
| PH_hs_0042352 | DPH1 | DPH1 homolog (S. cerevisiae) | 2.14 | 5.487E-07 | 1801 |
| PH_hs_0042138 | TOP1MT | topoisomerase (DNA) I, mitochondrial | 2.15 | 1.313E-10 | 116447 |
| PH_hs_0048065 | MCCC2 | methylcrotonoyl-CoA carboxylase 2 (beta) | 2.15 | 2.730E-15 | 64087 |
| PH_hs_0042096 | KLF3 | Kruppel-like factor 3 (basic) | 2.15 | 4.295E-18 | 51274 |
| PH_hs_0043410 | C6orf120 | chromosome 6 open reading frame 120 | 2.16 | 2.221E-03 | 387263 |
| PH_hs_0005636 | TNFAIP2 | tumor necrosis factor, alpha-induced protein 2 | 2.16 | 1.800E-07 | 7127 |
| PH_hs_0034663 | RORC | RAR-related orphan receptor C | 2.16 | 4.647E-04 | 6097 |
| PH_hs_0011427 | BANK1 | B-cell scaffold protein with ankyrin repeats 1 | 2.16 | 6.917E-09 | 55024 |
| PH_hs_0026987 | ZNF3 | zinc finger protein 3 | 2.16 | 4.880E-15 | 7551 |
| PH_hs_0033681 | HSD17B1 | hydroxysteroid (17-beta) dehydrogenase 1 | 2.16 | 3.834E-05 | 3292 |
| PH_hs_0019504 | MZB1 | marginal zone B and B1 cell-specific protein | 2.17 | 3.111E-11 | 51237 |
| PH_hs_0053842 | GOLGA8B\|GOLGA8A | golgin A8 family, member B\|golgin A8 family, member A | 2.17 | 3.102E-06 | 440270\|23015 |
| PH_hs_0049566 | FCGR2C\|FCGR2A | Fc fragment of IgG, low affinity IIc, receptor for (CD32) (gene/pseudogene)\|Fc fragment of IgG, low affinity IIa, receptor (CD32) | 2.17 | 1.666E-05 | 9103\|2212 |
| PH_hs_0016105 | NXF1 | nuclear RNA export factor 1 | 2.17 | 1.038E-18 | 10482 |
| PH_hs_0004859 | POLR1B | polymerase (RNA) I polypeptide B, 128 kDa | 2.18 | 4.434E-21 | 84172 |
| PH_hs_0005094 | PGAP3 | post-GPI attachment to proteins 3 | 2.18 | 1.526E-10 | 93210 |
| PH_hs_0025544 | CHCHD7 | coiled-coil-helix-coiled-coil-helix domain containing 7 | 2.19 | 1.002E-06 | 79145 |
| PH_hs_0001926 | IGSF1 | immunoglobulin superfamily, member 1 | 2.20 | 1.517E-06 | 3547 |
| PH_hs_0022674 | SARM1 | sterile alpha and TIR motif containing 1 | 2.20 | 7.343E-05 | 23098 |
| PH_hs_0048310 | ACACB | acetyl-CoA carboxylase beta | 2.20 | 4.412E-09 | 32 |
| PH_hs_0007296 | FBRSL1 | fibrosin-like 1 | 2.20 | 2.029E-07 | 57666 |
| PH_hs_0048590 | LRRTM1 | leucine rich repeat transmembrane neuronal 1 | 2.21 | 1.253E-02 | 347730 |
| PH_hs_0011345 | FAM160B1 | family with sequence similarity 160, member B1 | 2.21 | 3.142E-18 | 57700 |
| PH_hs_0013259 | ZNF219 | zinc finger protein 219 | 2.21 | 4.108E-23 | 51222 |
| PH_hs_0001482 | CNKSR3 | CNKSR family member 3 | 2.21 | 2.973E-06 | 154043 |
| PH_hs_0043183 | RARRES2 | retinoic acid receptor responder (tazarotene induced) 2 | 2.22 | 2.295E-02 | 5919 |
| PH_hs_0010802 | MAOA | monoamine oxidase A | 2.22 | 2.957E-05 | 4128 |
| PH_hs_0048914 | VASH2 | vasohibin 2 | 2.22 | 5.210E-13 | 79805 |
| PH_hs_0048534 | PRRT3 | proline-rich transmembrane protein 3 | 2.22 | 1.530E-14 | 285368 |
| PH_hs_0023814 | ARVCF | armadillo repeat gene deleted in velocardiofacial syndrome | 2.23 | 3.883E-11 | 421 |
| PH_hs_0015649 | PPP1R3C | protein phosphatase 1, regulatory (inhibitor) subunit 3C | 2.23 | 3.996E-12 | 5507 |
| PH_hs_0006585 | FLJ37453 | hypothetical LOC729614 | 2.24 | 4.036E-18 | 729614 |
| PH_hs_0043964 | SDHD\|LOC1005106 03 | succinate dehydrogenase complex, subunit D, integral membrane protein\|succinate dehydrogenase [ubiquinone] cytochrome b small subunit, mitochondrial-like | 2.24 | 9.084E-16 | 6392\|100510603 |
| PH_hs_0023677 | KIAA1370 | KIAA1370 | 2.24 | 1.360E-18 | 56204 |
| PH_hs_0043352 | ARID5B | AT rich interactive domain 5B (MRF1-like) | 2.24 | 3.422E-09 | 84159 |
| PH_hs_0048315 | ALDH7A1 | aldehyde dehydrogenase 7 family, member A1 | 2.24 | 3.189E-02 | 501 |
| PH_hs_0049579 | FHL1\|LOC10012816 4 | four and a half LIM domains 1\|four and a half LIM domains 1 pseudogene | 2.24 | 3.608E-17 | 2273\|100128164 |
| PH_hs_0024448 | RNASET2 | ribonuclease T2 | 2.25 | 2.587E-09 | 8635 |
| PH_hs_0048286 | GPSM1 | G-protein signaling modulator 1 | 2.25 | 7.803E-15 | 26086 |
| PH_hs_0004279 | ARFIP2 | ADP-ribosylation factor interacting protein 2 | 2.25 | 1.516E-16 | 23647 |
| PH_hs_0006351 | PANK1 | pantothenate kinase 1 | 2.25 | 5.179E-15 | 53354 |
| PH_hs_0044630 | DPM3 | dolichyl-phosphate mannosyltransferase polypeptide 3 | 2.25 | 2.580E-08 | 54344 |
| PH_hs_0000928 | TMEM47 | transmembrane protein 47 | 2.25 | 1.011E-14 | 83604 |
| PH_hs_0000894 | TRAF4 | TNF receptor-associated factor 4 | 2.26 | 7.043E-08 | 9618 |
| PH_hs_0048426 | C5orf4 | chromosome 5 open reading frame 4 | 2.28 | 6.610E-06 | 10826 |

-continued

| Probe ID | Gene_symbol | Description | Fold Change | p-value | Entrez_gene |
|---|---|---|---|---|---|
| PH_hs_0047163 | LOC646903 | hypothetical LOC646903 | 2.28 | 3.832E-03 | 646903 |
| PH_hs_0031245 | SEMA6C | sema domain, transmembrane domain (TM), and cytoplasmic domain, (semaphorin) 6C | 2.28 | 1.147E-04 | 10500 |
| PH_hs_0002744 | FIBIN | fin bud initiation factor homolog (zebrafish) | 2.28 | 1.079E-10 | 387758 |
| PH_hs_0004117 | CRIP2 | cysteine-rich protein 2 | 2.29 | 9.078E-10 | 1397 |
| PH_hs_0003170 | OLFML2B | olfactomedin-like 2B | 2.30 | 3.516E-10 | 25903 |
| PH_hs_0015627 | LOC100128822 | hypothetical LOC100128822 | 2.30 | 3.077E-10 | 100128822 |
| PH_hs_0023986 | ZBED3 | zinc finger, BED-type containing 3 | 2.30 | 3.866E-14 | 84327 |
| PH_hs_0006081 | PPIC | peptidylprolyl isomerase C (cyclophilin C) | 2.30 | 1.216E-10 | 5480 |
| PH_hs_0024897 | C9orf3 | chromosome 9 open reading frame 3 | 2.31 | 3.917E-22 | 84909 |
| PH_hs_0033390 | ALDH2 | aldehyde dehydrogenase 2 family (mitochondrial) | 2.31 | 1.362E-18 | 217 |
| PH_hs_0022133 | CH25H | cholesterol 25-hydroxylase | 2.31 | 2.040E-06 | 9023 |
| PH_hs_0003977 | EMILIN1 | elastin microfibril interfacer 1 | 2.32 | 4.220E-09 | 11117 |
| PH_hs_0026049 | CCDC25 | coiled-coil domain containing 25 | 2.32 | 8.264E-06 | 55246 |
| PH_hs_0022573 | C20orf108 | chromosome 20 open reading frame 108 | 2.33 | 4.187E-11 | 116151 |
| PH_hs_0023733 | CFI | complement factor I | 2.33 | 1.923E-12 | 3426 |
| PH_hs_0032079 | SREBF1 | sterol regulatory element binding transcription factor 1 | 2.34 | 3.370E-19 | 6720 |
| PH_hs_0027959 | RAB33B | RAB33B, member RAS oncogene family | 2.34 | 3.235E-11 | 83452 |
| PH_hs_0014152 | OSBPL7 | oxysterol binding protein-like 7 | 2.34 | 8.208E-09 | 114881 |
| PH_hs_0043392 | MST1 | macrophage stimulating 1 (hepatocyte growth factor-like) | 2.35 | 5.097E-11 | 4485 |
| PH_hs_0023030 | IL11RA | interleukin 11 receptor, alpha | 2.35 | 1.589E-14 | 3590 |
| PH_hs_0048783 | RBMS3 | RNA binding motif, single stranded interacting protein 3 | 2.35 | 1.340E-06 | 27303 |
| PH_hs_0004330 | BTG2 | BTG family, member 2 | 2.35 | 2.267E-03 | 7832 |
| PH_hs_0000450 | KLHL24 | kelch-like 24 (Drosophila) | 2.36 | 1.005E-02 | 54800 |
| PH_hs_0002217 | C8orf55 | chromosome 8 open reading frame 55 | 2.36 | 4.597E-17 | 51337 |
| PH_hs_0024193 | PNOC | prepronociceptin | 2.36 | 1.578E-09 | 5368 |
| PH_hs_0042673 | SSC5D | scavenger receptor cysteine-rich glycoprotein | 2.36 | 1.067E-03 | 284297 |
| PH_hs_0046183 | TUBA4B | tubulin, alpha 4b (pseudogene) | 2.37 | 1.416E-11 | 80086 |
| PH_hs_0035084 | C8orf82 | chromosome 8 open reading frame 82 | 2.37 | 5.209E-18 | 414919 |
| PH_hs_0042901 | C8orf85 | chromosome 8 open reading frame 85 | 2.37 | 6.166E-11 | 441376 |
| PH_hs_0048064 | GNAI3 | guanine nucleotide binding protein (G protein), alpha inhibiting activity polypeptide 3 | 2.37 | 3.866E-21 | 2773 |
| PH_hs_0048584 | UQCRQ | ubiquinol-cytochrome c reductase, complex III subunit VII, 9.5 kDa | 2.37 | 1.406E-05 | 27089 |
| PH_hs_0000823 | BTBD3 | BTB (POZ) domain containing 3 | 2.37 | 3.863E-18 | 22903 |
| PH_hs_0049536 | SYS1-DBNDD2|DBNDD2 | SYS1-DBNDD2 read-through transcript|dysbindin (dystrobrevin binding protein 1) domain containing 2 | 2.38 | 1.836E-15 | 76755755861 |
| PH_hs_0045687 | TMEM50B | transmembrane protein 50B | 2.39 | 2.451E-22 | 757 |
| PH_hs_0005174 | ZNF580 | zinc finger protein 580 | 2.39 | 5.629E-15 | 51157 |
| PH_hs_0047661 | RMND5A | required for meiotic nuclear division 5 homolog A (S. cerevisiae) | 2.40 | 5.614E-17 | 64795 |
| PH_hs_0047501 | CEP68 | centrosomal protein 68 kDa | 2.41 | 9.716E-16 | 23177 |
| PH_hs_0047853 | ITGA4 | integrin, alpha 4 (antigen CD49D, alpha 4 subunit of VLA-4 receptor) | 2.41 | 1.334E-08 | 3676 |
| PH_hs_0001117 | DHCR7 | 7-dehydrocholesterol reductase | 2.41 | 1.863E-19 | 1717 |
| PH_hs_0025402 | LOC100507739|LOC100506584 | hypothetical protein LOC100507739|hypothetical protein LOC100506584 | 2.41 | 8.618E-11 | 100507739|10006584 |
| PH_hs_0029926 | IFITM3 | interferon induced transmembrane protein 3 (1-8U) | 2.42 | 1.763E-06 | 10410 |
| PH_hs_0024827 | FKBP7 | FK506 binding protein 7 | 2.42 | 1.775E-03 | 51661 |
| PH_hs_0043317 | ZNF780B | zinc finger protein 780B | 2.42 | 3.160E-06 | 163131 |
| PH_hs_0032222 | TCEA2 | transcription elongation factor A (SII), 2 | 2.43 | 1.647E-12 | 6919 |
| PH_hs_0026600 | MCAM | melanoma cell adhesion molecule | 2.43 | 5.394E-14 | 4162 |
| PH_hs_0043577 | RALGDS | ral guanine nucleotide dissociation stimulator | 2.43 | 8.728E-17 | 5900 |
| PH_hs_0002620 | GAB2 | GRB2-associated binding protein 2 | 2.44 | 6.651E-04 | 9846 |
| PH_hs_0010073 | TLX2 | T-cell leukemia homeobox 2 | 2.45 | 4.051E-13 | 3196 |
| PH_hs_0010551 | OXCT1 | 3-oxoacid CoA transferase 1 | 2.45 | 1.030E-16 | 5019 |

| Probe ID | Gene_symbol | Description | Fold Change | p-value | Entrez_gene |
|---|---|---|---|---|---|
| PH_hs_0028982 | NFATC4 | nuclear factor of activated T-cells, cytoplasmic, calcineurin-dependent 4 | 2.45 | 1.727E-06 | 4776 |
| PH_hs_0048516 | AKT2 | v-akt murine thymoma viral oncogene homolog 2 | 2.45 | 4.172E-14 | 208 |
| PH_hs_0007721 | GBGT1 | globoside alpha-1,3-N-acetylgalactosaminyltransferase 1 | 2.46 | 1.028E-02 | 26301 |
| PH_hs_0034629 | GOLGA8G\|GOLGA8E\|GOLGA8C\|GOLGA8DP | golgin A8 family, member G\|golgin A8 family, member E\|golgin A8 family, member C\|golgin A8 family, member D (pseudogene) | 2.46 | 4.044E-08 | 283768\|390535\|729786\|100132979 |
| PH_hs_0010130 | THBS3 | thrombospondin 3 | 2.47 | 3.653E-12 | 7059 |
| PH_hs_0037351 | LRRC8B | leucine rich repeat containing 8 family, member B | 2.47 | 1.161E-03 | 23507 |
| PH_hs_0024837 | ALK | anaplastic lymphoma receptor tyrosine kinase | 2.48 | 1.529E-12 | 238 |
| PH_hs_0023592 | TNFRSF25 | tumor necrosis factor receptor superfamily, member 25 | 2.48 | 1.674E-12 | 8718 |
| PH_hs_0000585 | IMPA2 | inositol(myo)-1(or 4)-monophosphatase 2 | 2.49 | 1.115E-15 | 3613 |
| PH_hs_0022275 | NNT | nicotinamide nucleotide transhydrogenase | 2.49 | 8.497E-12 | 23530 |
| PH_hs_0043571 | FGF18 | fibroblast growth factor 18 | 2.49 | 8.249E-17 | 8817 |
| PH_hs_0023181 | MEGF9 | multiple EGF-like-domains 9 | 2.50 | 6.669E-16 | 1955 |
| PH_hs_0001401 | CLN8 | ceroid-lipofuscinosis, neuronal 8 (epilepsy, progressive with mental retardation) | 2.50 | 1.522E-17 | 2055 |
| PH_hs_0002930 | PRPH | peripherin | 2.50 | 7.181E-13 | 5630 |
| PH_hs_0045355 | NOVA1 | neuro-oncological ventral antigen 1 | 2.51 | 5.560E-08 | 4857 |
| PH_hs_0010165 | C9orf91 | chromosome 9 open reading frame 91 | 2.51 | 1.443E-07 | 203197 |
| PH_hs_0043531 | SDCBP2\|FKBP1A-SDCBP2 | syndecan binding protein (syntenin) 2\|FKBP1A-SDCBP2 read-through transcript | 2.52 | 2.938E-02 | 27111\|100528031 |
| PH_hs_0036494 | GDF11 | growth differentiation factor 11 | 2.52 | 5.433E-10 | 10220 |
| PH_hs_0002838 | LOC100510620\|LOC100505806 | hypothetical LOC100510620\|hypothetical LOC100505806 | 2.52 | 8.775E-03 | 100510620\|100505806 |
| PH_hs_0046356 | ZC3H12D | zinc finger CCCH-type containing 12D | 2.52 | 1.513E-04 | 340152 |
| PH_hs_0022824 | CBS | cystathionine-beta-synthase | 2.53 | 2.907E-09 | 875 |
| PH_hs_0042024 | LTC4S | leukotriene C4 synthase | 2.53 | 5.579E-09 | 4056 |
| PH_hs_0026552 | NKIRAS2 | NFKB inhibitor interacting Ras-like 2 | 2.53 | 4.443E-05 | 28511 |
| PH_hs_0005573 | TLE4 | transducin-like enhancer of split 4 (E(sp1) homolog, Drosophila) | 2.54 | 1.630E-15 | 7091 |
| PH_hs_0008177 | ARPM1 | actin related protein M1 | 2.55 | 2.096E-10 | 84517 |
| PH_hs_0047844 | JMY | junction mediating and regulatory protein, p53 cofactor | 2.56 | 1.357E-10 | 133746 |
| PH_hs_0002632 | RTN4R | reticulon 4 receptor | 2.56 | 6.548E-11 | 65078 |
| PH_hs_0020570 | PLK1S1 | polo-like kinase 1 substrate 1 | 2.57 | 3.262E-03 | 55857 |
| PH_hs_0010726 | LOC283663 | hypothetical LOC283663 | 2.57 | 3.149E-14 | 283663 |
| PH_hs_0024020 | FBP1 | fructose-1,6-bisphosphatase 1 | 2.57 | 8.036E-07 | 2203 |
| PH_hs_0024986 | DBP | D site of albumin promoter (albumin D-box) binding protein | 2.59 | 1.041E-07 | 1628 |
| PH_hs_0006020 | RAB38 | RAB38, member RAS oncogene family | 2.59 | 5.591E-08 | 23682 |
| PH_hs_0022113 | HNMT | histamine N-methyltransferase | 2.59 | 6.475E-05 | 3176 |
| PH_hs_0000672 | HECA | headcase homolog (Drosophila) | 2.59 | 1.240E-19 | 51696 |
| PH_hs_0008735 | HERPUD1 | homocysteine-inducible, endoplasmic reticulum stress-inducible, ubiquitin-like domain member 1 | 2.60 | 1.138E-32 | 9709 |
| PH_hs_0043702 | IL4I1 | interleukin 4 induced 1 | 2.61 | 5.545E-03 | 259307 |
| PH_hs_0032271 | SERPINH1 | serpin peptidase inhibitor, clade H (heat shock protein 47), member 1, (collagen binding protein 1) | 2.62 | 1.965E-14 | 871 |
| PH_hs_0032053 | PCMTD2 | protein-L-isoaspartate (D-aspartate) O-methyltransferase domain containing 2 | 2.62 | 1.743E-08 | 55251 |
| PH_hs_0013714 | VAV3 | vav 3 guanine nucleotide exchange factor | 2.62 | 5.423E-16 | 10451 |
| PH_hs_0017289 | CXXC5 | CXXC finger protein 5 | 2.62 | 4.773E-07 | 51523 |
| PH_hs_0043367 | EBF1 | early B-cell factor 1 | 2.63 | 2.407E-14 | 1879 |
| PH_hs_0047712 | YPEL2 | yippee-like 2 (Drosophila) | 2.64 | 8.930E-10 | 388403 |
| PH_hs_0007590 | BFSP1 | beaded filament structural protein 1, filensin | 2.65 | 3.302E-13 | 631 |
| PH_hs_0014251 | KCNT2 | potassium channel, subfamily T, member 2 | 2.65 | 7.297E-04 | 343450 |
| PH_hs_0030600 | C5orf13 | chromosome 5 open reading frame 13 | 2.65 | 5.858E-13 | 9315 |
| PH_hs_0010868 | STK38L | serine/threonine kinase 38 like | 2.67 | 2.557E-12 | 23012 |
| PH_hs_0000665 | KIF5C | kinesin family member 5C | 2.67 | 2.336E-17 | 3800 |

-continued

| Probe ID | Gene_symbol | Description | Fold Change | p-value | Entrez_gene |
|---|---|---|---|---|---|
| PH_hs_0005512 | NTF3 | neurotrophin 3 | 2.69 | 7.710E-09 | 4908 |
| PH_hs_0001171 | SYT13 | synaptotagmin XIII | 2.69 | 1.668E-08 | 57586 |
| PH_hs_0011484 | PALLD | palladin, cytoskeletal associated protein | 2.69 | 1.162E-29 | 23022 |
| PH_hs_0044091 | TNFSF12 | tumor necrosis factor (ligand) superfamily, member 12 | 2.70 | 1.382E-15 | 8742 |
| PH_hs_0047838 | IGFBP3 | insulin-like growth factor binding protein 3 | 2.70 | 4.299E-24 | 3486 |
| PH_hs_0024678 | LUM | lumican | 2.70 | 2.413E-08 | 4060 |
| PH_hs_0014995 | METTL7A | methyltransferase like 7A | 2.71 | 3.915E-28 | 25840 |
| PH_hs_0047451 | KAZ | kazrin | 2.71 | 2.906E-23 | 23254 |
| PH_hs_0025416 | TH | tyrosine hydroxylase | 2.73 | 4.850E-14 | 7054 |
| PH_hs_0025787 | ANK3 | ankyrin 3, node of Ranvier (ankyrin G) | 2.75 | 3.869E-04 | 288 |
| PH_hs_0005136 | PLA2G7 | phospholipase A2, group VII (platelet-activating factor acetylhydrolase, plasma) | 2.75 | 4.178E-04 | 7941 |
| PH_hs_0044320 | ZNF44 | zinc finger protein 44 | 2.75 | 1.545E-06 | 51710 |
| PH_hs_0002451 | PATZ1 | POZ (BTB) and AT hook containing zinc finger 1 | 2.75 | 6.470E-24 | 23598 |
| PH_hs_0047063 | WWOX | WW domain containing oxidoreductase | 2.77 | 1.938E-12 | 51741 |
| PH_hs_0004441 | SNCA | synuclein, alpha (non A4 component of amyloid precursor) | 2.77 | 2.671E-14 | 6622 |
| PH_hs_0031374 | KLF5 | Kruppel-like factor 5 (intestinal) | 2.78 | 6.622E-05 | 688 |
| PH_hs_0049102 | KCMF1 | potassium channel modulatory factor 1 | 2.80 | 4.836E-16 | 56888 |
| PH_hs_0034638 | HSD11B1L | hydroxysteroid (11-beta) dehydrogenase 1-like | 2.80 | 3.228E-28 | 374875 |
| PH_hs_0049706 | ABCC6/ABCC6P2 | ATP-binding cassette, sub-family C (CFTR/MRP), member 6\|ATP-binding cassette, sub-family C, member 6 pseudogene 2 | 2.81 | 3.829E-06 | 368\|730013 |
| PH_hs_0018551 | DDAH1 | dimethylarginine dimethylaminohydrolase 1 | 2.82 | 9.493E-09 | 23576 |
| PH_hs_0025514 | RARB | retinoic acid receptor, beta | 2.83 | 1.662E-06 | 5915 |
| PH_hs_0004753 | FASN | fatty acid synthase | 2.83 | 8.159E-36 | 2194 |
| PH_hs_0003251 | GAL3ST4 | galactose-3-O-sulfotransferase 4 | 2.85 | 1.143E-17 | 79690 |
| PH_hs_0043311 | KLHDC3 | kelch domain containing 3 | 2.85 | 5.179E-19 | 116138 |
| PH_hs_0026661 | DUSP8 | dual specificity phosphatase 8 | 2.85 | 2.407E-18 | 1850 |
| PH_hs_0005107 | WNT10B | wingless-type MMTV integration site family, member 10B | 2.86 | 1.239E-13 | 7480 |
| PH_hs_0005953 | LPHN1 | latrophilin 1 | 2.86 | 3.090E-16 | 22859 |
| PH_hs_0027347 | CTHRC1 | collagen triple helix repeat containing 1 | 2.87 | 9.534E-07 | 115908 |
| PH_hs_0001349 | SESN1 | sestrin 1 | 2.88 | 1.789E-09 | 27244 |
| PH_hs_0004398 | EFEMP1 | EGF-containing fibulin-like extracellular matrix protein 1 | 2.88 | 4.258E-20 | 2202 |
| PH_hs_0011876 | PCOLCE | procollagen C-endopeptidase enhancer | 2.89 | 5.904E-19 | 5118 |
| PH_hs_0029707 | KRTAP4-8\|KRTAP4-11 | keratin associated protein 4-8\|keratin associated protein 4-11 | 2.89 | 7.931E-13 | 728224\|653240 |
| PH_hs_0032521 | ACSF2 | acyl-CoA synthetase family member 2 | 2.91 | 2.628E-16 | 80221 |
| PH_hs_0006423 | SLC46A3 | solute carrier family 46, member 3 | 2.92 | 5.778E-14 | 283537 |
| PH_hs_0005145 | ZNF608 | zinc finger protein 608 | 2.94 | 5.480E-05 | 57507 |
| PH_hs_0043781 | ADAM21 | ADAM metallopeptidase domain 21 | 2.94 | 4.853E-08 | 8747 |
| PH_hs_0043599 | DCLK2 | doublecortin-like kinase 2 | 2.94 | 4.391E-23 | 166614 |
| PH_hs_0042059 | CALHM3 | calcium homeostasis modulator 3 | 2.95 | 5.820E-03 | 119395 |
| PH_hs_0027659 | HSPB7 | heat shock 27 kDa protein family, member 7 (cardiovascular) | 2.97 | 5.117E-08 | 27129 |
| PH_hs_0023711 | HSPA5 | heat shock 70 kDa protein 5 (glucose-regulated protein, 78 kDa) | 2.98 | 1.110E-23 | 3309 |
| PH_hs_0025905 | C8orf44 | chromosome 8 open reading frame 44 | 2.98 | 1.730E-18 | 56260 |
| PH_hs_0044361 | FAM179A | family with sequence similarity 179, member A | 2.98 | 1.235E-22 | 165186 |
| PH_hs_0047629 | ZNF74 | zinc finger protein 74 | 2.99 | 6.677E-17 | 7625 |
| PH_hs_0031241 | TNFSF13\|TNFSF12-TNFSF13 | tumor necrosis factor (ligand) superfamily, member 13\|TNFSF12-TNFSF13 readthrough | 3.00 | 3.526E-25 | 8741\|407977 |
| PH_hs_0025600 | EPB41L1 | erythrocyte membrane protein band 4.1-like 1 | 3.03 | 2.260E-26 | 2036 |
| PH_hs_0044803 | C2orf68 | chromosome 2 open reading frame 68 | 3.04 | 1.815E-12 | 388969 |
| PH_hs_0048509 | MFSD6 | major facilitator superfamily domain containing 6 | 3.05 | 6.095E-20 | 54842 |
| PH_hs_0028629 | ERV3 | endogenous retroviral sequence 3 | 3.05 | 7.309E-18 | 2086 |

-continued

| Probe ID | Gene_symbol | Description | Fold Change | p-value | Entrez_gene |
|---|---|---|---|---|---|
| PH_hs_0045976 | SEPT6 | septin 6 | 3.05 | 3.607E-08 | 23157 |
| PH_hs_0024713 | COL4A2 | collagen, type IV, alpha 2 | 3.06 | 2.495E-17 | 1284 |
| PH_hs_0000684 | DNAJB9 | DnaJ (Hsp40) homolog, subfamily B, member 9 | 3.06 | 6.398E-19 | 4189 |
| PH_hs_0037891 | NCRNA00157 | non-protein coding RNA 157 | 3.07 | 2.696E-03 | 54075 |
| PH_hs_0046015 | PDLIM3 | PDZ and LIM domain 3 | 3.07 | 4.844E-03 | 27295 |
| PH_hs_0014100 | ADCK3 | aarF domain containing kinase 3 | 3.07 | 6.298E-23 | 56997 |
| PH_hs_0030129 | PNKD | paroxysmal nonkinesigenic dyskinesia | 3.07 | 2.548E-29 | 25953 |
| PH_hs_0022416 | FRZB | frizzled-related protein | 3.08 | 4.430E-13 | 2487 |
| PH_hs_0043719 | HMGCS1 | 3-hydroxy-3-methylglutaryl-CoA synthase 1 (soluble) | 3.09 | 4.084E-28 | 3157 |
| PH_hs_0048642 | PITPNM3 | PITPNM family member 3 | 3.09 | 1.865E-03 | 83394 |
| PH_hs_0026436 | MXRA8 | matrix-remodelling associated 8 | 3.10 | 4.649E-22 | 54587 |
| PH_hs_0024709 | MYB | v-myb myeloblastosis viral oncogene homolog (avian) | 3.12 | 1.960E-12 | 4602 |
| PH_hs_0001428 | HEXIM1 | hexamethylene bis-acetamide inducible 1 | 3.19 | 2.520E-12 | 10614 |
| PH_hs_0049518 | SPRR2C | small proline-rich protein 2C (pseudogene) | 3.19 | 3.886E-08 | 6702 |
| PH_hs_0042334 | MT4 | metallothionein 4 | 3.23 | 4.564E-14 | 84560 |
| PH_hs_0044960 | MGC21881 | hypothetical locus MGC21881 | 3.24 | 7.026E-28 | 389741 |
| PH_hs_0047981 | DLX3 | distal-less homeobox 3 | 3.24 | 2.926E-22 | 1747 |
| PH_hs_0033195 | FOXN3 | forkhead box N3 | 3.25 | 1.798E-09 | 1112 |
| PH_hs_0007383 | F2R | coagulation factor II (thrombin) receptor | 3.28 | 4.070E-15 | 2149 |
| PH_hs_0048029 | CHRNB1 | cholinergic receptor, nicotinic, beta 1 (muscle) | 3.30 | 6.262E-21 | 1140 |
| PH_hs_0000763 | REEP1 | receptor accessory protein 1 | 3.30 | 9.573E-03 | 65055 |
| PH_hs_0005804 | AQP9 | aquaporin 9 | 3.31 | 1.817E-16 | 366 |
| PH_hs_0034837 | ARG2 | arginase, type II | 3.31 | 2.170E-15 | 384 |
| PH_hs_0046456 | TLCD2 | TLC domain containing 2 | 3.33 | 3.518E-13 | 727910 |
| PH_hs_0043744 | CITED1 | Cbp/p300-interacting transactivator, with Glu/Asp-rich carboxy-terminal domain, 1 | 3.38 | 1.733E-18 | 4435 |
| PH_hs_0000763 | SORT1 | sortilin 1 | 3.41 | 1.320E-21 | 6272 |
| PH_hs_0010359 | COL1A1 | collagen, type I, alpha 1 | 3.42 | 3.730E-20 | 1277 |
| PH_hs_0001086 | TP53INP2 | tumor protein p53 inducible nuclear protein 2 | 3.46 | 9.620E-13 | 58476 |
| PH_hs_0010384 | TMEM100 | transmembrane protein 100 | 3.46 | 3.184E-20 | 55273 |
| PH_hs_0000329 | ANGPT1 | angiopoietin 1 | 3.46 | 6.013E-21 | 284 |
| PH_hs_0047559 | ITGB8 | integrin, beta 8 | 3.46 | 2.278E-12 | 3696 |
| PH_hs_0033736 | TMEM119 | transmembrane protein 119 | 3.48 | 2.086E-24 | 338773 |
| PH_hs_0048420 | SNX18 | sorting nexin 18 | 3.48 | 1.143E-17 | 112574 |
| PH_hs_0046459 | LOC728819 | hCG1645220 | 3.50 | 6.811E-07 | 728819 |
| PH_hs_0047533 | MFAP5 | microfibrillar associated protein 5 | 3.50 | 2.947E-13 | 8076 |
| PH_hs_0046308 | FAM13C | family with sequence similarity 13, member C | 3.58 | 5.102E-09 | 220965 |
| PH_hs_0031653 | LIMS2 | LIM and senescent cell antigen-like domains 2 | 3.59 | 1.374E-08 | 55679 |
| PH_hs_0048185 | DPP6 | dipeptidyl-peptidase 6 | 3.61 | 2.384E-06 | 1804 |
| PH_hs_0023462 | COL5A2 | collagen, type V, alpha 2 | 3.68 | 7.659E-16 | 1290 |
| PH_hs_0043411 | IFITM2 | interferon induced transmembrane protein 2 (1-8D) | 3.72 | 1.855E-15 | 10581 |
| PH_hs_0001688 | LOC400043 | hypothetical LOC400043 | 3.72 | 0.000E+00 | 400043 |
| PH_hs_0026234 | VWA1 | von Willebrand factor A domain containing 1 | 3.73 | 2.020E-04 | 64856 |
| PH_hs_0043711 | ACTA2 | actin, alpha 2, smooth muscle, aorta | 3.76 | 0.000E+00 | 59 |
| PH_hs_0046297 | SYNPO2 | synaptopodin 2 | 3.77 | 5.301E-19 | 171024 |
| PH_hs_0009308 | CYP1B1 | cytochrome P450, family 1, subfamily B, polypeptide 1 | 3.84 | 1.065E-17 | 1545 |
| PH_hs_0048576 | MYL1P | myosin regulatory light chain interacting protein | 3.84 | 3.613E-26 | 29116 |
| PH_hs_0005971 | DOCK11 | dedicator of cytokinesis 11 | 3.89 | 1.155E-16 | 139818 |
| PH_hs_0049351 | C17orf103 | chromosome 17 open reading frame 103 | 3.89 | 6.017E-24 | 256302 |
| PH_hs_0027738 | PCDH18 | protocadherin 18 | 3.91 | 5.331E-29 | 54510 |
| PH_hs_0042917 | MT1M/MT1JP | metallothionein 1M/metallothionein 1J (pseudogene) | 3.92 | 3.262E-17 | 4499/4498 |
| | | | 3.93 | 7.594E-12 | |

| Probe ID | Gene_symbol | Description | Fold Change | p-value | Entrez_gene |
|---|---|---|---|---|---|
| PH_hs_0018667 | CHI3L1 | chitinase 3-like 1 (cartilage glycoprotein-39) | 3.94 | 9.415E-42 | 1116 |
| PH_hs_0043472 | GTF2IRD1 | GTF2I repeat domain containing 1 | 3.94 | 8.077E-28 | 9569 |
| PH_hs_0023673 | PDGFRB | platelet-derived growth factor receptor, beta polypeptide | 3.97 | 9.328E-18 | 5159 |
| PH_hs_0049327 | SEMA5A | sema domain, seven thrombospondin repeats (type 1 and type 1-like), transmembrane domain (TM) and short cytoplasmic domain, (semaphorin) 5A | 4.02 | 2.869E-37 | 9037 |
| PH_hs_0025365 | TRO | trophinin | 4.03 | 1.166E-13 | 7216 |
| PH_hs_0016327 | NAPRT1 | nicotinate phosphoribosyltransferase domain containing 1 | 4.06 | 1.289E-43 | 93100 |
| PH_hs_0025862 | GLUL | glutamate-ammonia ligase | 4.07 | 2.841E-24 | 2752 |
| PH_hs_0044095 | AQP1 | aquaporin 1 (Colton blood group) | 4.08 | 8.334E-19 | 358 |
| PH_hs_0026812 | CEACAM1 | carcinoembryonic antigen-related cell adhesion molecule 1 (biliary glycoprotein) | 4.13 | 1.153E-10 | 634 |
| PH_hs_0048943 | SLC26A4 | solute carrier family 26, member 4 | 4.14 | 6.415E-09 | 5172 |
| PH_hs_0004650 | NTS | neurotensin | 4.16 | 0.000E+00 | 4922 |
| PH_hs_0042871 | SAMD5 | sterile alpha motif domain containing 5 | 4.17 | 5.374E-23 | 389432 |
| PH_hs_0018380 | LOC100128288 | hypothetical LOC100128288 | 4.18 | 5.220E-26 | 100128288 |
| PH_hs_0000178 | TNFRSF8 | tumor necrosis factor receptor superfamily, member 8 | 4.18 | 1.939E-18 | 943 |
| PH_hs_0002147 | CXCL14 | chemokine (C-X-C motif) ligand 14 | 4.19 | 7.903E-14 | 9547 |
| PH_hs_0047359 | EPHA5 | EPH receptor A5 | 4.31 | 4.231E-15 | 2044 |
| PH_hs_0004979 | MSX2 | msh homeobox 2 | 4.39 | 8.493E-25 | 4488 |
| PH_hs_0015557 | PLXND1 | plexin D1 | 4.43 | 2.090E-10 | 23129 |
| PH_hs_0004661 | S100A4 | S100 calcium binding protein A4 | 4.52 | 1.578E-27 | 6275 |
| PH_hs_0001210 | FAM59A | family with sequence similarity 59, member A | 4.54 | 6.416E-07 | 64762 |
| PH_hs_0049690 | CT45A3|CT45A5|CT45A1|CT45A2|CT45A4|CT45A6 | cancer/testis antigen family 45, member A3|cancer/testis antigen family 45, member A5|cancer/testis antigen family 45, member A1|cancer/testis antigen family 45, member A2|cancer/testis antigen family 45, member A4|cancer/testis antigen family 45, member A6 | 4.60 | 7.478E-27 | 441519|441521|541466|728911|441520|541465 |
| PH_hs_0000109 | DMPK | dystrophia myotonica-protein kinase | 4.61 | 1.152E-14 | 1760 |
| PH_hs_0029735 | ZNF354A | zinc finger protein 354A | 4.62 | 7.967E-35 | 6940 |
| PH_hs_0045768 | LFNG | LFNG O-fucosylpeptide 3-beta-N-acetylglucosaminyltransferase | 4.65 | 2.451E-09 | 3955 |
| PH_hs_0048356 | PRUNE2 | prune homolog 2 (Drosophila) | 4.67 | 1.904E-35 | 158471 |
| PH_hs_0016832 | FOXC1 | forkhead box C1 | 4.84 | 1.498E-30 | 2296 |
| PH_hs_0044922 | HBE1 | hemoglobin, epsilon 1 | 4.84 | 2.811E-15 | 3046 |
| PH_hs_0048721 | TLR4 | toll-like receptor 4 | 4.85 | 8.187E-19 | 7099 |
| PH_hs_0034338 | MST1|MST1P2 | macrophage stimulating 1 (hepatocyte growth factor-like)|macrophage stimulating 1 (hepatocyte growth factor-like) pseudogene 2 | 4.90 | 3.752E-19 | 4485|11209 |
| PH_hs_0032306 | HOXC8 | homeobox C8 | 4.94 | 5.682E-19 | 3224 |
| PH_hs_0005473 | RCOR2 | REST corepressor 2 | 5.02 | 1.791E-18 | 283248 |
| PH_hs_0049120 | SORL1 | sortilin-related receptor, L(DLR class) A repeats-containing | 5.06 | 5.157E-10 | 6653 |
| PH_hs_0005110 | FRMPD4 | FERM and PDZ domain containing 4 | 5.12 | 1.692E-10 | 9758 |
| PH_hs_0003256 | DPP4 | dipeptidyl-peptidase 4 | 5.25 | 8.238E-31 | 1803 |
| PH_hs_0047293 | COL14A1 | collagen, type XIV, alpha 1 | 5.30 | 1.963E-19 | 7373 |
| PH_hs_0004689 | MDK | midkine (neurite growth-promoting factor 2) | 5.33 | 2.692E-32 | 4192 |
| PH_hs_0044718 | BCL2L11 | BCL2-like 11 (apoptosis facilitator) | 5.33 | 1.265E-27 | 10018 |
| PH_hs_0019846 | TP53 | tumor protein p53 | 5.49 | 1.540E-28 | 7157 |
| PH_hs_0010329 | DLX4 | distal-less homeobox 4 | 5.50 | 0.000E+00 | 1748 |
| PH_hs_0048809 | SGCD | sarcoglycan, delta (35 kDa dystrophin-associated glycoprotein) | 5.55 | 7.219E-35 | 6444 |
| PH_hs_0005015 | UGT2B4 | UDP glucuronosyltransferase 2 family, polypeptide B4 | 5.56 | 9.899E-13 | 7363 |
| PH_hs_0032424 | CALCB | calcitonin-related polypeptide beta | 5.58 | 0.000E+00 | 797 |
| PH_hs_0018212 | CD24 | CD24 molecule | 5.61 | 4.334E-22 | 100133941 |
| PH_hs_0049248 | PIK3R3 | phosphoinositide-3-kinase, regulatory subunit 3 (gamma) | 5.80 | 2.365E-18 | 8503 |
| PH_hs_0024090 | MEF2C | myocyte enhancer factor 2C | 5.86 | 6.404E-43 | 4208 |
| PH_hs_0013486 | BIRC7 | baculoviral IAP repeat-containing 7 | 5.98 | 2.513E-17 | 79444 |
| PH_hs_0018971 | SLC9A3R1 | solute carrier family 9 (sodium/hydrogen exchanger), member 3 regulator 1 | 6.02 | 0.000E+00 | 9368 |

| Probe ID | Gene_symbol | Description | Fold Change | p-value | Entrez_gene |
|---|---|---|---|---|---|
| PH_hs_0049050 | PCDH7 | protocadherin 7 | 6.04 | 1.538E−29 | 5099 |
| PH_hs_0044562 | ABLIM1 | actin binding LIM protein 1 | 6.12 | 1.623E−30 | 3983 |
| PH_hs_0031763 | THY1 | Thy-1 cell surface antigen | 6.30 | 8.381E−18 | 7070 |
| PH_hs_0042224 | CKB | creatine kinase, brain | 6.47 | 4.759E−42 | 1152 |
| PH_hs_0046222 | MEX3A | mex-3 homolog A (C. elegans) | 6.51 | 3.279E−21 | 92312 |
| PH_hs_0048541 | CCDC69 | coiled-coil domain containing 69 | 6.55 | 2.060E−28 | 26112 |
| PH_hs_0047226 | ZNF229 | zinc finger protein 229 | 6.58 | 2.415E−04 | 7772 |
| PH_hs_0003115 | F2RL2 | coagulation factor II (thrombin) receptor-like 2 | 6.59 | 4.881E−33 | 2151 |
| PH_hs_0010156 | FOXO1 | forkhead box O1 | 6.82 | 1.157E−14 | 2308 |
| PH_hs_0004671 | KIT | v-kit Hardy-Zuckerman 4 feline sarcoma viral oncogene homolog | 6.96 | 7.296E−37 | 3815 |
| PH_hs_0036356 | TNFRSF9 | tumor necrosis factor receptor superfamily, member 9 | 7.12 | 0.000E+00 | 3604 |
| PH_hs_0004774 | CD33 | CD33 molecule | 7.53 | 1.370E−40 | 945 |
| PH_hs_0006956 | EPHA3 | EPH receptor A3 | 7.53 | 0.000E+00 | 2042 |
| PH_hs_0048149 | ALX4 | ALX homeobox 4 | 7.62 | 8.080E−32 | 60529 |
| PH_hs_0044625 | CALCA | calcitonin-related polypeptide alpha | 7.63 | 3.890E−12 | 796 |
| PH_hs_0023865 | QPRT | quinolinate phosphoribosyltransferase | 8.31 | 3.435E−39 | 23475 |
| PH_hs_0049151 | CELF2 | CUGBP, Elav-like family member 2 | 8.36 | 0.000E+00 | 10659 |
| PH_hs_0000718 | CBLN2 | cerebellin 2 precursor | 8.73 | 1.580E−39 | 147381 |
| PH_hs_0003183 | SULF2 | sulfatase 2 | 9.21 | 4.223E−15 | 55959 |
| PH_hs_0011497 | WISP2 | WNT1 inducible signaling pathway protein 2 | 9.27 | 4.484E−44 | 8839 |
| PH_hs_0047211 | MGAT4A | mannosyl (alpha-1,3-)glycoprotein beta-1,4-N-acetylglucosaminyltransferase, isozyme A | 9.69 | 7.006E−45 | 11320 |
| PH_hs_0047434 | ARHGAP28 | Rho GTPase activating protein 28 | 10.03 | 4.151E−29 | 79822 |
| PH_hs_0001045 | CGNL1 | cingulin-like 1 | 10.41 | 5.063E−26 | 84952 |
| PH_hs_0048430 | MAF | v-maf musculoaponeurotic fibrosarcoma oncogene homolog (avian) | 10.52 | 2.694E−11 | 4094 |
| PH_hs_0009405 | RCAN2 | regulator of calcineurin 2 | 11.10 | 7.006E−45 | 10231 |
| PH_hs_0047260 | COL1A2 | collagen, type I, alpha 2 | 11.26 | 0.000E+00 | 1278 |
| PH_hs_0032279 | CSAG1|CSAG2|CSAG3 | chondrosarcoma associated gene 1|CSAG family, member 2|CSAG family, member 3 | 11.88 | 1.415E−15 | 158511|728461|389903 |
| PH_hs_0000559 | GPM6B | glycoprotein M6B | 11.94 | 1.514E−14 | 2824 |
| PH_hs_0009093 | CTNNA2 | catenin (cadherin-associated protein), alpha 2 | 12.75 | 0.000E+00 | 1496 |
| PH_hs_0024012 | SOX4 | SRY (sex determining region Y)-box 4 | 12.86 | 1.892E−26 | 6659 |
| PH_hs_0045549 | CSAG1 | chondrosarcoma associated gene 1 | 13.78 | 0.000E+00 | 158511 |
| PH_hs_0005438 | FAT3 | FAT tumor suppressor homolog 3 (Drosophila) | 14.40 | 0.000E+00 | 120114 |
| PH_hs_0042964 | UBE2QL1 | ubiquitin-conjugating enzyme E2Q family-like 1 | 15.93 | 0.000E+00 | 134111 |
| PH_hs_0024799 | SULF1 | sulfatase 1 | 16.35 | 5.879E−20 | 23213 |
| PH_hs_0035318 | PRL | prolactin | 16.66 | 1.067E−22 | 5617 |
| PH_hs_0023510 | LRRC17 | leucine rich repeat containing 17 | 21.54 | 0.000E+00 | 10234 |
| PH_hs_0022287 | APOE | apolipoprotein E | 24.59 | 0.000E+00 | 348 |
| PH_hs_0025581 | COL4A1 | collagen, type IV, alpha 1 | 30.33 | 1.375E−22 | 1282 |
| PH_hs_0023535 | NUP210 | nucleoporin 210 kDa | 34.18 | 5.084E−24 | 23225 |
| PH_hs_0044518 | MTUS1 | microtubule associated tumor suppressor 1 | 46.14 | 2.767E−10 | 57509 |
| PH_hs_0025910 | COL3A1 | collagen, type III, alpha 1 | 75.99 | 0.000E+00 | 1281 |
| PH_hs_0005961 | CCDC3 | coiled-coil domain containing 3 | 94.19 | 0.000E+00 | 83643 |

What is claimed is:

1. A method for treating a subject affiliated with glioblastoma multiforme comprising administering a therapeutically effective regime of temozolomide to the glioblastoma multiforme-afflicted subject, concurrently with radiation therapy delivered as 60 Gy/30 fractions and with concomitant administration of *Pneumocystis carinii* pneumonia prophylaxis during therapy, wherein the subject's glioblastoma multiforme cells are caveolin-1 positive.

2. The method of claim 1, wherein the subject is human.

3. The method of claim 2, wherein the glioblastoma multiforme is newly diagnosed in the subject, and wherein the glioblastoma multiforme cells are early apoptotic cells.

4. The method of claim 1, wherein the subject's glioblastoma multiforme cells express an amount of caveolin-1 that is a percentage of the amount of caveolin-1 expressed by a lentiviral transduced caveolin-1-overxpressing U-87MG cell.

5. A method for treating a subject affiliated with glioblastoma multiforme comprising; determining if said subject's glioblastoma multiforme cells are determined to be caveolin-1 positive by an antibody-based method; administering a therapeutically effective regime of temozolomide to the glioblastoma multiforme-afflicted subject, concurrently with radiation therapy delivered as 60 Gy/30 fractions and with concomitant administration of *Pneumocystis carinii* pneumonia prophylaxis during therapy, wherein the subject's glioblastoma multiforme cells are caveolin-1 positive.

6. The method of claim 5, wherein the subject is human.

7. The method of claim 5, wherein the glioblastoma multiforme is newly diagnosed in the subject, and wherein the glioblastoma multiforme cells are early apoptotic cells.

8. The method of claim 5, wherein the subject's glioblastoma multiforme cells express an amount of caveolin-1 that is a percentage of the amount of caveolin-1 expressed by a lentiviral transduced caveolin-1-overxpressing U-87MG cell.

9. The method of claim 8, wherein the percentage is above 200%.

* * * * *